US007410795B2

(12) United States Patent
Hermanson et al.

(10) Patent No.: US 7,410,795 B2
(45) Date of Patent: Aug. 12, 2008

(54) CODON-OPTIMIZED POLYNUCLEOTIDE-BASED VACCINES AGAINST HUMAN CYTOMEGALOVIRUS INFECTION

(75) Inventors: Gary G. Hermanson, Encinitas, CA (US); Andrew J. Geall, Del Mar, CA (US); Mary Kopke Wloch, San Diego, CA (US)

(73) Assignee: Vical Incorporated, San Diego, CA (US)

( * ) Notice: Subject to any disclaimer, the term of this patent is extended or adjusted under 35 U.S.C. 154(b) by 510 days.

(21) Appl. No.: 10/738,986

(22) Filed: Dec. 19, 2003

(65) Prior Publication Data

US 2004/0209241 A1 Oct. 21, 2004

Related U.S. Application Data

(60) Provisional application No. 60/435,549, filed on Dec. 23, 2002.

(51) Int. Cl.
  *C12N 5/00* (2006.01)
  *C12Q 7/00* (2006.01)
  *A61K 39/00* (2006.01)
(52) U.S. Cl. .................. 435/320.1; 435/15; 435/235.1; 424/184.1
(58) Field of Classification Search ........................ None
  See application file for complete search history.

(56) References Cited

U.S. PATENT DOCUMENTS

| | | | |
|---|---|---|---|
| 5,124,440 A | 6/1992 | Gehrz et al. | |
| 5,547,834 A | 8/1996 | Spaete et al. | |
| 5,800,981 A | 9/1998 | Bruggeman et al. | |
| 5,834,307 A | 11/1998 | Spaete et al. | |
| 6,074,648 A | 6/2000 | Lee | |
| 6,100,064 A | 8/2000 | Burke et al. | |
| 6,133,433 A | 10/2000 | Pande et al. | |
| 6,156,317 A | 12/2000 | Diamond et al. | |
| 6,162,620 A | 12/2000 | Smith et al. | |
| 6,242,567 B1 | 6/2001 | Pande et al. | |
| 6,251,399 B1 | 6/2001 | Diamond et al. | |
| 2002/0081318 A1 | 6/2002 | Zaia et al. | |
| 2002/0115067 A1 | 8/2002 | Volker et al. | |

FOREIGN PATENT DOCUMENTS

| | | |
|---|---|---|
| EP | 1 156 112 A1 | 11/2001 |
| WO | WO 89/07143 A1 | 8/1989 |
| WO | 0 609 580 A1 | 8/1994 |
| WO | WO 97/11086 A1 | 3/1997 |
| WO | WO 97/40165 A1 | 10/1997 |
| WO | WO 99/02694 A1 | 1/1999 |
| WO | WO 01/52888 A2 | 7/2001 |

OTHER PUBLICATIONS

Endresz et al. "Optimization of DNA immunization against human cytomegalovirus". Vaccine. Jul. 16, 2001;19(28-29):3972-80.*
Gonczol et al. "Development of a cytomegalovirus vaccine: lessons from recent clinical trials". Expert Opin Biol Ther. May 2001;1(3):401-12.*
Shiver et al. "Replication-incompetent adenoviral vaccine vector elicits effective anti-immunodeficiency-virus immunity". Nature. Jan. 17, 2002;415(6869):331-5.*
Kotsopoulou et al. "A Rev-independent human immunodeficiency virus type 1 (HIV-1)-based vector that exploits a codon-optimized HIV-1 gag-pol gene". J Virol. May 2000;74(10):4839-52.*
Baldridge "Monophosphoryl lipid A (MPL) formulations for the next generation of vaccines". Methods. Sep. 1999;19(1):103-7.*
Nagata T ey al. "Codon Optimization Effect on Translational Efficiency of DNA Vaccine in Mammalian Cells: Analysis of Plasmid DNA Encoding a CTL Epitope Derived from Microorganisms" Biochemical and Biophysical research Communication; 261 (1999): 445-451.*
European Examination Report for European Application No. 03 814 236.0-2405, European Patent Office, Munich.
Cranage, M.P., et al., "Identification of the human cytomegalovirus glycoprotein B gene and induction of neutralizing antibodies via its expression in recombinant vaccinia virus," *EMBO J.* 5:3057-3063, IRL Press Limited (1986).
Egan, M.A. and Israel, Z.R., "The use of cytokines and chemokines as genetic adjuvants for plasmid DNA vaccines," *Clin. Appl. Immunol. Rev.* 2:255-287, Elsevier Science Inc. (Jul.-Sep. 2002).
EMBL-EBI Database, Accession No. P06473, Cranage, M.P., et al., Entry Date 1988, Updated Feb. 2006.

(Continued)

*Primary Examiner*—Bruce Campell
*Assistant Examiner*—Bo Peng
(74) *Attorney, Agent, or Firm*—Sterne, Kessler, Goldstein & Fox P.L.L.C.

(57) ABSTRACT

The invention is related to polynucleotide-based cytomegalovirus vaccines. In particular, the invention is plasmids operably encoding HCMV antigens, in which the naturally-occurring coding regions for the HCMV antigens have been modified for improved translation in human or other mammalian cells through codon optimization. HCMV antigens which are useful in the invention include, but are not limited to pp65, glycoprotein B (gB), IE1, and fragments, variants or derivatives of either of these antigens. In certain embodiments, sequences have been deleted, e.g., the Arg435-Lys438 putative kinase in pp65 and the membrane anchor and endocellular domains in gB. The invention is further directed to methods to induce an immune response to HCMV in a mammal, for example, a human, comprising delivering a plasmid encoding a codon-optimized HCMV antigen as described above. The invention is also directed to pharmaceutical compositions comprising plasmids encoding a codon-optimized HCMV antigen as described above, and further comprising adjuvants, excipients, or immune modulators.

26 Claims, 32 Drawing Sheets

OTHER PUBLICATIONS

Shiver, J.W., et al., "Replication-incompetent adenoviral vaccine vector elicits effective anti-immunodeficiency-virus immunity," *Nature* 415:331-335, Macmillan Magazines Ltd. (Jan. 2002).

André, S., et al., "Increased Immune Response Elicited by DNA Vaccination with a Synthetic gp120 Sequence with Optimized Codon Usage," *J. Virol.* 72:1497-1503, American Society for Microbiology (1998).

Akrigg, A., et al., "The structure of the major immediate early gene of human cytomegalovirus strain AD169," *Virus Res.* 2:107-121, Elsevier (1985).

Allen, L.B., et al., "Novel Method for Evaluating Antiviral Drugs against Human Cytomegalovirus in Mice," *Antimicrob. Agents Chemother.* 36:206-208, American Society for Microbiology (1992).

Amadei, C., et al., "Human Anti-Cytomegalovirus (CMV) Immunoglobulins Secreted by EBV-Transformed B-Lymphocytes Cell Lines," *Dev. Biol. Stand.* 57:283-286, S. Karger (1984).

Arrode, G., et al., "Cross-Presentation of Human Cytomegalovirus pp65 (UL83) to $CD8^+$ T Cells IsRegulated by Virus-Induced, Soluble-Mediator-Dependent Maturation of Dendritic Cells," *J. Virol.* 76:142-150, American Society for Microbiology (Jan. 2002).

Berencsi, K., et al., "The N-terminal 303 amino acids of the human cytomegalovirus envelope glycoprotein B (UL55) and the exon 4 region of the major immediate early protein 1 (UL123) induce a cytotoxic T-cell response," *Vaccine* 14:369-374, Elsevier Science, Ltd. (1996).

Bidanset, D.J., et al., "Replication of Human Cytomegalovirus in Severe Combined Immunodeficient Mice Implanted with Human Retinal Tissue," *J. Infect. Dis.* 184:192-195, University of Chicago Press (Jul. 2001).

Chee, M.S., et al., "Analysis of the Protein-Coding Content of the Sequence of Human Cytomegalovirus Strain AD169," in *Cytomegaloviruses*, McDougall, J.K., ed., Springer-Verlag, Berlin, pp. 126-169 (1990).

Davignon, J-L., et al., "Anti-Human Cytomegalovirus Activity of Cytokines Produced by $CD4^+$ T-Cell Clones Specifically Activated by IE1 Peptides In Vitro," *J. Virol.* 70:2162-2169, American Society for Microbiology (1996).

Deml, L., et al., "Multiple Effects of Codon Usage Optimization on Expression and Immunogenicity of DNA Candidate Vaccines Encoding the Human Immunodeficiency Virus Type 1 Gag Protein," *J. Virol.* 75:10991-11001, American Society for Microbiology (Nov. 2001).

Diamond, D.J., et al., "Development of a Candidate HLA A*0201 Restricted Peptide-Based Vaccine Against Human Cytomegalovirus Infection," *Blood* 90:1751-1767, American Society of Hematology (1997).

Donnelly, J.J., et al., "DNA Vaccines," *Annu. Rev. Immunol.* 15:617-648, Annual Reviews, Inc. (1997).

Elek, S.D., and Stern, H., "Development of a Vaccine Against Mental Retardation Caused by Cytomegalovirus Infection in Utero," *Lancet* 1:1-5, The Lancet, Ltd. (1974).

Elkington, R., et al., "Ex Vivo Profiling of $CD8^+$-T-Cell Responses to Human Cytomegalovirus Reveals Broad and Multispecific Reactivities in Healthy Virus Carriers," *J. Virol.* 77:5226-5240, American Society for Microbiology (May 2003).

Endresz, V., et al., "Induction of human cytomegalovirus (HCMV)-glycoprotein B (gB)-specific neutralizing antibody and phosphoprotein 65 (pp65)-specific cytotoxic T lymphocyte responses by naked DNA immunization," *Vaccine* 17:50-58, Elsevier Science, Ltd. (1999).

Endresz, V., et al., "Optimization of DNA immunization against human cytomegalovirus," *Vaccine* 19:3972-3980, Elsevier Science, Ltd. (Jul. 2001).

Fowler, K.B., et al., "The Outcome of Congenital Cytomegalovirus Infection in Relation to Maternal Antibody Status," *N. Engl. J. Med.* 326:663-667, Massachusetts Medical Society (1992).

Gallez-Hawkins, G., et al., "Kinase-Deficient CMVpp65 Triggers a CMVpp65 Specific T-Cell Immune Response in HLA-A*0201.$K^b$ Transgenic Mice after DNA Immunization," *Scand. J. Immunol.* 55:592-598, Blackwell Science, Ltd. (Jun. 2002).

Gautier, N., et al., "Characterization of an epitope of the human cytomegalovirus protein IE1 recognized by a $CD4^+$ T cell clone," *Eur. J. Immunol.* 26:1110-1117, VCH Verlagsgesellschaft mbH (1996).

Geissler, M., et al., "Differential cellular and humoral immune responses to HCV core and HBV envelope proteins after genetic immunizations using chimeric constructs," *Vaccine* 16:857-867, Elsevier Science, Ltd. (1998).

Gonczol, E., and Plotkin, S., "Development of a cytomegalovirus vaccine: lessons from recent trials," *Exp. Opin. Biol. Ther.* 1:401-412, Ashley Publications, Ltd. (May 2001).

Griscelli, F., et al., "Quantification of Human Cytomegalovirus DNA in Bone Marrow Transplant Recipients by Real-Time PCR," *J. Clin. Microbiol.* 39:4362-4369, American Society for Microbiology (Dec. 2001).

Guiver, M., et al., "Evaluation of CMV Viral Load Using Taqman™ CMV Quantitative PCR and Comparison with CMV Antigenemia in Heart and Lung Transplant Recipients," *Transplantation* 71:1609-1615, Lippincott Williams & Wilkins, Inc. (Jun. 2001).

Gyulai, Z., et al., "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs," *J. Infect. Dis.* 181:1537-1546, University of Chicago Press (2000).

Hayward, G.S., and Alcendor, D.J., "Cytomegalovirus, Herpesviridae, Betaherpesvirinae," in *The Springer Index of Viruses*, Tidona, C.A., and Darai, G., eds., Springer, New York, NY, pp. 416-422 (Mar. 2002).

Kern, F., et al., "Cytomegalovirus (CMV) Phosphoprotein 65 Makes a Large Contribution to Shaping the T Cell Repertoire in CMV-Exposed Individuals," *J. Infect. Dis.* 185:1709-1716, University of Chicago Press (Jun. 2002).

Khan, N., et al., "Comparative Analysis of $CD8^+$ T Cell Responses against Human Cytomegalovirus Proteins pp65 and Immediate Early 1 Shows Similarities in Precursor Frequency, Oligoclonality, and Phenotype," *J. Infect. Dis.* 185:000-000, University of Chicago Press (Apr. 2002).

Khattub, B.A-M., et al., "Three T-Cell Epitopes Within the C-Terminal 265 Amino Acids of the Matrix Protein pp65 of Human Cytomegalovirus Recognized by Human Lymphocytes," *J. Med. Virol.* 52:68-76, Wiley-Liss, Inc. (1997).

Laycock, K.A., et al., "An In Vivo Model of Human Cytomegalovirus Retinal Infection," *Am. J. Ophthalmol.* 124:181-189, Elsevier Science (1997).

Limaye, A.P., et al., "High Incidence of Ganciclovir-Resistant Cytomegalovirus Infection among Lung Transplant Recipients Receiving Preemptive Therapy," *J. Infect. Dis.* 185:20-27, University of Chicago Press (Jan. 2002).

Liu, Y.-N., et al., "Molecular analysis of the immune response to human cytomegalovirus glycoprotein B. I. Mapping of HLA-restricted helper T cell epitopes on gp93," *J. Gen. Virol.* 74:2207-2214, Society for General Microbiology (1993).

Loomis-Huff, J.E., et al., "Immunogenicity of a DNA vaccine against herpes B virus in mice and *rhesus macaques*," *Vaccine* 19:4865-4873, Elsevier Science, Ltd. (Sep. 2001).

Lurain, N.S., et al., "Human Cytomegalovirus UL144 Open Reading Frame: Sequence Hypervariability in Low-Passage Clinical Isolates," *J. Virol.* 73:10040-10050, American Society for Microbiology (1999).

Malone, C.L., et al., "Transactivation of a Human Cytomegalovirus Early Promoter by Gene Products from the Immediate-Early Gene IE2 and Augmentation by IE1: Mutational Analysis of the Viral Proteins," *J. Virol.* 64:1498-1506, American Society for Microbiology (1990).

Manickan, E., et al., "DNA Vaccines—A Modern Gimmick or a Boon to Vaccinology?" *Crit. Rev. Immunol.* 17:139-154, Begell House, Inc. (1997).

Masuoka, M., et al., "Identification of the HLA-A24 Peptide Epitope within Cytomegalovirus Protein pp65 Recognized by CMV-Specific Cytotoxic T Lymphocytes," *Viral. Immunol.* 14:369-377, Mary Ann Liebert, Inc. (Dec. 2001).

Minamishima, Y., et al., "Murine Model for Immunoprophylaxis of Cytomegalovirus Infection," *Microbiol. Immunol.* 22:693-700, Japanese Society for Bacteriology (1978).

Mocarski, Jr., E.S., "Cytomegaloviruses (Herpesviridae)," in *Encyclopedia of Virology*, 2nd ed., vol. I., Granoff, A., and Webster, R.G., eds., Academic Press, San Diego, CA, pp. 344-358.

Mocarski, Jr., E.S., and Courcelle, C.T., "Cytomegaloviruses and Their Replication," in *Fields Virology*, 4th ed., Knipe, D.M., et al., eds., Lippincott Williams & Wilkins, Philadelphia, PA, pp. 2629-2674 (Jul. 2001).

Morello, C.S., et al., "Development of a Vaccine against Murine Cytomegalovirus (MCMV), Consisting of Plasmid DNA and Formalin-Inactivated MCMV, That Provides Long-Term, Complete Protection against Viral Replication," *J. Virol.* 76:4822-4835, American Society for Microbiology (May 2002).

Nakamura, Y., et al., "Codon usage tabulated from international DNA sequence databases: status for the year 2000," *Nucl. Acids Res.* 28:292, Oxford University Press (2000).

Narum, D.L., et al., "Codon Optimization of Gene Fragments Encoding *Plasmodium falciparum* Merzoite Proteins Enhances DNA Vaccine Protein Expression and Immunogenicity in Mice," *Infect. Immun.* 69:7250-7523, American Society for Microbiology (Dec. 2001).

Navarro, D., et al., "Humoral Immune Response to Functional Regions of Human Cytomegalovirus Glycoprotein B," *J. Med. Virol.* 52:451-459, Wiley-Liss, Inc. (1997).

Nossal, G., "Living up to the legacy," *Nat. Med.* 4:475-476, Nature America, Inc. (1998).

Ohlin, M., et al., "Characterization of human monoclonal antibodies directed against the pp65-kD matrix antigen of human cytomegalovirus," *Clin. Exp. Immunol.* 84:508-514, Blackwell Scientific Publications (1991).

Ohlin, M., et al., "Fine Specificity of the Human Immune Response to the Major Neutralization Epitopes Expressed on Cytomegalovirus gp58/116 (gB), as Determined with Human Monoclonal Antibodies," *J. Virol.* 67:703-710, American Society for Microbiology (1993).

Pajovic, S., et al., "Identification of a Viral Kinase That Phosphorylates Specific E2Fs and Pocket Proteins," *Mol. Cell. Biol.* 17:6459-6464, American Society for Microbiology (1997).

Pande, H., et al., "Human Cytomegalovirus Strain Towne pp65 Gene: Nucleotide Sequence and Expression in *Escherichia coli*," *Virology* 182:220-228, Academic Press, Inc. (1991).

Pari, G.S., et al., "Generation of a Nude Mouse Tumor Model for In Vivo Replication of Human Cytomegalovirus," *J. Infect. Dis.* 177:523-528, University of Chicago Press (1998).

Pass, R.F., et al., "Cytomegalovirus," in *Fields Virology*, 4th ed., vol. 2, Knipe, D.M., et al., eds., Lippincott Williams & Wilkins, Philadelphia, PA, pp. 2675-2698 (Aug. 2001).

Plotkin, S.A., "Vaccination against cytomegalovirus, the changeling demon," *Pediatr. Infect. Dis. J.* 18:313-326, Lippincott Williams & Wilkins, Inc. (1999).

Rüger, B., et al., "Primary Structure and Transcription of the Genes Coding for the Two Virion Phosphoproteins pp65 and pp71 of Human Cytomegalovirus," *J. Virol.* 61:446-453, American Society for Microbiology (1987).

Schmolka, I.R., "A Review of Block Polymer Surfactants," *J. Am. Oil Chem. Soc.* 54:110-116, The American Oil Chemists' Society (1977).

Segondy, M., et al., "Cytomegalovirus-Specific In Vitro Antibody Production by Peripheral Blood Lymphocytes From Renal Treatment Recipients With CMV Infection," *J. Med. Virol.* 40:200-203, Wiley-Liss, Inc. (1993).

Sequar, G., et al., "Experimental Coinfection of *Rhesus macaques* with Rhesus cytomegalovirus and Simian Immunodeficiency Virus: Pathogenesis," *J. Virol.* 76:7661-7671, American Society for Microbiology (Aug. 2002).

Solache, A., et al., "Identification of Three HLA-A*0201-Restricted Cytotoxic T Cell Epitopes in the Cytomegalovirus Protein pp65 That Are Conserved Between Eight Strains of the Virus," *J. Immunol.* 163:5512-5518, American Assocation of Immunologists (1999).

Spaete, R.R., et al., "Human cytomegalovirus structural proteins," *J. Gen. Virol.* 75:3287-3308, Society for General Microbiology (1994).

Speckner, A., et al., "Antigenic domain 1 of human cytomegalovirus glycoprotein B induces a multitude of different antibodies which, when combined, results in incomplete virus neutralization," *J. Gen. Virol.* 80:2183-2191, Society for General Microbiology (1999).

Spiller, O.B., et al., "Development of a model for cytomegalovirus infection of oligodendrocytes," *J. Gen. Virol.* 78:3349-3356, Society for General Microbiology (1997).

Staczek, J., "Animal Cytomegaloviruses," *Microbiol. Rev.* 54:247-265, American Society for Microbiology (1990).

Storch, G.A., et al., "Comparison of PCR and pp65 Antigenemia Assay with Quantitative Shell Vial Culture for Detection of Cytomegalovirus in Blood Leukocytes from Solid-Organ Transplant Recipients," *J. Clin. Microbiol.* 32:997-1003, American Society for Microbiology (1994).

Tang, J., et al., "Building a mouse model hallmarking the congenital human cytomegalovirus infection in central nervous system," *Arch. Virol.* 147:1189-1195, Springer-Verlag (Jun. 2002).

Tugizov, S., et al., "Mutated Forms of Human Cytomegalovirus Glycoprotein B Are Impaired in Inducing Syncytium Formation," *Virology* 209:580-591, Academic Press, Inc. (1995).

Vaz-Santiago, J., et al., "IE1-pp65 recombinant protein from human CMV combined with a nanoparticulate carrier, SMBV, as a potential source for the development of anti-human CMV adoptive immunotherapy," *Cytotherapy* 4:11-19, Martin Dunitz Taylor & Francis Group (Jan. 2002).

Yang, Z-y., et al., "Overcoming Immunity to a Viral Vaccine by DNA Priming before Vector Boosting," *J. Virol.* 77:799-803, American Society for Microbiology (Jan. 2003).

Yao, Z-Q., et al., "Site-directed mutation in a conserved kinase domain of human cytomegalovirus-pp65 with preservation of cytotoxic T lymphocyte targeting," *Vaccine* 19:1628-1635, Elsevier (Feb. 2001).

Ye, M., et al., "Strong CD8 T-Cell Responses following Colmmunization with Plasmids Expressing the Dominant pp89 and Subdominant M84 Antigens of Murine Cytomegalovirus Correlate with Long-Term Protection against Subsequent Viral Challenge," *J. Virol.* 76:2100-2112, American Society for Microbiology (Mar. 2002).

Zaia, J.A., et al., "Status of Cytomegalovirus Prevention and Treatment in 2000," *Hematology*, pp. 339-355, Taylor & Francis Health Sciences (2000).

Zheng, Z., et al., "Mutations in the Carboxyl-Terminal Hydrophobic Sequence of Human Cytomegalovirus Glycoprotein B Alter Transport and Protein Chaperone Binding," *J. Virol.* 70:8029-8040, American Society for Mirobiology (1996).

"Performance Chemical Products: Pluronic® and Pluronic® R Block Copolymer Surfactants," BASF Corporation, at http://www.basf.com/static/OpenMarket/Xcelerate/Preview_cid-982931199819_pubid-974236, viewed Dec. 13, 2002.

NCBI Entrez, GenBank Report, Accession No. X17403, from Chee et al. (Feb. 1999).

* cited by examiner

Figure 1A
PRETTYSEQ of from 1 to 1683

```
  1 atggagtcgcgcggtcgccgttgtcccgaaatgatatccgtactgggtcccatttcgggg  60
  1 M   E   S   R   G   R   R   C   P   E   M   I   S   V   L   G   P   I   S   G    20

61 cacgtgctgaaagccgtgtttagtcgcggcgatacgccggtgctgccgcacgagacgcga 120
 21 H   V   L   K   A   V   F   S   R   G   D   T   P   V   L   P   H   E   T   R    40

121 ctcctgcagacgggtatccacgtacgcgtgagccagccctcgctgatcttggtatcgcag 180
 41 L   L   Q   T   G   I   H   V   R   V   S   Q   P   S   L   I   L   V   S   Q    60

181 tacacgcccgactcgacgccatgccaccgcggcgacaatcagctgcaggtgcagcacacg 240
 61 Y   T   P   D   S   T   P   C   H   R   G   D   N   Q   L   Q   V   Q   H   T    80

241 tactttacgggcagcgaggtggagaacgtgtcggtcaacgtgcacaaccccacgggccga 300
 81 Y   F   T   G   S   E   V   E   N   V   S   V   N   V   H   N   P   T   G   R   100

301 agcatctgccccagccaggagcccatgtcgatctatgtgtacgcgctgccgctcaagatg 360
101 S   I   C   P   S   Q   E   P   M   S   I   Y   V   Y   A   L   P   L   K   M   120

361 ctgaacatccccagcatcaacgtgcaccactacccgtcggcggccgagcgcaaacaccga 420
121 L   N   I   P   S   I   N   V   H   H   Y   P   S   A   A   E   R   K   H   R   140

421 cacctgcccgtagctgacgctgtgattcacgcgtcgggcaagcagatgtggcaggcgcgt 480
141 H   L   P   V   A   D   A   V   I   H   A   S   G   K   Q   M   W   Q   A   R   160

481 ctcacggtctcgggactggcctggacgcgtcagcagaaccagtggaaagagcccgacgtc 540
161 L   T   V   S   G   L   A   W   T   R   Q   Q   N   Q   W   K   E   P   D   V   180

541 tactacacgtcagcgttcgtgtttcccaccaaggacgtggcactgcggcacgtggtgtgc 600
181 Y   Y   T   S   A   F   V   F   P   T   K   D   V   A   L   R   H   V   V   C   200

601 gcgcacgagctggtttgctccatggagaacacgcgcgcaaccaagatgcaggtgataggt 660
201 A   H   E   L   V   C   S   M   E   N   T   R   A   T   K   M   Q   V   I   G   220

661 gaccagtacgtcaaggtgtacctggagtccttctgcgaggacgtgccctccggcaagctc 720
221 D   Q   Y   V   K   V   Y   L   E   S   F   C   E   D   V   P   S   G   K   L   240

721 tttatgcacgtcacgctgggctctgacgtggaagaggacctgacgatgacccgcaacccg 780
241 F   M   H   V   T   L   G   S   D   V   E   E   D   L   T   M   T   R   N   P   260

781 caacccttcatgcgcccccacgagcgcaacggctttacggtgttgtgtcccaaaaatatg 840
261 Q   P   F   M   R   P   H   E   R   N   G   F   T   V   L   C   P   K   N   M   280

841 ataatcaaaccgggcaagatctcgcacatcatgctggatgtggcttttacctcacacgag 900
281 I   I   K   P   G   K   I   S   H   I   M   L   D   V   A   F   T   S   H   E   300

901 cattttgggctgctgtgtcccaagagcatcccgggcctgagcatctcaggtaacctgttg 960
301 H   F   G   L   L   C   P   K   S   I   P   G   L   S   I   S   G   N   L   L   320

961 atgaacgggcagcagatcttcctggaggtacaagccatacgcgagaccgtggaactgcgt 1020
321 M   N   G   Q   Q   I   F   L   E   V   Q   A   I   R   E   T   V   E   L   R   340

1021 cagtacgatcccgtggctgcgctcttcttttttcgatatcgacttgctgctgcagcgcggg 1080
341 Q   Y   D   P   V   A   A   L   F   F   F   D   I   D   L   L   L   Q   R   G   360
```

Figure 1B

```
1081 cctcagtacagcgagcaccccaccttcaccagccagtatcgcatccagggcaagcttgag 1140
 361  P  Q  Y  S  E  H  P  T  F  T  S  Q  Y  R  I  Q  G  K  L  E   380

1141 taccgacacacctgggaccggcacgacgagggtgccgcccagggcgacgacgacgtctgg 1200
 381  Y  R  H  T  W  D  R  H  D  E  G  A  A  Q  G  D  D  D  V  W   400

1201 accagcggatcggactccgacgaagaactcgtaaccaccgagcgcaagacgccccgcgtc 1260
 401  T  S  G  S  D  S  D  E  E  L  V  T  T  E  R  K  T  P  R  V   420

1261 accggcggcggcgccatggcgggcgcctccacttccgcgggccgcaaacgcaaatcagca 1320
 421  T  G  G  A  M  A  G  A  S  T  S  A  G  R  K  R  K  S  A   440

1321 tcctcggcgacggcgtgcacgtcgggcgttatgacacgcggccgccttaaggccgagtcc 1380
 441  S  S  A  T  A  C  T  S  G  V  M  T  R  G  R  L  K  A  E  S   460

1381 accgtcgcgcccgaagaggacaccgacgaggattccgacaacgaaatccacaatccggcc 1440
 461  T  V  A  P  E  E  D  T  D  E  D  S  D  N  E  I  H  N  P  A   480

1441 gtgttcacctggccgccctggcaggccggcatcctggcccgcaacctggtgcccatggtg 1500
 481  V  F  T  W  P  P  W  Q  A  G  I  L  A  R  N  L  V  P  M  V   500

1501 gctacggttcagggtcagaatctgaagtaccaggaattcttctgggacgccaacgacatc 1560
 501  A  T  V  Q  G  Q  N  L  K  Y  Q  E  F  F  W  D  A  N  D  I   520

1561 taccgcatcttcgccgaattggaaggcgtatggcagcccgctgcgcaacccaaacgtcgc 1620
 521  Y  R  I  F  A  E  L  E  G  V  W  Q  P  A  A  Q  P  K  R  R   540

1621 cgccaccggcaagacgccttgcccgggccatgcatcgcctcgacgcccaaaaagcacga 1680
 541  R  H  R  Q  D  A  L  P  G  P  C  I  A  S  T  P  K  K  H  R   560

1681 ggt 1683
 561  G    561
```

Figure 2A

| | Met | Glu | Ser | Arg | Gly | Arg | Arg | Cys | Pro | Glu | Met | Ile | Ser | Val | Leu | Gly | Pro |

ATGGAGTCCC GCGGTCGCCG CTGTCCCGAA ATGATATCCG TACTGGGTCC  50

| | Ile | Ser | Gly | His | Val | Leu | Lys | Ala | Val | Phe | Ser | Arg | Gly | Asp | Thr | Pro | Val |

CATTTCCGGG CACGTGCTGA AAGCCGTGTT TAGTCGCGGC GATACCCCG  100

| | Leu | Pro | His | Glu | Thr | Arg | Leu | Leu | Gln | Thr | Gly | Ile | His | Val | Arg | Val |

TGCTGCCCCA CGAGACCCGA CTCCTGCAGA CCGGTATCCA CGTACGCGTG  150

| | Ser | Gln | Pro | Ser | Leu | Ile | Leu | Val | Ser | Gln | Tyr | Thr | Pro | Asp | Ser | Thr | Pro |

AGCCAGCCCT CCCTGATCTT GGTATCCCAG TACACCCCG ACTCCACCCC  200

| | Cys | His | Arg | Gly | Asp | Asn | Gln | Leu | Gln | Val | Gln | His | Thr | Tyr | Phe | Thr | Gly |

ATGCCACCGC GGCGACAATC AGCTGCAGGT GCAGCACACC TACTTTACCG  250

| | Ser | Glu | Val | Glu | Asn | Val | Ser | Val | Asn | Val | His | Asn | Pro | Thr | Gly | Arg |

GCAGCGAGGT GGAGAACGTG TCCGTCAACG TGCACAACCC CACCGGCCGA  300

| | Ser | Ile | Cys | Pro | Ser | Gln | Glu | Pro | Met | Ser | Ile | Tyr | Val | Tyr | Ala | Leu | Pro |

AGCATCTGCC CCAGCCAGGA GCCCATGTCC ATCTATGTGT ACGCCCTGCC  350

| | Leu | Lys | Met | Leu | Asn | Ile | Pro | Ser | Ile | Asn | Val | His | His | Tyr | Pro | Ser | Ala |

CCTCAAGATG CTGAACATCC CCAGCATCAA CGTGCACCAC TACCCCTCCG  400

| | Ala | Glu | Arg | Lys | His | Arg | His | Leu | Pro | Val | Ala | Asp | Ala | Val | Ile | His |

CCGCCGAGCG CAAACACCGA CACCTGCCCG TAGCTGACGC TGTGATTCAC  450

| | Ala | Ser | Gly | Lys | Gln | Met | Trp | Gln | Ala | Arg | Leu | Thr | Val | Ser | Gly | Leu | Ala |

GCCTCCGGCA AGCAGATGTG GCAGGCCGC CTCACCGTCT CCGGACTGGC  500

| | Trp | Thr | Arg | Gln | Gln | Asn | Gln | Trp | Lys | Glu | Pro | Asp | Val | Tyr | Tyr | Thr | Ser |

CTGGACCCGC CAGCAGAACC AGTGGAAAGA GCCCGACGTC TACTACACCT  550

| | Ala | Phe | Val | Phe | Pro | Thr | Lys | Asp | Val | Ala | Leu | Arg | His | Val | Val | Cys |

CAGCCTTCGT GTTTCCCACC AAGGACGTGG CACTGCGGCA CGTGGTGTGC  600

| | Ala | His | Glu | Leu | Val | Cys | Ser | Met | Glu | Asn | Thr | Arg | Ala | Thr | Lys | Met | Gln |

GCCCACGAGC TGGTTTGCTC CATGGAGAAC ACCCGCGCAA CCAAGATGCA  650

Figure 2B

```
+1   -Val  Ile  Gly  Asp  Gln  Tyr  Val  Lys  Val  Tyr  Leu  Glu  Ser  Phe  Cys  Glu  Asp

GGTGATAGGT GACCAGTACG TCAAGGTGTA CCTGGAGTCC TTCTGCGAGG 700

+1        Val  Pro  Ser  Gly  Lys  Leu   Phe  Met  His  Val  Thr  Leu  Gly  Ser  Asp  Val

ACGTGCCCTC CGGCAAGCTC TTTATGCACG TCACCCTGGG CTCTGACGTG 750

+1   Glu  Glu  Asp  Leu  Thr  Met  Thr  Arg  Asn  Pro   Gln  Pro  Phe  Met  Arg  Pro  His

GAAGAGGACC TGACCATGAC CCGCAACCCC CAACCCTTCA TGCGCCCCA 800

+1        Glu  Arg  Asn  Gly  Phe  Thr  Val  Leu  Cys  Pro  Lys  Asn  Met   Ile  Ile  Lys  Pro

CGAGCGCAAC GGCTTTACCG TGTTGTGTCC CAAAAATATG ATAATCAAAC 850

+1        Gly  Lys  Ile  Ser  His  Ile   Met  Leu  Asp  Val  Ala  Phe  Thr  Ser  His  Glu

CCGGCAAGAT CTCCCACATC ATGCTGGATG TGGCTTTTAC CTCACACGAG 900

+1   His  Phe  Gly  Leu  Leu  Cys  Pro  Lys  Ser  Ile   Pro  Gly  Leu  Ser  Ile  Ser  Gly

CATTTTGGGC TGCTGTGTCC AAGAGCATC CCCGGCCTGA GCATCTCAGG 950

+1        Asn  Leu  Leu  Met  Asn  Gly  Gln  Gln  Ile  Phe  Leu  Glu  Val  Gln  Ala  Ile  Arg

TAACCTGTTG ATGAACGGGC AGCAGATCTT CCTGGAGGTA CAAGCCATAC 1000

+1        Glu  Thr  Val  Glu  Leu  Arg  Gln  Tyr  Asp  Pro  Val  Ala  Ala  Leu  Phe  Phe

GCGAGACCGT GGAACTGCGC CAGTACGATC CCGTGGCTGC CCTCTTCTTT 1050

-1   Phe  Asp  Ile  Asp  Leu  Leu  Leu  Gln  Arg  Gly  Pro  Gln  Tyr  Ser  Glu  His  Pro

TTCGATATCG ACTTGCTGCT GCAGCGCGGG CCTCAGTACA GCGAGCACCC 1100

+1        Thr  Phe  Thr  Ser  Gln  Tyr  Arg  Ile  Gln  Gly  Lys  Leu  Glu  Tyr  Arg  His  Thr

CACCTTCACC AGCCAGTATC GCATCCAGGG CAAGCTTGAG TACCGACACA 1150

+1        Trp  Asp  Arg  His  Asp  Glu  Gly  Ala  Ala  Gln  Gly  Asp  Asp  Asp  Val  Trp

CCTGGGACCG GCACGACGAG GGTGCCGCCC AGGGCGACGA CGACGTCTGG 1200

+1   Thr  Ser  Gly  Ser  Asp  Ser  Asp  Glu  Glu  Leu  Val  Thr  Thr  Glu  Arg  Lys  Thr

ACCAGCGGAT CCGACTCCGA CGAAGAACTC GTAACCACCG AGCGCAAGAC 1250

+1        Pro  Arg  Val  Thr  Gly  Gly  Gly  Ala  Met  Ala  Gly  Ala  Ser  Thr  Ser  Ala  Gly

CCCCCGCGTC ACCGGCGGCG GCGCCATGGC CGGCGCCTCC ACTTCCGCCG 1300
```

Figure 2C

```
+1        Arg  Lys   Arg   Lys  Ser   Ala    Ser   Ser   Ala   Thr    Ala  Cys   Thr    Ser   Gly   Val
     GCCGCAAACG CAAATCAGCA TCCTCCGCCA CCGCCTGCAC CTCCGGCGTT        1350

+1    Met   Thr   Arg    Gly    Arg    Leu    Lys    Ala   Glu  Ser    Thr   Val   Ala    Pro    Glu   Gln   Asp
     ATGACACGCG GCCGCCTTAA GGCCGAGTCC ACCGTCGCCC CCGAAGAGGA        1400

+1    Thr   Asp   Glu    Asp   Ser   Asp    Asn    Glu   Ile   His   Asn   Pro   Ala    Val   Phe   Thr   Trp
     CACCGACGAG GATTCCGACA ACGAAATCCA CAATCCCGCC GTGTTCACCT        1450

+1       Pro   Pro   Trp    Gln  Ala   Gly    Ile   Leu  Ala   Arg   Asn   Leu    Val   Pro   Met   Val
     GGCCACCCTG GCAGGCCGGC ATCCTGGCCC GCAACCTGGT GCCCATGGTG        1500

+1    Ala   Thr   Val    Gln    Gly   Gln   Asn    Leu   Lys   Tyr    Gln   Glu   Phe    Phe   Trp   Asp   Ala
     GCTACCGTTC AGGGTCAGAA TCTGAAGTAC CAGGAATTCT TCTGGGACGC        1550

+1    Asn   Asp   Ile    Tyr   Arg   Ile    Phe   Ala   Glu   Leu    Glu   Gly   Val    Trp   Gln   Pro   Ala
     CAACGACATC TACCGCATCT TCGCCGAATT GGAAGGCGTA TGGCAGCCCG        1600

+1       Ala   Gln   Pro    Lys   Arg   Arg    Arg   His   Arg   Gln    Asp   Ala   Leu    Pro   Gly   Pro
     CTGCCCAACC CAAACGCCGC CGCCACCGGC AAGACGCCTT GCCCGGGCCA        1650

+1    Cys   Ile   Ala    Ser   Thr   Pro    Lys   Lys   His   Arg    Gly
     TGCATCGCCT CCACCCCCAA AAAGCACCGA GGT                           1700
```

Figure 3A

```
1   ATGGAGTCGCGCGGTCGCCGTTGTCCCGAAATGATATCCGTACTGGGTCC      50
    ||||·||·||·||·.||·.|||||||||·||·.|||·||·.||·.||
1   ATGGAAATCTCGAGGTAGACGTTGTCCGGAGATGATCAGCCGTGCTAGGACC    50

51  CATTTCGGGGCACGTGCTGAAAGCCGTGTTTAGTCGGCGGCGATACGCCGG     100
    ||·.|||||||·||·||||·|||·|||·||·|||||·||||||||
51  AATAAGTGGGCACGTCCTGAAGGCTGTGTTTTCAAGGGGGATACGCCAG       100

101 TGCTGCCCGCACGAGACGCGACTCCTGCAGACGGGTATCCACGTACGCGTG     150
    ||||·||·||||||||·||·||·||·||·||||·.||·.|||·.||·.
101 TGCTCCCACACGAGACCCGCCTGCTACACAACAGTATTCACGTTAGGGTC      150

151 AGCCAGCCCTGCTGATCTTGGTATCGCAGTACACGCCCGACTGACGCC       200
    ·||·.|||||||·||·|||||·.||·.||||·||·|||||·|||||
151 TCACAGCCCAGCCTAATTTTGGTTAGCCAGTATACAGACCCGACTCCACCCC    200

201 ATGCCACCGGCGACAATCAGCTGCAGGTGCAGCACACGTACTTTACGG       250
    ·||·|||·||·|||||||·.|||||||·||·.|||||·.|||·.||·.||
201 TTGTCATCGGCGGCGACAACCAGCTGCAAGTGCCAAGTCCATAACCTACGGGCGT 250

251 GCAGCGAGGTGTGAGAGAACGTGTCGGTCAACGTGCACAACCCCACGGGCCGA   300
    |||||||·||·||||||·.||·||||||·.||·||·||||·.|·.||·.||·.
251 GCAGCGAGGTGGAAAATGTGTCGGTCAATGTGCATAACCCTACCGGGCGT      300

301 AGCATCTGCCCCCAGCCCCAGGAGCCCATGTCGATCTATGTGTACGCGCTGCC   350
    ·.|||||||·||·.|||·.|||·.||·.|||·|||·|||·.||·.|·.||
301 TCCATCTGCCCTTCACAGGAGCCTATGTCTATCTACGTGTATGCTTTACC     350

351 GCTCAAGATGCTGAACATCCCCAGCATCAACGTGCACCACTACCCGTCGG      400
    ·.|·.||·|||·||||·.||·.|·.||·.|·.|||·||·||·.||||·.
351 TTTGAAAGATGTTAAACATCCCCTCTATCAATGTGCACCATTATCCTTTCAG    400
```

Figure 3B

```
401 CGGCCCGAGCCGCAAACACCGACACCTGCCCGTAGCTGACGCTGTGATTCAC    450
        ||||||||||||||| || || |||||  ||||||||| |||||| | |||
401 CGGCTGAGCGGAAACACCGCCACTTACCCGTGCTGACGCAGTCATACAC      450

451 GCGTCGGGCAAGCAGATGTGGCAGGCGCGTCTCACGGTCTCGGGACTGGC     500
    |||| ||| |||||||||||||| |||  ||| |||||| |  |||||||
451 GCGAGCGGTAAGCAGATGTGGCAAGCACGACTGACGGTCTCCGGTCTGGC    500

501 CTGGACGCGTCAGCAGAACCAGTGGAAAGAGCCCGACGTCTACTACACGT     550
    ||||||||| ||||||||||| ||||||| |||||||| |||||| ||
501 TTGGACTAGACAGCAGAATCAGTGGAAGGAACCTGATGTGTACTACACCA    550

551 CAGCGTTCGTGTTCTCCCACCAAGGACGTGGCACTGCGCGCACGTGGTGC   600
     |  ||| ||| ||||| ||  || |||||||||| | || |||||||||
551 GCGCATTTGTCTTCCCAACCAAAGACGTGGCACTGCGCCACGTAGTGTGC    600

601 GCGCACGAGCTGGTTTGCTCCATGGAGAACACGCGCCAACCAAGATGCA   650
    |||| ||| |||| ||||||||||||||||| ||||  ||||||||||||
601 GCCCATGAACTGGTCGTGTTCCATGGAGAACACCCCGGCAACCAAGATGCA  650

651 GGTGATAGGTGACCAGTACGTCAAGGTGTACCTGGAGTCCTTCTGCGAGG   700
    ||| |||  || |||| |||||||||||||| |||||| ||| |||||||
651 GGTAATTGGCGATCAGTATGTGAAAGTTTACCTTGAGTCCTTTTGTGAGG   700

701 ACGTGCCCCTCCGGCAAGCTCTTTATGCACGTCACGCTCTGACGTG      750
    || |||||  |||| ||||| || ||||| ||| |||| |||||| |
701 ATGTACCCAGCGGCAAGCTGTTCATGCATGTGGGCAGTGACGTG         750

751 GAAGAGGACCTGACAATGACTCGAAATCCACAACCATTTATGAGGCCGCA   800
    ||||||||||||||| ||||||   ||||||   ||   |  |||||||
751 GAAGAGGACCTGACAATGACTCGAAATCCACAACCATTTATGAGGCCGCA   800
```

Figure 3C

```
 801 CGAGCGCAACGGCTTTACGGTGTTGTGTCCCAAAAATATGATAATCAAAC  850
     |||.|.||||||||||||.|||.||.|.||.||.|||||.|||||||.|.
 801 CGAAAGAAACGGGTTTACAGTGCTCTGCCCAAAGAACATGATCATCAAGC  850

851 CGGGCAAGATCTCGCACATCATGCTGGATGTGGCTTTTACCTCACACGAG  900
     |.||.|||||||||||||.|.||.|||||.||||.|||.|||...|.||.
 851 CCGGGAAGATTAGTCATATTATGCTCGATGTTGCCTTCACCAGTCACGAA  900

901 CATTTTGGGCTGCTGTGTCCCAAGAGCATCCCGGGCCTGAGCATCTCAGG  950
     |||||||.||||||||||||||.|||.|.||.||||.|||.||.|||||
 901 CATTTTGGACTCCTTGCCCCAAATCCATCCCAGGCTTGTCAATTTCAGG  950

951 TAACCTGTTGATGAACGGGCAGCAGATCTTCCTGGAGGTACAAGCCATAC 1000
     .||.|.||||||||.|||||||||||.|||||||||||.|.||.|.|.|
 951 CAATCTCCTCATGAACGGACAGCAGATTTTCCTGGAGGTGCAAGCGATCC 1000

1001 GCGAGACCGTGGAACTGCCTCAGTACGATCCCGTGGCTCGCTCTTCTTT 1050
     |.|||.|.||.|||.|.||.||||||.||.||||.||.||.||||.||.
1001 GGGAGACTGTGTAGAGCTGAGACAGTATGATCCTGTTGCAGCCCTGTTCTTC 1050

1051 TTCGATATCGACTTGCTGCTGCAGCGCGGGGCCTCAGTACAGCGAGCACCC 1100
     |||||||||||||||.|||||.||||||||||.|||||||||||.|||||
1051 TTCGATATCGACCTTCTCCTTCAGCGCGGGGCCAGTACAGCGAACACCC 1100

1101 CACCTTCACCAGCCAGTATCGCCATCCAGGGCAAGCTTGAGTACCGACACA 1150
     .|||||||.|.|||||.|||||||.|||||.||||.|.|.|.|||||.||.
1101 AACCTTTACATCTCAGTACCGCATCCAAGGGAAACTGGAGTATCGTCATA 1150

1151 CCTGGGACCGGCACGACGAGGGTGCCGCCCAGGGCGACGACGTCTGG 1200
     ||||||||.||||.||||||||||||||||.||.|||||||.|.|||
1151 CCTGGGACAGGCATGACGAAGGGGCCGCTCAAGGAGAGACGATGATGTGTGG 1200
```

Figure 3D

```
1201 ACCAGCGGATCGGACTCCGACGAAGAACTCGTAACCACCGAGCGCAAGAC 1250
      ||.||.||||||.||.||...|.|.||||.....|.||||||
1201 ACAAGTGGCTCGGATTCCGATGAGGAGTTGGTGACAACCGAAAGAAAGAC 1250

1251 GCCCCGCGTCACCGGCGGCGGCGCCATGGCGGCCTCCACTTCCGCGG    1300
      ||.|.||||||.||.|||...|||..|||.|
1251 TCCCAGGGTTACCGGAGGAGGAGCAATGGCCAGGTGCTTCCACTAGCGCTG 1300

1301 GCCGCAAACGCCAAATCAGCATCCTCGGCGACGGCGTGCACGTCGGGCGTT 1350
      ||.|.||||||....||.|||||||.||||.|
1301 GCAGGAAACGGAAAAAGCGCCTCCAGTGCCACAGCCTGCACTTCTGGCGTC 1350

1351 ATGACACGCGGCCGCCTTAAGGCCGAGTCCACCGTCGCGCCCGAAGAGGA 1400
      ||||.|.|||.|||||||.||||||||
1351 ATGACGAGGAGGCGGCTGAAAGCCGGAATCTACTGTAGCCCCCTGAGGAGGA 1400

1401 CACCGACGAGGATTCCGACAACGAAATCCACAATCCGGCCGTGTTCACCT 1450
      ||.|.|||||||.||.||||.|.||||.||.||.||.|.||.
1401 CACTGACGAGGATTCTGACAATGAAATTCACAATCCCGCGGTTTTTACAT 1450

1451 GGCCGCCCTGGCAGGCCGGCATCCTGCCCGCCAACCTGGTGTGCCATGGTG 1500
      |||||||.||||.||||||||.||.|.|||||.||||.||||||||
1451 GGCCCCCCTGGCAGGCCCGGAATTCTGGCCCGGGAACCTTGTGCCCATGGTC 1500

1501 GCTACGGTTCAGGGTCAGAGAATCTGAAGTACCAGGAATTCTTCTGGGACGC 1550
      ||.|.||.||.|.|||||.||.|||||||||||||||||||.|
1501 GCCACAGTCCAAGGCCAGAACCTGAAGTACCAGGAATTTTTCTGGGATGC 1550

1551 CAACGACACATCTACCGCCATCTTCGCCGAATTGGAAGGCGTATGGCAGCCCG 1600
      |||||||.|||||.|.||||.||||.|||||||||||||||||||||
1551 CAACGACATATACAGAATCTTCGCAGAACTGGAGGGAGTTTGGCAGCCCG 1600
```

Figure 3E

```
1601 CTGCGGCAACCCAAACGTCGCCGCCACCGGCAAGACGCCTTGCCCGGGCCA    1650
     ||||·||·||·|||··|·||·||·|||·||·||·||||·|·|||·|||
1601 CTGCTCAGCCCTAAACGCAGACGGCACAGAGACGCCCTCCCAGGGCCG        1650

1651 TGCATCGCCTCGACGCCCAAAAAGCACCGAGGT    1683
     |||||·|||||·||·||·||||·|||||||·|||
1651 TGCATAGCCCTCTACCCCAAAGAAGCACCGCGGT    1683
```

Figure 4A

```
  1 atggaatccaggatctggtgcctgtagtctgcgttaacctgtgtatcgtgtctgggt   60
  1  M  E  S  R  I  W  C  L  V  V  C  V  N  L  C  I  V  C  L  G   20

61 gctgcggttcctcttctagtacttccatgcaacttcttctactccacaatgaagccat  120
 21  A  A  V  S  S  S  S  T  S  H  A  T  S  S  T  H  N  G  S  H   40

121 acttctcgtacgacgtctgctcaaaccggtcagtctattctcaacgtaacgtcttct  180
 41  T  S  R  T  T  S  A  Q  T  R  S  V  Y  S  Q  H  V  T  S  S   60

181 gaagccgtcagtcatagagccaacgagactatctacaacactaccctcaagtacggagat  240
 61  E  A  V  S  H  R  A  N  E  T  I  Y  N  T  T  L  K  Y  G  D   80

241 gtggtgggagtcaacactaccaagtaccctatcgtgtgttctatgccaagggtacg  300
 81  V  V  G  V  N  T  T  K  Y  P  Y  R  V  C  S  M  A  Q  G  T  100

301 gatcttattcgctttgaacgtaatatcatctgcacctcgatgaagcctatcaatgaagac  360
101  D  L  I  R  F  E  R  N  I  I  C  T  S  M  K  P  I  N  E  D  120

361 ttggatgagggcatcatgtggtctacaagcgcaacatcgtggcgcacacctttaaggta  420
121  L  D  E  G  I  M  V  V  Y  K  R  N  I  V  A  H  T  F  K  V  140

421 cgggtctaccaaaaggtttgacgttcgtcgttcgttcttcgtcgtagctacgcttacatctacaccactat  480
141  R  V  Y  Q  K  V  L  T  F  R  R  S  Y  A  Y  I  Y  T  T  Y  160

481 ctgctgggcagcaatacggaatacgtggcgcctcctatgtgggagattcatcacatcaac  540
161  L  L  G  S  N  T  E  Y  V  A  P  P  M  W  E  I  H  H  I  N  180

541 aagtttgctcaatgctacagttcctacagccgcgttataggaggcacggtttcgtggca  600
181  K  F  A  Q  C  Y  S  S  Y  S  R  V  I  G  G  T  V  F  V  A  200
```

Figure 4B

```
601  tatcatagggacagttatgaaaacaaaccatgcaattaattcccgacgattattccaac  660
201   Y  H  R  D  S  Y  E  N  K  T  M  Q  L  I  P  D  D  Y  S  N   220

661  acccacagtacccgttacgtgacggtcaaggatcagtggcacagccgcggcagcacctgg  720
221   T  H  S  T  R  Y  V  V  T  V  K  D  Q  W  H  S  R  G  S  W   240

721  ctctatcgtgagacctgtaatctgaactgtatgctgaccatcactactgcgcgtccaag  780
241   L  Y  R  E  T  C  N  L  N  C  M  L  T  I  T  T  A  R  S  K   260

781  tatccttatcattttttgcaacttccacgggtgatgtggtttacattctctcctttctac  840
261   Y  P  Y  H  F  F  A  T  S  T  G  D  V  V  Y  I  S  P  F  Y   280

841  aacggaaccaatgcaatgccagctgactttggagaaaacgccgacaagttttcattttc  900
281   N  G  T  N  R  N  A  S  Y  F  G  E  N  A  D  K  F  F  I  F   300

901  ccgaactacaccatcgttcctgacttggaagacccaacgctgccgccagaaaccatagg  960
301   P  N  Y  T  I  V  S  D  F  G  R  P  N  A  A  P  E  T  H  R   320

961  ttggtggcttttctcgaacgtgccgactcggtgatctcttgggatatacaggacgagaag  1020
321   L  V  A  F  L  E  R  A  D  S  V  I  S  W  D  I  Q  D  E  K   340

1021 aatgtcacctgccagctcacctttctgggaagcctcggaacgtactatccgttccgaagcc  1080
341   N  V  T  C  Q  L  T  F  W  E  A  S  E  R  T  I  R  S  E  A   360

1081 gaagactcgtaccactttctctgccaaaatgactgcaacttttctgtctaagaaacaa  1140
361   E  D  S  Y  H  F  S  S  A  K  M  T  A  T  F  L  S  K  K  Q   380

1141 gaagtgaacatgtccgactccgcgctgactgtacgtgatgaggctataaataagtta  1200
381   E  V  N  M  S  D  S  A  L  D  C  V  R  D  E  A  I  N  K  L   400
```

Figure 4C

```
1201 cagcagatttcaatacttcatacaatcaaacatatgaaaatacgaaacgtgtccgtc 1260
 401  Q  Q  I  F  N  T  S  Y  N  Q  T  Y  E  K  Y  G  N  V  S  V  420

1261 ttcgaaaccagcggcggtctggtcgtgttctggcaaggcatcaagcaaaaatctttggtg 1320
 421  F  E  T  S  G  G  L  V  V  F  W  Q  G  I  K  Q  K  S  L  V  440

1321 gaattggaacgtttggccaatcgatccagtctgaatatcactcataggaccagaagaagt 1380
 441  E  L  E  R  L  A  N  R  S  S  L  N  I  T  H  R  T  R  R  S  460

1381 acgagtgacaataatacaactcatttgtccagcatggaatcggtgcacaatctggtctac 1440
 461  T  S  D  N  N  T  T  H  L  S  S  M  E  S  V  H  N  L  V  Y  480

1441 gcccagctgcagttcacctatgacacgttgcgcggttacatcaaccgggcgctggcgcaa 1500
 481  A  Q  L  Q  F  T  Y  D  T  L  R  G  Y  I  N  R  A  L  A  Q  500

1501 atcgcagaagcctgctgggatcgtgtggatcagcgacgcacccctagaggtcttcaaggaactcagc 1560
 501  I  A  E  A  W  C  V  D  Q  R  R  T  L  E  V  F  K  E  L  S  520

1561 aagatcaacccgtcagccattctctcggccatttacaacaaccgattgccgcgcgtttc 1620
 521  K  I  N  P  S  A  I  L  S  A  I  Y  N  K  P  I  A  A  R  F  540

1621 atgggtgatgtctttggcctggcgctgctcagccgtgtcaaggtg 1680
 541  M  G  D  V  L  G  L  A  S  C  V  T  I  N  Q  T  S  V  K  V  560

1681 ctgcgtgatatgaacgtgaaggaatcgccaggacgctgctactcacgaccgtggtcatc 1740
 561  L  R  D  M  N  V  K  E  S  P  G  R  C  Y  S  R  P  V  V  I  580

1741 tttaatttcgccaacagctcgtacgtgcagtacgtcaactgggcgaggacaacgaaatc 1800
 581  F  N  F  A  N  S  Y  V  Q  Y  G  Q  L  G  E  D  N  E  I  600
```

Figure 4D

```
1801 ctgttgggcaaccaccgcactgaggaatgtcagcttcccagcctcaagatcttcatcgcc 1860
 601  L  L  G  N  H  R  T  E  E  C  Q  L  P  S  L  K  I  F  I  A   620

1861 gggaactcggctacgagtacgtggactacctcttcaaacgcatgattgacctcagcagt 1920
 621  G  N  S  A  Y  E  Y  V  D  Y  L  F  K  R  M  I  D  L  S  S   640

1921 atctccaccgtcgacagcatgatcgccctggatatcgacccgctggaaataccgacttc 1980
 641  I  S  T  V  D  S  M  I  A  L  D  I  D  P  L  E  N  T  D  F   660

1981 agggtactggaacttactcgcagaaagagctgcgttccagcaacgttttgacctcgaa 2040
 661  R  V  L  E  L  Y  S  Q  K  E  L  R  S  S  N  V  F  D  L  E   680

2041 gagatcatgcgcgaattcaactcgtacaagcagcgggtaaagtacgtggaggacaagta 2100
 681  E  I  M  R  E  F  N  S  Y  K  Q  R  V  K  Y  V  E  D  K  V   700

2101 gtcgacccgctaccgcctacctcaaggtgctggacgactcatgagcggcctggggcgcc 2160
 701  V  D  P  L  P  P  Y  L  K  G  L  D  D  L  M  S  G  L  G  A   720

2161 gcgggaaaggccgttggcgtagccattggggtggccgtgggcggcgtggcctccgtggtc 2220
 721  A  G  K  A  V  G  V  A  I  G  A  V  G  G  A  V  A  S  V  V   740

2221 gaaggcgttgccaccttcctcaaaaaccccttcggagccttcaccatcatcctcgtgcc 2280
 741  E  G  V  A  T  F  L  K  N  P  F  G  A  F  T  I  I  L  V  A   760

2281 atagccgtagtcattatcacttatttgatctatactcgacagcggctctgtgcacgcag 2340
 761  I  A  V  V  I  I  T  Y  L  I  Y  T  R  Q  R  R  L  C  T  Q   780

2341 ccgctgcagaacctcttccctatctggtccgccgacggaccaccgtgactgtcggggc 2400
 781  P  L  Q  N  L  F  P  Y  L  V  S  A  D  G  T  T  V  T  S  G   800
```

Figure 4E

```
2401 agcaccaaagagacacgtcgttacaggctccgcctcctacgaggaaagtgttataattct 2460
 801  S  T  K  D  T  S  L  Q  A  P  P  S  Y  E  E  S  V  Y  N  S   820

2461 ggtcgcaaggaccgggaccaccgtctgtctgatgcatccacggcgcctccgcttacacc 2520
 821  G  R  K  G  P  G  P  P  S  S  D  A  S  T  A  A  P  P  Y  T   840

2521 aacgagcaggcttaccagatgcttctggccctgtctggacgcagagcagcgagcg 2580
 841  N  E  Q  A  Y  Q  M  L  L  A  L  A  R  L  D  A  E  Q  R  A   860

2581 cagcagaacggtacagattctttggacgacggcacgcaggacaagggacagaag 2640
 861  Q  Q  N  G  T  D  S  L  D  G  Q  T  G  T  Q  D  K  G  Q  K   880

2641 cctaacctgctagaccggctgcgacatcgcaaaaacggctacagacacttgaaagactcc 2700
 881  P  N  L  L  D  R  L  R  H  R  K  N  G  Y  R  H  L  K  D  S   900

2701 gacgaagaagagaacgtc 2718
 901  D  E  E  E  N  V   906
```

Figure 5A

```
  1 atggaatccaggatctgtggtgcctgttagtctgcgttaacctgtgtatcgtgtctgtctggt  60
  1  M  E  S  R  I  W  C  L  V  V  C  V  N  L  C  I  V  C  L  G     20

61 gctgccgtttcctcttctagtacttcttctactcacaatggaagccat                120
 21  A  A  V  S  S  S  T  S  H  A  T  S  S  T  H  N  G  S  H        40

121 acttctcgcaccacctctgctcaaaccggtcagtctgtctattctcaacacgtaacctcttct 180
 41  T  S  R  T  T  S  A  Q  T  R  S  V  Y  S  Q  H  V  T  S  S     60

181 gaagccgtcagtcatagagccaacgagactatctacaacactacccctcaagtacggagat  240
 61  E  A  V  S  H  R  A  N  E  T  I  Y  N  T  T  L  K  Y  G  D     80

241 gtggtgggagtcaacactaccaagtaccccatcgcgtgtgttctatggcccaggggtacc  300
 81  V  V  G  V  N  T  T  K  Y  P  Y  R  V  C  S  M  A  Q  G  T    100

301 gatcttattcgctttgaacgcaatatcatctgcacctccatgaagcctatcaatgaagac  360
101  D  L  I  R  F  E  R  N  I  I  C  T  S  M  K  P  I  N  E  D    120

361 ttggatgagggcatcatggtggtctacaagcgcaacatcgtggcccacacctttaaggta  420
121  L  D  E  G  I  M  V  V  Y  K  R  N  I  V  A  H  T  F  K  V    140

421 cgggtctaccaaaaggttttgacctttcgccgcagctacgcttacatctacaccacttat  480
141  R  V  Y  Q  K  V  L  T  F  R  R  S  Y  A  Y  I  Y  T  T  Y    160

481 ctgctgggcagcaataccgaatacgtggcccctcctatgtgggagattcatcacatcaac  540
161  L  L  G  S  N  T  E  Y  V  A  P  P  M  W  E  I  H  H  I  N    180

541 aagtttgctcaatgctacagttcctacagccgcgttataggaggcaccgttttcgtggca  600
181  K  F  A  Q  C  Y  S  S  Y  S  R  V  I  G  G  T  V  F  V  A    200
```

Figure 5B

```
601  tatcataggga cagttatgaa aaacaaacca tgcaattaat tccgacgatt attccaac  660
201   Y  H  R  D   S  Y  E  N   K  T  M  Q   L  I  P  D   D  Y  S  N   220

661  acccacagta cccgctacgt gaccgtcaag gatcagtgga cagccgggca gcacctgg  720
221   T  H  S  T   R  Y  V  T   V  K  D  Q   W  H  S  R   G  S  T  W   240

721  ctctatcgcg agacctgtaa tctgaactgt atgctgacca tcactactgc ccgctccaag  780
241   L  Y  R  E   T  C  N  L   C  M  L  T   I  T  T  A   R  S  K   260

781  tatcctttat cattttttgc aacttccacc ggtgatgtgg ttacatttct cctttctac  840
261   Y  P  Y  H   F  F  A  T   S  T  G  D   V  V  Y  I   S  P  F  Y   280

841  aacggaacca atcgcagcta cttttggaga gaaaacgcca gtttttcatttc  900
281   N  G  T  N   R  N  A  S   Y  F  G  E   N  A  D  K   F  F  I  F   300

901  cccaactaca ccatcgtttc cgactttgga agaccaacgc tgccccagaa acccatagg  960
301   P  N  Y  T   I  V  S  D   F  G  R  P   N  A  A  P   E  T  H  R   320

961  ttggtggttt tctgaacgcg ccagctccgt gatctcttgg gatatacagg acgagaag  1020
321   L  V  A  F   L  E  R  A   D  S  V  I   S  W  D  I   Q  D  E  K   340

1021 aatgtcacct gccagctcac ctttctggga agcctccgaa cgcactatcc gctccgaagcc  1080
341   N  V  T  C   Q  L  T  F   W  E  A  S   E  R  T  I   R  S  E  A   360

1081 gaagactcct accactttct ctgccaaaat gactgcaact tttctgtcta agaaacaa  1140
361   E  D  S  Y   H  F  S  S   A  K  M  T   A  T  F  L   S  K  K  Q   380

1141 gaagtgaaca tgtccgactc cgctacgcgc tgcgatgagg ctataaataa gtta  1200
381   E  V  N  M   S  D  S  A   L  D  C  V   R  D  E  A   I  N  K  L   400
```

Figure 5C

```
1201 cagcagatttcaatacttcatacaatcaaacatatgaaaaatacggaaacgtgtccgtc 1260
 401  Q  Q  I  F  N  T  S  Y  N  Q  T  Y  E  K  Y  G  N  V  S  V   420

1261 ttcgaaaccagcggcggtctggtggtgttctggcaaggcatcaagcaaaaatctttggtg 1320
 421  F  E  T  S  G  G  L  V  V  F  W  Q  G  I  K  Q  K  S  L  V   440

1321 gaattgaacgcttggccaatcgatccagtctgaatatcactcataggaccagaagaagt 1380
 441  E  L  E  R  L  A  N  R  S  S  L  N  I  T  H  R  T  R  R  S   460

1381 accagtgacaataataacactcattgtccagcatgaatccgtgcacaatctggtctac 1440
 461  T  S  D  N  N  T  H  L  S  S  M  E  S  V  H  N  L  V  Y   480

1441 gcccagctgcagttcacctatgacacctttgcgcggttacatcaacgggccctggccccaa 1500
 481  A  Q  L  Q  F  T  Y  D  T  L  R  G  Y  I  N  R  A  L  A  Q   500

1501 atcgcagaagcctgctgggtgtgtgtggatcaacgtggatcaacaggtctttcaaggaactcagc 1560
 501  I  A  E  A  W  C  V  D  Q  R  R  T  L  E  V  F  K  E  L  S   520

1561 aagatcaaccccctcagcgctgaagctatcctctctccgccattacaacaaaccattgccgcccgcttc 1620
 521  K  I  N  P  S  A  I  L  S  A  I  Y  N  K  P  I  A  A  R  F   540

1621 atgggtgatgtcttgggcctggcctggcagctgcgtgaccatcaaccagcgtcaaggtg 1680
 541  M  G  D  V  L  G  L  A  S  C  V  T  I  N  Q  T  S  V  K  V   560

1681 ctgcgcgatatgaacgtgaaggaatcccaggacgctgtactcacgaccgtggtcatc 1740
 561  L  R  D  M  N  V  K  E  S  P  G  R  C  Y  S  R  P  V  V  I   580

1741 tttaatttcgccaacagctcctacgtgcagtacgtcaactgggcgaggacaacgaaatc 1800
 581  F  N  F  A  N  S  Y  V  Q  Y  G  Q  L  G  E  D  N  E  I   600
```

Figure 5D

```
1801 ctgttgggcaaccaccgcactgaggaatgtcagcttcccagcctcaagatcttcatcgcc 1860
601   L  L  G  N  H  R  T  E  E  C  Q  L  P  S  L  K  I  F  I  A  620

1861 gggaactccgcctacgagtacgtggactacctcttcaaacgcatgattgacctcagcagt 1920
621   G  N  S  A  Y  E  Y  V  D  Y  L  F  K  R  M  I  D  L  S  S  640

1921 atctccacgtcgacagcatgatcgccctggatatcgacccctgaaaataccgacttc 1980
641   I  S  T  V  D  S  M  I  A  L  D  I  D  P  L  E  N  T  D  F  660

1981 agggtactggaacttactcccagaaagagctgcgctccagcaacgttttgacctcgaa 2040
661   R  V  L  E  L  Y  S  Q  K  E  L  R  S  S  N  V  F  D  L  E  680

2041 gagatcatgcgcgaattcaactcctacaagcagcgggtaaagtacgtggaggacaaggta 2100
681   E  I  M  R  E  F  N  S  Y  K  Q  R  V  K  Y  V  E  D  K  V  700

2101 gtcgaccactacctcccctacctcaagggtctggacgac 2139
701   V  D  P  L  P  P  Y  L  K  G  L  D  D  713
```

Figure 6A

```
  1 ATGGAATCCAGGATCTGGTGTGCCTGGTAGTCTGCGTTAACCTGTGTATCGT    50
    ||||||||||||||||||||||||||||||||.||||.||||||||||||||
  1 ATGGAATCCAGGATCTGGTGTGCCTGGTCGTCGTGTCTGTGTCAACCTTTGTATCGT    50

51 CTGTCTGGGTGCTGCGGGTTTC---CTCTTCTAGTACTTCCCATGCAACTT    97
    .|...|||..|||||.|||.||    ...|.|..|..|
 51 TTGCTTGGGAGCTGCGCCGTTAGTAGCAGCTCCACAAGT---CATGCCACCA    97

98 CTTCTACTCACAATGGAAGCCATACTTCTCGTACGACGTCTGCTCAAACC   147
    .|||||||||||.||||||||||||||.|||...|||||.|||.||||||
 98 GCAGTACCCATAAACGGTAGCCACACCTCACGGACAACGAGCGCTCAGACT   147

148 CGGTCAGTCTATTCTCAACACGTAACGTCTTCTGAAGCCGTCAGTCATAG   197
    |.|.||||||.|||.||.||.||||||.||...||||.||||..|||.|
148 CGTTCCCGTGTACTCGCAGCACGTTACCTCCTCAGAGAGGCAGTGTCCCATCG   197

198 AGCCAACGAGACTATCTACAACACTACCCTCAAGTACGGAGATGTGGTGG   247
    .|.||||||||||.||||||||||||.|||||||||||.||.|||.||||
198 CGCTAACGAAACTATCTACAACACCACACTCAAGTATGCGACGTAGTGG   247

248 GAGTCAACACTACCAAGTACCCCTATCGCGTGTGTTCTATGCCCAGGGT   297
    |.||.|||||.|.||||.|||||||||||||.|||||||||||||||.
248 GTGTAAATACGACACAAAATACCCATATAGAGTGTGCTCAATGCCCAGGGC   297

298 ACGGATCTTATTCGCTTTGAACGTAATATCATCTGCACCTGATGAAGCC   347
    ||.||||||||||.||||.|||.|||.||||||||||||||||||||||
298 ACCGATCTGATCCGGTTCGAGAGAAATATAATCTGCACCTCTATGAAACC   347

348 TATCAATGAAGACTTGGATGAGGGCATCATGGTGGTCTACAAGCGCAACA   397
    |||||||||||||||||||||||||||||||||||||||||||.|||.|
348 TATCAATGAGGACTTGGACGAGGGGATCATGGTGGTGTATAAGAGAAATA   397
```

FIGURE 6B

```
398  TCGTGGCGCACACCTTTAAGGTACGGGTCTACCAAAAGGTTTTGACGTTT  447
     |.||..||||.||.||.|||||.|||||||.||.|||.|||.||.||.||.|
398  TTGTCGCCCATACCTTTAAAGTGCGCGTTTATCAAAAGGTGTTAACTTTC   447

448  CGTCGTAGCTACGCTTACATCTACACCACTTATCTGCTGGGCAGCAATAC   497
     .|.|||||||||||||||||.|||.|||.|||.||..|||.||.|.|||||
448  AGAAGGTCCTACGCTTATATCTACACCACGTACCTGCTCGGCTCCAATAC   497

498  GGAATACGTGGCGCCTCCTATGTGGGAGATTCATCACATCAACAAGTTTG   547
     .|.||||||||||||.|.|||.||.|.|||||||||||.||||||||.|.|
498  AGAGTACGTCGCTCCTCCCATGTGGGAAATTCACCATATCAACAAGTTCG   547

548  CTCAATGCTACAGTTCCTACAGCCGCGTTATAGGAGGCACGGTTTTCGTG   597
     .|.||||||||||.|..|.||.||.|||||.|||||.||.||||.|||||
548  CCCAGTGCTACTCCTCCTTACTCACGCGTGATCGGAGGACCGTGTTCGTG   597

598  GCATATCATAGGGACAGTTATGAAAACAAAACCATGCAATTAATTCCCGA   647
     ||||||||.|.||.|||.|.||.|||||.|||||.||.||..|.||.|||
598  GCATATCACCGAGATTCTTACGAAAACAAGACAATGCAGCTGATCCCTGA   647

648  CGATTATTCCAACACCCACAGTACCCGTTACGTGACGGTCAAGGATCAGT   697
     .|.|||.||||..|.||.|||..|||.||||.||||||.|||.||||.||
648  TGACTACTCTAATACACACTCAACCCGTTATGTGACCGTAAAGGATCAAT   697

698  GGCACAGCCGGCGACCAGCACCTGGCTCTATCGTGAGACCTGTAATCTGAAC  747
     ||||.||||.||...||.||||||||||.||.||||.||.|.||.|.|||.
698  GGCACTCCCGGGTCTACCTGGCTCTACAGGGAAACGTGCAACCTGAAT    747

748  TGTATGCTGACCATCACTACTGCGCGCTCCAAGTATCCTTATCATTTTT   797
     ||||||||||||..|||..|||.|.||||||||||.||.|.|||.||||
748  TGTATGCTGACAATAACGACTGCTAGTGTCAAAGTCAAAGTACCCCTACCACTTTT  797
```

Figure 6C

```
798  TGCAACTTCCACGGGTGATGTGGTTTACATTTCTCCTTTCTACAACGGAA  847
     |||||||||||||||||||||||.||.|||||||||...|||||||||||
798  TGCAACCTCTACCGGCGACGTGGTTTATATTAGTCCTTTCTACAACGGAA  847

848  CCAATCGCAATGCCAGCTACTTTGGAGAAAACGCCGACAAGTTTTTCATT  897
     |||.|||||||.||||||.|.||.|||||..||||||.||||||||||||
848  CCAACCGTAATGCGAGTTATTCGGTGAAAACGCAGACAAGTTTTTCATT  897

898  TTCCCGAACTACACCATCGTTCCGACTTTGGAAGACCCAACGCTGCGCC  947
     |||||.|||.|||.|.||.|||||.||||||||||||.|||||.|.||.
898  TTCCCCAACTATACTATCGTGAGTGACTTCGGAAGACCTAATGCAGCCCC  947

948  AGAAACCCATAGGTTGGTGGCTTTTCTCGAACGTGCCGACTCGGTGATCT  997
     |||||.||||.|.||.|||.|||||||.||.|||..|||...|||||||
948  AGAGACTCATCGCCTGGTGCCTTCCTCGAAAGAGCCGATAGCGTGATCT  997

998  CTTGGGATATACAGGACGAGAAGAATGTCACCTGCCAGCTCGCCTTCTGG  1047
     |.|||||||.|||.||||.|||||.|||.||.|||||||.|||.|||||
998  CCTGGGATATTCAGGACGAGAAGAACGTGACTTGCCAACTCACCTTTTGG  1047

1048 GAAGCCCTCGGAACGTACTATCCGTTCCGAAGCCGAAGACTCGTACCACTT  1097
     ||.||.|||.||||.|||||.||.|||||.|||||||||||.||.||.||
1048 GAGGCGTCTGAGCGCACTATACGAAGCGAAGCCGAAGACTCTTATCATTT  1097

1098 TTCTTCTGCCAAAATGACTGCAACTTTTCTGTCTAAGAAAACAAGAAGTGA  1147
     ....|.||||||||.|||.||.|||.||.||||.|||||||.||||.|.|
1098 CAGCAGTGCAAAGATGACAGCCACTTTCTTGTCCAAAAAACAGGAGGTTA  1147

1148 ACATGTCCGACTCCGCGCTGACTGCTAGCGTGATGAGGCTATAAATAAG  1197
     |||||||.|||||.||.|||||||||||.||||||.||||.|.|||.|.
1148 ACATGTCTGACTCAGCGCTAGACTGTGTGCGGGACGAGGCGATCAACAAA  1197
```

Figure 6D

```
1198  TTACAGCAGATTTTCAATACTTCATACAATCAAACATATGAAAAATACGG  1247
      .|.||.||.|||||||||.....|||||||.||..||.||.||.||.||
1198  CTGCAACAAATATTCAACACGAGCTACAACCAGACCTACGAGAAGTATGG  1247

1248  AAACGTGTCCGTCTTCGAAACCAGCGGCGGTCTGGTGGTGTTCTGGCAAG  1297
      .|.|||||.|.||.||.|.|||||.||.|.||||.|||.||||||.|.|
1248  CAATGTGTCAGTATTTGAGACTAGCGGCGGACTGGTAGTATTTGGCAGG  1297

1298  GCATCAAGCAAAAATCTTTGGTGGAATTGGAACGTTTGGCCAATCGATCC  1347
      |.|.||.||.||.|.||.|.|||.|.|||.||.|||||||||||||||
1298  GGATTAAACAGAAGTCTCTCGTCGAACTCGAGCGGCTGGCCAATCGCAGT  1347

1348  AGTCTGAATATCACTCATAGGACCAGAAGAAGTACGAGTGACAATAATAC  1397
      |||||||.|.|.|.|||.|.||||.||.|....||.|||||||||||||
1348  AGTCTGAACATCACACAGGACACGAAGGTCTACTTCCGATAATAATAC  1397

1398  AACTCATTTGTCCAGCATGGAATCGGTGCACAATCTGGTCTACGCCCAGC  1447
      .|.|||||||||.|||||.|.||||||||||||.||.|||||.||||||
1398  CACCCACCCTCTCCTATGGAGTCGGTGCACAACCTGGTACGCTCAGT  1447

1448  TGCAGTTCACCTATGACACGTTGCGCGGTTACATCAACGGGGCGCTGGCG  1497
      ||||||||.|.|||.|.||.|.|||.|||||||.|||||.|||.||.|.
1448  TGCAGTTTACATACGACACCCCTGCGCGGGTATATTAACAGAGCGCTGGCA  1497

1498  CAAATCGCAGAAGCCTGGTGTGTGGATCAACGGCGCCACCCTAGAGGTCTT  1547
      ||.|||||.|||||..|||.||.||||||||.|||||.||||||||.|||
1498  CAGATCGCCGAAGCATGGTGCGTCGACCAACGTCGAACGCTGGAGGTCTT  1547

1548  CAAGGAACTCAGCAAGATCAACCCGTCAGCCATTCTCTCGGCCATTTACA  1597
      |||||.||||||||.|.||.|||..|.||..|.|.|.|||..||||||||
1548  CAAGGAGCTATCCAAGATTAACCCAAGTGCCATTCTATCTGCAATTTACA  1597
```

Figure 6E

```
1598  ACAAACCGATTGCCGCGCGTTTCATGGGTGATGTCTTGGGCCTGGCCAGC  1647
      | ||  ||||||||||   ||  |||||||||  ||||| |||||  |||
1598  ATAAGCCGATTGCCGCTAGGTTTATGGGCGATGTTCTGGGACTGGCGAGC  1647

1648  TGCGTGACCATCAACCAGTCAAACCAGCGTCAAGGTGCTGCGTGATATGAACGT  1697
      |  ||  || || || |||  |||| ||  |||||  | ||||| ||||||
1648  TGTGTGACTATAAACCAAACGTCAGTCAAGGTGCTTAGGACATGAACGT  1697

1698  GAAGGAATCGCCAGGACGCTGCTACTCACGACCCGTGGTCATCTTTAATT  1747
      |   |||||||| ||  |  | ||  || |  ||| ||| ||| ||||||
1698  TAAGGAATCCCCTGGCCGGTGTTATTCGCGCCTGTTGTCATATTTAATT  1747

1748  TCGCCAACAGCTCGTGCAGTACGGTCAACTGGGCGAGGACAACGAA  1797
      | ||||| ||| | |   ||| ||| ||| ||||| ||||||||||
1748  TTGCCAATTCCCTCTTACGTGCAGTACGACGGCCAGTTAGGCGAGGACAACGAA  1797

1798  ATCCTGTTGGGCAACCACCGCACTGAGGAATGTCAGCTTCCCAGCCTCAA  1847
      || |  ||||||||||  | ||| |||| |||| |||  |||  ||||
1798  ATTTTATTGGGCAATCATCGCACCGAGGAATGCCAGTTGCCGAGCCTGAA  1847

1848  GATCTTCATCGCCGGAACTCGGCCTACGAGTACGTGGACTACCTCTTCA  1897
      . |   || || ||  ||| |  || ||| || ||  ||| |||| ||
1848  AATCTTTATAGCTGGAACAGCGCTTACGAGTACGTCGACTATCTCTTTA  1897

1898  AACGCATGATTGACCTCAGCAGTATCTCCACCGTCGACAGCATGATCGCC  1947
      | |||||||||||| ||||| | |   ||| |||||| || ||||||||
1898  AGCGGATGATTGATCTGAGCTGTCGATCAGCACAGTCGACTCTATGATCGCC  1947

1948  CTGGATATCGACCCGCTGGAAAATACCGACTTCAGGGTACTGGAACTTTA  1997
      |||||||| ||||| |||||   ||| |  |||||||| ||||| |||||
1948  CTGGATATTGACCCGCTGGAGAATACAGATTTCAGAGTGCTTGAATTATA  1997
```

Figure 6F

```
1998  CTCGCAGAAAGAGCTGCGTTCCAGCAACGTTTTGACCTCGAAGAGATCA  2047
      .||.||||||||||||||||.||||||..||.|||.||.||.||.|..|
1998  TTCACAGAAAGAGCTGCGGAGCTCAAATGTGTTCGATCTTGAGGAAATTA  2047

2048  TGCGCGAATTCAACTCGTACAAGCAGCGGGTAAAGTACGTGGAGGACAAG  2097
      ||||.|||||||||||.||..|||||||| ||||.|||||||||||||||
2048  TGCGGGAATTCAACAGCTACAAGCGGTCAACGGGTCAAGTACGTGGAGGACAAG  2097

2098  GTAGTCGACCCGCTACCGGCCCTACCTCAAGGGTCTGGACGACCTCATGAG  2147
      ||.||.|||||.||.||.||.|||||.|||.|||||||||||||||||||
2098  GTGGTGGACCCACTGCCCCCCCTACTTGAAAGGTCTGGATGATCTCATGAG  2147

2148  CGGCCTGGGCGCCGGGGAAAGGCCGTTGGCGTAGCCATTGGGCCGTGG  2197
      |||.|.||.|||.||.||.|||.||.||..||||||||..||||.|.||.
2148  CGGTCTTGGAGCGGCTGGCAAAGCCGTTGGAGTAGCAATCGGCGCCGTTG  2197

2198  CGGCCTGGGCGGTGGCCTCCGTGGTCGAAGGCCGTTGCCACCTTCCTCAAAAAC  2247
      |.|||.||.|||.||.||.|.||.|.||.||.|||.|.||.|.|.|||.|||
2198  GAGGGGCCCGTGGCCTGTGTAGTGGAAGGGCGTTGCTACCTTTTTGAAGAAC  2247

2248  CCCTTCGGAGCCTTCACCATCATCCTCGTGGCCATAGCCGTAGTCATTAT  2297
      ||||||||.|||.||.||.|||.||.|||||||.|.||..||.||||.||
2248  CCCTTCGGGGCCTTTACTATCATTCTAGTGCTATTGCAGTCGTGATAAT  2297

2298  CACTTATTTGATCTATATACTCGACAGCGGGCCGTCTGTGCACGCAGCCGCTGC  2347
      |||.||.|||||||||||||||||||||||||||.|..|.||.|.|.||
2298  CACATATTTGATCTATATACTCGGCAGAGACGCTTATGCACACAGCCCCTTC  2347

2348  AGAACCTCTTTCCCTATCTGGTGTCCGCCGACGGGACCACCGTGACGTCG  2397
      ||.|.||||||.|||.||.|.|||||.|||||||||||.||.||||||.
2348  AGAATCTCTTCCCCTATCTGGTCTCCGCAGATGGGACAACAGTGACAAGT  2397
```

Figure 6G

```
2398  GGCAGCACCAAAGACACGTCGTTACAGGCTCCGCCTTCCTACGAGGAAAG  2447
      ||   |  ||   |     ||  ||  |||||| |  ||||  || ||
2398  GGCTCGACTAAGGATACCAGCTTGCAAGCTCCCCCAAGTTACGAAGAGAG  2447

2448  TGTTTATAATTCTGGTCGCAAAGGACCGGGACCACCGTCGTCTGATGCAT  2497
       |||||||| |   ||   || || ||| |  ||| ||||||||||||||
2448  CGTTTATAACTCCGGTAGGAAAGGACCAGGTCCACCTAGCTCAGATGCAT  2497

2498  CCACGGCGGCTCCGCCCTTACACCAACGAGCAGGCTTACCAGATGCTTCTG  2547
      |  ||| || | ||||| ||||||| |||||||||| ||||||||||| |
2498  CAACCGCTGCCCCACCCTATACTAATGAGCAGGCCTATCAGATGCTGCTT  2547

2548  GCCCTGGCCCCGTCTGGACGCAGCAGCGAGCGGCAGAACGGTACAGA  2597
      ||  |||||| ||| ||||| | ||||||||||||| |  ||||||
2548  GCACTCGCCAGACTGGACGCCGAGCAGCGAGCCCAGCAGAATGGGACAGA  2597

2598  TTCTTTGGACGGACAGACTGGCACGCAGGACAAGGGACAGAAGCCTAACC  2647
       | ||| ||| | |||| |||| |||||||| ||   |||| ||| |||
2598  CTCCCCTCGACGGGCAGACTGGAACCCAGGATAAAGGACAGAAACCTAATC  2647

2648  TGCTAGACCGGCTGCCGACATCGCAAAAACGGCTACAGACACTTGAAAGAC  2697
      ||| | |||| |||| ||| ||||||| |||||||||| ||||||||| |
2648  TGCTTGACCGACTAAGACACAGGAGAAAAATGGCTACAGGCACCTTAAAGAT  2697

2698  TCCGAGAAGAGAGAACGTC  2718
         ||| | |||||||||||
2698  AGTGATGAAGAAGAGAACGTC  2718
```

Figure 7A

```
  1 atggagtcctctgccaagagaaagatgaccctgataatcctgacgagggcccttcctcc    60
  1  M  E  S  S  A  K  R  K  M  D  P  D  N  P  D  E  G  P  S  S    20

61 aaggtgccacggcccgagacacccgtgaccaaggccacgacgttcctgcagactatgttg   120
 21  K  V  P  R  P  E  T  P  V  T  K  A  T  T  F  L  Q  T  M  L    40

121 aggaaggaggttaacagtcagtcagctgagtctgggagacccgctgtttccagagttggccgaa   180
 41  R  K  E  V  N  S  Q  L  S  L  G  D  D  P  L  F  P  E  L  A  E   60

181 gaatcccctcaaaacttttgaacaagtgaccgagattgcaacgagaacccagaaagat   240
 61  E  S  L  K  T  F  F  E  Q  V  T  E  D  C  N  E  N  P  E  K  D    80

241 gtcctggcagaactcgtcaaacagattaaggttcgagtggacatggtgcggcatagaatc   300
 81  V  L  A  E  L  V  K  Q  I  K  V  R  V  D  M  V  R  H  R  I    100

301 aaggagcacatgctgaaaaaatataccagacggaagagaaattcactggcgccctttaat   360
101  K  E  H  M  L  K  K  Y  T  Q  T  E  E  K  F  T  G  A  F  N    120

361 atgatgggaggatgtttgcagaatgccttagatatcttagataaggttcatgagccttc   420
121  M  M  G  G  C  L  Q  N  A  L  D  I  L  D  K  V  H  E  P  F    140

421 gaggagatgaagtgtattgggctaactatgcagagcatgtatgagaactacattgtacct   480
141  E  E  M  K  C  I  G  L  T  M  Q  S  M  Y  E  N  Y  I  V  P    160

481 gaggataagcgggagatgtggatggcttgtattaaggagctgcatgatgtgagcaagggc   540
161  E  D  K  R  E  M  W  M  A  C  I  K  E  L  H  D  V  S  K  G    180

541 gccgctaacaagttgggggtgcactgcaggctgcagcaggcccgtgctaaaaggatgaactt   600
181  A  A  N  K  L  G  G  A  L  Q  A  K  A  R  A  K  K  D  E  L    200
```

Figure 7B

```
 601 aggagaaagatgatgtatatgtgctacaggaatatagagttctcttaccaagaactcagcc  660
 201  R  R  K  M  M  Y  M  C  Y  R  N  I  E  F  F  T  K  N  S  A   220

661 ttccctaagaccaccaatggctgcagtcaggcatggcggcactgcagaacttgcctcag    720
 221  F  P  K  T  T  N  G  C  S  Q  A  M  A  A  L  Q  N  L  P  Q   240

721 tgctcccctgatgagattatggcttatgcccagaaaatatttaagattttggatgaggag   780
 241  C  S  P  D  E  I  M  A  Y  A  Q  K  I  F  K  I  L  D  E  E   260

781 agagacaaggtgctcacgcacattgatcacgcacatttatgatatcctcactacatgtgtg  840
 261  R  D  K  V  L  T  H  I  D  H  I  F  M  D  I  L  T  T  C  V   280

841 gaaacaatgtgtaatgagtacaaggtcactagtgacgcttgtatgatgaccatgtacggg   900
 281  E  T  M  C  N  E  Y  K  V  T  S  D  A  C  M  M  T  M  Y  G   300

901 ggcatctctctcttaagtgagttctgtcgggtgctgtgctgctatgtcttagaggagact   960
 301  G  I  S  L  L  S  E  F  C  R  V  L  C  C  Y  V  L  E  E  T   320

961 agtgtgatgctggccaagcggcctctgataaccaagcctgaggttatcagtgtaatgaag  1020
 321  S  V  M  L  A  K  R  P  L  I  T  K  P  E  V  I  S  V  M  K   340

1021 cgccgcattgaggagatctgcatgaaggtctttgcccagtacattctgggggccgatcct  1080
 341  R  R  I  E  E  I  C  M  K  V  F  A  Q  Y  I  L  G  A  D  P   360

1081 ctgagagtctgtctcctagtgtggatgacctacgggccatcgccgaggagtcagatgag   1140
 361  L  R  V  C  S  P  S  V  D  D  L  R  A  I  A  E  E  S  D  E   380

1141 gaagaggctattgtagcctacactttggccaccgctgtgtcagtcgtcctcctgattctctg 1200
 381  E  E  A  I  V  A  Y  T  L  A  T  A  G  V  S  S  S  D  S  L   400
```

Figure 7C

```
1201 gtgtcacccccagagtccccctgtacccgcgactatcccctgtcctcagtaattgtggct 1260
401    V  S  P  P  E  S  P  V  P  A  T  I  P  L  S  S  V  I  V  A   420

1261 gagaacagtgatcaggaagaaagtgagcagagtgatgaggaggaggaggggtgctcag 1320
421    E  N  S  D  Q  E  E  S  E  Q  S  D  E  E  E  E  E  G  A  Q   440

1321 gaggagcggggaggacactgtgtctgtcaagtctgagccagtgtctgagatagaggaagtt 1380
441    E  E  R  E  D  T  V  S  V  K  S  E  P  V  S  E  I  E  E  V   460

1381 gccccagagaagaggaggatggtgctgaggaaccaccgcctctggaggcaagagcacc 1440
461    A  P  E  E  E  E  D  G  A  E  E  P  T  A  S  G  G  K  S  T   480

1441 cacccctatggtgactagaagcaaggctgaccag 1473
481    H  P  M  V  T  R  S  K  A  D  Q   491
```

CODON-OPTIMIZED POLYNUCLEOTIDE-BASED VACCINES AGAINST HUMAN CYTOMEGALOVIRUS INFECTION

CROSS-REFERENCE TO RELATED APPLICATIONS

The present application claims the benefit of the filing date of U.S. Provisional Application No. 60/435,549, filed Dec. 23, 2002, which is incorporated herein by reference in its entirety.

BACKGROUND OF THE INVENTION

Human cytomegalovirus ("HCMV") infects between 50% and 85% of adults by 40 years of age (Gershon A. A., et al., in *Viral Infections of Humans*, Evans A. S. and Kaslow, R. A., eds., Plenum Press, New York, N.Y. (1997)). Although HCMV infection is benign in most healthy adults, it can result in deadly pneumonitis, as well as colitis, esophagitis, leukopenia, and retinitis in transplant and other immuno-compromised patients, especially those with HIV. In solid organ transplant (SOT) or hematopoeitic cell transplant (HCT) populations, HCMV disease can occur either from new infection transmitted from the donor organ or HCT, or can recur as a result of reactivation of latent virus in the recipient.

Despite licensed therapies, HCMV-associated disease remains severely debilitating and life-threatening in HIV patients and the allogeneic related HCT and SOT settings. In addition, HCMV is the most common intrauterine infection in the United States, and results in death or severe sequelae in over 8,000 infants per year. For these reasons, HCMV was ranked in the list of the top 10 vaccines most in need of development in the United States (*Vaccines for the 21st century: a tool for decision making*, National Academy of Sciences (1999)).

Existing therapies include the use of immunoglobulins and anti-viral agents such as ganciclovir and its derivatives, which are most effective when used prophylactically or very early during infection in at risk populations. However, these therapies are characterized by significant toxicity and limited efficacy, especially for late onset disease (onset after the first 100 days) (Fillet, A. M., *Drugs Aging* 19:343-354 (2002); von Bueltzingsloewen, A., et al., *Bone Marrow Transplant* 12:197-202 (1993); Winston, D. J., et al., *Ann. Intern. Med.* 118:179-184 (1993); Goodrich, J. M., et al., *Ann. Intern. Med.* 118:173-178 (1993); Boeckh, M., et al., *Blood* 88:4063-4071 (1996); Salzberger, B., et al., *Blood* 90:2502-2508 (1997); Preiser, W., et al., *J. Clin. Virol.* 20:59-70 (2001); Grangeot-Keros, L., and Cointe, D., *J. Clin. Virol.* 21:213-221 (2001); Boeckh, M., and Bowden, R., *Cancer Treat. Res.* 76:97-136 (1995); Zaia, J. A., et al., *Hematology* (Am. Soc. Hematol. Educ. Program) 339-355 (2000)).

In addition to developing more rapid and sensitive diagnostics, molecular biological methods enable the development of defined subunit vaccines for human pathogens. Indeed, safe, effective recombinant subunit vaccines would significantly reduce, and perhaps eliminate, the need for therapeutic treatments. In the case of HCMV, control of infection has been correlated with antibody and T cell recognition of at least three viral proteins: pp65, glycoprotein B (gB), and the immediate early-1 protein (IE1).

The 65 kD viral protein pp65, also known as ppUL83, lower matrix protein, ICP27, PK68, and pp64, is one of the most abundantly expressed structural proteins (FIG. 1). It is encoded by the UL83 gene of the viral genome (nucleotides 119352-121037 of the HCMV strain AD169 genomic sequence, Genbank X17403). This protein is believed to be processed for MHC presentation shortly after viral entry into cells, which allows it to be presented before other viral proteins shut down the antigen processing pathway in infected cells. Therefore, T cell recognition of this protein is important for infection control (Solache, et al. *J. Immunol.* 163:5512-5518 (1999)), which is herein incorporated by reference in its entirety.

Glycoprotein B (gB) is a 906 amino acid envelope glycoprotein (FIG. 4) encoded by UL55, nucleotides 80772-83495 of Genbank X17403). It is a type I integral membrane protein that participates in the fusion of the virion envelope with the cell membrane, is required for infectivity, is highly immunogenic, and has a high degree of conservation among HCMV strains, making this protein an attractive target for vaccines. The full-length protein contains an amino-terminal signal peptide (amino acids 1-24), an extracellular domain (amino acids 25-713), a putative trans-membrane anchor domain (amino acids 714-771) and an intracellular domain (amino acids 772-906). Deletion of the transmembrane anchor domain results in secretion of gB (Zheng et al. *J. Virol.* 70:8029-8040 (1996)). Additionally, the full-length protein is cleaved by host furin proteases between amino acids 460 and 461 to form the gp93 and gp55 cleavage products that remain tightly associated as a heterodimer. (Mocarski E. S. and C. T. Courcelle, pp. 2629-2674, Field's Virology, 4th ed., Eds. Knipe D M and Howley P M, Lippincott Williams & Wilkins, Philadelphia (2001)). Each of the references cited in this paragraph is incorporated herein by reference in its entirety.

IE1 is a 491 amino acid protein (FIG. 7) encoded by HCMV ORF UL123 (Genbank X17403, nucleotides 171006-172765). The gene encodes a 1.9 Kb mRNA comprising four exons, with only exons 2-4 being translated. The 85 N-terminal amino acids are encoded by exons 2 and 3, with the remainder encoded by exon 4. IE2 is a related family of proteins that share exons 1-3 and an exon 5, with many splice variations. Together, IE1 and IE2 transactivate the HCMV major immediate early promoter to regulate viral transcription (Malone, C L. et al. *J. Virol.* 64:1498-1506 (1990); Mocarski, E. *Fields Virology* Ed. Field et al., $3^{rd}$ ed., pp. 2447-2491, Lippincott-Raven Publishers, Philadelphia (1996); Chee M. S. et al., *Curr Topics Microbiol. Immunol.* 154:125-169 (1990)). Each of the references cited in this paragraph is incorporated herein by reference in its entirety.

IE1 has a kinase activity that is dependent on an ATP binding site encoded by amino acids 173-196. IE1 can autophosphorylate or phosphorylate cellular factors to transactivate E2F dependent transcription. Both exons 3 and 4 are required for viral transactivation, with the required regions in exon 4 being broadly distributed throughout the exon. The portion of the protein encoded by exon 4 is known to have a high degree of secondary structure. Although IE1 is transported to the nucleus, no nuclear localization signal has been identified. (Pajovic, S. et al. *Mol. Cell. Bio.* 17:6459-6464 (1997)). Gyulai et al. showed high levels of CTL response in vitro to effector cells expressing a nucleotide fragment consisting of exon 4 (Gyulai et al. *J. Infectious Diseases* 181: 1537-1546 (2000)). Each of the references cited in this paragraph is incorporated herein by reference in its entirety.

No vaccine is currently available for HCMV. However, clinical trials have been performed with live-attenuated HCMV vaccines, a canarypox-based vaccine, and a recombinant gB vaccine (Plotkin, S. A., *Pediatr. Infect. Dis. J.* 18:313-325 (1999)). The first HCMV vaccine tested in humans was a live attenuated virus vaccine made from the AD169 laboratory-adapted strain (Elek, S. D. and Stern, H., Lancet 1:1-5 (1974)). Local reactions were common, but HCMV was not isolated from any of the vaccine recipients. This vaccine was not investigated beyond initial Phase I studies.

Immune responses to HCMV have been determined by the study of acute and chronic HCMV infections in both animal models and in man. Antibody appears critical in the prevention of maternal-fetal transmission, and is primarily directed to the envelope glycoproteins, especially gB (Plotkin, S. A., *Pediatr. Infect. Dis. J.* 18:313-325 (1999); Fowler, K. B., *N. Engl. J. Med.* 326:663-667 (1992)).

In contrast, the control of HCMV infection in transplant recipients and HIV-infected persons is associated with preserved cellular immune responses, including CD4+, CD8+, and NK T cells. The CD8+ T-cell responses are directed primarily at the immediate early (IE) protein of HCMV and at the abundant tegument protein pp65 (Gyulai, Z., et al., *J. Infect. Dis.* 181:1537-1546 (2000); Tabi, Z., et al., *J. Immunol.* 166:5695-5703 (2001); Wills, M. R., et al., *J. Virol.* 70:7569-7579 (1996); Frankenberg, N., et al., *Virology* 295:208-216 (2002); Retiere, C., et al., *J. Virol.* 74:3948-3952 (2000); Koszinowski, U. H., et al., *J. Virol.* 61:2054-2058 (1987); Kern, F., et al., *J. Infect. Dis.* 185:1709-1716 (2002)). Approximately 92% of persons have CD8+ responses to pp65 and another 76% to exon 4 of IE1 (Gyulai, Z., et al., *J. Infect. Dis.* 181:1537-1546 (2000); Kern, F., et al., *J. Infect. Dis.* 185:1709-1716 (2002)). In addition, another one third of infected individuals have CTL responses to gB. Almost all infected persons have CD4+ responses to HCMV, although the gene and epitope mapping of these responses is not as fully investigated as those for CD8+ T cells (Kern, F., et al., *J. Infect. Dis.* 185:1709-1716 (2002); Davignon, J. L., et al., *J. Virol.* 70:2162-2169 (1996); He, H., et al., *J. Gen. Virol.* 76:1603-1610 (1995); Beninga, J., et al., *J. Gen. Virol.* 76:153-160 (1995). The helper T-cell responses in infected, healthy persons are sufficiently robust that HCMV is frequently used as a positive control in the development of methods for the measurement of CD4+ T-cell responses (Kern, F., et al., *J. Infect. Dis.* 185:1709-1716 (2002); Currier, J. R., et al., *J. Immunol. Methods* 260:157-172 (2002); Picker, L. J., et al., *Blood* 86:1408-1419 (1995)).

Other attempts to develop vaccines for HCMV have focused on administering purified or recombinant viral polypeptides, either full-length, modified, or short epitopes, to induce immune responses. In a review published by the American Society for Hematology, Zaia et al. describes various peptide-based approaches to developing HCMV vaccines, including using DNA vaccines to express wild-type and mutated proteins (Zaia, J. A. et al. *Hematology* 2000, *Am Soc Hematol Educ Program*, pp. 339-355, Am. Soc. Hematol. (2000)). Endresz et al. describes eliciting HCMV-specific CTL in mice immunized with plasmids encoding HCMV Towne strain full-length gB, expressed constitutively or under a tetracycline-regulatable promoter, and pp65 or a gB with the deletion of amino acids 715-772 (Endresv, V. et al. *Vaccine* 17:50-8 (1999); Endresz, V. et al. *Vaccine* 19:3972-80 (2001)). U.S. Pat. No. 6,100,064 describes a method of producing secreted gB polypeptides lacking the transmembrane domain but retaining the C terminal domain. U.S. Pat. Nos. 5,547,834 and 5,834,307 describe a gB polypeptide with amino acid substitutions at the endoproteolytic cleavage site to prevent proteolytic processing. U.S. Pat. Nos. 6,251,399 and 6,156,317 describe vaccines using short peptide fragments of pp65 comprising immunogenic epitopes. A number of other groups have analyzed epitopes in HCMV pp65 and gB for eliciting a strong immune response (Liu, Y N. et al. *J. Gen. Virol.* 74:2207-14 (1993); Ohlin, M. et al. *J. Virol.* 67:703-10 (1993); Navarro, D. et al. *J. Med. Virol.* 52:451-9 (1997); Khattab B A. et al. *J. Med. Virol.* 52:68-76 (1997); Diamond, D J. et al. *Blood* 90:1751067 (1997); Solache, A. et al. *J. Immunol.* 163:5512-8 (1999). U.S. Pat. No. 6,162,620 is directed to a polynucleotide encoding a wild-type gB or a gB lacking the membrane sequences. U.S. Pat. No. 6,133,433 is directed to a nucleotide encoding a full-length, wild-type pp65 or a specific 721 nt fragment thereof. Each of the references cited in this paragraph is incorporated herein by reference in its entirety.

During the past few years there has been substantial interest in testing DNA-based vaccines for a number of infectious diseases where the need for a vaccine, or an improved vaccine, exists. Several well-recognized advantages of DNA-based vaccines include the speed, ease and cost of manufacture, the versatility of developing and testing multivalent vaccines, the finding that DNA vaccines can produce a robust cellular response in a wide variety of animal models as well as in man, and the proven safety of using plasmid DNA as a delivery vector (Donnelly, J. J., et al., *Annu. Rev. Immunol.* 15:617-648 (1997); Manickan, E., et al., *Crit. Rev. Immunol.* 17(2):139-154 (1997)). DNA vaccines represent the next generation in the development of vaccines (Nossal, G., *Nat. Med.* 4:475-476 (1998)) and numerous DNA vaccines are in clinical trials. Each of the references cited in this paragraph is incorporated herein by reference in its entirety.

The immunotherapeutic product design is based on the concept of immunization by direct gene transfer. Plasmid-based immunotherapeutics offer the positive attributes of immune stimulation inherent to live-attenuated vaccines combined with the safety of recombinant subunit vaccines in an adjuvant formulation.

In the transplant population, control of HCMV disease is associated with a cellular immune response (Riddell, S. R., "Pathogenesis of cytomegalovirus pneumonia in immuno-compromised hosts," *Semin. Respir. Infect.* 10:199-208 (1995)) and thus an effective product should induce CD4+ and CD8+ T-cell responses. Formulated plasmid has been shown to induce such cellular immune responses, and does not have the safety concerns associated with the use of live vectors in the transplant setting (Shiver, J. W., et al., *Nature* 415:331-335 (2002)).

Retooling coding regions encoding polypeptides from pathogens using codon frequencies preferred in a given mammalian species often results in a significant increase in expression in the cells of that mammalian species, and concomitant increase in immunogenicity. See, e.g., Deml, L., et al., *J. Virol.* 75:10991-11001 (2001), and Narum, D L, et al., *Infect. Immun.* 69:7250-7253 (2001), all of which are herein incorporated by reference in its entirety.

There remains a need in the art for convenient, safe, and efficacious immunogenic compounds to protect humans against HCMV infection. The present invention provides safe yet effective immunogenic compounds and methods to protect humans, especially transplant recipients and immuno-compromised individuals, against HCMV infection using such immunogenic compounds.

SUMMARY OF THE INVENTION

The present invention is directed to enhancing immune response of a human in need of protection against HCMV infection by administering in vivo, into a tissue of the human, a polynucleotide comprising a codon-optimized coding region encoding an HCMV polypeptide or a nucleic acid fragment of such a coding region encoding a fragment, a variant, or a derivative thereof. Nucleic acid fragments of the present invention are altered from their native state in one or more of the following ways. First, a nucleic acid fragment which encodes an HCMV polypeptide may be part or all of a codon-optimized coding region, optimized according to codon usage in humans. In addition, a nucleic acid fragment which encodes an HCMV polypeptide may be a fragment which encodes only a portion of a full-length polypeptide, and/or may be mutated so as to, for example, remove from the encoded polypeptide adventitious protein motifs present in the encoded polypeptide or virulence factors associated with the encoded polypeptide. For example, the nucleic acid sequence could be mutated so as not to encode adventitious anchoring motifs that prevent secretion of the polypeptide. Upon delivery, the polynucleotide of the invention is incorporated into the cells of the human in vivo, and a prophylactically or therapeutically effective amount of an HCMV polypeptide or fragment thereof is produced in vivo.

The invention further provides immunogenic compositions comprising a polynucleotide which comprises one or more codon-optimized coding regions encoding polypeptides of HCMV or nucleic acid fragments of such coding regions encoding fragments, variants, or derivatives thereof. Such compositions may include various transfection facilitating or immunity enhancing agents, such as poloxamers, cationic lipids, or adjuvants.

The present invention further provides plasmids and other polynucleotide constructs for delivery of nucleic acid coding sequences to a vertebrate which provide expression of HCMV polypeptides, or fragments, variants, or derivatives thereof. The present inventions further provides carriers, excipients, transfection-facilitating agents, immunogenicity-enhancing agents, e.g. adjuvants, or other agent or agents to enhance the transfection, expression, or efficacy of the administered gene and its gene product.

The invention further provides methods for enhancing the immune response of a human to HCMV infection by administering to the tissues of a human one or more polynucleotides comprising one or more codon-optimized coding regions encoding polypeptides of HCMV or nucleic acid fragments of such coding regions encoding fragments, variants, or derivatives thereof. In certain embodiments, the invention further provides methods for enhancing the immune response of a human patient to HCMV infection by sequentially administering two or more different immunogenic compositions to the tissues of the vertebrate. Such methods comprise initially administering one or more polynucleotides comprising one or more codon-optimized coding regions encoding polypeptides of HCMV or nucleic acid fragments of such coding regions encoding fragments, variants, or derivatives thereof, to prime immunity, and then administering subsequently a different vaccine composition, for example a recombinant viral vaccine, a protein subunit vaccine, or a recombinant or killed bacterial vaccine or vaccines to boost the anti-HCMV immune response in a human.

The invention further provides methods for enhancing the immune response of a human patient to HCMV by administering to the tissues of a human one or more polynucleotides comprising one or more codon-optimized coding regions encoding polypeptides of HCMV, and also HCMV polypeptides or fragments, variants or derivatives thereof; or one or more non-optimized polynucleotides encoding HCMV polypeptides, fragments, variants or derivatives thereof.

The combination of HCMV polypeptides or polynucleotides encoding HCMV polypeptides or fragments, variants or derivatives thereof, with the codon-optimized nucleic acid compositions provides for therapeutically beneficial effects at dose sparing concentrations. For example, immunological responses sufficient for a therapeutically beneficial effect may be attained by using less of a conventional-type vaccine when supplemented or enhanced with the appropriate amount of a codon-optimized nucleic acid.

Conventional-type vaccines, include vaccine compositions comprising either dead, inert or fragments of a virus or bacteria, or bacterial or viral proteins or protein fragments, injected into the patient to elicit action by the immune system. With regard to the present invention, conventional-type vaccines include compositions comprising immunogenic polypeptides or nucleotides encoding immunogenic polypeptides, fragments, variants, or derivatives thereof, and vectors comprising nucleotides encoding immunogenic polypeptides, fragments, variants, or derivatives thereof, that are not products of, or do not contain codon-optimized polynucleotides as described herein. Thus, genetically engineered vaccines, are included in conventional-type vaccines, such as genetically engineered live vaccines, live chimeric vaccines, live replication-defective vaccines, subunit vaccines, peptide vaccines in various modifications of monovalent, multivalent, or chimeric subunit vaccines delivered as individual components or incorporated into virus-like particles for improved immunogenicity, and polynucleotide vaccines. Auxiliary agents, as described herein, are also considered components of conventional-type vaccines.

Thus, dose sparing is contemplated by administration of the combinatorial polynucleotide vaccine compositions of the present invention.

In particular, the dose of conventional-type vaccine may be reduced by at least 5%, at least 10%, at least 20%, at least 30%, at least 40%, at least 50%, at least 60% or at least 70% when administered in. combination, or prior to, or subsequent to, the codon-optimized nucleic acid compositions of the invention.

Similarly, a desirable level of an immunological response afforded by a DNA based pharmaceutical alone may be attained with less DNA by including a conventional-type DNA vaccine. Further, using a combination of a conventional-type vaccine and a codon-optimized DNA-based vaccine may allow both materials to be used in lesser amounts while still affording the desired level of immune response arising from administration of either component alone in higher amounts (e.g. one may use less of either immunological product when they are used in combination). This reduction in amounts of materials being delivered may be for each administration, in addition to reducing the number of administrations, in a vaccination regimen (e.g. 2 versus 3 or 4 injections). Further, the combination may also provide for reducing the kinetics of the immunological response (e.g. desired response levels are attained in 3 weeks instead of 6 after immunization).

In particular, the dose of a DNA based pharmaceutical, may be reduced by at least 5%, at least 10%, at least 20%, at least 30%, at least 40%, at least 50%, at least 60% or at least 70% when administered in combination with conventional CMV vaccines.

Determining the precise amounts of DNA based pharmaceutical and conventional antigen is based on a number of factors as described herein, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional-type vaccine; adding a conventional-type vaccine to a DNA pharmaceutical to enhanced humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by various standard immunological assays specific for the desirable response spectrum, which are described in more detail herein.

Both broadening and dose sparing may be obtained simultaneously.

BRIEF DESCRIPTION OF THE FIGURES

FIG. 1 shows the wild-type nucleotide sequence (SEQ ID NO:1) and amino acid translation (SEQ ID NO:2) of full-length, native HCMV pp65 (Genbank WMBE65) from HCMV strain AD169. The putative kinase site at amino acids Arg435-Lys438 is underlined.

FIG. 2 shows a fully codon-optimized nucleotide sequence (SEQ ID NO:3) and amino acid translation (SEQ ID NO:4) of native HCMV pp65.

FIG. 3 shows the alignment of wild-type ("wt") (SEQ ID NO:1) and fully codon-optimized ("opt") (SEQ ID NO:8) nucleotide sequences encoding native HCMV pp65.

FIG. 4 shows the wild-type nucleotide sequence (SEQ ID NO:11) and amino acid translation (SEQ ID NO:12) of HCMV gB strain AD169. SEQ ID NO:11 contains a nucleic acid fragment encoding the open reading frame for full-length HCMV gB (nucleotides 157-3125 of Genbank X04606). The host proteolytic cleavage site between amino acids 460 and 461 is marked by a colon.

FIG. 5 shows a fully codon-optimized nucleotide sequence (SEQ ID NO:13) and amino acid sequence (SEQ ID NO:14) of a truncated, secreted HCMV gB. SEQ ID NO:13 contains a nucleic acid encoding a minimal human codon-optimized secreted gB (SEQ ID NO:14).

FIG. 6 shows the alignment of wild-type ("wt") (SEQ ID NO:11) and fully codon-optimized ("opt") (SEQ ID NO:16) nucleotide sequences encoding full-length wild-type HCMV gB.

FIG. 7 shows the wild-type IE1 nucleotide sequence (SEQ ID NO:19), and amino acid translation (SEQ ID NO:20) of full-length, native IE1.

DETAILED DESCRIPTION OF THE INVENTION

Figure 8:
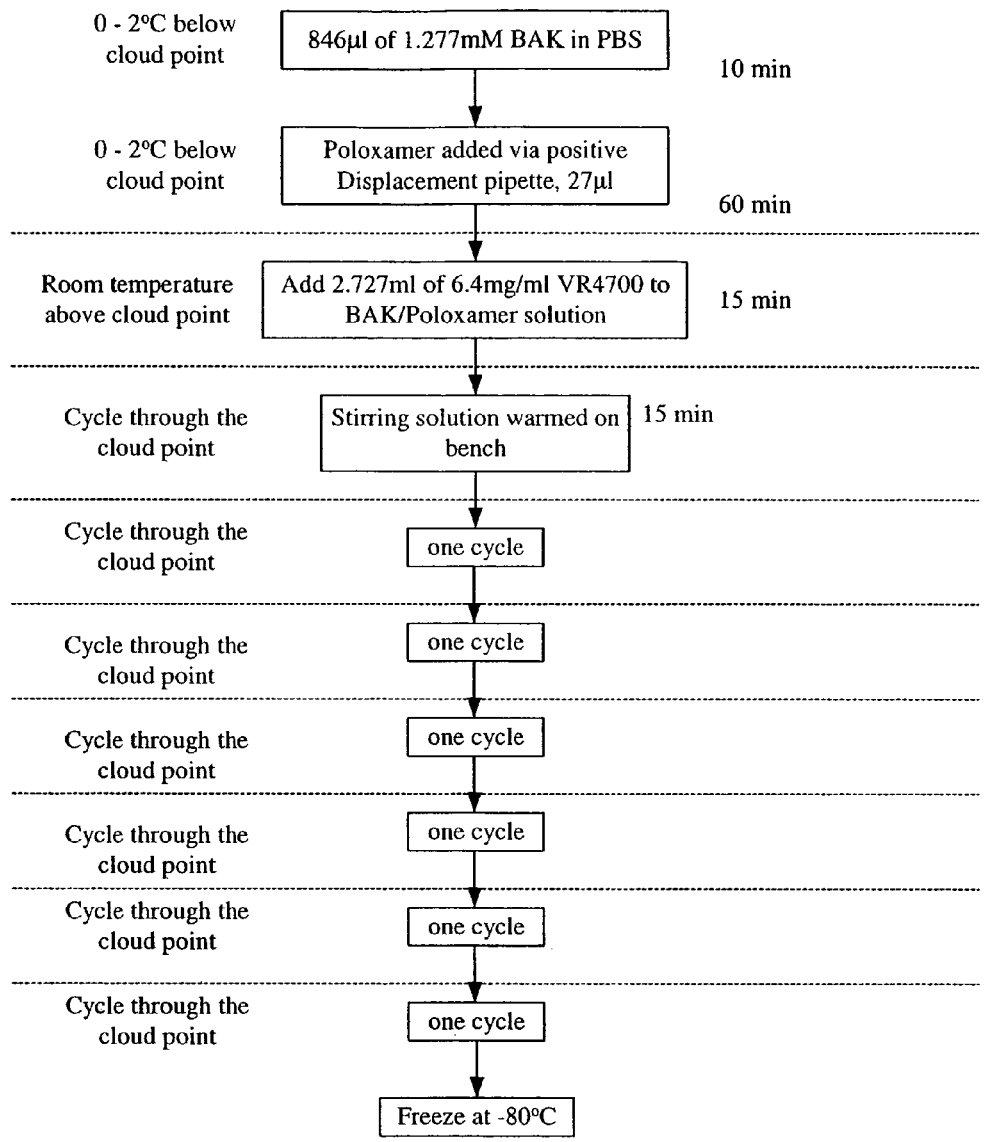
FIG. 8 shows the protocol for the preparation of a formulation comprising 0.3 mM BAK, 7.5 mg/ml CRL 1005, and 5 mg/ml of DNA in a final volume of 3.6 ml, through the use of thermal cycling.

The present invention is directed to compositions and methods for enhancing the immune response of a human in need of protection against HCMV infection by administering in vivo, into a tissue of a human, a polynucleotide comprising a human codon-optimized coding region encoding a polypeptide of HCMV, or a nucleic acid fragment of such a coding region encoding a fragment, variant, or derivative thereof. The polynucleotides are incorporated into the cells of the human in vivo, and an immunologically effective amount of the HCMV polypeptide, or fragment or variant is produced in vivo.

The present invention provides polynucleotide-based vaccines and methods for delivery of HCMV coding sequences to a human with optimal expression and safety conferred through codon optimization and/or other manipulations. These polynucleotide-based vaccines are prepared and administered in such a manner that the encoded gene products are optimally expressed in humans. As a result, these compositions and methods are useful in stimulating an immune response against HCMV infection. Also included in the invention are expression systems, delivery systems, and codon-optimized HCMV coding regions.

A polynucleotide vaccine of the present invention is capable of eliciting an immune response in a human against HCMV when administered to that human. Such polynucleotides are referred to herein as polynucleotide vaccines.

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The terms "nucleic acid" or "nucleic acid fragment" refers to any one or more nucleic acid segments, e.g., DNA or RNA fragments, present in a polynucleotide or construct. While the terms "nucleic acid," as used herein, is meant to include any nucleic acid, the term "nucleic acid fragment" is used herein to specifically denote a fragment of a designed or synthetic codon-optimized coding region encoding a polypeptide, or fragment, variant, or derivative thereof, which has been optimized according to the codon usage of a given species. As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate plasmids. Furthermore, any nucleic acid or nucleic acid fragment may encode a single polypeptide, e.g., a single antigen, cytokine, or regulatory polypeptide, or may encode more than one polypeptide, e.g., a nucleic acid may encode two or more polypeptides. In addition, a nucleic acid may encode a regulatory element such as a promoter or a transcription terminator, or may encode heterologous coding regions, e.g. specialized elements or motifs, such as a secretory signal peptide or a functional domain.

The terms "fragment," "variant," "derivative" and "analog" when referring to HCMV polypeptides of the present invention include any polypeptides which retain at least some of the immunogenicity or antigenicity of the corresponding native polypeptide. Fragments of HCMV polypeptides of the present invention include proteolytic fragments, deletion fragments and in particular, fragments of HCMV polypeptides which exhibit increased secretion from the cell or higher immunogenicity when delivered to an animal. Polypeptide fragments further include any portion of the polypeptide which comprises an antigenic or immunogenic epitope of the native polypeptide, including linear as well as three-dimensional epitopes. Variants of HCMV polypeptides of the present invention includes fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome or genome of an organism or virus. *Genes II*, Lewin, B., ed., John Wiley & Sons, New York (1985), which is incorporated herein by reference. For example, as used herein, variations in a given gene product, e.g., pp65, between HCMV strains, e.g. Towne and AD169, would be considered "allelic variants." Non-naturally occurring variants may be produced using art-known mutagenesis techniques. Variant polypeptides may comprise conservative or non-conservative amino acid substitutions, deletions or additions. Derivatives of HCMV polypeptides of the present invention, are polypeptides which have been altered so as to exhibit additional features not found on the native polypeptide. Examples include fusion proteins. An analog is another form of an HCMV polypeptide of the present invention. An example is a proprotein which can be activated by cleavage of the proprotein to produce an active mature polypeptide.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349 (1997)) comprising a polynucleotide. A nucleic acid may be provided in linear (e.g., mRNA), circular (e.g., plasmid), or branched form as well as double-stranded or single-stranded forms. A polynucleotide may comprise a conventional phosphodiester bond or a non-conventional bond (e.g., an amide bond, such as found in peptide nucleic acids (PNA)).

The terms "infectious polynucleotide" or "infectious nucleic acid" are intended to encompass isolated viral polynucleotides and/or nucleic acids which are solely sufficient to mediate the synthesis of complete infectious virus particles upon uptake by permissive cells. "Isolated" means that the viral nucleic acid does not require pre-synthesized copies of any of the polypeptides it encodes, e.g., viral replicases, in order to initiate its replication cycle.

The terms "non-infectious polynucleotide" or "non-infectious nucleic acid" as defined herein are polynucleotides or nucleic acids which cannot, without additional added materials, e.g, polypeptides, mediate the synthesis of complete infectious virus particles upon uptake by permissive cells. An infectious polynucleotide or nucleic acid is not made "non-infectious" simply because it is taken up by a non-permissive cell. For example, an infectious viral polynucleotide from a virus with limited host range is infectious if it is capable of mediating the synthesis of complete infectious virus particles when taken up by cells derived from a permissive host (i.e., a host permissive for the virus itself). The fact that uptake by cells derived from a non-permissive host does not result in the synthesis of complete infectious virus particles does not make the nucleic acid "non-infectious." In other words, the term is not qualified by the nature of the host cell, the tissue type, or the species.

In some cases, an isolated infectious polynucleotide or nucleic acid may produce fully-infectious virus particles in a host cell population which lacks receptors for the virus particles, i.e., is non-permissive for virus entry. Thus viruses produced will not infect surrounding cells. However, if the supernatant containing the virus particles is transferred to cells which are permissive for the virus, infection will take place.

The terms "replicating polynucleotide" or "replicating nucleic acid" are meant to encompass those polynucleotides and/or nucleic acids which, upon being taken up by a permissive host cell, are capable of producing multiple, e.g., one or more copies of the same polynucleotide or nucleic acid. Infectious polynucleotides and nucleic acids are a subset of replicating polynucleotides and nucleic acids; the terms are not synonymous. For example, a defective virus genome lacking the genes for virus coat proteins may replicate, e.g., produce multiple copies of itself, but is NOT infectious because it is incapable of mediating the synthesis of complete infectious virus particles unless the coat proteins, or another nucleic acid encoding the coat proteins, are exogenously provided.

In certain embodiments, the polynucleotide, nucleic acid, or nucleic acid fragment is DNA. In the case of DNA, a polynucleotide comprising a nucleic acid which encodes a polypeptide normally also comprises a promoter operably associated with the polypeptide-encoding nucleic acid. An operable association is when a nucleic acid encoding a gene product, e.g., a polypeptide, is associated with one or more regulatory sequences in such a way as to place expression of the gene product under the influence or control of the regulatory sequence(s). Two DNA fragments (such as a polypeptide-encoding nucleic acid and a promoter associated with the 5' end of the nucleic acid) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), retroviruses (such as Rous sarcoma virus), and picornaviruses (particularly an internal ribosome entry site, or IRES, also referred to as a CITE sequence). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

In one embodiment, a DNA polynucleotide of the present invention is a circular or linearized plasmid, or other linear DNA which is, in certain embodiments, non-infectious and nonintegrating (i.e., does not integrate into the genome of vertebrate cells). A linearized plasmid is a plasmid that was previously circular but has been linearized, for example, by digestion with a restriction endonuclease.

Alternatively, DNA virus genomes may be used to administer DNA polynucleotides into vertebrate cells. In certain embodiments, a DNA virus genome of the present invention is noninfectious, and nonintegrating. Suitable DNA virus genomes include herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

In other embodiments, a polynucleotide of the present invention is RNA. In a suitable embodiment, the RNA is in the form of messenger RNA (mRNA). Methods for introducing RNA sequences into vertebrate cells are described in U.S. Pat. No. 5,580,859, the disclosure of which is incorporated herein by reference in its entirety.

Polynucleotide, nucleic acids, and nucleic acid fragments of the present invention may be associated with additional nucleic acids which encode secretory or signal peptides, which direct the secretion of a polypeptide encoded by a nucleic acid or polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native leader sequence is used, or a functional derivative of that sequence that retains the ability to direct the secretion of the polypeptide that is operably associated with it. Alternatively, a heterologous mammalian leader sequence, or a functional derivative thereof, may be used. For example, the wild-type leader sequence may be substituted with the leader sequence of human tissue plasminogen activator (TPA) or mouse β-glucuronidase.

In accordance with one aspect of the present invention, there is provided a plasmid for expression of an HCMV gB-derived or pp65-derived coding sequence optimized for expression in human cells, to be delivered to a human to be treated or immunized. Additional HCMV-derived coding sequences, e.g. coding for IE1, may also be included on the plasmid, or on a separate plasmid, and expressed, either using native codons or codons optimized for expression in humans to be treated or immunized. When such a plasmid encoding one or more optimized HCMV sequences is delivered, in vivo to a tissue of the human to be treated or immunized, the transcriptional unit will thus express the one or more encoded gene product(s). The level of expression of the gene product(s) will depend to a significant extent on the strength of the associated promoter and the presence and activation of an associated enhancer element, as well as the optimization of the coding region.

As used herein, the term "plasmid" refers to a construct made up of genetic material (i.e., nucleic acids). Typically a plasmid contains an origin of replication which is functional in bacterial host cells, e.g., *Eschericha coli*, and selectable markers for detecting bacterial host cells comprising the plasmid. Plasmids of the present invention may include genetic elements as described herein arranged such that an inserted coding sequence can be transcribed and translated in eukaryotic cells. Also, while the plasmid may include a sequence from a viral nucleic acid, such viral sequence normally does not cause the incorporation of the plasmid into a viral particle, and the plasmid is therefore a non-viral vector. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is translated to form a polypeptide product which has a relevant biological activity. Also, the process of expression may involve further processing steps to the RNA product of transcription, such as splicing to remove introns, and/or post-translational processing of a polypeptide product.

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

Also included as polypeptides of the present invention are fragments, derivatives, analogs, or variants of the foregoing polypeptides, and any combination thereof. Polypeptides, and fragments, derivatives, analogs, or variants thereof of the present invention can be antigenic and immunogenic polypeptides related to HCMV polypeptides, which are used to prevent or treat, i.e., cure, ameliorate, lessen the severity of, or prevent or reduce contagion of infectious disease caused by HCMV.

As used herein, an antigenic polypeptide or an immunogenic polypeptide is a polypeptide which, when introduced into a human, reacts with the human's immune system molecules, i.e., is antigenic, and/or induces an immune response in the human, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides of the present invention include, but are not limited to, HCMV pp65 or fragments or variants thereof, e.g. pp65-delArg435-Lys468; gB, or fragments thereof, e.g. consisting of amino acids 1-713, or variants thereof; and IE1 or fragments or variants thereof, e.g. ex4-IE1-delATP and derivatives thereof, e.g., any of the foregoing polypeptides fused to a TPA signal peptide.

The term "epitopes," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic.

In the present invention, antigenic epitopes preferably contain a sequence of at least 4, at least 5, at least 6, at least 7, at least 8, at least 9, at least 10, at least 15, at least 20, at least 25, or between about 15 to about 30 amino acids contained within the amino acid sequence of a polypeptide of the invention. Certain polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic as well as immunogenic epitopes may be linear, i.e., be comprised of contiguous amino acids in a polypeptide, or may be three dimensional, i.e., where an epitope is comprised of non-contiguous amino acids which come together due to the secondary or tertiary structure of the polypeptide, thereby forming an epitope.

As to the selection of peptides or polypeptides bearing an antigenic epitope (e.g., that contain a region of a protein molecule to which an antibody or T cell receptor can bind), it is well known in that art that relatively short synthetic peptides that mimic part of a protein sequence are routinely capable of eliciting an antiserum that reacts with the partially mimicked protein. See, e.g., Sutcliffe, J. G., et al., *Science* 219:660-666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins. Non-limiting examples of antigenic polypeptides or peptides for HCMV pp65, gB and IE1 epitopes known to elicit cellular or humoral immune responses are listed in Table 1.

TABLE 1

Epitopes for immune recognition for HCMV proteins pp65, gB, and IE1. All of the references herein are incorporated by reference in its entirety.

| HCMV polypeptide | Position | Reference |
| --- | --- | --- |
| gB | aa 178-194<br>aa 190-204<br>aa 250-264<br>aa 420-434 | Liu, Y N. et al. J. Gen. Virol. 74: 2207-14 (1993) |
| gB | aa 67-86<br>aa 549-635<br>aa 570-579<br>aa 606-619 | Ohlin, M. et al. J. Virol. 67: 703-10 (1993). |
| gB | aa 548-618 | Navarro, D. et al. J. Med. Virol. 52: 451-9 (1997) |
| pp65 | aa 361-376<br>aa 485-499 | Khattab B A. et al. J. Med. Virol. 52: 68-76 (1997) |
| pp65 | aa 495-503 | Diamond, D J. et al. Blood 90: 1751067 (1997) |
| pp65 | aa 14-22<br>aa 120-128<br>aa 495-503 | Solache, A. et al. J. Immunol. 763: 5512-8 (1999) |
| IE1 (UL123) | aa 199-207<br>aa 279-287<br>aa 309-317<br>aa 315-323<br>aa 378-389<br>aa 379-387 | Khan, N. et al. J. Inf. Dis. 185: 000-000 (2002);<br>Elkington, R. et al. J. Virol. 77(9): 5226-5240 (2003). |
| IE1 Class II | aa 91-110<br>aa 162-175<br>aa 96-115 | Davignon, J. et al. J. Virol. 70: 2162-2169(1996);<br>Gautier, N. et al. Eur. J. Immunol. 26(5): 1110-7 (1996). |

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson, et al., *Cell* 37:767-778 (1984) at 777. The anti-peptide antibodies of the invention also are useful for purification of the mimicked protein, for instance, by adsorption chromatography using methods well known in the art.

In certain embodiments, the present invention is directed to polynucleotides comprising nucleic acids and fragments thereof comprising codon-optimized coding regions which encode polypeptides of HCMV, and in particular, HCMV gB or pp65, and fragments, variants, or derivatives thereof, alone or in combination with additional codon-optimized or non-codon-optimized HCMV-derived coding sequences, for example IE1 (SEQ ID NO:19).

"Codon optimization" is defined as modifying a nucleic acid sequence for enhanced expression in the cells of the vertebrate of interest, e.g. human, by replacing at least one, more than one, or a significant number, of codons of the native sequence with codons that are more frequently or most frequently used in the genes of that vertebrate. Various species exhibit particular bias for certain codons of a particular amino acid.

The present invention relates to polynucleotides comprising nucleic acid fragments of codon-optimized coding regions which encode HCMV polypeptides, or fragments, variants, or derivatives thereof, with the codon usage adapted for optimized expression in human cells. These polynucleotides are prepared by incorporating codons preferred for use in human genes into the DNA sequence. Also provided are polynucleotide expression constructs, vectors, and host cells comprising nucleic acid fragments of codon-optimized coding regions which encode HCMV polypeptides, and fragments, variants, or derivatives thereof, and various methods of using the polynucleotide expression constructs, vectors, host cells to treat or prevent HCMV disease in a human.

Polynucleotides comprising nucleic acid fragments of codon-optimized coding regions which encode polypeptides from nonhuman cytomegaloviruses, or fragments, variants, or derivatives thereof, may be optimized for expression in the cells of the vertebrate that can be infected by the nonhuman cytomegalovirus using the methods described herein. A partial list of known vertebrate cytomegaloviruses include murine CMV (MCMV), hamster CMV, guinea pig CMV, rat CMV, rabbit CMV, porcine CMV, bovine CMV, equine CMV, rhesus macaque CMV, African green monkey CMV, and chimpanzee CMV, as well as others (Staczek, J., *Am. Soc. Microbiol.* 545:247-265 (1990)). For example, an MCMV gene would be optimized for expressing in mouse cells, and an equine CMV gene would be optimized for expression in horse cells.

Codon Optimization

As used herein the term "codon-optimized coding region" means a nucleic acid coding region that has been adapted for expression in the cells of a given vertebrate by replacing at least one, or more than one, or a significant number, of codons with one or more codons that are more frequently used in the genes of that vertebrate.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 2

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). The codon usage table for human, calculated from GenBank Release 128.0 [15 Feb. 2002], is reproduced below as Table 3. These tables use mRNA nomenclature, and so instead of thymine (T) which is found in DNA, the tables use uracil (U) which is found in RNA. The tables have been adapted so that frequencies are calculated for each amino acid, rather than for all 64 codons. For comparison, the codon usage table for human cytomegalovirus is reproduced below as Table 4.

TABLE 3

Codon Usage Table for Human Genes (*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 430946 | 1.0000 |
| Total | | 430946 | |
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |
| Ala | GCU | 360146 | 0.2637 |
| Ala | GCC | 551452 | 0.4037 |

TABLE 3-continued

Codon Usage Table for Human Genes (Homo sapiens)

| Amino Acid | Codon | Number | Frequency |
|---|---|---|---|
| Ala | GCA | 308034 | 0.2255 |
| Ala | GCG | 146233 | 0.1071 |
| Total | | 1365865 | |
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 4

Codon Usage Table for Human Cytomegalovirus (human herpesvirus 5)

| Amino Acid | Codon | Number | Frequency |
|---|---|---|---|
| Phe | UUU | 5435 | 0.5456 |
| Phe | UUC | 4527 | 0.4544 |
| Total | | 9962 | |
| Leu | UUA | 1191 | 0.0510 |
| Leu | UUG | 3683 | 0.1578 |
| Leu | CUU | 2162 | 0.0926 |
| Leu | CUC | 5473 | 0.2344 |

TABLE 4-continued

Codon Usage Table for Human Cytomegalovirus (human herpesvirus 5)

| Amino Acid | Codon | Number | Frequency |
|---|---|---|---|
| Leu | CUA | 1771 | 0.0759 |
| Leu | CUG | 9066 | 0.3883 |
| Total | | 23346 | |
| Ile | AUU | 2452 | 0.2538 |
| Ile | AUC | 6135 | 0.6350 |
| Ile | AUA | 1075 | 0.1113 |
| Total | | 9662 | |
| Met | AUG | 5051 | 1.0000 |
| Total | | 430946 | |
| Val | GUU | 2271 | 0.1167 |
| Val | GUC | 5082 | 0.2611 |
| Val | GUA | 2570 | 0.1320 |
| Val | GUG | 9541 | 0.4902 |
| Total | | 19464 | |
| Ser | UCU | 2350 | 0.1234 |
| Ser | UCC | 3911 | 0.2054 |
| Ser | UCA | 1296 | 0.0681 |
| Ser | UCG | 4876 | 0.2561 |
| Ser | AGU | 1927 | 0.1012 |
| Ser | AGC | 4677 | 0.2457 |
| Total | | 19037 | |
| Pro | CCU | 1817 | 0.1439 |
| Pro | CCC | 4425 | 0.3506 |
| Pro | CCA | 1391 | 0.1102 |
| Pro | CCG | 4990 | 0.3953 |
| Total | | 12623 | |
| Thr | ACU | 2156 | 0.1368 |
| Thr | ACC | 5648 | 0.3584 |
| Thr | ACA | 1782 | 0.1131 |
| Thr | ACG | 6173 | 0.3917 |
| Total | | 15759 | |
| Ala | GCU | 2559 | 0.1491 |
| Ala | GCC | 8013 | 0.4668 |
| Ala | GCA | 1386 | 0.0807 |
| Ala | GCG | 5209 | 0.3034 |
| Total | | 17167 | |
| Tyr | UAU | 2321 | 0.2629 |
| Tyr | UAC | 6509 | 0.7371 |
| Total | | 8830 | |
| His | CAU | 1906 | 0.2753 |
| His | CAC | 5018 | 0.7247 |
| Total | | 6924 | |
| Gln | CAA | 2894 | 0.3398 |
| Gln | CAG | 5623 | 0.6602 |
| Total | | 8517 | |
| Asn | AAU | 2268 | 0.2892 |
| Asn | AAC | 5574 | 0.7108 |
| Total | | 7842 | |
| Lys | AAA | 3313 | 0.4408 |
| Lys | AAG | 4203 | 0.5592 |
| Total | | 7516 | |
| Asp | GAU | 3514 | 0.3023 |
| Asp | GAC | 8110 | 0.6977 |
| Total | | 11624 | |
| Glu | GAA | 4310 | 0.3684 |
| Glu | GAG | 7390 | 0.6316 |
| Total | | 11700 | |

TABLE 4-continued

Codon Usage Table for Human
Cytomegalovirus (human herpesvirus 5)

| Amino Acid | Codon | Number | Frequency |
|---|---|---|---|
| Cys | UGU | 3059 | 0.4265 |
| Cys | UGC | 4113 | 0.5735 |
| Total |  | 7172 |  |
| Trp | UGG | 2797 | 1.0000 |
| Total |  | 2797 |  |
| Arg | CGU | 3747 | 0.2186 |
| Arg | CGC | 6349 | 0.3703 |
| Arg | CGA | 1826 | 0.1065 |
| Arg | CGG | 3285 | 0.1916 |
| Arg | AGA | 1185 | 0.0691 |
| Arg | AGG | 752 | 0.0439 |
| Total |  | 17144 |  |
| Gly | GGU | 3521 | 0.2430 |
| Gly | GGC | 6952 | 0.4797 |
| Gly | GGA | 1885 | 0.1301 |
| Gly | GGG | 2133 | 0.1472 |
| Total |  | 14491 |  |
| Stop | UAA | 310 |  |
| Stop | UAG | 169 |  |
| Stop | UGA | 234 |  |

By utilizing these or similar tables, one of ordinary skill in the art can apply the frequencies to any given polypeptide sequence, and produce a nucleic acid fragment of a codon-optimized coding region which encodes the polypeptide, but which uses codons more optimal for a given species. Codon-optimized coding regions can be designed by various different methods.

In one method, termed "uniform optimization," a codon usage table is used to find the single most frequent codon used for any given amino acid, and that codon is used each time that particular amino acid appears in the polypeptide sequence. For example, referring to Table 3 above, for leucine, the most frequent codon is CUG, which is used 41% of the time. Thus all the leucine residues in a given amino acid sequence would be assigned the codon CUG. Human "uniform" codon-optimized nucleotide sequences encoding native pp65 from HCMV strain AD169 (SEQ ID NO:2)) (FIG. 1) and full-length gB from strain AD169 (SEQ ID NO:12) (FIG. 4) are presented herein as SEQ ID NO:7 and SEQ ID NO: 15, respectively.

In another method, termed "full-optimization," the actual frequencies of the codons are distributed randomly throughout the coding region. Thus, using this method for optimization, if a hypothetical polypeptide sequence had 100 leucine residues, referring to Table 3 for frequency of usage in the humans, about 7, or 7% of the leucine codons would be UUA, about 13, or 13% of the leucine codons would be UUG, about 13, or 13% of the leucine codons would be CUU, about 20, or 20% of the leucine codons would be CUC, about 7, or 7% of the leucine codons would be CUA, and about 41, or 41% of the leucine codons would be CUG. These frequencies would be distributed randomly throughout the leucine codons in the coding region encoding the hypothetical polypeptide. As will be understood by those of ordinary skill in the art, the distribution of codons in the sequence can vary significantly using this method, however, the sequence always encodes the same polypeptide. Three different human codon-optimized nucleotide sequences encoding native pp65 (SEQ ID NO:2) which have been optimized using this method are presented herein as SEQ ID NO:8, SEQ ID NO:9, and SEQ ID NO:10. Three different human codon-optimized sequences encoding native gB (SEQ ID NO:12) which have been fully optimized using this method are presented herein as SEQ ID NO:16, SEQ ID NO:17 and SEQ ID NO:18, respectively.

In using the "full-optimization" method, an entire polypeptide sequence, or fragment, variant, or derivative thereof is codon-optimized by any of the methods described herein. Various desired fragments, variants or derivatives are designed, and each is then codon-optimized individually. Alternatively, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

When using the "full-optimization" method, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

In a third method termed "minimal, optimization," coding regions are only partially optimized. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a vertebrate species, e.g., humans, in place of a codon that is normally used in the native nucleic acid sequence. Codons that are rarely found in human genes are changed to codons more commonly utilized in human coding regions. To illustrate this method, a comparative chart showing codon usage per thousand of human and HCMV coding regions is presented in Table 5. The data is expressed as the number of times a given codon is used per 1000 codons. For instance, the asterisked codons in Table 5 for alanine, arginine, proline, serine, and threonine are frequently used in the genome of HCMV, but less frequently used in human genes. Starting with the native coding region of the HCMV gene of interest, one or more codons which are infrequently-used may be changed to more commonly-used human codons either by substituting one of the codons more frequently used in human genes. According to this method, these HCMV codons which are used at the same or higher frequency in human genes as compared to HCMV genes are left unchanged.

TABLE 5

Codon Usage Table for Human Genes and HCMV

| Amino Acid | | Codon | Human | hCMV |
|---|---|---|---|---|
| Ala | A | GCA | 16 | 6 |
| * | | GCG | 8 | 22 |
| | | GCC | 19 | 34 |
| | | GCT | 19 | 11 |
| Arg | R | AGA | 12 | 5 |
| | | AGG | 11 | 3 |
| | | CGA | 6 | 8 |
| | | CGG | 12 | 14 |
| | | CGC | 11 | 27 |
| * | | CGT | 5 | 16 |
| Asn | N | AAC | 20 | 24 |
| | | AAT | 17 | 10 |
| Asp | D | GAC | 26 | 34 |
| | | GAT | 22 | 15 |
| Cys | C | TGC | 12 | 17 |
| | | TGT | 10 | 13 |
| Gln | Q | CAA | 12 | 12 |
| | | CAG | 35 | 24 |
| Glu | E | GAA | 30 | 18 |
| | | GAG | 40 | 31 |
| Gly | G | GGA | 16 | 8 |
| | | GGG | 16 | 9 |
| | | GGC | 23 | 29 |
| | | GGT | 11 | 15 |
| His | H | CAC | 15 | 21 |
| | | CAT | 11 | 8 |
| Ile | I | ATA | 7 | 5 |
| | | ATC | 22 | 26 |
| | | ATT | 16 | 10 |
| Leu | L | CTA | 7 | 8 |
| | | CTG | 40 | 38 |
| | | CTC | 20 | 23 |
| | | CTT | 13 | 9 |
| | | TTA | 7 | 5 |
| | | TTG | 13 | 16 |
| Lys | K | AAA | 24 | 14 |
| | | AAG | 33 | 18 |
| Met | M | ATG | 22 | 21 |
| Phe | F | TTC | 21 | 19 |
| | | TTT | 17 | 23 |
| Pro | P | CCA | 17 | 6 |
| * | | CCG | 7 | 21 |
| | | CCC | 20 | 19 |
| | | CCT | 17 | 8 |
| Ser | S | AGC | 19 | 20 |
| | | AGT | 12 | 8 |
| | | TCA | 12 | 6 |
| * | | TCG | 5 | 21 |
| | | TCC | 18 | 17 |
| | | TCT | 15 | 10 |
| Thr | T | ACA | 15 | 8 |
| * | | ACG | 6 | 26 |
| | | ACC | 19 | 24 |
| | | ACT | 13 | 9 |
| Trp | W | TGG | 13 | 12 |
| Tyr | Y | TAC | 16 | 27 |
| | | TAT | 12 | 10 |
| Val | V | GTA | 7 | 11 |
| | | GTG | 29 | 40 |
| | | GTC | 15 | 21 |
| | | GTT | 11 | 10 |
| Term | | TAA | 1 | 1 |
| | | TAG | 0.5 | 0 |
| | | TGA | 1 | 1 |

Thus, those codons which are used more frequently in the HCMV genome than in human genes are substituted with the most frequently-used human codon. The difference in frequency at which the HCMV codons are substituted may vary based on a number factors as discussed below. For example, codons used at least twice more per thousand in HCMV genes as compared to human genes are substituted with the most frequently used human codon for that amino acid. This ratio may be adjusted higher or lower depending on various factors such as those discussed below. Accordingly, a codon in an HCMV native coding region would be substituted with the codon used most frequently for that amino acid in human coding regions if the codon is used 1.1 times, 1.2 times, 1.3 times, 1.4 times, 1.5 times, 1.6 times, 1.7 times, 1.8 times, 1.9 times, 2.0 times, 2.1 times, 2.2 times, 2.3 times, 2.4 times, 2.5 times, 2.6 times, 2.7 times, 2.8 times, 2.9 times, 3.0 times, 3.1 times, 3.2 times, 3.3 times, 3.4 times, 3.5 times, 3.6 times, 3.7 times, 3.8 times, 3.9 times, 4.0 times, 4.1 times, 4.2 times, 4.3 times, 4.4 times, 4.5 times, 4.6 times, 4.7 times, 4.8 times, 4.9 times, 5.0 times, 5.5 times, 6.0 times, 6.5 times, 7.0 times, 7.5 times, 8.0 times, 8.5 times, 9.0 times, 9.5 times, 10.0 times, 10.5 times, 11.0 times, 11.5 times, 12.0 times, 12.5 times, 13.0 times, 13.5 times, 14.0 times, 14.5 times, 15.0 times, 15.5 times, 16.0 times, 16.5 times, 17.0 times, 17.5 times, 18.0 times, 18.5 times; 19.0 times, 19.5 times, 20 times, 21 times, 22 times, 23 times, 24 times, 25 times, or greater more frequently in HCMV coding regions than in human coding regions.

This minimal human codon optimization for highly variant codons has several advantages, which include but are not limited to the following examples. Since fewer changes are made to the nucleotide sequence of the gene of interest, fewer manipulations are required, which leads to reduced risk of introducing unwanted mutations and lower cost, as well as allowing the use of commercially available site-directed mutagenesis kits, reducing the need for expensive oligonucleotide synthesis. Further, decreasing the number of changes in the nucleotide sequence decreases the potential of altering the secondary structure of the sequence, which can have a significant impact on gene expression in certain host cells. The introduction of undesirable restriction sites is also reduced, facilitating the subcloning of the genes of interest into the plasmid expression vector.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTl Suite, available from InforMax, Inc., Bethesda, Md., and the "backtranslate" function in the GCG--Wisconsin Package, available from Accelrys, Inc., San Diego, Calif. In addition, various resources are publicly available to codon-optimize coding region sequences. For example, the "backtranslation" function is proved on the world wide web by Entelechon GMBH at www.entelechon.com/eng/backtranslation.html (visited Jul. 9, 2002), "backtranseq" function available at bioinfo.pbi.nrc.ca:-8090/EMBOSS/index.html (visited Oct. 15, 2002). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

The codon-optimized coding regions can be versions encoding any gene products from any strain of HCMV, or fragments, variants, or derivatives of such gene products. Described herein are nucleic acid fragments of codon-optimized coding regions encoding the HCMV pp65 polypeptide and the HCMV glycoprotein B (gB) polypeptide, the nucleic acid fragments encoding the complete polypeptide, as well as various fragments, variants, and derivatives thereof, although other pp65 or gB-encoding nucleic acid sources are not excluded. Codon-optimized coding regions encoding other HCMV polypeptides (e.g. IE1), or fragments, variants and derivatives thereof, are included within the present invention. Additional, non-codon-optimized polynucleotides encoding HCMV polypeptides may be included as well.

The present invention is directed to compositions and methods of enhancing the immune response of a human in need of protection against HCMV infection by administering in vivo, into a tissue of a human, a polynucleotide comprising a codon-optimized coding region encoding a polypeptide of HCMV, or a nucleic acid fragment of such a coding region encoding a fragment, variant or derivative thereof. Human-codon optimization is carried out by the methods described herein, for example, in certain embodiments codon-optimized coding regions encoding polypeptides of HCMV, or nucleic acid fragments of such coding regions encoding fragments, variants, or derivatives thereof are optimized according to human codon usage. The polynucleotides of the invention are incorporated into the cells of the human in vivo, and an immunologically effective amount of an HCMV polypeptide is produced in vivo.

In particular, the present invention relates to codon-optimized coding regions encoding polypeptides of HCMV, or nucleic acid fragments of such coding regions fragments, variants, or derivatives thereof which have been optimized according to human codon usage. For example, human codon-optimized coding regions encoding polypeptides of HCMV, or nucleic acid fragments of such coding regions encoding fragments, variants, or derivatives thereof are prepared by substituting one or more codons preferred for use in human genes for the codons naturally used in the DNA sequence encoding the HCMV polypeptide. Also provided are polynucleotides, vectors, and other expression constructs comprising codon-optimized coding regions encoding polypeptides of HCMV, or nucleic acid fragments of such coding regions encoding fragments, variants, or derivatives thereof, and various methods of using such polynucleotides, vectors and other expression constructs. Coding regions encoding HCMV polypeptides may be uniformly optimized, fully optimized, or minimally optimized, as described herein.

The present invention is further directed towards polynucleotides comprising codon-optimized coding regions encoding polypeptides of HCMV antigens, for example, HCMV pp65, gB, and optionally in conjunction with other HCMV antigens, e.g. IE1. The invention is also directed to polynucleotides comprising codon-optimized nucleic acid fragments encoding fragments, variants and derivatives of these polypeptides.

The present invention provides isolated polynucleotides comprising codon-optimized coding regions of HCMV pp65, or fragments, variants, or derivatives thereof. In certain embodiments described herein, a codon-optimized coding region encoding SEQ ID NO:2 is optimized according to codon usage in humans (Homo sapiens).

Codon-optimized coding regions encoding SEQ ID NO:2, fully optimized according to codon usage in humans are designed as follows. The amino acid composition of SEQ ID NO:2 is shown in Table 6.

TABLE 6

Amino Acid Composition of Wild-Type HCMV pp65 from strain AD169 (SEQ ID NO:2).

| | Amino Acid | Number in SEQ ID NO:2 |
|---|---|---|
| A | Ala | 38 |
| R | Arg | 36 |
| C | Cys | 10 |
| G | Gly | 36 |
| H | His | 24 |
| I | Ile | 25 |
| L | Leu | 41 |
| K | Lys | 22 |
| M | Met | 16 |
| F | Phe | 19 |
| P | Pro | 38 |
| S | Ser | 41 |
| T | Thr | 37 |
| W | Trp | 9 |
| Y | Tyr | 15 |
| V | Val | 44 |
| N | Asn | 18 |
| D | Asp | 28 |
| Q | Gln | 31 |
| E | Glu | 33 |

Using the amino acid composition shown in Table 6, and the human codon usage table shown in Table 3, a human codon-optimized coding region which encodes SEQ ID NO:2 can be designed by any of the methods discussed herein.

In the "uniform optimization" approach, each amino acid is assigned the most frequent codon used in the human genome for that amino acid as indicated on Table 3. According to this method, codons are assigned to the coding region encoding SEQ ID NO:2 as follows: the 19 phenylalanine codons are TTC, the 41 leucine codons are CTG, the 25 isoleucine codons are ATC, the 16 methionine codons are ATG, the 44 valine codons are GTG, the 41 serine codons are AGC, the 38 proline codons are CCC, the 37 threonine codons are ACC, the 38 alanine codons are GCC, the 15 tyrosine codons are TAC, the 24 histidine codons are CAC, the 31 glutamine codons are CAG, the 18 asparagine codons are AAC, the 22 lysine codons are AAG, the 28 aspartic acid codons are GAC, the 33 glutamic acid codons are GAG, the 10 cysteine codons are TGC, the 9 tryptophan codons are TGG, the 36 arginine codons are CGG, AGA, or AGG (the frequencies of usage of these three codons in the human genome are not significantly different), and the 36 glycine codons are GGC. The codon-optimized pp65 coding region designed by this method is presented herein as SEQ ID NO:7.

Alternatively, a "fully codon-optimized" coding region which encodes SEQ ID NO:2 can be designed by randomly assigning each of any given amino acid a codon based on the frequency that codon is used in the human genome. These frequencies are shown in Table 3 above. Using this latter method, codons are assigned to the coding region encoding SEQ ID NO:2 as follows: about 9 of the 19 phenylalanine codons are TTT, and about 10 of the phenylalanine codons are TTC; about 3 of the 41 leucine codons are TTA, about 5 of the leucine codons are TTG, about 5 of the leucine codons are CTT, about 8 of the leucine codons are CTC, about 3 of the leucine codons are CTA, and about 17 of the leucine codons are CTG; about 9 of the 25 isoleucine codons are ATT, about 12 of the isoleucine codons are ATC, and about 4 of the isoleucine codons are ATA; the 16 methionine codons are ATG; about 8 of the 44 valine codons are GTT, about 10 of the valine codons are GTC, about 5 of the valine codons are GTA, and about 21 of the valine codons are GTG; about 8 of the 41 serine codons are TCT, about 9 of the serine codons are TCC, about 6 of the serine codons are TCA, about 2 of the serine codons are TCG, about 6 of the serine codons are AGT, and about 10 of the serine codons are AGC; about 11 of the 38 proline codons are CCT, about 12 of the proline codons are CCC, about 10 of the proline codons are CCA, and about 4 of the proline codons are CCG; about 9 of the 37 threonine codons are ACT, about 13 of the threonine codons are ACC, about 11 of the threonine codons are ACA, and about 4 of the threonine codons are ACG; about 10 of the 38 alanine codons are GCT, about 15 of the alanine codons are GCC, about 9 of the alanine codons are GCA, and about 4 of the alanine codons are GCG; about 7 of the 15 tyrosine codons are TAT and about 8 of the tyrosine codons are TAC; about 10 of the 24 histidine codons are CAT and about 14 of the histidine codons are CAC; about 8 of the 31 glutamine codons are CAA and about 23 of the glutamine codons are CAG; about 8 of the 18 asparagine codons are AAT and about 10 of the asparagine codons are AAC; about 9 of the 22 lysine codons are AAA and about 13 of the lysine codons are AAG; about 13 of the 28 aspartic acid codons are GAT and about 15 of the aspartic acid codons are GAC; about 14 of the 33 glutamic acid codons are GAA and about 19 of the glutamic acid codons are GAG; about 4 of the 10 cysteine codons are TGU and about 6 of the cysteine codons are TGC; the 9 tryptophan codons are TGG; about 3 of the 36 arginine codons are CGT, about 7 of the arginine codons are CGC, about 4 of the arginine codons are CGA, about 8 of the arginine codons are CGG, about 7 of the arginine codons are AGA, and about 7 of the arginine codons are AGG; and about 6 of the 36 glycine codons are GGT, about 12 of the glycine codons are GGC, about 9 of the glycine codons are GGA, and about 9 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid.

Representative fully-codon-optimized pp65 coding regions designed by this method are presented herein as SEQ ID NOs:8-10.

Additionally, a minimally codon-optimized nucleotide sequence encoding SEQ ID NO:2 can be designed by changing only certain codons found more frequently in HCMV genes than in human genes, as shown in Table 5. For example, if it is desired to substitute more frequently used codons in humans for those codons that occur at least 2.7 times more frequently in HCMV genes, Ala CGC, which occurs 2.75 times more frequently in HCMV genes than in human genes, is changed to, e.g., GCC; Pro CCG, which occurs 3.0 times more frequently in HCMV genes than is human, is changed to, e.g., CCC; Arg CGT, which occurs 3.2 times more frequently in HCMV genes than is human, is changed to, e.g., CGC; Ser TCG, which occurs 4.2 times more frequently in HCMV genes than in human, is changed to, e.g., TCC; and Thr ACG, which occurs 4.3 times more frequently in HCMV genes than is human, is changed to, e.g., ACC. The minimally codon-optimized pp65 coding region designed by this method encoding native HCMV pp65 is presented herein as SEQ ID NO:3. Other methods of "minimal" optimization can be carried out by methods well known to those of ordinary skill in the art.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:2, where the nucleic acid fragment is a fragment of a codon-optimized coding region encoding SEQ ID NO:2. The human codon-optimized coding region can be optimized by any of the methods described herein.

In certain embodiments, the present invention provides an isolated polynucleotide comprising a nucleic acid fragment which encodes a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to SEQ ID NO:2, and where the nucleic acid fragment is a variant of a human codon-optimized coding region encoding SEQ ID NO:2. The human codon-optimized coding region can be optimized by any of the methods described herein.

Further provided is an isolated polynucleotide comprising a minimally codon-optimized nucleic acid (SEQ ID NO:5) which encodes a polypeptide variant of pp65, i.e., SEQ ID NO:6, in which amino acids 435-438 of SEQ ID NO:2 have been deleted. This deletion in the amino acid sequence of pp65 removes putative adventitious substrates for kinase activity present in the amino acid sequence. A human codon-optimized coding region encoding this variant can be optimized by any of the methods described herein. alternatively amino acids 435-438 could be substituted with different amino acids, or an insertion could be made to remove the motif. Additional fragments, variants, or derivatives of SEQ ID NO:2 may be utilized as well.

The present invention further provides isolated polynucleotides comprising human codon-optimized coding regions of HCMV gB, or fragments, variants, or derivatives thereof. In certain embodiments described herein, a human codon-optimized coding region encoding SEQ ID NO:12 is optimized according to codon usage in humans (*Homo sapiens*). The human codon-optimized coding region can be optimized by any of the methods described herein.

Codon-optimized coding regions encoding SEQ ID NO:12, optimized according to codon usage in humans are designed as follows. The amino acid composition of SEQ ID NO:12 is shown in Table 7, and the amino acid composition of truncated, secreted gB (SEQ ID NO: 14) is shown in Table 8.

TABLE 7

Amino Acid Composition of wild type HCMV gB (SEQ ID NO:12)

| | Amino Acid | Number in SEQ ID NO:12 |
|---|---|---|
| A | Ala | 62 |
| R | Arg | 53 |
| C | Cys | 16 |
| G | Gly | 46 |
| H | His | 20 |
| I | Ile | 48 |
| L | Leu | 70 |
| K | Lys | 39 |
| M | Met | 17 |
| F | Phe | 34 |
| P | Pro | 30 |
| S | Ser | 87 |
| T | Thr | 71 |
| W | Trp | 8 |
| Y | Tyr | 51 |
| V | Val | 71 |
| N | Asn | 52 |
| D | Asp | 45 |
| Q | Gln | 37 |
| E | Glu | 49 |

TABLE 8

Amino Acid Composition of secreted HCMV gB, amino acids 1-713 (SEQ ID NO:14)

| | Amino Acid | Number in SEQ ID NO:14 |
|---|---|---|
| A | Ala | 41 |
| R | Arg | 43 |
| C | Cys | 15 |
| G | Gly | 27 |
| H | His | 18 |
| I | Ile | 41 |
| L | Leu | 51 |
| K | Lys | 31 |
| M | Met | 15 |
| F | Phe | 30 |
| P | Pro | 19 |
| S | Ser | 73 |
| T | Thr | 56 |
| W | Trp | 8 |
| Y | Tyr | 43 |
| V | Val | 57 |
| N | Asn | 44 |
| D | Asp | 35 |
| Q | Gln | 25 |
| E | Glu | 41 |

Using the amino acid composition shown in Table 7 and the human codon usage table shown in Table 3, a human codon-optimized coding region which encodes SEQ ID NO:12 can be designed by any of the methods discussed herein. In the "uniform optimization" approach, each amino acid is assigned the most frequent codon used in the human genome for that amino acid as indicated, e.g., in Table 3. According to this method, codons are assigned to the coding region encoding SEQ ID NO:12 as follows: the 34 phenylalanine codons are TTC, the 70 leucine codons are CTG, the 48 isoleucine codons are ATC, the 17 methionine codons are ATG, the 71 valine codons are GTG, the 87 serine codons are AGC, the 30 proline codons are CCC, the 71 threonine codons are ACC, the 62 alanine codons are GCC, the 51 tyrosine codons are TAC, the 20 histidine codons are CAC, the 37 glutamine codons are CAG, the 52 asparagine codons are AAC, the 39 lysine codons are AAG, the 45 aspartic acid codons are GAC, the 49 glutamic acid codons are GAG, the 16 cysteine codons are TGC, the 8 tryptophan codons are TGG, the 53 arginine codons are CGG, AGA, or AGG (the frequencies of usage of these three codons in the human genome are not significantly different), and the 46 glycine codons are GGC. The codon-optimized full-length gB coding region designed by this method is presented herein as SEQ ID NO:15.

Alternatively, a "fully codon-optimized" coding region which encodes SEQ ID NO:12 can be designed by randomly assigning each of any given amino acid a codon based on the frequency that codon is used in the human genome. These frequencies are shown in Table 3 above. Using this latter method, codons are assigned to the coding region encoding SEQ ID NO:12 as follows: about 15 of the 34 phenylalanine codons are TTT and about 19 of the phenylalanine codons are TTC; about 5 of the 70 leucine codons are TTA, about 9 of the leucine codons are TTG, about 9 of the leucine codons are CTT, about 10f the leucine codons are CTC, about 5 of the leucine codons are CTA, and about 28 of the leucine codons are CTG; about 17 of the 48 soleucine codons are ATT, about 23 of the isoleucine codons are ATC, and about 8 of the isoleucine codons are ATA; the 17 methionine codons are ATG; about 13 of the 71 valine codons are GTT, about 17 of the valine codons are GTC, about 8 of the valine codons are GTA, and about 33 of the valine codons are GTG; about 16 of the 87 serine codons are TCT, about 19 of the serine codons are TCC, about 13 of the serine codons are TCA, about 5 of the serine codons are TCG, about 13 of the serine codons are AGT, and about 21 of the serine codons are AGC; about 9 of the 30 proline codons are CCT, about 10 of the proline codons are CCC, about 8 of the proline codons are CCA, and about 3 of the proline codons are CCG; about 17 of the 71 threonine codons are ACT, about 26 of the threonine codons are ACC, about 20 of the threonine codons are ACA, and about 8 of the threonine codons are ACG; about 16 of the 62 alanine codons are GCT, about 25 of the alanine codons are GCC, about 14 of the alanine codons are GCA, and about 7 of the alanine codons are GCG; about 22 of the 51 tyrosine codons are TAT and about 29 of the tyrosine codons are TAC; about 8 of the 20 histidine codons are CAT and about 12 of the histidine codons are CAC; about 9 of the 37 glutamine codons are CAA and about 28 of the glutamine codons are CAG; about 24 of the 52 asparagine codons are AAT and about 28 of the asparagine codons are AAC; about 16 of the 39 lysine codons are AAA and about 23 of the lysine codons are AAG; about 21 of the 45 aspartic acid codons are GAT and about 24 of the aspartic acid codons are GAC; about 20 of the 49 glutamic acid codons are GAA and about 29 of the glutamic acid codons are GAG; about 7 of the 16 cysteine codons are TGT and about 9 of the cysteine codons are TGC; the 8 tryptophan codons are TGG; about 4 of the 53 arginine codons are CGT, about 10 of the arginine codons are CGC, about 6 of the arginine codons are CGA, about 11 of the arginine codons are CGG, about 11 of the arginine codons are AGA, and about 11 of the arginine codons are AGG; and about 7 of the 46 glycine codons are GGT, about 16 of the glycine codons are GGC, about 12 of the glycine codons are GGA, and about 11 of the glycine codons are GGG.

As described above, the term "about" means that the number of amino acids encoded by a certain codon may be one more or one less than the number given. It would be understood by those of ordinary skill in the art that the total number of any amino acid in the polypeptide sequence must remain constant, therefore, if there is one "more" of one codon encoding a give amino acid, there would have to be one "less" of another codon encoding that same amino acid. Representative fully codon-optimized gB coding regions designed by this method encoding full-length HCMV gB are presented herein as SEQ ID NOs:16-18.

Additionally, a minimally codon-optimized nucleotide sequence encoding SEQ ID NO:14 can be designed by referring to the amino acid composition of Table 8 and changing only certain codons found more frequently in highly expressing human genes, as shown in Table 5. For example, if it is desired to substitute more frequently used codons in humans for those codons that occur at least 2.7 times more frequently in HCMV genes, Ala CGC, which occurs 2.75 times more frequently in HCMV genes than in human genes, is changed to, e.g., GCC; Pro CCG, which occurs 3.0 times more frequently in HCMV genes than is human, is changed to, e.g., CCC; Arg CGT, which occurs 3.2 times more frequently in HCMV genes than is human, is changed to, e.g., CGC; Ser TCG, which occurs 4.2 times more frequently in HCMV genes than in human, is changed to, e.g., TCC; and Thr ACG, which occurs 4.3 times more frequently in HCMV genes than is human, is changed to, e.g., ACC. The minimally codon-optimized secreted gB coding region encoding SEQ ID NO:14 designed by this method is presented herein as SEQ ID NO:13.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, or at least 100 or more contiguous amino acids of SEQ ID NO:12 or SEQ ID NO:14, where the nucleic acid fragment is a fragment of a human codon-optimized coding region encoding SEQ ID NO:12 or SEQ ID NO:14. The human codon-optimized coding region can be optimized by any of the methods described herein.

In certain embodiments, the present invention provides an isolated polynucleotide comprising a nucleic acid which encodes a polypeptide at least 60%, 65%, 70%, 75%, 80%, 85%, 86%, 87%, 88%, 89%, 90%, 91%, 92%, 93%, 94%, 95%, 96%, 97%, 98%, or 99% identical to gB, i.e., SEQ ID NO:12 or SEQ ID NO:14, and where the nucleic acid is a variant of a codon-optimized coding region encoding SEQ ID NO:12 or SEQ ID NO:14. The human codon-optimized coding region can be optimized by any of the methods described herein.

In this manner, the present invention provides a method of enhancing the level of polypeptide expression from delivered polynucleotides in vivo and/or facilitating uptake of the polynucleotides by the cells of a desired species, for example a vertebrate species, for example a mammalian species, for example humans. Accordingly, the present invention provides a method of treatment and prevention against HCMV infection.

Methods and Administration

The present invention further provides methods for delivering an HCMV polypeptide to a human, which comprise administering to a human one or more of the compositions described herein; such that upon administration of compositions such as those described herein, an HCMV polypeptide is expressed in human cells, in an amount sufficient generate an immune response to HCMV.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equines such as horses, donkeys, and zebras, food animals such as cows, pigs, and sheep; ungulates such as deer and giraffes; and ursids such as bears. In particular, the mammal can be a human subject, a food animal or a companion animal.

The present invention further provides a method for generating, enhancing or modulating an immune response to HCMV comprising administering to a vertebrate one or more of the compositions described herein. In this method, the composition includes an isolated polynucleotide comprising a human codon-optimized coding region encoding a polypeptide of HCMV, or a nucleic acid fragment of such a coding region encoding a fragment, variant, or derivative thereof. The polynucleotides are incorporated into the cells of the vertebrate in vivo, and an antigenic amount of the HCMVs polypeptide, or fragment, variant, or derivative thereof, is produced in vivo. Upon administration of the composition according to this method, the HCMV polypeptide is expressed in the vertebrate in an amount sufficient to elicit an immune response. Such an immune response might be used, for example, to generate antibodies to HCMV for use in diagnostic assays or as laboratory reagents.

The present invention further provides a method for generating, enhancing, or modulating a protective and/or therapeutic immune response to HCMV in a human, comprising administering to a human in need of therapeutic and/or preventative immunity one or more of the compositions described herein. In this method, the composition includes an isolated polynucleotide comprising a human codon-optimized coding region encoding a polypeptide of HCMV, or a nucleic acid fragment of such a coding region encoding a fragment, variant, or derivative thereof. The polynucleotides are incorporated into the cells of the human in vivo, and an immunologically effective amount of the HCMV polypeptide, or fragment or variant is produced in vivo. Upon administration of the composition according to this method, the HCMV polypeptide is expressed in the human in a therapeutically or prophylactically effective amount.

As used herein, an "immune response" refers to the ability of a vertebrate to elicit an immune reaction to a composition delivered to that vertebrate. Examples of immune responses include an antibody response or a cellular, e.g., cytotoxic T-cell, response. One or more compositions of the present invention may be used to prevent HCMV infection in humans, e.g., as a prophylactic vaccine, to establish or enhance immunity to HCMV in a healthy individual prior to exposure to HCMV or contraction of HCMV disease, thus preventing the disease or reducing the severity of disease symptoms.

One or more compositions of the present invention may also be used to treat individuals already exposed to HCMV, or already suffering from HCMV disease to further stimulate the immune system of the human, thus reducing or eliminating the symptoms associated with that disease or disorder. As defined herein, "treatment " refers to the use of one or more compositions of the present invention to prevent, cure, retard, or reduce the severity of HCMV disease symptoms in a human, and/or result in no worsening of HCMV disease over a specified period of time. It is not required that any composition of the present invention provide total immunity to HCMV or totally cure or eliminate all HCMV disease symptoms. As used herein, a "human in need of therapeutic and/or preventative immunity" refers to an individual for whom it is desirable to treat, i.e., to prevent, cure, retard, or reduce the severity of HCMV disease symptoms, and/or result in no worsening of HCMV disease over a specified period of time.

In other embodiments, one or more compositions of the present invention are utilized in a "prime boost" regimen. An example of a "prime boost" regimen may be found in Yang, Z. et al. *J. Virol.* 77:799-803 (2002). In these embodiments, one or more polynucleotide vaccine compositions of the present invention are delivered to a human, thereby priming the immune response of the human to HCMV, and then a second immunogenic composition is utilized as a boost vaccination. One or more polynucleotide vaccine compositions of the present invention are used to prime immunity, and then a second immunogenic composition, e.g., a recombinant viral vaccine or vaccines, a different polynucleotide vaccine, one or more purified subunit HCMV proteins, e.g., gB or pp65, with or without additional HCMV antigens, e.g. IE1, or a variant, fragment, or derivative thereof, is used to boost the anti-HCMV immune response. The polynucleotide vaccine compositions may comprise one or more vectors for expression of one or more HCMV genes as described herein. In addition, a polynucleotide prime vaccine and the later boost vaccine may elicit an immune response to the same or similar antigens, or may elicit responses to different antigens.

In another embodiment, vectors are prepared for expression in the recombinant virus vaccine and in transfected mammalian cells as part of a polynucleotide vaccine.

The terms "priming" or "primary" and "boost" or "boosting" are used herein to refer to the initial and subsequent immunizations, respectively, i.e., in accordance with the definitions these terms normally have in immunology.

The invention further provides methods for enhancing the immune response of a human patient to HCMV by administering to the tissues of a human one or more polynucleotides comprising one or more codon-optimized coding regions encoding polypeptides of HCMV, and also HCMV polypeptides or fragments, variants or derivatives thereof, or one or more non-optimized polynucleotides encoding HCMV polypeptides, fragments, variants or derivatives thereof.

The combination of HCMV polypeptides or polynucleotides encoding HCMV polypeptides or fragments, variants or derivatives thereof, with the codon-optimized nucleic acid compositions provides for therapeutically beneficial effects at dose sparing concentrations. For example, immunological responses sufficient for a therapeutically beneficial effect may be attained by using less of a conventional-type vaccine (that is a vaccine comprising immunogenic polypeptides or nucleotides encoding immunogenic polypeptides, fragments, variants, or derivatives thereof, that are not products of, or have not been codon-optimized as described herein) when supplemented or enhanced with the appropriate amount of a codon-optimized nucleic acid.

Conventional-type vaccines, include vaccine compositions comprising either dead, inert or fragments of a virus or bacteria, or bacterial or viral proteins or protein fragments, injected into the patient to elicit action by the immune system. With regard to the present invention, conventional-type vaccines include compositions comprising immunogenic polypeptides or nucleotides encoding immunogenic polypeptides, fragments, variants, or derivatives thereof, and vectors comprising nucleotides encoding immunogenic polypeptides, fragments, variants, or derivatives thereof, that are not products of, or do not contain codon-optimized polynucleotides as described herein. Thus, genetically engineered vaccines, are included in conventional-type vaccines, such as genetically engineered live vaccines, live chimeric vaccines, live replication-defective vaccines, subunit vaccines, peptide vaccines in various modifications of monovalent, multivalent, or chimeric subunit vaccines delivered as individual components or incorporated into virus-like particles for improved immunogenicity, and polynucleotide vaccines. Auxiliary agents, as described herein, are also considered components of conventional-type vaccines.

Thus, dose sparing is contemplated by administration of the combinatorial polynucleotide vaccine compositions of the present invention.

In particular, the dose of conventional-type vaccines may be reduced by at least 5%, at least 10%, at least 20%, at least 30%, at least 40%, at least 50%, at least 60% or at least 70% when administered in combination with the codon-optimized nucleic acid compositions of the invention.

Similarly, a desirable level of an immunological response afforded by a DNA based pharmaceutical alone may be attained with less DNA by including a conventional-type DNA vaccine. Further, using a combination of a conventional-type vaccine and a codon-optimized DNA-based vaccine may allow both materials to be used in lesser amounts while still affording the desired level of immune response arising from administration of either component alone in higher amounts (e.g. one may use less of either immunological product when they are used in combination). This reduction in amounts of materials being delivered may be for each administration, in addition to reducing the number of administrations, in a vaccination regimen (e.g. 2 versus 3 or 4 injections). Further, the combination may also provide for reducing the kinetics of the immunological response (e.g. desired response levels are attained in 3 weeks instead of 6 after immunization).

In particular, the dose of DNA based pharmaceuticals, may be reduced by at least 5%, at least 10%, at least 20%, at least 30%, at least 40%, at least 50%, at least 60% or at least 70% when administered in combination with conventional IV vaccines.

Determining the precise amounts of DNA based pharmaceutical and a conventional antigen is based on a number of factors as described herein, and is readily determined by one of ordinary skill in the art.

In addition to dose sparing, the claimed combinatorial compositions provide for a broadening of the immune response and/or enhanced beneficial immune responses. Such broadened or enhanced immune responses are achieved by: adding DNA to enhance cellular responses to a conventional-type vaccine; adding a conventional-type vaccine to a DNA pharmaceutical to enhanced humoral response; using a combination that induces additional epitopes (both humoral and/or cellular) to be recognized and/or more desirably responded to (epitope broadening); employing a DNA-conventional vaccine combination designed for a particular desired spectrum of immunological responses; obtaining a desirable spectrum by using higher amounts of either component. The broadened immune response is measurable by one of ordinary skill in the art by standard immunological assay specific for the desirable response spectrum.

Both broadening and dose sparing may be obtained simultaneously.

In certain embodiments, one or more compositions of the present invention are delivered to a human by methods described herein, thereby achieving an effective therapeutic and/or an effective preventative immune response.

More specifically, the compositions of the present invention may be administered to any tissue of a human, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

Furthermore, the compositions of the present invention may be administered to any internal cavity of a human, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, the ocular cavities, the lumen of a duct of a salivary gland or a liver. When the compositions of the present invention is administered to the lumen of a duct of a salivary gland or liver, the desired polypeptide is expressed in the salivary gland and the liver such that the polypeptide is delivered into the blood stream of the human from each of the salivary gland or the liver. Certain modes for administration to secretory organs of a gastrointestinal system using the salivary gland, liver and pancreas to release a desired polypeptide into the bloodstream is disclosed in U.S. Pat. Nos. 5,837,693 and 6,004,944, both of which are incorporated herein by reference in their entireties.

In one embodiment, the compositions are administered to muscle, either skeletal muscle or cardiac muscle, or to lung tissue. Specific, but non-limiting modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention can be administered by intramuscular (i.m.), subcutaneous (s.c.), or intrapulmonary routes. Other suitable routes of administration include, but not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intraatrial (i.e., into the heart atrium) and sub arachnoid (i.e., into the sub arachnoid spaces of the brain) administration.

Any mode of administration can be used so long as the mode results in the expression of the desired peptide or protein, in the desired tissue, in an amount sufficient to generate an immune response to HCMV and/or to generate a prophylactically or therapeutically effective immune response to HCMV in a human in need of such response. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171:11-22 (1994)), Pigjet (Schrijver, R., et al., *Vaccine* 15: 1908-1916 (1997)), Biojector (Davis, H., et al., *Vaccine* 12: 1503-1509 (1994); Gramzinski, R., et al., *Mol. Med.* 4: 109-118 (1998)), AdvantaJet (Linmayer, I., et al., *Diabetes Care* 9:294-297 (1986)), Medi-jector (Martins, J., and Roedl, E. *J. Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65: 2193-2203 (1999)) or topical applications during surgery. Certain modes of administration are intramuscular needle-based injection and pulmonary application via catheter infusion. Energy-assisted plasmid delivery (EAPD) methods may also be employed to administer the compositions of the invention. One such method involves the application of brief electrical pulses to injected tissues, a procedure commonly known as electroporation. See generally Mir, L. M. et al., *Proc. Natl. Acad. Sci USA* 96:4262-7 (1999); Hartikka, J. et al., *Mol. Ther.* 4:407-15 (2001); Mathiesen, I., *Gene Ther.* 6:508-14(1999); Rizzuto G. et al., *Hum. Gen. Ther.* 11:1891-900 (2000). Each of the references cited in this paragraph is incorporated herein by reference in its entirety.

Further, antigen constructs alone or in combination may be formulated to enhance the type of immune response (e.g. humoral, cellular, mucosal, etc.) believed to be most beneficial to mount in the host for that particular antigen or antigens. Each such formulation may be administered individually at a separate site in the host, and/or combined and administered with some or all of the other antigen formulations at one or more sites in the host. Each administration may be accomplished using the same or different physical means of administration. Thus, as a non-limiting example, a gB plasmid could be formulated with cationic lipids and administered as a mist intranasaly, in conjunction with administration of a poloxamer formulation of pp65 using a needle free device into skin and muscle of one limb, in conjunction with transdermal intramuscular administration using a conventional syringe and needle of an IE1 plasmid in PBS into a second limb.

Determining an effective amount of one or more compositions of the present invention depends upon a number of factors including, for example, the antigen being expressed, e.g. gB, pp65 or IE1; or fragments, variants, or derivatives thereof, the age and weight of the subject, the precise condition requiring treatment and its severity, and the route of administration. Based on the above factors, determining the precise amount, number of doses, and timing of doses are within the ordinary skill in the art and will be readily determined by the attending physician.

Compositions of the present invention may include various salts, excipients, delivery vehicles and/or auxiliary agents as are disclosed, e.g., in U.S. Patent Application Publication 2002/0019358, published Feb. 14, 2002, which is incorporated herein by reference in its entirety.

Furthermore, compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, e.g., in addition to facilitating delivery of polynucleotides to the interior of a cell, the compound acts to alter or increase the immune response to the antigen encoded by that polynucleotide. Examples of the transfection facilitating compounds include, but are not limited to inorganic materials such as calcium phosphate, alum (aluminum sulfate), and gold particles (e.g., "powder" type delivery vehicles); peptides that are, for example, cationic, intercell targeting (for selective delivery to certain cell types), intracell targeting (for nuclear localization or endosomal escape), and ampipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); and polymers such as dendrimers, star-polymers, "homogenous" poly-amino acids (e.g., poly-lysine, poly-arginine), "heterogenous" poly-amino acids (e.g., mixtures of lysine & glycine), co-polymers, polyvinylpyrrolidinone (PVP), poloxamers (e.g. CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., *Biochim. Biophys. Acta* 1380(3):354-368 (1988)), mechanical mixing (e.g., free moving materials in liquid or solid phase such as "polylysine+cationic lipids") (Gao and Huang, *Biochemistry* 35:1027-1036 (1996); Trubetskoy, et al., *Biochem. Biophys. Acta* 1131:311-313 (1992)), and aggregation (e.g., co-precipitation, gel forming such as in cationic lipids+poly-lactide, and polylysine+gelatin).

One category of transfection facilitating materials is cationic lipids. Examples of cationic lipids are 5-carboxyspermylglycine dioctadecylamide (DOGS) and dipalmitoylphophatidylethanolamine-5-carboxyspermylamide (DPPES). Cationic cholesterol derivatives are also useful, including {3β-[N-N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino)propyl-ammonium bromide (PA-TELO), and N1-(3-aminopropyl)((2-dodecyloxy)ethyl)-N2-(2-dodecyloxy)ethyl-1-piperazinaminium bromide (GA-LOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other specific but non-limiting cationic surfactants for use in certain embodiments of the present invention include Bn-DHRIE, DhxRIE, DhxRIE-OAc, DhxRIE-OBz and Pr-DOctRIE-OAc. These lipids are disclosed in copending U.S. Patent Application Ser. No. 60/435,303. In another aspect of the present invention, the cationic surfactant is Pr-DOctRIE-OAc.

Other cationic lipids include (±)-N,N-dimethyl-N-[2-(sperminecarboxamido) ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., *Biochim. Biophys. Acta* 1280:1-11 (1996)), and (±)-N-(3-aminopropyl)-N,N-dimethyl-2,3-bis(dodecyloxy)-1-propaniminium bromide (GAP-DLRIE) (Wheeler, et al., *Proc. Natl. Acad. Sci. USA* 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAPP-DMRIE), (±)-N-((N"-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

In the embodiments where the immunogenic composition comprises a cationic lipid, the cationic lipid may be mixed with one or more co-lipids. For purposes of definition, the term Aco-lipid refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE, which comprises two phytanoyl substituents incorporated into the diacylphosphatidylethanolamine skeleton. In other embodiments, the co-lipid is DOPE, CAS name 1,2-diolyeoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the plasmid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a codon-optimized polynucleotide of the present invention, according to methods known to those skilled in the art. For example, the sonication of a lipid solution is described in Felgner et al., *Proc. Natl. Acad. Sci. USA* 8: 7413-7417 (1987) and in U.S. Pat. No. 5,264,618, the disclosures of which are incorporated herein by reference.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

Additional embodiments of the present invention are drawn to compositions comprising an auxiliary agent which is administered before, after, or concurrently with the polynucleotide. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, cationic, or zwitterionic surfactants or detergents; chelators, DNAse inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 630® CA 630, NONIDET® NP-40, NONIDET® P40 (2-[2-[4-(2,4,4-trimethylpentan-2-yl)phenoxy]ethoxy]ethanol), TWEEN-20™ (2-[2-[3,4-bis (2-hydroxyethoxy)oxolan-2-yl]-2-(2-hydroxyethoxy) ethoxy]ethyl dodecanoate), TWEEN-80™, Pluronic® F68, Pluronic® F77, Pluronic® P65, Triton X-100™, and Triton X-114™; the anionic detergent sodium dodecyl sulfate (SDS); the sugar stachyose; the condensing agent DMSO; and the chelator/DNAse inhibitor EDTA, CRL 1005, and BAK. In certain specific embodiments, the auxiliary agent is DMSO, NONIDET® P40 (2-[2-[4-(2,4,4-trimethylpentan-2-yl)phenoxy]ethoxy]ethanol), Pluronic® F68, Pluronic® F77, Pluronic® P65, Pluronic® L64, and Pluronic® F108. See, e.g., U.S. Patent Application Publication 20020019358, published Feb. 14, 2002, which is incorporated herein by reference in its entirety.

Certain compositions of the present invention may further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," may be a transfection facilitating material. Similarly, certain "transfection facilitating materials" described supra, may also be an "adjuvant." An adjuvant may be used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; pluronic block polymers, such as TiterMax™; depot formers, such as Freunds adjuvant, surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) tri-block copolymers. Also included as adjuvants are transfection-facilitating materials, such as those described above.

Poloxamers which may be screened for their ability to enhance the immune response according to the present invention include, but are not limited to commercially available poloxamers such as Pluronic® L121 (ave. MW: 4400; approx. MW of hydrophobe, 3600; approx. wt. % of hydrophile, 10%), Pluronic® L101 (ave. MW: 3800; approx. MW of hydrophobe, 3000; approx. wt. % of hydrophile, 10%), Pluronic® L81 (ave. MW: 2750; approx. MW of hydrophobe, 2400; approx. wt. % of hydrophile, 10%), Pluronic® L61 (ave. MW: 2000; approx. MW of hydrophobe, 1800; approx. wt. % of hydrophile, 10%), Pluronic® L31 (ave. MW: 1100; approx. MW of hydrophobe, 900; approx. wt. % of hydrophile, 10%), Pluronic® L122 (ave. MW: 5000; approx. MW of hydrophobe, 3600; approx. wt. % of hydrophile, 20%), Pluronic® L92 (ave. MW: 3650; approx. MW of hydrophobe, 2700; approx. wt. % of hydrophile, 20%), Pluronic® L72 (ave. MW: 2750; approx. MW of hydrophobe, 2100; approx. wt. % of hydrophile, 20%), Pluronic® L62 (ave. MW: 2500; approx. MW of hydrophobe, 1800; approx. wt. % of hydrophile, 20%), Pluronic® L42 (ave. MW: 1630; approx. MW of hydrophobe, 1200; approx. wt. % of hydrophile, 20%), Pluronic® L63 (ave. MW: 2650; approx. MW of hydrophobe, 1800; approx. wt. % of hydrophile, 30%), Pluronic® L43 (ave. MW: 1850; approx. MW of hydrophobe, 1200; approx. wt. % of hydrophile, 30%), Pluronic® L64 (ave. MW: 2900; approx. MW of hydrophobe, 1800; approx. wt. % of hydrophile, 40%), Pluronic® L44 (ave. MW: 2200; approx. MW of hydrophobe, 1200; approx. wt. % of hydrophile, 40%), Pluronic® L35 (ave. MW: 1900; approx. MW of hydrophobe, 900; approx. wt. % of hydrophile, 50%), Pluronic® P123 (ave. MW: 5750; approx. MW of hydrophobe, 3600; approx. wt. % of hydrophile, 30%), Pluronic® P103 (ave. MW: 4950; approx. MW of hydrophobe, 3000; approx. wt. % of hydrophile, 30%), Pluronic® P104 (ave. MW: 5900; approx. MW of hydrophobe, 3000; approx. wt. % of hydrophile, 40%), Pluronic® P84 (ave. MW: 4200; approx. MW of hydrophobe, 2400; approx. wt. % of hydrophile, 40%), Pluronic® P105 (ave. MW: 6500; approx. MW of hydrophobe, 3000; approx. wt. % of hydrophile, 50%), Pluronic® P85 (ave. MW: 4600; approx. MW of hydrophobe, 2400; approx. wt. % of hydrophile, 50%), Pluronic® P75 (ave. MW: 4150; approx. MW of hydrophobe, 2100; approx. wt. % of hydrophile, 50%), Pluronic® P65 (ave. MW: 3400; approx. MW of hydrophobe, 1800; approx. wt. % of hydrophile, 50%), Pluronic® F127 (ave. MW: 12600; approx. MW of hydrophobe, 3600; approx. wt. % of hydrophile, 70%), Pluronic® F98 (ave. MW: 13000; approx. MW of hydrophobe, 2700; approx. wt. % of hydrophile, 80%), Pluronic® F87 (ave. MW: 7700; approx. MW of hydrophobe, 2400; approx. wt. % of hydrophile, 70%), Pluronic® F77 (ave. MW: 6600; approx. MW of hydrophobe, 2100; approx. wt. % of hydrophile, 70%), Pluronic® F108 (ave. MW: 14600; approx. MW of hydrophobe, 3000; approx. wt. % of hydrophile, 80%), Pluronic® F98 (ave. MW: 13000; approx. MW of hydrophobe, 2700; approx. wt. % of hydrophile, 80%), Pluronic® F88 (ave. MW: 11400; approx. MW of hydrophobe, 2400; approx. wt. % of hydrophile, 80%), Pluronic® F68 (ave. MW: 8400; approx. MW of hydrophobe, 1800; approx. wt. % of hydrophile, 80%), Pluronic® F38 (ave. MW: 4700; approx. MW of hydrophobe, 900; approx. wt. % of hydrophile, 80%).

Reverse poloxamers of the present invention include, but are not limited to Pluronic® R 31R1 (ave. MW: 3250; approx. MW of hydrophobe, 3100; approx. wt. % of hydrophile, 10%), Pluronic® R 25R1 (ave. MW: 2700; approx. MW of hydrophobe, 2500; approx. wt. % of hydrophile, 10%), Pluronic® R 17R1 (ave. MW: 1900; approx. MW of hydrophobe, 1700; approx. wt. % of hydrophile, 10%), Pluronic® R 31R2 (ave. MW: 3300; approx. MW of hydrophobe, 3100; approx. wt. % of hydrophile, 20%), Pluronic® R 25R2 (ave. MW: 3100; approx. MW of hydrophobe, 2500; approx. wt. % of hydrophile, 20%), Pluronic® R 17R2 (ave. MW: 2150; approx. MW of hydrophobe, 1700; approx. wt. % of hydrophile, 20%), Pluronic® R 12R3 (ave. MW: 1800; approx. MW of hydrophobe, 1200; approx. wt. % of hydrophile, 30%), Pluronic® R 31R4 (ave. MW: 4150; approx. MW of hydrophobe, 3100; approx. wt. % of hydrophile, 40%), Pluronic® R 25R4 (ave. MW: 3600; approx. MW of hydrophobe, 2500; approx. wt. % of hydrophile, 40%), Pluronic® R 22R4 (ave. MW: 3350; approx. MW of hydrophobe, 2200; approx. wt. % of hydrophile, 40%), Pluronic® R 17R4 (ave. MW: 3650; approx. MW of hydrophobe, 1700; approx. wt. % of hydrophile, 40%), Pluronic R 25R5 (ave. MW: 4320; approx. MW of hydrophobe, 2500; approx. wt. % of hydrophile, 50%), Pluronic® R 10R5 (ave. MW: 1950; approx. MW of hydrophobe, 1000; approx. wt. % of hydrophile, 50%), Pluronic® R 25R8 (ave. MW: 8550; approx. MW of hydrophobe, 2500; approx. wt. % of hydrophile, 80%), Pluronic® R 17R8 (ave. MW: 7000; approx. MW of hydrophobe, 1700; approx. wt. % of hydrophile, 80%), and Pluronic® R 10R8 (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as Synperonic® L121, Synperonic® L122, Synperonic® P104, Synperonic® P105, Synperonic® P123, Synperonic® P85 and Synperonic® P94; and compounds that are nonylphenyl polyethylene glycol such as Synperonic® NP10, Synperonic® NP30 and Synperonic® NP5.

Other poloxamers which may be screened for their ability to enhance the immune response according to the present invention include a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—R$^o$, wherein R$^o$ is a straight chain aliphatic group of 2 to 6 carbon atoms, which may be substituted, wherein said polyether segments comprise at least one of an A-type of B-type segment. See U.S. Pat. No. 5,656,611, by Kabonov, et al., which is incorporated herein by reference in its entirety.

Other auxiliary agents which may be screened for their ability to enhance the immune response according to the present invention include, but are not limited to Acacia (gum arabic); the poloxyethylene ether R—O—(C$_2$H$_4$O)$_x$—H (BRIJ®), e.g., polyethylene glycol dodecyl ether (BRIJ® 35, x=23), polyethylene glycol dodecyl ether (BRIJ® 30, x=4), polyethylene glycol hexadecyl ether (BRIJ® 52 x=2), polyethylene glycol hexadecyl ether (BRIJ® 56, x=10), polyethylene glycol hexadecyl ether (BRIJ® 58, x=20), polyethylene glycol octadecyl ether (BRIJ® 72, x=2), polyethylene glycol octadecyl ether (BRIJ® 76, x=10), polyethylene glycol octadecyl ether (BRIJ® 78P, x=20), polyethylene glycol oleyl ether (BRIJ® 92V, x=2), and polyoxyl 10 oleyl ether (BRIJ® 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40®); octylphenoxypolyethoxyethanol (NONIDET NP-40 from Amresco); ethyl phenol poly (ethylene glycol ether)$^n$, n=11 (Nonidet® P40 from Roche); octyl phenol ethylene oxide condensate with about 9 ethylene oxide units (nonidet P40); IGEPAL CA 630® ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20®); polyoxyethylene sorbitan monooleate (polysorbate 80, or TWEEN-80®); propylene glycol diacetate; propylene glycol monstearate; protamine sulfate; proteolytic enzymes; sodium dodecyl sulfate (SDS); sodium monolaurate; sodium stearate; sorbitan derivatives (SPAN®), e.g., sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly(ethyleneglycolether)$_9$ (Thesit®) MW 582.9; octyl phenol ethylene oxide condensate with about 9-10 ethylene oxide units (Triton X-100™); octyl phenol ethylene oxide condensate with about 7-8 ethylene oxide units (Triton X-114™); tris(2-hydroxyethyl) amine (trolamine); and emulsifying wax.

In certain adjuvant compositions, the adjuvants are cytokines. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), Leishmania elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-propanaminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising ;GAP-DMORIE and DPyPE at a 1:1 molar ratio is referred to herein as Vaxfectin™. See, e.g., PCT Publication No. WO 00/57917, which is incorporated herein by reference in its entirety.

The ability of an adjuvant to increase the immune response to an antigen is typically manifested by a significant increase in immune-mediated protection. For example, an increase in humoral immunity is typically manifested by a significant increase in the titer of antibodies raised to the antigen, and an increase in T-cell activity is typically manifested in increased cell proliferation, increased cytokine production and/or antigen specific cytolytic activity. An adjuvant may also alter an immune response, for example, by changing a Th$_2$ response into a Th$_1$ response.

Nucleic acid molecules and/or polynucleotides of the present invention, e.g., pDNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in *Remington's Pharmaceutical Sciences,* 16th Edition, A. Osol, ed., Mack Publishing Co., Easton, Pa. (1980), and *Remington's Pharmaceutical Sciences,* 19th Edition, A. R. Gennaro, ed., Mack Publishing Co., Easton, Pa. (1995), both of which are incorporated herein by reference in their entireties. Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims. All references cited in the Examples are incorporated herein by reference in their entireties.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual,* 2nd Ed., Sambrook et al., ed., Cold Spring Harbor Laboratory Press: (1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); and in Ausubel et al., *Current Protocols in Molecular Biology,* John Wiley and Sons, Baltimore, Md. (1989).

Gene Construction

Constructs of the present invention are constructed based on the sequence information provided herein or in the art utilizing standard molecular biology techniques, including, but not limited to the following. First, a series complementary oligonucleotide pairs of 80-90 nucleotides each in length and spanning the length of the construct are synthesized by standard methods. These oligonucleotide pairs are synthesized such that upon annealing, they form double stranded fragments of 80-90 base pairs, containing cohesive ends. The single-stranded ends of each pair of oligonucleotides are designed to anneal with a single-stranded end of an adjacent oligonucleotide duplex. Several adjacent oligonucleotide pairs prepared in this manner are allowed to anneal, and approximately five to six adjacent oligonucleotide duplex fragments are then allowed to anneal together via the cohesive single stranded ends. This series of annealed oligonucleotide duplex fragments is then ligated together and cloned into a suitable plasmid, such as the TOPO® vector available from Invitrogen Corporation, Carlsbad, Calif. The construct is then sequenced by standard methods. Constructs prepared in this manner, comprising 5 to 6 adjacent 80 to 90 base pair fragments ligated together, i.e., fragments of about 500 base pairs, are prepared, such that the entire desired sequence of the construct is represented in a series of plasmid constructs. The inserts of these plasmids are then cut with appropriate restriction enzymes and ligated together to form the final construct. The final construct is then cloned into a standard bacterial cloning vector, and sequenced. Alternatively, wild sequences can be cloned directly from HCMV-infected cells (e.g. MRC-5 cells, ATCC Accession No. CCL-171, available from the American Type Culture Collection, Manassas, Va.) using PCR primers that amplify the gene of interest. The oligonucleotides and primers referred to herein can easily be designed by a person of skill in the art based on the sequence information provided herein and in the art, and such can be synthesized by any of a number of commercial nucleotide providers, for example Retrogen, San Diego, Calif., and GENEART, Regensburg, Germany.

Plasmid Vector

Constructs of the present invention were inserted into eukaryotic expression vector V10551. This vector is built on a modified pUC18 background (see Yanisch-Perron, C., et al. *Gene* 33:103-119 (1985)), and contains a kanamycin resistance gene, the human cytomegalovirus immediate early 1 promoter/enhancer and intron A, and the bovine growth hormone transcription termination signal, and a polylinker for inserting foreign genes. See Hartikka, J., et al., *Hum. Gene Ther.* 7:1205-1217 (1996). However, other standard commercially available eukaryotic expression vectors may be used in the present invention, including, but not limited to: plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.).

Plasmid DNA Purification

Plasmid DNA was transformed into *Escherichia coli* DH5α competent cells and highly purified covalently closed circular plasmid DNA was isolated by a modified lysis procedure (Horn, N. A., et al., *Hum. Gene Ther.* 6:565-573 (1995)) followed by standard double CsCl-ethidium bromide gradient ultracentrifugation (Sambrook, J., et al., *Molecular Cloning: A Laboratory Manual*, 2nd Ed., Cold Spring Harbor Laboratory Press, Plainview, N.Y. (1989)). Alternatively, plasmid DNAs are purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using Limulus Amebocyte Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in an appropriate solution, e.g., 150 mM sodium phosphate (for other appropriate excipients and auxiliary agents, see U.S. Patent Application Publication 20020019358, published Feb. 14, 2002). DNA was stored at −20° C. until use. DNA was diluted by mixing it with 300 mM salt solutions and by adding appropriate amount of USP water to obtain 1 mg/ml plasmid DNA in the desired salt at the desired molar concentration.

Plasmid Expression in Mammalian Cell Lines

The expression plasmids were analyzed in vitro by transfecting the plasmids into a well characterized mouse melanoma cell line (VM-92, also known as UM-449) available from the American Type Culture Collection, Manassas, Va. Other well-characterized human cell lines may also be used, e.g. MRC-5 cells, ATCC Accession No. CCL-171. The transfection was performed using cationic lipid-based transfection procedures well known to those of skill in the art. Other transfection procedures are well known in the art and may be used, for example electroporation and calcium chloride-mediated transfection (Graham F. L. and A. J. van der Eb *Virology* 52:456-67 (1973)). Following transfection, cell lysates and culture supernatants of transfected cells were evaluated to compare relative levels of expression of HCMV antigen proteins. The samples were assayed by western blots and ELISAs, using commercially available anti-pp65 and anti-gB monoclonal antibodies (available, e.g., from Research Diagnostics Inc., Flanders N.J.), so as to compare both the quality and the quantity of expressed antigen. Additionally, in vitro transfection assays were used to determine the effect of mixing the various plasmids comprising codon-optimized coding regions encoding HCMV pp65 and gB on levels of expression in human cells.

Expression products derived from human cells transfected with the various polynucleotide constructs were examined for molecular weight, and immunoreactive antigens (i.e., to react with HCMV antisera). In addition, a comparison of expression levels (both intra- and extra-cellular) of each class of expression plasmid (e.g., wild-type vs. human codon-optimized; truncated vs. full-length) was made.

Injections of Plasmid DNA

The quadriceps muscles of restrained awake mice (e.g., female 6-12 week old BALB/c mice from Harlan Sprague Dawley, Indianapolis, Ind.) are injected using a disposable sterile, plastic insulin syringe and 28 G ½ needle (Becton-Dickinson, Franklin Lakes, N.J., Cat. No. 329430) fitted with a plastic collar cut from a micropipette tip, all as previously described (Hartikka, J., et al., *Hum. Gene Ther.* 7:1205-1217 (1996)). The mice are injected bilaterally in the rectus femoris muscle with 25 μg of plasmid DNA (50 μg total per mouse) formulated in a salt solution (e.g. 150 mM Sodium Phosphate or phosphate buffered saline (PBS)) or with a lipid-based delivery system.

Animal care throughout the study is in compliance with the "Guide for the Use and Care of Laboratory Animals," Institute of Laboratory Animal Resources, Commission on Life Sciences, National Research Council, National Academy Press, Washington, D.C., 1996 as well as with Vical's Institutional Animal Care and Use Committee.

Immune Correlates

Although HCMV can only infect human cells, a number of reliable animal models for HCMV infection are known in the art, as reviewed by Staczek, and may be used with the methods of the present invention, e.g. to test immunogenicity or expression (Staczek, J. *Microbiol Rev* 54:247-65 (1990)). For example, the transgenic human leukocyte antigen (HLA) A*0201.Kb mouse model may be used (Gallez-Hawkins, G.

et al. *Scand J Immunol* 55:592-8 (2002)). A mouse model of vertical HCMV transmission is described in Tang, et al., (Tang, J L, et al. *Arch Virol* 147:1189-95 (2002)). Several models infecting human tissue implanted onto immunodeficient SCID or nude mice have been described (Bidanset, D J, et al., *J Infect Dis* 184:192-5 (2001); Pari, G S, et al, *J Infect Dis* 177:523-8 (1998); Mocarski, E S, et al. *Proc Natl Acad Sci USA* 90:104-8 (1993)). Athymic rats have been used to model cytomegalovirus retinitis using HCMV (Laycock, Kans., et al. *Am J Ophthalmol* 124:181-9 (1997)). Additionally, animal models using animal cytomegaloviruses to mimic HCMV infection have been described, including primate models in which rhesus macaques are infected with rhesus cytomegalovirus, and murine models infected with murine cytomegalovirus (Sequar, G. et al. *J Virol* 76:7661-71 (2002); Lockridge, K M, et al. *J Virol* 73:9576-83 (1999); Minamishima, Y, et al., *Microbiol Immunol* 22:693-700 (1978)).

Example 1

Construction of an Isolated Polynucleotide Comprising a Minimally Human Codon-Optimized pp65 Coding Region, Encoding Human Cytomegalovirus pp65 with Kinase Site Deleted VCL-6368 encodes an optimized and mutated form of the human CMV antigen pp65 cloned into the expression vector VR10551 described supra. This plasmid encodes a 557 amino acid protein (SEQ ID NO:6) in which amino acids Arg435-Lys438 of the human CMV pp65 antigen have been deleted. The coding sequence was minimally optimized for expression in humans by changing five codons that are rarely used in humans to corresponding codons that are used more frequently. The five codons and changes are: Ala GCG to GCC, Arg CGT to CGC, Pro CCG to CCC, and CCA, Ser TCG to TCC, and Thr ACG to ACC. The optimized sequence is SEQ ID NO:5.

The pp65delArg435-Lys438 insert of VCL-6368 was constructed in two steps by PCR amplification of an optimized hCMV pp65 plasmid synthesized at Retrogen Inc. (San Diego). The TOPO-hCMV-opti-pp65 plasmid (Retrogen product # 8041-8081-4) was amplified with Expand DNA polymerase (Boehringer Mannheim) using the primer set T7 (Invitrogen Cat. #N650-02) (SEQ ID NO:21) and 65-delta-rev (SEQ ID NO:22) and the resulting product was gel purified as a 1330 bp fragment. An overlapping 400 bp fragment was amplified from the same parent TOPO plasmid using the primer set M13rev (Invitrogen Cat. # 18430017) (SEQ ID NO:23) and 65-delta-for (SEQ ID NO:24) and the product was gel purified. Ten microliters of each of the two PCR fragments were combined in a second PCR reaction and amplified with the T7 (SEQ ID NO:21) and M13rev primer (SEQ ID NO:23) and the 1704 bp fragment was gel purified. This fragment was cut with the restriction enzymes Avr II and Nhe I and ligated with similarly digested plasmid backbone DNA. The ligation mix was transformed into *E. coli* (XL-2 from Stratagene, Inc.) and screened by PCR for recombinant clones using the primers VR10551FOR (SEQ ID NO:25) and hCMVpp65-R (SEQ ID NO:26). Several PCR positive clones were picked and sequenced. A minimally human codon-optimized clone encoding the correct Arg435-Lys438 deletion form of the human CMV pp65 antigen was selected and used for further analysis.

Expression of VR6368 was shown by transfection of VM92 cells and Western blot analysis using a monoclonal anti-pp65 antibody (ViroGen, lot# hCMV-pp65-4). The predicted sized protein was detected in the supernatant and cell lysate. Even though this construct encodes an intracellular protein, a significant amount ends up in the supernatant. This is not a unique or particularly unusual phenomenon.

Example 2

Construction of an Isolated Polynucleotide Comprising a Minimally Human Codon-Optimized Glycoprotein B Coding Region, Encoding the Secreted Human Cytomegalovirus Glycoprotein B VCL-6365 encodes a secreted form of the human CMV antigen gB cloned into the expression vector VR10551 described supra. This plasmid encodes amino acids 1-713 of the human CMV gB antigen (SEQ ID NO:14). Nucleotides 1-2139 of the wild-type gB coding sequence (SEQ ID NO:11) were minimally optimized for expression in humans by changing five codons that are rarely used in humans to five corresponding codons that are used more frequently. The five codons and changes are: Ala GCG to GCC, Arg CGT to CGC, Pro CCG to CCC, CCT, and CCA, Ser TCG to TCC, and Thr ACG to ACC. The optimized sequence is SEQ ID NO:13.

VR6365 was constructed by inserting a 2160 bp synthesized fragment encoding amino acids 1-713 of the human CMV gB antigen inserted into the expression vector VR-10551. Specifically, VR-10551 was digested with the restriction enzymes Nhe I and Avr II, and the 4.5 kb linear vector was gel purified. The gB insert was obtained by digesting the minimally human codon-optimized coding region encoding the secreted gB fragment synthesized by Retrogen Inc. (San Diego, product # 7981-8031(2)-1) with the restriction enzymes Nhe I and Avr II, then gel purifying the resulting 2160 bp fragment. The vector and insert fragments were ligated together, transformed into *E. coli* (XL-2 from Stratagene, Inc.) and screened by PCR for recombinant clones using the primers 1055 IF (SEQ ID NO:25) and hCMVgB-R (SEQ ID NO:27). Several PCR positive clones were sequenced. A clone with the correct nucleotide sequence and was given the designation VR6365. This clone encodes a secreted form of the human CMV antigen gB cloned into the Nhe I-Avr II sites of the expression vector VR10551.

Purified plasmid DNA was used to transfect the murine cell line VM92 to determine secretion of the minimally human-codon-optimized gB.

Secretion of the minimally human-codon-optimized gB was confirmed with an ELISA assay using plates coated with supernatants from the transfected VM92 cells. Expression and secretion was visualized with polyclonal anti-gB serum and a commercially available anti-gB monoclonal antibody (available from Research Diagnostics Inc., Flanders, N.J.).

Example 3

Construction of an Isolated Polynucleotide Comprising a Human Codon-Optimized CMV IE1 Coding Region, Encoding Human Cytomegalovirus IE1

Plasmid VCL-6520 comprises a 1236 base-pair human codon-optimized synthetic DNA construct encoding exons 2 and 4 of the human CMV IE1 gene, inserted into the expression vector VR-10551. The wild type sequence for exons 2 and 4 of the human CMV IE1 gene follows (SEQ ID NO: 50):

```
GAATTCGCCGCCACCATGGAGTCCTCTGCCAAGAGAAAGATGGACCCTGATAATCCTGAC
GAGGGCCCTTCCTCCAAGGTGCCACGGGTCAAACAGATTAAGGTTCGAGTGGACATGGTG
CGGCATAGAATCAAGGAGCACATGCTGAAAAAATATACCCAGACGGAAGAGAAATTCACT
GGCGCCTTTAATATGATGGGAGGATGTTTGCAGAATGCCTTAGATATCTTAGATAAGGTT
CATGAGCCTTTCGAGGAGATGAAGTGTATTGGGCTAACTATGCAGAGCATGTATGAGAAC
TACATTGTACCTGAGGATAAGCGGGAGATGTGGATGGCTTGTATTGATGAACTTAGGAGA
AAGATGATGTATATGTGCTACAGGAATATAGAGTTCTTTACCAAGAACTCAGCCTTCCCT
AAGACCACCAATGGCTGCAGTCAGGCCATGGCGGCACTGCAGAACTTGCCTCAGTGCTCC
CCTGATGAGATTATGGCTTATGCCCAGAAAATATTTAAGATTTTGGATGAGGAGAGAGAC
AAGGTGCTCACGCACATTGATCACATATTTATGGATATCCTCACTACATGTGTGGAAACA
ATGTGTAATGAGTACAAGGTCACTAGTGACGCTTGTATGATGACCATGTACGGGGCATC
TCTCTCTTAAGTGAGTTCTGTCGGTGCTGTGCTGCTATGTCTTAGAGGAGACTAGTGTG
ATGCTGGCCAAGCGGCCTCTGATAACCAAGCCTGAGGTTATCAGTGTAATGAAGCGCCGC
ATTGAGGAGATCTGCATGAAGGTCTTTGCCCAGTACATTCTGGGGGCCGATCCTCTGAGA
GTCTGCTCTCCTAGTGTGGATGACCTACGGGCCATCGCCGAGGAGTCAGATGAGGAAGAG
GCTATTGTAGCCTACACTTTGGCCACCGCTGGTGTCAGCTCCTCTGATTCTCTGGTGTCA
CCCCCAGAGTCCCCTGTACCCGCGACTATCCCTCTGTCCTCAGTAATTGTGGCTGAGAAC
AGTGATCAGGAAGAAAGTGAGCAGAGTGATGAGGAAGAGGAGGAGGGTGCTCAGGAGGAG
CGGGAGGACACTGTGTCTGTCAAGTCTGAGCCAGTGTCTGAGATAGAGGAAGTTGCCCCA
GAGGAAGAGGAGGATGGTGCTGAGGAACCCACCGCCTCTGGAGGCAAGAGCACCCACCCT
ATGGTGACTAGAAGCAAGGCTGACCAGTGAGGATCC
```

The insert in the VCL-6250 construct was synthesized by GENEART www.geneart.de/, Regensburg, Germany). VCL-6250 has the following sequence (SEQ ID NO:28):

```
10ATATCGCCGCCACCATGGAGTCTAGCGCCAAGAGGAAGATGGACCCCGACAACCCTGAT
GAGGGCCCTAGCAGCAAGGTGCCCCGGGTGAAGCAGATCAAGGTGCGGGTGGACATGGTG
CGGCACAGGATCAAGGAACACATGCTGAAGAAGTACACCCAGACCGAGGAGAAGTTCACC
GGCGCCTTCAATATGATGGGCGGCTGCCTGCAGAATGCCCTGGACATCCTGGACAAGGTG
CACGAGCCCTTCGAGGAGATGAAGTGCATCGGCCTGACCATGCAGAGCATGTACGAGAAC
TACATCGTGCCCGAGGACAAGAGGGAGATGTGGATGGCCTGCATCGACGAGCTGCGGCGG
AAGATGATGTACATGTGCTACCGGAACATCGAGTTCTTCACCAAG-AACAGCGCCTTCCCC
AAGACCACCAACGGATGCTCTCAGGCCATGGCCGCCCTGCAGAATCTGCCTCAGTGCAGC
CCCGATGAGATCATGGCCTACGCCCAGAAGATCTTCAAGATCCTGGACGAGGAGAGGGAT
AAGGTGCTGACCCACATCGACCACATCTTCATGGACATCCTGACCACCTGCGTGGAGACC
ATGTGCAACGAGTACAAGGTGACCAGCGACGCCTGCATGATGACAATGTACGGCGGCATC
AGCCTGCTGAGCGAGTTCTGCAGAGTGCTGTGCTGCTACGTGCTGGAGGAGACCTCTGTG
ATGCTGGCCAAGAGGCCCCTGATCACCAAGCCTGAGGTGATCAGCGTGATGAAGCGGCGG
ATCGAGGAGATCTGCATGAAGGTGTTCGCCCAGTACATCCTGGGAGCCGACCCTCTGAGA
GTGTGTAGCCCCAGCGTGGATGACCTGAGAGCCATCGCCGAGGAATCTGATGAAGAGGAG
```

```
                           -continued
GCCATCGTGGCCTATACACTGGCCACAGCCGGCGTGTCTAGCAGCGATAGCCTGGTGAGC

CCTCCTGAGTCTCCTGTGCCTGCCACAATCCCTCTGAGCAGCGTGATCGTGGCCGAGAAC

AGCGATCAGGAGGAGAGCGAGCAGTCTGATGAGGAAGAGGAAGAGGGAGCCCAGGAGGAG

AGAGAGGATACCGTGAGCGTGAAGAGCGAGCCTGTGAGCGAGATCGAAGAGGTGGCCCCT

GAGGAAGAAGAGGATGGCGCCGAGGAGCCTACAGCCAGCGGCGGCAAGTCAACACACCCC

ATGGTGACCAGAAGCAAGGCCGACCAGTAAGGATCC
```

VCL-6250 was constructed by isolating the EcoR5-BamHI IE1 synthetic insert and ligating it into the expression vector VR-10551, described above. Specifically, VR-10551 was digested with restriction enzymes and gel purified, as described in the preceding examples. The vector and insert fragments were ligated together, transformed into *E. coli* DH10B cells (available, e.g., from Invitrogen). Selected recombinant plasmids were completely sequences using the primers synthesized according to the following table:

TABLE 9

Primers

| Primer | Sequence | SEQ ID NO |
|---|---|---|
| 2944S | CTG CGC CTT ATC CGG TAA CT | SEQ ID NO:33 |
| 5876 | CAG TGA GGC ACC TAT CTC AG | SEQ ID NO:34 |
| 5760 | CAC CAT GAG TGA CGA CTG AA | SEQ ID NO:35 |
| 5761 | TTA ATC GCG GCC TCG AGC AA | SEQ ID NO:36 |
| 5762 | GGC TCA TGT CCA ACA TTA CC | SEQ ID NO:37 |
| 931S | GAG ACG CCA TCC ACG CTG TT | SEQ ID NO:38 |
| 5874 | CAG ACT TAG GCA CAG CAC AA | SEQ ID NO:39 |
| 5104 | GAG CGA GGA AGC GGA AGA GT | SEQ ID NO:40 |
| 3054A | CCG CCT ACA TAC CTC GCT CT | SEQ ID NO:41 |
| 5767 | GAG CAT TAC GCT GAC TTG AC | SEQ ID NO:42 |
| 5768 | ATG CCT CTT CCG ACC ATC AA | SEQ ID NO:43 |
| 5770 | GGC GGT AAT GTT GGA CAT GA | SEQ ID NO:44 |
| 847A | GGC GGA GTT GTT ACG ACA TT | SEQ ID NO:45 |
| 5772 | CAT TGT GCT GTG CCT AAG TC | SEQ ID NO:46 |
| GA seqF1 | CCA GAC CGA GGA GAA GTT CA | SEQ ID NO:47 |
| GA seqF2 | TGC TGG AGG AGA CCT CTG TG | SEQ ID NO:48 |
| GA seqR2 | TCG ATC GCG CGC TTC ATC AC | SEQ ID NO:49 |

Purified VCL-6250 DNA was used to transfect the murine cell line VM92 to determine expression of the IE1 protein. Expression of IE1 was confirmed with a Western Blot assay. Expression was visualized with a commercially available anti-IE1 monoclonal antibody (available from Chemicon International, Temecula, Calif.).

Example 4

Preparation of Vaccine Formulations

In each of the following methods, HCMV antigen-encoding plasmids of the present invention are formulated with the poloxamer system, described herein as VF-P1205-02A. VF-P1205-02A refers to a poloxamer-based delivery system consisting of the non-ionic block copolymer, CRL 1005, and a cationic surfactant, BAK (Benzalkonium chloride 50% solution, available from Ruger Chemical Co. Inc.). Specific final concentrations of each component of the formulae are described in the following methods, but for any of these methods, the concentrations of each component may be varied by basic stoichiometric calculations known by those of ordinary skill in the art to make a final solution having the desired concentrations.

For example, the concentration of CRL 1005 is adjusted depending on, for example, transfection efficiency, expression efficiency, or immunogenicity, to achieve a final concentration of between about 1 mg/ml to about 75 mg/ml, for example, about 1 mg/ml, about 2 mg/ml, about 3 mg/ml, about 4 mg/ml, about 5 mg/ml, about 6.5 mg/ml, about 7 mg/ml, about 7.5 mg/ml, about 8 mg/ml, about 9 mg/ml, about 10 mg/ml, about 15 mg/ml, about 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, or about 75 mg/ml of CRL 1005.

Similarly the concentration of DNA is adjusted depending on many factors, including the amount of a formulation to be delivered, the age and weight of the subject, the delivery method and route and the immunogenicity of the antigen being delivered. In general, formulations of the present invention are adjusted have a final concentration from about 1 ng/ml to about 30 mg/ml of plasmid (or other polynucleotide). For example, a formulation of the present invention may have a final concentration of about 1 ng/ml, about 5 ng/ml, about 10 ng/ml, about 50 ng/ml, about 100 ng/ml, about 500 ng/ml, about 1 µg/ml, about 5 µg/ml, about 10 µg/ml, about 50 µg/ml, about 200 µg/ml, about 400 µg/ml, about 600 µg/ml, about 800 µg/ml, about 1 mg/ml, about 2 mg/ml, about 2.5, about 3 mg/ml, about 3.5, about 4 mg/ml, about 4.5, about 5 mg/ml, about 5.5 mg/ml, about 6 mg/ml, about 7 mg/ml, about 8 mg/ml, about 9 mg/ml, about 10 mg/ml, about 20 mg/ml, or about 30 mg mg/ml of a plasmid.

Certain formulations of the present invention include a cocktail of plasmids, for example, a mixture of two or more of plasmids VCL-6365, VCL-6368, or VCL-6520 of the present invention, and optionally plasmids comprising codon-optimized or non-codon-optimized coding regions encoding other HCMV antigens, e.g., an antigenic portion if HCMV IE1, and/or plasmids encoding immunity enhancing proteins, e.g., cytokines. Various plasmids desired in a cocktail are combined together in PBS or other diluent prior to the addition to the other ingredients. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or up to twice or three times, or more, as much of one plasmid may be included relative to other plasmids in the cocktail.

Additionally, the concentration of BAK may be adjusted depending on, for example, a desired particle size and improved stability. Indeed, in certain embodiments, formulations of the present invention include CRL 1005 and DNA, but are free of BAK. In general BAK-containing formulations of the present invention are adjusted to have a final concentration of BAK from about 0.05 mM to about 0.5 mM. For example, a formulation of the present invention may have a final BAK concentration of about 0.05 mM, 0.1 mM, 0.2 mM, 0.3 mM, 0.4 mM, or 0.5 mM.

The total volume of the formulations produced by the methods below may be scaled up or down, by choosing apparatus of proportional size. Finally, in carrying out any of the methods described below, the three components of the formulation, BAK, CRL 1005, and plasmid DNA, may be added in any order. In each of these methods described below the term "cloud point" refers to the point in a temperature shift, or other titration, at which a clear solution becomes cloudy, i.e., when a component dissolved in a solution begins to precipitate out of solution.

A. Thermal Cycling of a Pre-Mixed Formulation

This example describes the preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is thermally cycled to room temperature (above the cloud point) several times, according to the protocol outlined in FIG. 8.

A 1.28 mM solution of BAK is prepared in PBS, 846 µl of the solution is placed into a 15 ml round bottom flask fitted with a magnetic stirring bar, and the solution is stirred with moderate speed, in an ice bath on top of a stirrer/hotplate (hotplate off) for 10 minutes. CRL 1005 (27 µl) is then added using a 100 µl positive displacement pipette and the solution is stirred for a further 60 minutes on ice. Plasmids VCL-6365 and VCL-6368, and optionally, additional plasmids encoding, e.g., additional HCMV antigens, e.g., VLC-6520, are mixed together at desired proportions in PBS. In the present example, 2.73 ml of a solution containing 3.2 mg/ml VCL-6365 and 3.2 mg/ml VCL-6368 (6.4 mg/ml total DNA) is added drop wise, slowly, to the stirring solution over 1 min using a 5 ml pipette. The solution at this point (on ice) is clear since it is below the cloud point of the poloxamer and is further stirred on ice for 15 min. The ice bath is then removed, and the solution is stirred at ambient temperature for 15 minutes to produce a cloudy solution as the poloxamer passes through the cloud point.

The flask is then placed back into the ice bath and stirred for a further 15 minutes to produce a clear solution as the mixture is cooled below the poloxamer cloud point. The ice bath is again removed and the solution stirred at ambient temperature for a further 15 minutes. Stirring for 15 minutes above and below the cloud point (total of 30 minutes), is defined as one thermal cycle. The mixture is cycled six more times. The resulting formulation may be used immediately, or may be placed in a glass vial, cooled below the cloud point, and frozen at −80° C. for use at a later time.

B. Thermal Cycling, Dilution and Filtration of a Pre-mixed Formulation, using Increased Concentrations of CRL 1005

Figure 9:
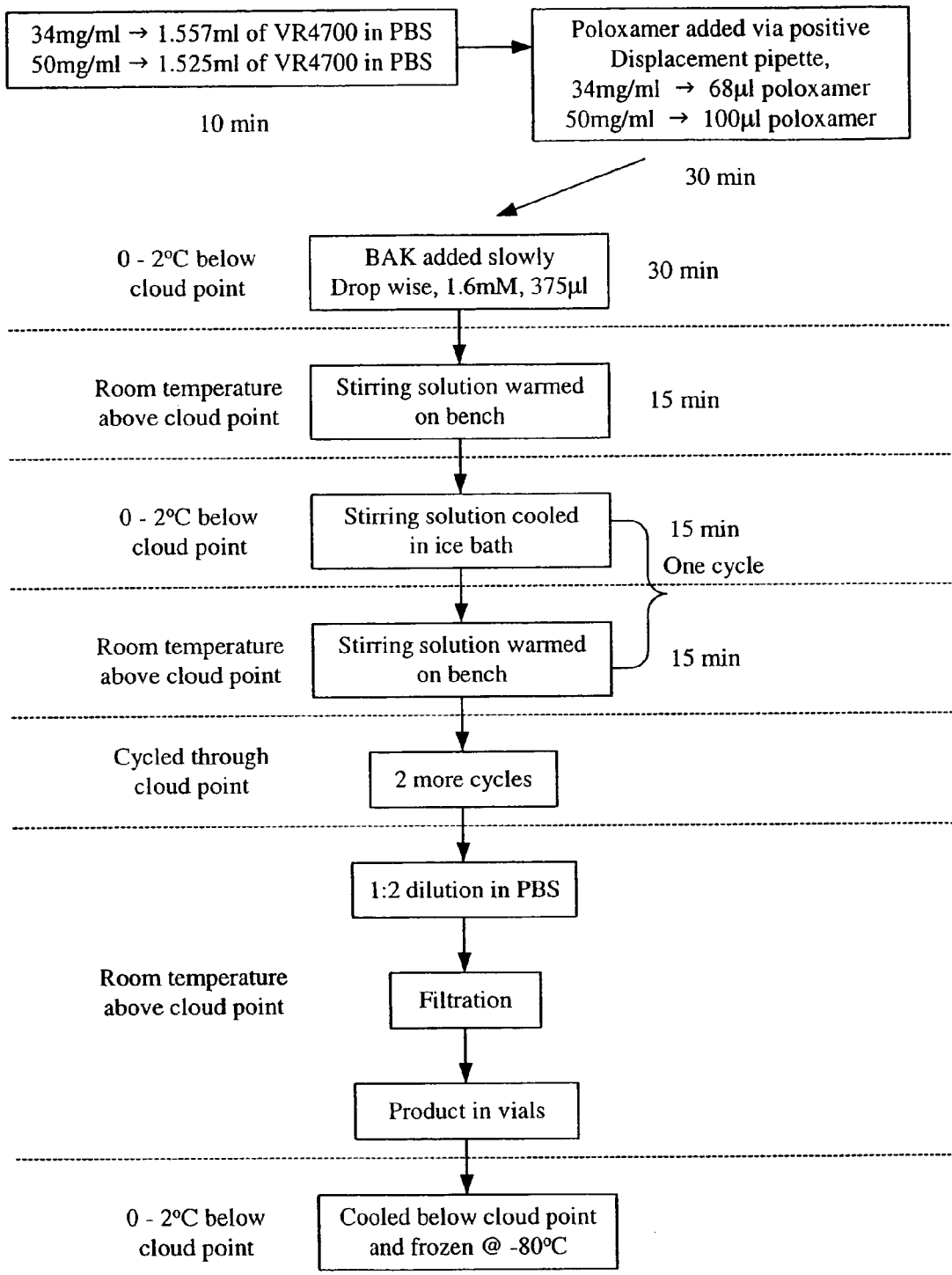
FIG. 9 shows the protocol for the preparation of a formulation comprising 0.3 mM BAK, 34 mg/ml or 50 mg/ml CRL 1005, and 2.5 mg/ml DNA in a final volume of 4.0 ml, through the use of thermal cycling.

This example describes the preparation of a formulation comprising 0.3 mM BAK, 34 mg/ml or 50 mg/ml CRL 1005, and 2.5 mg/ml of DNA in a final volume of 4.0 ml. The ingredients are combined together at a temperature below the cloud point, then the formulation is thermally cycled to room temperature (above the cloud point) several times, diluted, and filtered according to the protocol outlined in FIG. 9.

Plasmids VCL-6365 and VCL-6368, and optionally, additional plasmids encoding, e.g., additional HCMV antigens, e.g., VLC-6520, are mixed together at desired proportions in PBS. For the formulation containing 34 mg/ml CRL 1005, 1.55 ml of a solution containing about 3.2 mg/ml VCL-6365 and about 3.2 mg/ml VCL-6368 (about 6.4 mg/ml total DNA) is placed into the 15 ml round bottom flask fitted with a magnetic stirring bar, and for the formulation containing 50 mg/ml CRL 1005, 1.52 ml of a solution containing about 3.2 mg/ml VCL-6365 and about 3.2 mg/ml VCL-6368 (about 6.4 mg/ml total DNA) is placed into the 15 ml round bottom flask fitted with a magnetic stirring bar, and the solutions are stirred with moderate speed, in an ice bath on top of a stirrer/hotplate (hotplate off) for 10 minutes. CRL 1005 (68 µl for 34 mg/ml final concentration, and 100 µl for 50 mg/ml final concentration) is then added using a 100 µl positive displacement pipette and the solution is stirred for a further 30 minutes on ice. A 1.6 mM solution of BAK is prepared in PBS, and 375 µl is then added drop wise, slowly, to the stirring 34 mg/ml or 50 mg/ml mixtures, over 1 min using a 1ml pipette. The solutions at this point are clear since they are below the cloud point of the poloxamer and are stirred on ice for 30 min. The ice baths are then removed; the solutions stirred at ambient temperature for 15 minutes to produce cloudy solutions as the poloxamer passes through the cloud point.

The flasks are then placed back into the ice baths and stirred for a further 15 minutes to produce clear solutions as the mixtures cooled below the poloxamer cloud point. The ice baths are again removed and the solutions stirred for a further 15 minutes. Stirring for 15 minutes above and below the cloud point (total of 30 minutes), is defined as one thermal cycle. The mixtures are cycled two more times.

In the meantime, two Steriflip® 50 ml disposable vacuum filtration devices, each with a 0.22 µm Millipore Express® membrane (available from Millipore, cat # SCGP00525) are placed in an ice bucket, with a vacuum line attached and left for 1 hour to allow the devices to equilibrate to the temperature of the ice. The poloxamer formulations are then diluted to 2.5 mg/ml DNA with PBS and filtered under vacuum.

The resulting formulations may be used immediately, or may be transferred to glass vials, cooled below the cloud point, and frozen at −80° C. for use at a later time.

C. A Simplified Method without Thermal Cycling

Figure 10:
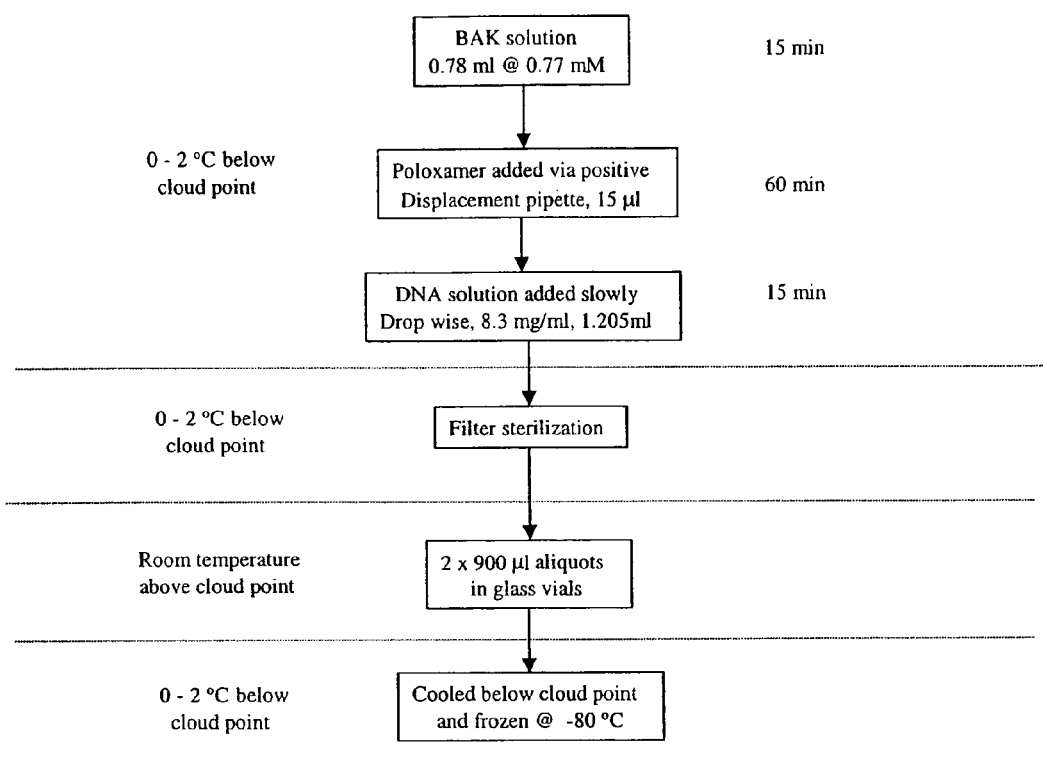
FIG. 10 shows the protocol for the simplified preparation (without thermal cycling) of a formulation comprising 0.3 mM BAK, 7.5 mg/ml CRL 1005, and 5 mg/ml DNA.

This example describes a simplified preparation of a formulation comprising 0.3 mM BAK, 7.5 mg/ml CRL 1005, and 5 mg/ml of DNA in a total volume of 3.6 ml. The ingredients are combined together at a temperature below the cloud point and then the formulation is simply filtered and then used or stored, according to the protocol outlined in FIG. 10.

A 0.77 mM solution of BAK is prepared in PBS, and 780 µl of the solution is placed into a 15 ml round bottom flask fitted with a magnetic stirring bar, and the solution is stirred with moderate speed, in an ice bath on top of a stirrer/hotplate (hotplate off) for 15 minutes. CRL 1005 (15 µl) is then added using a 100 µl positive displacement pipette and the solution is stirred for a further 60 minutes on ice. Plasmids VCL-6365 and VCL-6368, and optionally, additional plasmids encoding, e.g., additional HCMV antigens, e.g., VLC-6250, are mixed together at desired proportions in PBS. In the present example, about 1.2 ml of a solution containing about 4.1 mg/ml VCL-6365 and about 4.2 mg/ml VCL-6368 (about 8.3 mg/ml total DNA) is added drop wise, slowly, to the stirring solution over 1 min using a 5 ml pipette. The solution at this point (on ice) is clear since it is below the cloud point of the poloxamer and is further stirred on ice for 15 min.

In the meantime, two Steriflip® 50 ml disposable vacuum filtration devices, each with a 0.22 μm Millipore Express® membrane (available from Millipore, cat # SCGP00525) are placed in an ice bucket, with a vacuum line attached and left for 1 hour to allow the devices to equilibrate to the temperature of the ice. The poloxamer formulation was then filtered under vacuum, below the cloud point and then allowed to warm above the cloud point. The resulting formulations may be used immediately, or may be transferred to glass vials, cooled below the cloud point and then frozen at −80° C. for use at a later time.

Example 5

Animal Immunization

The immunogenicity of expression products encoded by one or more of the codon-optimized polynucleotides described in Examples 1, 2 and 3, and optionally the codon-optimized polynucleotides described in Example 4, are evaluated based on each plasmid's ability to mount an immune response in vivo. Plasmids are tested individually and in combinations by injecting single constructs as well as multiple constructs. Immunizations are initially carried out in animals, such as mice, rabbits, goats, sheep, primates, or other suitable animal, by intramuscular (IM) injections. Serum is collected from immunized animals, and the immune response is quantitated. The tests of immunogenicity further include measuring antibody titer, neutralizing antibody titer, T cell cytokine production and T cell cytolytic activity. Correlation to protective levels in humans are made according to methods well known by those of ordinary skill in the art. See "immune correlates," above.

A. DNA Formulations

Plasmid DNA is formulated by any of the methods described in Example 4. Alternatively, plasmid DNA is prepared as described above and dissolved at a concentration of about 0.1 mg/ml to about 10 mg/ml, preferably about 1 mg/ml, in PBS with or without transfection-facilitating cationic lipids, e.g., DMRIE/DOPE at a 4:1 DNA:lipid mass ratio. Alternative DNA formulations include 150 mM sodium phosphate instead of PBS, adjuvants, e.g., Vaxfectin™ at a 4:1 DNA: Vaxfectin™ mass ratio, mono-phosphoryl lipid A (detoxified endotoxin) from *S. minnesota* (MPL) and trehalosedicorynomycolateAF (TDM), in 2% oil (squalene)-Tween 80-water (MPL+TDM, available from Sigma/Aldrich, St. Louis, Mo., (catalog # M6536)), a solubilized monophosphoryl lipid A formulation (AF, available from Corixa), or (±)-N-(3-Acetoxypropyl)-N,N-dimethyl-2,3-bis(octyloxy)-1-propanaminium chloride (compound # VC1240) (see Shriver, J. W. et al., *Nature* 415:331-335 (2002), and P.C.T. Publication No. WO 02/00844 A2, each of which is incorporated herein by reference in its entirety).

B. Animal Immunizations

Codon-optimized and wild type DNA plasmids encoding secreted gB and pp65, and their respective mutant variants, as described above, are injected into BALB/c mice as single plasmids, as either DNA in PBS or formulated with the poloxamer-based delivery system: 3 mg/ml DNA, 34 or 50 mg/ml CRL 1005, and 0.3 mM BAK. Groups of 10 mice are immunized three times, at biweekly intervals, and serum is obtained to determine antibody titers to each of the antigens. Groups are also included in which mice are immunized with a trivalent preparation, containing each of the three plasmids in equal mass. The study design for each plasmid is shown in Table 10, and a typical immunization protocol is shown in Table 11.

TABLE 10

Study Design for Plasmids

| Group | Number of animals |
|---|---|
| DNA in PBS | 10 |
| DNA formulated with CRL 1005 and BAK | 10 |
| Plasmid backbone (VR10551), DNA in PBS | 5 |

TABLE 11

Immunization Schedule

| Day | Immunization |
|---|---|
| −3 | Pre-bleed |
| 0 | Plasmid injections, intramuscular, bilateral in rectus femoris, 25 μg/leg |
| 14 | Plasmid injections, intramuscular, bilateral in rectus femoris, 25 μg/leg |
| 20 | Serum collection |
| 28 | Plasmid injections, intramuscular, bilateral in rectus femoris, 25 μg/leg |
| 35 | Serum collection |

Serum antibody titers are determined by ELISA with recombinant proteins or transfection supernatants and lysates from transfected VM-92 cells or virus-infected cell lysates.

C. Production of HCMV pp65 and gB Antisera in Animals

Plasmid DNA encoding HCMV pp65, gB, IE1 or fragments, variants or derivatives therof is prepared according to the immunization scheme described above and injected into a suitable animal for generating polyclonal antibodies. Serum is collected and the antibody titered as above. The titer of anti-HCMV peptide antibodies in serum from immunized animals may be increased by selection of anti-peptide antibodies, for instance, by adsorption to the peptide on a solid support and elution of the selected antibodies according to methods well known in the art.

Monoclonal antibodies are also produced using hybridoma technology (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal antibodies and T-Cell Hybridomas*, Elsevier, N.Y., (1981), pp. 563-681, each of which is incorporated herein by reference in its entirety). In general, such procedures involve immunizing an animal (preferably a mouse) as described above. Suitable cells can be recognized by their capacity to bind anti-HCMV pp65, gB antibody or IE1 antibody. Such cells may be cultured in any suitable tissue culture medium; however, it is preferable to culture cells in Earl's modified Eagle's medium supplemented with 10% fetal bovine serum (inactived at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2/0), available from the American Type Culture Collection, Rockville, Md. After fusion, the resulting hybridoma cells are selectively maintained in HAT medium, and then cloned by limiting dilution as described by Wands et al., *Gastroenterology* 80:225-232 (1981), incorporated herein by reference in its entirety. The hybridoma cells obtained through such a selection are then assayed to identify clones which secrete antibodies capable of binding HCMV pp65 or gB.

Alternatively, additional antibodies capable of binding to HCMV pp65 or gB may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, HCMV pp65 or gB specific antibodies are used to immunize an animal, preferably a mouse. The splenocytes of such an animal are then used to produce hybridoma cells, and the hybridoma cells are screened to identify clones which produce an antibody whose ability to bind to the HCMV protein-specific antibody can be blocked by HCMV pp65 or gB. Such antibodies comprise anti-idiotypic antibodies to the HCMV protein-specific antibody and can be used to immunize an animal to induce formation of further HCMV pp65 or gB-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, HCMV pp65 or gB-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

These antibodies are used, for example, in diagnostic assays, as a research reagent, or to further immunize animals to generate HCMV-specific anti-idiotypic antibodies. Non-limiting examples of uses for anti-HCMV antibodies include use in Western blots, ELISA (competitive, sandwich, and direct), immunofluorescence, immunoelectron microscopy, radioimmunoassay, immunoprecipitation, agglutinations assays, immunodiffisuon, immunoelectrophoresis, and epitope mapping (Weir, D. Ed. *Handbook of Experimental Immunology*, 4$^{th}$ ed. Vols. I and II, Blackwell Scientific Publications (1986)).

Example 6

Quantitative, Real Time RT-PCR Analysis of mRNA Expression of Constructs Encoding HCMV pp65 and gB, and Fragments, Variants and Derivatives Thereof Quantitation of the mRNA levels expressed from the HCMV pp65, gB and IE1 constructs is a valuable biological marker for gene activity. Various methods can be used to measure the levels of mRNA, such as Northern blots, slot blots, and other techniques known to those skilled in the art. However, a rapid method based on real-time RT-PCR provides an efficient, reliable means to monitor gene activity. One such system is the TaqMan® RT-PCR assay used with an ABI PRISM® Sequence Detection System, both available from Applied Biosystems, Inc. (Foster City, Calif.).

Briefly, RNA is extracted using conventional or commercially available techniques. After extraction, the RNA is aliquotted into optically transparent tubes or wells of a microtiter plate containing the provided buffers, enzymes, and reagents supplied with the appropriate kit, e.g., TaqMan® Gold RT-PCR Kit (Applied Biosystems, Inc., Foster City, Calif.). Additionally, the construct specific primers and probe, which can be designed by a person skilled in the art based on the sequences described herein, or commercially, e.g., ABI PRISM®. Primers & TaqMan® Probes Synthesis Service (Applied Biosystems, Inc., Foster City, Calif.) are added. The samples are placed in the ABI PRISM® Sequence Detection System, a thermocycler coupled to a laser capable of exciting the fluorophores present on the probe and a suitable detection system. Initially, the RNA is reverse transcribed into DNA, then thermostable DNA polymerase and sequence-specific primers contained in the reaction solution initiate the temperature-controlled amplification cycles. The probe used for detection of the amplification product is labeled with a low energy fluorophore (the reporter) and a high energy fluorophore (the quencher), which prevents emissions of the reporter from being detected if the quencher is closely associated with the reporter through fluorescence resonance energy transfer (FRET). At the beginning of the reaction cycle, the probe is in excess, so the majority remains unhybrized and intact, resulting in no signal. However, as the DNA product accumulates, a higher proportion of the probe is bound to the DNA. The bound probe is then degraded by the 5' nuclease activity of the DNA polymerase used for the amplification, which releases the reporter from the quencher and creates a detectable signal. As the PCR reaction progresses and the amplified product accumulates, more of the probe is degraded, inducing a greater signal that is recorded. The number of amplification cycles necessary to detect a signal (Ct) is directly proportional to the amount of starting template, or construct mRNA. By comparing Ct values between the sample and controls starting with a known amount of RNA, it is possible to quantitate the amount of mRNA expressed in cells transfected with plasmids containing the HCMV constructs. See the Applied Biosystem, Inc. tutorial "Real-Time PCR Vs. Traditional PCR" on the world wide web at www.appliedbiosystems.com/support/tutorials/, visited Nov. 15, 2002. Other real time detection systems include "Molecular Beacon" probes, see, e.g., U.S. Pat. No. 6,103,476 to Kramer and Tyagi, which is incorporated herein by reference.

For the in vitro studies, suitable cells are seeded into 24 well tissue culture plates. Once the cells are at an appropriate cell density, plasmid DNA containing codon-optimized and non-codon-optimized HCMV constructs or appropriate controls, e.g. negative controls containing the plasmid backbone with no HCMV construct, is used to transfect the cells. At various time-points post-transfection, the cells are collected for RNA extraction, for example with 4M guanidinium thiocyanate followed by phenol extraction. Cells collected from in vivo studies are also used for RNA extraction. The extracted total RNA is quantitated by measuring the absorbance of the sample at 260 nm, diluted according to the Taqman® kit instructions (Applied Biosystems, Inc., Foster City, Calif.), and aliquotted into 386 well plates suitable for real-time PCR containing the buffers, nucleotides, and enzymes necessary. Controls containing known amounts of starting RNA are included in the assay, and optionally an internal standard may be included in the samples for quality assurance. This internal standard is typically an unrelated gene product, usually an abundant endogenous RNA. Primers and probes specific for the construct and optionally internal standard are also included. The primers are designed and synthesized in the same manner as conventional PCR primers, which is a routine task for one of skill in the art. To ensure reproducibility and specificity, multiple primer sets are used in the reaction, each targeting different regions of the construct. The primer is synthesized in a similar manner, but the fluorophores, e.g. FAM and TAMRA, are covalently attached by conventional methods. The reaction proceeds as described above, and the resulting Ct values of the samples are compared to those of the controls. Starting quantities of the mRNA are interpolated using the control Ct values.

After mRNA quantitation, the mRNA level is correlated with protein expression, both intracellular and secreted. Supernatant is collected from the tissue culture medium (or from the supernatant of centrifuged cells collected in vivo) at various time-points post-transfection. Additionally, a suitable number of cells are retained after harvesting for use in protein extraction. Western blots, slot blots, ELISA and other protein quantitation techniques are used to measure the HCMV protein levels produced by the transfected cells.

Example 7

Demonstration of Immunogenicity Plasmids Encoding Human CMV Antigens

General Experimental Procedure

The experimental procedure for the following example is as described above, with particular parameters and materials employed as described herein.

Plasmids

As described above, constructs of the present invention were inserted into the expression vector VR10551.

VR10551 is an expression vector without any transgene insert (backbone for the HCMV plasmids).

VR6365 contains the coding sequence for a secreted version of human CMV gB (amino acids 1-713) cloned into the VR10551 expression vector (Example 1). The DNA was prepared using Qiagen plasmid purification kits, and was characterized and formulated with the VF-P1205-02A poloxamer-based delivery system.

VR6368 contains the coding sequence of the full-length HCMV pp65, deleted of residues $^{435}$RKRK$^{438}$ in the putative kinase domain, cloned into the VR10551 expression vector (Example 2). The DNA was prepared using Qiagen plasmid purification kits, and was characterized and formulated with the VF-P1205-02A poloxamer-based delivery system, as above.

Poloxamer Formulation

The VF-P1205-02A poloxamer-based delivery system was formulated using a protocl equivalent to Example 4B, with an initial DNA, poloxamer and BAK concentration of 5.0 mg/ml, 7.5 mg/ml and 0.3 mM, respectively. Formulations were diluted with PBS at room temperature to the required experimental concentrations prior to injection.

Vaccination Regimen

Groups of nine, 6- to 8-week old female BALB/c mice (Harlan-Sprague-Dawley) received intramuscular (rectus femoris) injections containing 100 μg of pp65 DNA, 100 μg of gB DNA, or 100 μg each of pp65 and gB DNA delivered with PBS or the CRL 1005 poloxamer formulation described above. Control mice received 100 μg of pp65 DNA or 100 μg of gB DNA mixed with 100 μg of non-coding, vector DNA (VR10551) delivered with PBS or VF-P1205-02A. All mice received two vaccinations (administered on days 0 and 13) containing a total of 200 μg of DNA, 100 μg pp65 DNA and the 100 μg gB DNA. Sera were collected after the first (day 11) and second (day 22) vaccinations, and gB- and pp65-specific antibody responses were measured by ELISA and immunoblot analysis, respectively.

Recombinant gB Enzyme Linked Immunosorbent Assay (ELISA)

Sera were collected from the mice vaccinated according to the regimen described above. Anti-gB IgG titers were determined using a recombinant CMV gB Enzyme Linked Immunosorbent Assay (ELISA).

Ninety six-well, half area, high-binding EIA (Enzyme ImmunoAssay) plates were coated with recombinant CMV gB at a concentration of 0.05 μg/well (50 μL/well) in Borate Buffered Saline (BBS) buffer at 4° C. overnight. Plates were covered with an adhesive plate sealer for all incubations. After coating, plates were blotted on paper towels and 100 μL of blocking buffer (0.1% [w/v] BSA in BBS) was added to each well. Sealed plates were incubated at room temperature for 2 hours and were then stored at 4° C. until sera had been diluted. Sera were diluted in 0.5% (w/v) BSA in BBS in Eppendorf tubes, and were mixed by inversion and brief vortexing. Blocked plates were blotted and 100 μL of diluted serum was added to each well. Plates were sealed and incubated overnight at 4° C. Plates were then washed on a four wash cycle on an automated plate washer with 0.1% (v/v) Tween-20 in BBS and were blotted on paper towels. Alkaline phosphate labeled anti-mouse IgG Fc secondary antibody was diluted 1:2000 in 0.5% (w/v) BSA in BBS and 80 μL of diluted secondary antibody was added to each well. Plates were sealed and were incubated at room temperature for 2 hours. Plates were washed again on the four wash cycle on the automated plate washer and were blotted on paper towels. Fifty microliters of developing solution (1 mg/ml para-nitrophenyl phosphate in 50 mM sodium bicarbonate buffer, pH 9.8 and 1 mM MgCl$_2$) was added to each well, plates were sealed and incubated at room temperature. Absorbance at 405 nm, A405, (single wavelength) was read on the plate reader. Titers were determined as the dilution at which the mean absorbance value of the immune serum was at least twice that of the mean absorbance value for the pre-immune serum at a dilution of 1:100.

Immunoblots to Detect pp65

Lysates from murine melanoma VM92 cells transfected with either VR6368 or VR10551 were made directly in 1× NuPAGE LDS sample buffer and were stored at −80° C. until needed. After thawing at room temperature, one tenth of the sample volume of 0.5 MM dithiothreitol was added to each sample. Samples were then heated at 85° C. for 10 min and were cooled immediately on ice prior to loading on NuPAGE 4-12% Bis-Tris gels. Electrophoresis was carried out at 200 V for 60 minutes at room temperature. For transfer of proteins, polyvinylidene difluoride (PVDF) membranes were first soaked in methanol for 30 s and then equilibrated in 1× NuPAGE transfer buffer containing 20% (v/v) methanol. Proteins were transferred from gels to PVDF membranes at 30V for 60 min at room temperature. After protein transfer, membranes were rinsed in milli-Q water and then blocked for 45 min at room temperature in 1% (w/v) BSA in BBS on an orbital shaker. After blocking, membranes were stored at 4° C. in 1% (w/v) BSA in BBS for no longer than 24 hr. Blots were cut into strips and were incubated in mouse immune serum diluted in 0.5% (w/v) BSA in BBS at room temperature overnight on an orbital shaker. After washing in BBS, the strips were incubated in secondary antibody (goat anti-mouse IgG Fcγ conjugated to alkaline phosphatase) at room temperature for 2.5 hr. Strips were then washed again in BBS and were developed in alkaline phosphatase substrate solution for 10 min at room temperature. Strips were then rinsed thoroughly in distilled water and were allowed to dry at room temperature between paper towels.

Mice were vaccinated with gB plasmid (VR6365) or gB/pp65 plasmid combination, as described above. The anti-gB IgG titers, measured after two vaccinations in mice vaccinated with gB plasmid (VR6365), alone or in combination with pp65 plasmid (VR6368) are given below:

TABLE 12

Anti-gB IgG titers Following 2$^{nd}$ Vaccination

| Group | mean reciprocal titer (range) | geometric mean reciprocal titer |
|---|---|---|
| gB (poloxamer formulation) | 42,667 (12,800-102,400) | 34,836 |
| Combination (poloxamer formulation) | 17,244 (1,600-25,600) | 13,825 |
| gB (naked DNA) | 29,867 (12,800-51,200) | 27,650 |
| Combination (naked DNA) | 10,667 (3,200-25,600) | 8,709 |

All mice vaccinated with plasmid DNA encoding HCMV gB alone or in combination, either with or without VF-P1205-02A, had detectable anti-gB IgG titers after two injections of DNA. Sera from mice injected with pp65 DNA only were pooled and tested. The binding activity for the pp65 only group was the same as for the pre-bleed sera, indicating that gB specific antibodies were not detected.

pp65 Immunoblots

Mouse sera collected after the second DNA vaccination were tested on immunoblots of lysates from cells transfected with pp65 plasmid (VR6368) as described above to determine, qualitatively, the difference in the antibody responses to pp65 in mice vaccinated with VR6368 alone and mice vaccinated with the plasmid combination. In the first set of immunoblots, pooled sera from each group of mice vaccinated with VR6368 were tested at dilutions of 1:200, 1:400, 1:800, 1:1000 and 1:2000. A sample of pooled sera from mice vaccinated with VR6365 (gB) formulated in VF-P1205-02A was included as a negative control. A pp65-specific murine monoclonal antibody was included as a positive control. Each immunoblot strip had a lane of molecular weight standards, a lane containing VR6368-transfected cell lysate, and a VR10551 transfected cell lysate control lane. All mice (nine of nine) vaccinated with pp65 DNA formulated with VF-P1205-02A had detectable antibody to pp65 by immunoblot when sera were tested at dilution of 1:200. Six of nine mice vaccinated with the bivalent HCMV plasmid vaccine formulated with VF-P1205-02A had detectable antibody to pp65 by immunoblot when tested at dilution of 1:200. Immunoblot titration of pooled sera from the mice vaccinated with either the pp65 DNA formulated with VF-P1205-02A, or the bivalent HCMV plasmid vaccine formulated with VF-P1205-02A did not reveal a marked difference in the antibody response to pp65 between the groups. No pp65 antibody was detected in mice vaccinated with gB DNA alone.

Thus, plasmids VR6365 (gB) and VR6368 (pp65) elicited the production of antigen-specific antibodies in mice that received two injections of the plasmids either alone or in combination. Although we cannot quantify the anti-pp65 antibody response using immunoblots, they do show that the majority of mice had a detectable antibody response to pp65, and that the combination of the two plasmids did not result in complete suppression of the response to pp65. Antibody responses to pp65 in this study served as an additional readout for confirmation of production of this protein in vivo after vaccination with VR6368.

pp65-specific IFN-γ ELISpot Assay

T cell responses to the DNA-encoded pp65 were determined by IFN-γ ELISpot assay. Splenocytes of vaccinated mice were stimulated with two separate pools of overlapping peptides, that, together, span the entire pp65 protein and should contain all possible T cell epitopes. Therefore, the type of the T cell (e.g., $CD8^+$ or $CD4^+$) that is producing IFN-γ in response to the peptide stimulation cannot be distinguished by this assay method. Theoretically, these peptides can be presented in the context of class I or class II MHC, thus stimulating both $CD8^+$ and $CD4^+$ T cells within the same splenocyte preparation.

In these assays the number of antigen-specific spots were usually >10-fold more than the number in control wells. IFN-γ producing cells were detected in splenocyte preparations from VR6368-vaccinated mice stimulated with either of the peptide pools, but approximately three times as many spots were detected in response to Pool I than to Pool II. Few to no spots were produced by splenocytes of gB-vaccinated mice in response to stimulation with either of the peptide pools.

These data demonstrate that the HCMV DNA vaccine component pp65 was expressed in vivo at levels sufficient to induce cellular immune responses, either when it was administered alone or in combination, in the VF-P1205-02A formulation.

Example 8

Confirmation of Immunogenicity Plasmids Encoding Human CMV Antigens

General Experimental Procedure

The experimental procedure for the following example is as described above, with particular parameters and materials employed as described herein.

Plasmids

As described above, constructs of the present invention, VR6365 and VR 6368 were constructed by inserting the appropriate inserts into the expression vector VR10551, and were formulated with poloxamer formulation VF-P1205-02A where noted.

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without VF-P1205-02A on days 0, 21, and 49. Each mouse received 200 μg of DNA per vaccination. For formulations containing a single gB or pp65 coding plasmid, 100 μg of blank DNA (VCL10551), which served as a filler, was included. The effect of the blank DNA was tested by vaccinating mice with 100 µg of the single plasmid DNAs delivered with or without VF-P1205-02A in the absence of the filler DNA. Serum samples were collected prior to the first vaccination (day −1) and after each vaccination (days 20, 48, and 63) and gB-specific antibodies were measured by ELISA.

Recombinant gB Enzyme Linked Immunosorbent Assay (ELISA)

Sera were collected from the vaccinated mice, and anti-gB IgG titers were determined using a recombinant CMV gB Enzyme Linked Immunosorbent Assay (ELISA) as described in Example 7.

The anti-gB IgG titers in sera from mice vaccinated with VCL-6365, either alone or in combination with VCL-6368 are given below:

TABLE 13

Anti-gB IgG Titers

| Immunogen | Bleed 2 (Day 48) $Log_{10}$ mean titer (range) | Bleed 3 (Day 63) $Log_{10}$ mean titer (range) |
| --- | --- | --- |
| gB + pp65 in PBS | 4.6 (4.4-4.7) | 4.78 (4.4-5.0) |
| gB + pp65 + VF-P1205-02A | 4.7 (4.1-5.0) | 4.96 (4.7-5.3) |
| gB + neg. control plasmid | 4.98 (3.8-5.3) | 5.25 (4.1-5.6) |
| gB + neg. control plasmid + VF-P1205-02A | 4.87 (4.4-5.3) | 5.14 (4.7-5.6) |
| gB in PBS | 4.82 (4.4-5.3) | 5.15 (4.7-5.6) |
| gB + VF-P1205-02A | 4.73 (4.4-5.0) | 5.1 (4.7-5.3) |

Plasmid VCL6365 (gB) elicited the production of gB-specific antibodies in mice that received three injections of the plasmids either alone or in combination. All mice vaccinated with VCL6365 had detectable anti-gB IgG titers after two injections. These data confirm the immunogenicity of the gB plasmid product in vivo when VCL6365 is delivered in combination with VCL6368 in the VF-P1205-02A formulation.

Example 9

Plasmid Encoding Human CMV IE1 is Immunogenic

General Experimental Procedure

The experimental procedure for the following example is as described above, with particular parameters and materials employed as described herein.

Vaccination Regimen

Mice received bilateral, intramuscular injections into the rectus femoris of the IE1 plasmid VR6250. The total DNA doses as shown below were each in a 100 µl volume in PBS, but was administered as two equal volume injections, one into each rectus femoris muscle of each mouse. The negative control group contained 5 mice and all other groups contained 10 mice. Mice received injections on days 0 and 14. Splenocytes were analyzed for IE1 reactivity by ELISpot assay in which splenocytes were stimulated with a pool of 98 overlapping 15 mer peptides (overlapping by 11 amino acids) that span the entire IE1 protein encoded on the VR6250 construct. Splenocytes from the negative control group were harvested on day 24 and were analyzed for non-specific stimulation of IFN-γ secreting T-cells with the IE1 peptide pool. Splenocytes from the groups injected with IE1 DNA were harvested for analysis of antigen specific, IFN-γ secreting, T-cell responses on days 27-29. Two spleens from each group were pooled for the assay. Two pools from each group were analyzed on days 27 and 28, one pool from each group was analyzed on day 29. The values reported below represent the average of 5 splenocyte pools per experimental group.

IFN-γ ELISpot Assay

T cell responses to the DNA vaccines were determined by quantifying the number of splenocytes secreting IFN-γ in response to antigen-specific stimulation as measured by IFN-γ ELISpot assay. ImmunoSpot plates (Cellular Technology Limited, Cleveland, Ohio) were coated with rat anti-mouse IFN-γ monoclonal antibody (BD Biosciences, San Diego, Calif.), and blocked with RPMI-1640 medium. Splenocyte suspensions were isolated from individual vaccinated mice and added to ELISpot plates at $1 \times 10^6$ or $3.3 \times 10^5$ cells/well in RPMI medium containing 5 µg/mL of each of the overlapping IE1 peptides as stimulating antigen. Control wells contained $1 \times 10^6$ splenocytes incubated in medium (no antigen). After a 20-hour incubation at 37° C., captured IFN-γ was detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), were quantified by an ImmunoSpot Analyzer (Cellular Technology Limited, Cleveland, Ohio). The results are expressed as spot forming units (SFU) per $10^6$ cells.

TABLE 14

IE1 ELISpot Results

| DNA & Dose | 100 µg Blank | 1 µg VR6250 | 3 µg VR6250 | 10 µg VR6250 | 30 µg VR6250 | 100 µg VR6250 |
| --- | --- | --- | --- | --- | --- | --- |
| SFU/$10^6$ cells | 6 | 5 | 77 | 289 | 367 | 501 |

The data shows that administering the IE1 plasmid VR6250 induced an antigen specific immune response, and that the immune response was DNA dose dependent. Additionally, this indirectly confirms that the IE1 protein was expressed in vivo.

Example 10

Formulation Selection Studies

The potency of different vaccine formulations was evaluated in two experimental mouse immunogenicity studies using murine CMV M84. Murine CMV M84 is considered a homolog of the human CMV pp65, and thus served as a surrogate for the pp65 antigen. The first study measured lipid dose responses using a fixed quantity of DNA while the second study evaluated clinically relevant doses of DNA by dose escalation.

Formulations

DMRIE/DOPE in a 1:1 molar ration was produced as a lipid film containing 46.2% DMRIE and 53.8% DOPE by weight (5.14 mg total dried lipid). Prior to injection, the dried, mixed lipid film was hydrated in sterile water for injection to form cationic liposomes that were then added to DNA at the appropriate concentration in 2×PBS. DNA was formulated with DMRIE/DOPE as follows:

TABLE 15

DNA Formulations

| DNA Concentration (mg/mL) | DNA:Lipid* |
|---|---|
| 0.5 | 2:1 |
| 1.0 | 4:1 |
| 3.0 | 10:1 |

*DNA(assigned MW = 333 gr/mol):cationic lipid molar ratio

For the lipid dose response studies the DMRIE/DOPE formulations listed above were diluted to a final vaccinating concentration of 0.5 mg/mL of M84 DNA. For the DNA dose escalation studies the formulations were not diluted prior to injection.

Poloxamer formulations for the lipid dose response study were produced with 5 mg/mL of M84 DNA, 7.5 mg/mL of CRL 1005, and 0.3 mM of benzylalkonium chloride (BAK) surfactant. Prior to injection, the formulations for the lipid dose response study were diluted to a final vaccinating concentration of 0.5 mg/mL of M84 DNA. In the DNA dose escalation studies, the formulations were produced with 3 mg/mL of the appropriate plasmid DNA, 4.5 mg/mL of CRL 1005, and 0.18 mM BAK. These formulations were not diluted prior to injection.

Vaccination Regimen

Groups of nine, six- to eight-week old BALB/c mice (Harlan-Sprague-Dawley) received bilateral (50 μL/leg) intramuscular (rectus femoris) injections of plasmid DNA formulated with DMRIE/DOPE or CRL 1005 in PBS. Control mice received DNA in PBS alone. All mice were boosted on (approximately) days 21 and 49. Two weeks after the last immunization, splenocytes were harvested from three mice/group/day for three sequential days, and antigen specific T cell responses were measured by IFN-γ ELISpot assay.

Cell Culture Media

Splenocyte cultures were grown in RPMI-1640 medium containing 25 mM HEPES buffer and L-glutamine and supplemented with 10% (v/v) FBS, 55 μM β-mercaptoethanol, 100 U/mL of penicillin G sodium salt, and 100 μg/mL of streptomycin sulfate.

IFN-γ ELISpot Assay

T cell responses to the DNA vaccines were determined by quantifying the number of splenocytes secreting IFN-γ in response to antigen-specific stimulation as measured by IFN-γ ELISpot assay. ImmunoSpot plates (Cellular Technology Limited, Cleveland, Ohio) were coated with rat anti-mouse IFN-γ monoclonal antibody (BD Biosciences, San Diego, Calif.), and blocked with RPMI-1640 medium. Splenocyte suspensions were produced from individual vaccinated mice and seeded in ELISpot plates at $1\times10^6$, $3\times10^5$, or $1\times10^5$ cells/well in RPMI medium containing 1 μg/mL of the appropriate MHC class I-restricted peptide (M84, $^{297}$AYAGLFTPL$^{305}$, (SEQ ID NO:32) lmgenex, San Diego, Calif.), 1 U/mL of recombinant murine IL-2 (Roche, Indianapolis, Ind.). Control wells contained $1\times10^6$ splenocytes incubated in medium with IL-2 only (no antigen). After a 20-hour incubation at 37° C., captured IFN-γ was detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), were quantified by an ImmunoSpot reader (Cellular Technology Limited, Cleveland, Ohio). Statistically significant differences between the T cell responses of mice vaccinated with lipid- or poloxamer-formulated DNA and naked DNA was determined using a Student's t-test with α=0.05.

The M84-specific CD8+ T cell responses of mice vaccinated with 50 μg of M84 DNA formulated with DMRIE/DOPE ("D/D") at the DNA:lipid molar ratios indicated, CRL 1005, or PBS alone are given below.

TABLE 16

CD8 + T Cell Responses

| Vaccine Formulation | Mean SFU/$10^6$ Splenocytes CD8 + T cells |
|---|---|
| PBS | 299 |
| 2:1 D/D | 243 |
| 4:1 D/D | 179 |
| 10:1 D/D | 299 |
| CRL 1005 | 344 |

The M84-specific CD8+ T cell responses of mice vaccinated with escalating doses of M84 DNA formulated with DMRIE/DOPE (D/D) at the DNA:lipid molar ratios indicated versus M84 DNA formulated with CRL 1005 or PBS alone are given below.

TABLE 17

CD8 + T Cell Responses

| Vaccine Formulation (DNA Dose) | Mean SFU/$10^6$ Splenocytes CD8 + T cells |
|---|---|
| PBS (300 μg) | 533 |
| 2:1 D/D(50 μg) | 184 |
| 4:1 D/D(100 μg) | 158 |
| 10:1 D/D(300 μg) | 243 |
| CRL 1005 (300 μg) | 416 |

Example 11

Experiments Employing HCMV Antigens

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without CRL 1005 (the VF-P1205-02A formulation) on days 0 and 13. Each mouse received 200 μg of DNA per vaccination. For formulations containing a single gB or pp65 coding plasmid, 100 μg of blank DNA (VR10551) was added to yield 200 μg of total DNA. Beginning approximately three weeks after the primary immunization (on day 22), splenocytes were harvested from vaccinated mice and pp65-specific T cell responses were measured by IFN-g ELISpot assay. Three ELISpot assays were performed: assay one measured the immune response from a pool of splenocytes from three mice per group and assays two and three measured the immune response from a pool of splenocytes from two mice per group. The immune responses of the additional two mice in each group were not measured in this series of assays.

IFN-γ ELISpot Assay

T cell responses to DNA-encoded pp65 were determined by quantifying the number of splenocytes secreting IFN-γ in response to stimulation with pp65-derived peptides (Bio-Synthesis, Lewisville, Tex.). ImmunoSpot plates (Millipore, Billerica, Mass.) were coated with rat anti-mouse IFN-γ monoclonal antibody (BD Biosciences, San Diego, Calif.) and blocked with RPMI-1640 medium containing 25 mM HEPES buffer and L-glutamine and supplemented with 10% (v/v) heat inactivated FBS, 55 mM b-mercaptoethanol, 100 U/mL of penicillin G sodium salt, and 100 μg/mL of streptomycin sulfate (10% RPMI). Splenocyte suspensions were produced from vaccinated mice, resuspended in 10% RPMI medium at a density of $2 \times 10^7$ cells/mL, and seeded in triplicate wells of two separate ImmunoSpot plates at a density of $5 \times 10^5$ or $2.5 \times 10^5$ cells/well. Splenocytes were stimulated with two separate pools of overlapping pp65 peptides (one pool per plate) that, together, span the entire pp65 protein and should include all possible T cell epitopes. Therefore, the type of T cell (e.g., CD8+ or CD4+) that is producing IFN-γ in response to the peptide stimulation cannot be distinguished by this assay method. Theoretically, these peptides can be presented in the context of class I or class II MHC, thus stimulating both CD8+ and CD4+ T cells within the same splenocyte preparation. The peptide pools contained 68 (pool I) or 69 (pool II) peptides of 15 amino acids each (except one 13 amino acid peptide in pool II), and each peptide was represented at a final concentration of 5 μg/mL in the assay well. Control wells contained $5 \times 10^5$ cells in medium only (no peptide antigen). After a 21-hour incubation at 37° C., captured IFN-γ was detected by the sequential addition of biotin-labeled rat anti-mouse IFN-γ monoclonal antibody (BD Biosciences, San Diego, Calif.) and avidin-horseradish peroxidase. Spots produced by the conversion of the colorimetric substrate, 3-amino-9-ethylcarbazole (AEC), were quantified by an ImmunoSpot reader (Cellular Technology Limited, Cleveland, Ohio). Data are presented as the number of Spot Forming Units (SFU), produced in response to antigen-specific stimulation, per million cells assayed. The antigen-specific stimulation was calculated by subtracting the mean number of spots in wells containing splenocytes incubated in medium alone (the non-specific, background response) from the number of spots in wells containing the identical splenocyte preparation incubated with a pool of pp65-derived peptides. Three replicate wells were used to determine the mean non-specific background response. Each SFU corresponds to one pp65-specific T cell. Due to the small sample size (n=3), a statistical analysis of the difference of the means was not performed.

Experiment 1—See Tables 18 and 19.

TABLE 18

T Cell Responses to CMV pp65 Peptide Pool I

| DNA Vaccine | Mean SFU/$10^6$ Cells | Fold Increase versus pp65 + gB |
|---|---|---|
| pp65 + gB | 170 | — |
| pp65 + gB + CRL 1005 | 705 | 4.1 |
| pp65 + Blank | 681 | 4.0 |
| pp65 + Blank + CRL 1005 | 780 | 4.6 |
| gB + Blank | 1 | 0 |
| gB + Blank + CRL 1005 | 2 | 0 |

TABLE 19

T Cell Responses to CMV pp65 Peptide Pool II

| DNA Vaccine | Mean SFU/$10^6$ Cells | Fold Increase versus pp65 + gB |
|---|---|---|
| pp65 + gB | 80 | — |
| pp65 + gB + CRL 1005 | 208 | 2.6 |
| pp65 + Blank | 374 | 4.7 |
| pp65 + Blank + CRL 1005 | 225 | 2.8 |
| gB + Blank | 0 | 0 |
| gB + Blank + CRL 1005 | 0 | 0 |

Experiment 2

The experiment above was repeated, and although the pp65+gB group had responses to peptide pool I that were 2.4-fold higher than that measured in the study reported in detail above, the results were similar.

TABLE 20

T CELL RESPONSES TO CMV PP65 PEPTIDE POOL I

| DNA Vaccine | Mean SFU/$10^6$ Cells | Fold Increase versus pp65 + gB |
|---|---|---|
| pp65 + gB | 407 | — |
| pp65 + gB + CRL 1005 | 444 | 1.1 |
| pp65 + Blank | 435 | 1.1 |
| pp65 + Blank + CRL 1005 | 762 | 1.9 |
| gB + Blank | ND | — |
| gB + Blank + CRL 1005 | ND | — |

TABLE 21

T Cell Responses to CMV pp65 Peptide Pool II

| DNA Vaccine | Mean SFU/$10^6$ Cells | Fold Increase versus pp65 + gB |
|---|---|---|
| pp65 + gB | 100 | — |
| pp65 + gB + CRL 1005 | 158 | 1.6 |
| pp65 + Blank | 140 | 1.4 |
| pp65 + Blank + CRL 1005 | 225 | 2.3 |
| gB + Blank | 0 | — |
| gB + Blank + CRL 1005 | 0 | — |

Experiment 3

Vaccination Regimen

Groups of nine, 6- to 8-week old female BALB/c mice (Harlan-Sprague-Dawley) received bilateral, intramuscular (rectus femoris) injections (50 μl/leg) containing plasmid DNA encoding pp65, gB, or pp65 and gB with or without CRL 1005 (the VF-P1205-02A formulation) on days 0, 21, and 49. Each mouse received 200 μg of DNA per vaccination. For formulations containing a single gB or pp65 coding plasmid, 100 μg of blank DNA (VCL10551) was added to yield a 200 μg dose of total DNA. The effect of the blank DNA was tested by vaccinating mice with 100 μg of the single plasmid DNAs delivered with or without CRL 1005 in the absence of the blank DNA. Splenocytes were harvested beginning day 66 and pp65-specific T cell responses were analyzed by IFN-γ ELISpot as above. Based on previous results, no pp65-specific T cell responses were anticipated for mice vaccinated with gB+blank DNA or gB+blank DNA+CRL 1005. Therefore, these mice were not evaluated in the ELISpot assays. Statistically significant differences between the mean T cell responses of vaccinated mice versus pp65+gB was determined using a Student's t-test with α=0.05.

TABLE 22

T Cell Responses to CMV pp65 Peptide Pool I

| DNA Vaccine | Mean SFU/$10^6$ Cells | Fold Increase versus pp65 + gB | p-value |
|---|---|---|---|
| pp65 + gB | 783 | — | — |
| pp65 + gB + CRL 1005 | 1360 | 1.7 | 0.03 |
| pp65 + Blank | 1265 | 1.6 | 0.02 |
| pp65 + Blank + CRL 1005 | 1308 | 1.7 | 0.03 |
| pp65 | 1184 | 1.5 | NS |
| pp65 + CRL 1005 | 1767 | 2.3 | 0.01 |

NS = not significant

TABLE 23

T Cell Responses to CMV pp65 Peptide Pool II

| DNA Vaccine | Mean SFU/$10^6$ Cells | Fold Increase versus pp65 + gB | p-value |
|---|---|---|---|
| pp65 + gB | 234 | — | — |
| pp65 + gB + CRL 1005 | 544 | 2.3 | 0.04 |
| pp65 + Blank | 496 | 2.1 | 0.04 |
| pp65 + Blank + CRL 1005 | 651 | 2.8 | 0.008 |
| pp65 | 581 | 2.5 | 0.02 |
| pp65 + CRL 1005 | 704 | 3.0 | 0.01 |

Example 12

Vaccine Combinations—DNA and Protein Combination

General Experimental Procedure

The experimental procedure for the following example is as described above, with particular parameters and materials employed as described herein.

Vaccination Regimen

BALB/c female mice, 6/group, were injected in each rectus femoris with 20 μg of HCMV bivalent DNA vaccine in a 50 μl volume+/−poloxamer VF-P1205-02A ("02A"), DMRIE: DOPE, ("D/D") and/or gB protein as indicated below. Plasmid VR6365 encodes HCMV gB, plasmid VR6368 encodes HCMV pp65. Full-length gB protein purfied from CHO cells was obtained from Austral Biologicals. (San Ramon, Calif.). Mice received injections on days 0 and 14 and were bled for determination of gB antibody titers on day 13 and day 26. Splenocytes from two mice per group were harvested on days 26, 27, and 28 for pp65 IFN-γ ELISpot analyses (splenocytes from individual mice were assayed, n=6 per group).

TABLE 24

Immunization Schedule

| Group | DNA (total/injection/mouse) |
|---|---|
| A | 10 μg VR 6368 + 10 μg VR6365 + 02A |
| B | 10 μg VR 6368 + 10 μg VR6365 + 02A + 4.5 μg gB protein |
| C | 10 μg VR 6368 + 10 μg VR6365 + 02A + 1.5 μg gB protein |
| D | 10 μg VR 6368 + 10 μg VR6365 + 02A + 0.5 μg gB protein |
| E | 10 μg VR 6368 + 10 μg VR6365 + D/D + 4.5 μg gB protein |
| F | 10 μg VR 6368 + 10 μg VR6365 |

Recombinant gB Enzyme Linked Immunosorbent Assay (ELISA)

The ELISA for detecting gB specific serum antibodies was performed with 96 well Costar ½ well EIA plates coated with recombinant CMV gB at a concentration of 0.1 μg/well in borate buffered saline (BBS) buffer. After coating with antigen, the plates were sealed and incubated at 4° C. overnight. Plates were washed 4× with BBS containing 0.1% Tween-20 (BBST) using an automated plate washer. Non-specific binding was blocked by incubating plates for 1 hr at room temperature with 100 μL of assay buffer (10% fetal calf serum in BBS). Blocking buffer was then decanted and serially diluted sera (diluted in assay buffer) added at 50 μl/well. Plates were sealed, incubated at room temperature for 2 hours, then washed 4× with BBS containing 0.1% Tween-20 (BBST) using an automated plate washer. Goat anti-mouse IgG Fc specific secondary antibody diluted at 1:5000 in assay buffer was added at 50 μl/well; plates were sealed and incubated at room temperature for 2 hours. Plates were washed 4× with BBS containing 0.1% Tween-20 (BBST) using an automated plate washer. Substrate, consisting of p-nitrophenylphosphate at 1 mg/ml in 50 nM Sodium Bicarbonate buffer, pH 9.8 and $MgCl_2$ at 1 mM was added at 50 μl/well, plates were sealed and incubated at room temperature for 60 minutes. Absorbance of each well was determined at 405 nm. Endpoint titer=the reciprocal of the last dilution resulting in a mean absorbance value that is greater than or equal to twice the mean absorbance value of background wells.

TABLE 25

Anti-gB IgG Titers and ELISpot Results

| Group | HCMV pp65 SFU/$10^6$ splenocytes | HCMV gB antibody titers Day 13 | HCMV gB antibody titers Day 26 |
|---|---|---|---|
| A | 368 | 325 | 5867 |
| B | 576 | 467 | 22400 |
| C | 451 | 717 | 25600 |

TABLE 25-continued

Anti-gB IgG Titers and ELISpot Results

| Group | HCMV pp65 SFU/10$^6$ splenocytes | HCMV gB antibody titers Day 13 | HCMV gB antibody titers Day 26 |
|---|---|---|---|
| D | 260 | 500 | 14400 |
| E | 523 | 1800 | 187733 |
| F | 465 | 75 | 1867 |

Adding gB protein to the bivalent gB, pp65 DNA vaccine formulated in poloxamer increased the anti-gB antibody response up to 14-fold vs. the bivalent vaccine alone (bivalent vaccine+02A+1.5 µg gB protein (Group C) vs. bivalent vaccine alone (Group F), p=0.005) and up to 4-fold vs. bivalent DNA in poloxamer (bivalent vaccine+02A+1.5 µg gB protein (Group C) vs. bivalent vaccine+02A (Group A), p=0.01). Adding gB protein to the bivalent DNA vaccine formulated in cationic lipid increased the anti-gb antibody response 101-fold vs. bivalent vaccine alone (bivalent vaccine+D/D+4.5 µg gB protein (Group E) vs. bivalent vaccine alone (Group F), p=0.00006) and 32-fold vs. bivalent DNA in poloxamer (bivalent vaccine+D/D+4.5 µg gB protein (Group E) vs. bivalent vaccine+02A (Group A), p=0.00005). The pp65 response was similar for all groups indicating that combining protein with the bivalent DNA vaccine to improve the antibodycomponent of the response did not decrease the cellular component of the response.

Example 13

Vaccine Combinations—Trivalent Vaccine Combination

Vaccination Regimen

Groups of 10 mice were injected in each rectus femoris with 50 µL of PBS containing multiple DNA plasmids as shown below. Plasmid VR6365 encodes HCMV gB, Plasmid VR6368 encodes HCMV pp65, Plasmid VR6250 encodes HCMV IE1, and "blank" refers to an equivalent plasmid backbone but lacking any antigen coding sequence. All DNA was formulated with the "02A" poloxamer based formulation as described in Example 4. Two sets of injections were given on days 0 and 14. Serum was drawn at day 26 for determination of gB antibody titers.

TABLE 26

Immunization Schedule

| Group | Dose (per leg) |
|---|---|
| A | 6.6 µgr VR6368 (pp65) + 6.6 µgr VR6250 (IE1) + 6.6 µgr VR6365 (gB) |
| B | 6.6 µgr VR6368 (pp65) + 6.6 µgr blank + 6.6 µgr VR6365 (gB) |
| C | 6.6 µgr blank + 6.6 µgr VR6250 (IE1) + 6.6 µgr VR6365 (gB) |

Recombinant gB Enzyme Linked Immunosorbent Assay (ELISA)

Sera were collected from the vaccinated mice according to the regimen described in Example 7 above. Anti-gB IgG titers were determined using a recombinant CMV gB Enzyme Linked Immunosorbent Assay (ELISA), as described in Example 12 above.

IFN-γ ELISpot Assay

Spleens were harvested for analysis of antigen specific, IFN-γ secreting, T-cell responses on days 27-29. Two spleens from each group were pooled for the assay. Two pools from each group were analyzed on days 27 and 28, one pool from each group was analyzed on day 29. Splenocytes were processed and analyzed for pp65 reactivity by ELISpot assay as described in Example 7. Splenocytes were analyzed for IE1 reactivity by ELISpot assay as described for pp65 ELISpot assay except, splenocytes were stimulated with a pool of 98 overlapping 15 mer peptides (overlapping by 11 amino acids) that span the entire IE1 protein encoded on the VR6250 construct. (See Example 3).

TABLE 27

Anti-gB IgG Titers and ELISpot Results

| Analysis | Group A | Group B | Group C |
|---|---|---|---|
| gB antibody titer | 18,560 | 24,320 | 62,720 |
| pp65 ELISpot (SFU/10$^6$ splenocytes) | 348 | 231 | 1 |
| IE1 ELISpot (SFU/10$^6$ splenocytes) | 218 | 1 | 319 |

Earlier experiments showed that administering each antigen encoding DNA alone elicits an immune response in vivo. The present data show that each antigen encoding DNA induces a specific immunological response when combined with other antigens. Thus, combining the antigens and simultaneously administering multiple antigen encoding DNAs allows generation of immune responses to all the antigens simultaneously.

Example 14

Electrically-assisted Plasmid Delivery

In vivo gene delivery may be enhanced through the application of brief electrical pulses to injected tissues, a procedure referred to herein as electrically-assisted plasmid delivery. See, e.g., Aihara, H. & Miyazaki, J. *Nat. Biotechnol.* 16:867-70 (1998); Mir, L. M. et al., *Proc. Natl Acad. Sci. USA* 96:4262-67 (1999); Hartikka, J. et al., *Mol. Ther.* 4:407-15 (2001); and Mir, L. M. et al.; Rizzuto, G. et al., *Hum Gene Ther* 11:1891-900 (2000); Widera, G. et al, *J. of Immuno.* 164: 4635-4640 (2000). The use of electrical pulses for cell electropermeabilization has been used to introduce foreign DNA into prokaryotic and eukaryotic cells in vitro. Cell permeabilization can also be achieved locally, in vivo, using electrodes and optimal electrical parameters that are compatible with cell survival.

The electroporation procedure can be performed with various electroporation devices. These devices include external plate type electrodes or invasive needle/rod electrodes and can possess two electrodes or multiple electrodes placed in an array. Distances between the plate or needle electrodes can vary depending upon the number of electrodes, size of target area and treatment subject.

The TriGrid needle array, as described herein, is a three electrode array comprising three elongate electrodes in the approximate shape of a geometric triangle. Needle arrays may include single, double, three, four, five, six or more needles arranged in various array formations. The electrodes are connected through conductive cables to a high voltage switching device that is connected to a power supply.

The electrode array is placed into the muscle tissue, around the site of nucleic acid injection, to a depth of approximately 3 mm to 3 cm. The depth of insertion varies depending upon the target tissue and size of patient receiving electroporation. After injection of foreign nucleic acid, such as plasmid DNA, and a period of time sufficient for distribution of the nucleic acid, square wave electrical pulses are applied to the tissue. The amplitude of each pulse ranges from about 100 volts to about 1500 volts, e.g., about 100 volts, about 200 volts, about 300 volts, about 400 volts, about 500 volts, about 600 volts, about 700 volts, about 800 volts, about 900 volts, about 1000 volts, about 1100 volts, about 1200 volts, about 1300 volts, about 1400 volts, or about 1500 volts or about 1-1.5 kV/cm, based on the spacing between electrodes. Each pulse has a duration of about 1 μs to about 1000 μs, e.g., about 1 μs, about 10 μs, about 50 μs, about 100 μs, about 200 μs, about 300 μs, about 400 μs, about 500 μs, about 600 μs, about 700 μs, about 800 μs, about 900 μs, or about 1000 μs, and a pulse frequency on the order of about 1-10 Hz. The polarity of the pulses may be reversed during the electroporation procedure by switching the connectors to the pulse generator. Pulses are repeated multiple times. The electroporation parameters (e.g. voltage amplitude, duration of pulse, number of pulses, depth of electrode insertion and frequency) will vary based on target tissue type, number of electrodes used and distance of electrode spacing, as would be understood by one of ordinary skill in the art.

Immediately after completion of the pulse regimen, subjects receiving electroporation can be optionally treated with membrane stabilizing agents to prolong cell membrane permeability as a result of the electroporation. Examples of membrane stabilizing agents include, but are not limited to, steroids (e.g. dexamethasone, methylprednisone and progesterone), angiotensin II and vitamin E. A single dose of dexamethasone, approximately 0.1 mg per kilogram of body weight, should be sufficient to achieve a beneficial affect.

EAPD techniques such as electroporation can also be used for plasmids contained in liposome formulations. The liposome—plasmid suspension is administered to the animal or patient and the site of injection is treated with a safe but effective electrical field generated, for example, by a TriGrid needle array, or a four needle array. The electroporation may aid in plasmid delivery to the cell by destabilizing the liposome bilayer so that membrane fusion between the liposome and the target cellular structure occurs. Electroporation may also aid in plasmid delivery to the cell by triggering the release of the plasmid, in high concentrations, from the liposome at the surface of the target cell so that the plasmid is driven across the cell membrane by a concentration gradient via the pores created in the cell membrane as a result of the electroporation.

Electroporation Study in Rabbits

Electroporation assisted DNA vaccine delivery was compared to DNA formulated with DMRIE:DOPE or CRL 1005 and DNA in PBS in a New Zealand White Rabbit model using CMV gB DNA. Rabbits (5 per group) were injected in the tibialis muscle at 0 and 28 days with 50 μg DNA/500 μl/leg. Electroporation was performed immediately after injection using the BTX-ECM830 pulse generator with a 5 mm×8.6 mm 4 needle array at 200V (232 V/cm), 60 msec, 2 pulses, and 2 Hz.

Serum endpoint titers were measured at days 2, 14, 28, 42 and 56 by gB ELISA. The ELISA for detecting gB specific serum antibodies was performed with 96 well Costar ½ well EIA plates coated with recombinant CMV gB at a concentration of 0.1 μg/well in borate buffered saline (BBS) buffer. After coating with antigen, the plates were sealed and incubated at 4° C. overnight. Plates were washed 4× with BBS containing 0.1% Tween-20 (BBST) using an automated plate washer. Non-specific binding was blocked by incubating plates for 1 hr at room temperature with 100 μL of assay buffer (10% fetal calf serum in BBS). Blocking buffer was then decanted and serially diluted sera (diluted in assay buffer) added at 50 μl/well. Plates were sealed, incubated at room temperature for 2 hours, then washed 4× with BBS containing 0.1% Tween-20 (BBST) using an automated plate washer. Goat anti-rabbit IgG Fc specific secondary antibody diluted at 1:5000 in assay buffer was added at 50 μl/well; plates were sealed and incubated at room temperature for 2 hours. Plates were washed 4× with BBS containing 0.1% Tween-20 (BBST) using an automated plate washer. Substrate, consisting of p-nitrophenylphosphate at 1 mg/ml in 50 μnM Sodium Bicarbonate buffer, pH 9.8 and $MgCl_2$ at 1 mM was added at 50 μl/well, plates were sealed and incubated at room temperature for 60 minutes. Absorbance was determined at 405 nm using an automated 96 well plate reader. Endpoint titer=the reciprocal of the last dilution resulting in a mean absorbance value that is greater than or equal to twice the mean absorbance value of background wells.

TABLE 28

| | Serum endpoint titers | | | | |
|---|---|---|---|---|---|
| Group | Pre-bleed | Day 14 | Day 28 | Day 42 | Day 56 |
| CRL 1005 | 140 | 420 | 4830 | 46720 | 55040 |
| DMRIE:DOPE | 240 | 1360 | 5120 | 354987 | 218453 |
| PBS + Electroporation | 180 | 79360 | 221867 | 2703360 | 1884160 |
| PBS | 115 | 135 | 2240 | 35840 | 35840 |

The mean anti-gB titers for the CRL 1005 group were slightly higher (up to 3 fold higher) than the titers for the PBS group, but the differences were not statistically significant at any time point. The mean anti-gB titers for the DMRIE:DOPE group were 2-10 fold higher (p<0.05 at all post-injection time points) than for gB DNA in PBS. Electroporation after injection of gB DNA in PBS increased anti-gb titers 53-588 fold over gB DNA in PBS without electroporation (p<0.05 at all post-injection time points), 34-189 fold over the CRL 1005 group (p<0.05 at all post-injection time points) and 8-58 fold over the DMRIE:DOPE group (p<0.05 at all post-injection time points).

Example 15

Treating Patients using Compositions Comprising Human Codon-Optimized HCMV pp65 and gB, and Fragments and Variants Thereof The plasmid immunotherapeutic products are produced according to current FDA Good Manufacturing Procedures (GMP) and are administered to human subjects under an approved Investigational New Drug application.

A. Initial Studies

Thirty-two healthy adults are immunized by i.m. injection with 0.5 mg or 2.5 mg each of plasmid DNA encoding optimized gB and pp65 on separate plasmids at 0, 2, and 8 weeks. Blood samples are drawn preimmunization and at 2, 4, 8, 10, and 16 weeks for immunogenicity studies, including ELISpot assays to measure CD4+ and CD8+ T cell responses and antibody titers for HCMV gB.

B. Administration to Hematopoetic Stem Cell (HSC) Transplant Donors and Recipients Following the procedures above, healthy HSC donors are immunized with the plasmid compositions at 4 and 2 weeks prior to donation. Immunogenicity assays are performed using blood drawn from the donors at preimmunization, and every two weeks for 16 weeks post immunization. Recipients are divided into two groups. The first group receives the HSC from the immunized donors, but not be immunized themselves. The second group receives the HSC from the immunized donors and are immunized with the same plasmid compositions as the donors approximately four weeks after HSC transplantation, and immunogenicity assays are performed at pretransplantation and every two weeks as above. Immunizations may be repeated every two weeks for both donors and recipients.

What is claimed is:

1. A composition comprising the plasmids VR6365 and VR6368.

2. The composition of claim 1, further comprising an additional polynucleotide encoding an HCMV polypeptide, fragment, variant or derivative thereof, or a component selected from the group consisting of inactivated virus, attenuated virus, a viral vector expressing an isolated HCMV polypeptide, and an isolated polypeptide from an HCMV virus protein, fragment, or derivative thereof.

3. The composition of claim 2, comprising a component selected from the group consisting of an adjuvant, and a transfection facilitating compound.

4. The composition of claim 2, wherein said additional polynucleotide comprises a codon-optimized coding region encoding said HCMV polypeptide, fragment, variant or derivative thereof.

5. The composition of claim 4, wherein said HCMV polypeptide is IE-1.

6. The composition of claim 5, wherein said additional polynucleotide comprises plasmid VR6250.

7. The composition of claim 1, comprising a component selected from the group consisting of an adjuvant, and a transfection facilitating compound.

8. The composition of claim 7, wherein said adjuvant or said transfection facilitating compound is selected from the group consisting of:
(±)-N-(3-aminopropyl)-N,N-dimethyl-2,3-bis(syn-9-tetradeceneyloxy)-1-propanaminium bromide (GAP-DMORIE) and a neutral lipid;
a cytokine;
mono-phosphoryl lipid A and trehalosedicorynomycolateAF (MPL+TDM);
a solubilized mono-phosphoryl lipid A formulation; CRL1005/BAK; and
(±)-N-(2-hydroxyethyl)-N,N-dimethyl-2,3-bis(tetradecyloxy)-1-propanaminium bromide) (DMRIE).

9. The composition of claim 7, wherein said adjuvant or said transfection facilitating compound comprises CRL1005 and benzalkonium chloride (BAK).

10. The composition of claim 7, wherein said CRL1005 and BAK are present at concentrations selected from the group consisting of:
0.3 mM BAK and 7.5 mg/ml CRL 1005,
0.3 mM BAK and 34 mg/ml CRL 1005, and
0.3 mM BAK and 50 mg/ml CRL 1005.

11. The composition of claim 10, which is formulated by combining together the CRL10050, BAK, and polynucleotide at a temperature below the cloud point, without thermal cycling to a temperature above the cloud point.

12. A method of eliciting an immune response to CMV in a human comprising administering the composition of claim 1.

13. A method of eliciting an immune response to CMV in a human comprising administering the composition of claim 3.

14. A composition comprising the plasmid VR6368.

15. The composition of claim 14, further comprising an additional polynucleotide encoding an HCMV polypeptide, fragment, variant or derivative thereof, or a component selected from the group consisting of inactivated virus, attenuated virus, a viral vector expressing an isolated HCMV polypeptide, and an isolated polypeptide from an HCMV virus protein, fragment, or derivative thereof.

16. The composition of claim 15, comprising a component selected from the group consisting of an adjuvant, and a transfection facilitating compound.

17. The composition of claim 15, wherein said additional polynucleotide comprises a codon-optimized coding region encoding said HCMV polypeptide, fragment, variant or derivative thereof.

18. The composition of claim 17, wherein said HCMV polypeptide is IE-1.

19. The composition of claim 18, wherein said additional polynucleotide comprises plasmid VR6250.

20. The composition of claim 14, comprising a component selected from the group consisting of an adjuvant, and a transfection facilitating compound.

21. The composition of claim 19, wherein said adjuvant or said transfection facilitating compound is selected from the group consisting of:
(±)-N-(3-aminopropyl)-N,N-dimethyl-2,3-bis(syn-9-tetradeceneyloxy)-1-propanaminium bromide (GAP-DMORIE) and a neutral lipid;
a cytokine;
mono-phosphoryl lipid A and trehalosedicorynomycolateAF (MPL+TDM);
a solubilized mono-phosphoryl lipid A formulation; CRL1005/BAK; and
(±)-N-(2-hydroxyethyl)-N,N-dimethyl-2,3-bis(tetradecyloxy)-1-propanaminium bromide) (DMRIE).

22. The composition of claim 19, wherein said adjuvant or said transfection facilitating compound comprises CRL1005 and benzalkonium chloride (BAK).

23. The composition of claim 19, wherein said CRL1005 and BAK are present at concentrations selected from the group consisting of:
0.3 mM BAK and 7.5 mg/ml CRL 1005,
0.3 mM BAK and 34 mg/ml CRL 1005, and
0.3 mM BAK and 50 mg/ml CRL 1005.

24. The composition of claim 22, which is formulated by combining together the CRL10050, BAK, and polynucleotide at a temperature below the cloud point, without thermal cycling to a temperature above the cloud point.

25. A method of eliciting an immune response to CMV in a human comprising administering the composition of claim 14.

26. A method of eliciting an immune response to CMV in a human comprising administering the composition of claim 16.

* * * * *

UNITED STATES PATENT AND TRADEMARK OFFICE
CERTIFICATE OF CORRECTION

PATENT NO. : 7,410,795 B2
APPLICATION NO. : 10/738986
DATED : August 12, 2008
INVENTOR(S) : Gary G. Hermanson, Andrew J. Geall and Mary Kopke Wloch It is certified that error appears in the above-identified patent and that said Letters Patent is hereby corrected as shown below:

Column 7, line 19: cancel the text "The putative kinase" to and ending "is underlined."

Column 7, line 25: the phrase "(SEQ ID NO:8)" should read --(SEQ ID NO:9)--

Signed and Sealed this
Thirty-first Day of May, 2011

David J. Kappos
*Director of the United States Patent and Trademark Office*

```
                         SEQUENCE LISTING

<160> NUMBER OF SEQ ID NOS: 50

<210> SEQ ID NO 1
<211> LENGTH: 1683
<212> TYPE: DNA
<213> ORGANISM: Human cytomegalovirus
<220> FEATURE:
<221> NAME/KEY: CDS
<222> LOCATION: (1)..(1683)

<400> SEQUENCE: 1 atg gag tcg cgc ggt cgc cgt tgt ccc gaa atg ata tcc gta ctg ggt        48
Met Glu Ser Arg Gly Arg Arg Cys Pro Glu Met Ile Ser Val Leu Gly
1               5                   10                  15 ccc att tcg ggg cac gtg ctg aaa gcc gtg ttt agt cgc ggc gat acg        96
Pro Ile Ser Gly His Val Leu Lys Ala Val Phe Ser Arg Gly Asp Thr
                20                  25                  30 ccg gtg ctg ccg cac gag acg cga ctc ctg cag acg ggt atc cac gta       144
Pro Val Leu Pro His Glu Thr Arg Leu Leu Gln Thr Gly Ile His Val
            35                  40                  45 cgc gtg agc cag ccc tcg ctg atc ttg gta tcg cag tac acg ccc gac       192
Arg Val Ser Gln Pro Ser Leu Ile Leu Val Ser Gln Tyr Thr Pro Asp
        50                  55                  60 tcg acg cca tgc cac cgc ggc gac aat cag ctg cag gtg cag cac acg       240
Ser Thr Pro Cys His Arg Gly Asp Asn Gln Leu Gln Val Gln His Thr
65                  70                  75                  80 tac ttt acg ggc agc gag gtg gag aac gtg tcg gtc aac gtg cac aac       288
Tyr Phe Thr Gly Ser Glu Val Glu Asn Val Ser Val Asn Val His Asn
                85                  90                  95 ccc acg ggc cga agc atc tgc ccc agc cag gag ccc atg tcg atc tat       336
Pro Thr Gly Arg Ser Ile Cys Pro Ser Gln Glu Pro Met Ser Ile Tyr
                100                 105                 110 gtg tac gcg ctg ccg ctc aag atg ctg aac atc ccc agc atc aac gtg       384
Val Tyr Ala Leu Pro Leu Lys Met Leu Asn Ile Pro Ser Ile Asn Val
            115                 120                 125 cac cac tac ccg tcg gcg gcc gag cgc aaa cac cga cac ctg ccc gta       432
His His Tyr Pro Ser Ala Ala Glu Arg Lys His Arg His Leu Pro Val
        130                 135                 140 gct gac gct gtg att cac gcg tcg ggc aag cag atg tgg cag gcg cgt       480
Ala Asp Ala Val Ile His Ala Ser Gly Lys Gln Met Trp Gln Ala Arg
145                 150                 155                 160 ctc acg gtc tcg gga ctg gcc tgg acg cgt cag cag aac cag tgg aaa       528
Leu Thr Val Ser Gly Leu Ala Trp Thr Arg Gln Gln Asn Gln Trp Lys
                165                 170                 175 gag ccc gac gtc tac tac acg tca gcg ttc gtg ttt ccc acc aag gac       576
Glu Pro Asp Val Tyr Tyr Thr Ser Ala Phe Val Phe Pro Thr Lys Asp
                180                 185                 190 gtg gca ctg cgg cac gtg gtg tgc gcg cac gag ctg gtt tgc tcc atg       624
Val Ala Leu Arg His Val Val Cys Ala His Glu Leu Val Cys Ser Met
            195                 200                 205 gag aac acg cgc gca acc aag atg cag gtg ata ggt gac cag tac gtc       672
```

```
                Glu Asn Thr Arg Ala Thr Lys Met Gln Val Ile Gly Asp Gln Tyr Val
                    210                 215                 220 aag gtg tac ctg gag tcc ttc tgc gag gac gtg ccc tcc ggc aag ctc        720
Lys Val Tyr Leu Glu Ser Phe Cys Glu Asp Val Pro Ser Gly Lys Leu
225                 230                 235                 240 ttt atg cac gtc acg ctg ggc tct gac gtg gaa gag gac ctg acg atg        768
Phe Met His Val Thr Leu Gly Ser Asp Val Glu Glu Asp Leu Thr Met
                245                 250                 255 acc cgc aac ccg caa ccc ttc atg cgc ccc cac gag cgc aac ggc ttt        816
Thr Arg Asn Pro Gln Pro Phe Met Arg Pro His Glu Arg Asn Gly Phe
            260                 265                 270 acg gtg ttg tgt ccc aaa aat atg ata atc aaa ccg ggc aag atc tcg        864
Thr Val Leu Cys Pro Lys Asn Met Ile Ile Lys Pro Gly Lys Ile Ser
            275                 280                 285 cac atc atg ctg gat gtg gct ttt acc tca cac gag cat ttt ggg ctg        912
His Ile Met Leu Asp Val Ala Phe Thr Ser His Glu His Phe Gly Leu
        290                 295                 300 ctg tgt ccc aag agc atc ccg ggc ctg agc atc tca ggt aac ctg ttg        960
Leu Cys Pro Lys Ser Ile Pro Gly Leu Ser Ile Ser Gly Asn Leu Leu
305                 310                 315                 320 atg aac ggg cag cag atc ttc ctg gag gta caa gcc ata cgc gag acc       1008
Met Asn Gly Gln Gln Ile Phe Leu Glu Val Gln Ala Ile Arg Glu Thr
                325                 330                 335 gtg gaa ctg cgt cag tac gat ccc gtg gct gcg ctc ttt ttc gat            1056
Val Glu Leu Arg Gln Tyr Asp Pro Val Ala Ala Leu Phe Phe Phe Asp
                340                 345                 350 atc gac ttg ctg ctg cag cgc ggg cct cag tac agc gag cac ccc acc       1104
Ile Asp Leu Leu Leu Gln Arg Gly Pro Gln Tyr Ser Glu His Pro Thr
            355                 360                 365 ttc acc agc cag tat cgc atc cag ggc aag ctt gag tac cga cac acc       1152
Phe Thr Ser Gln Tyr Arg Ile Gln Gly Lys Leu Glu Tyr Arg His Thr
        370                 375                 380 tgg gac cgg cac gac gag ggt gcc gcc cag ggc gac gac gac gtc tgg       1200
Trp Asp Arg His Asp Glu Gly Ala Ala Gln Gly Asp Asp Asp Val Trp
385                 390                 395                 400 acc agc gga tcg gac tcc gac gaa gaa ctc gta acc acc gag cgc aag       1248
Thr Ser Gly Ser Asp Ser Asp Glu Glu Leu Val Thr Thr Glu Arg Lys
                405                 410                 415 acg ccc cgc gtc acc ggc ggc ggc gcc atg gcg ggc gcc tcc act tcc       1296
Thr Pro Arg Val Thr Gly Gly Gly Ala Met Ala Gly Ala Ser Thr Ser
                420                 425                 430 gcg ggc cgc aaa cgc aaa tca gca tcc tcg gcg acg gcg tgc acg tcg       1344
Ala Gly Arg Lys Arg Lys Ser Ala Ser Ser Ala Thr Ala Cys Thr Ser
            435                 440                 445 ggc gtt atg aca cgc ggc cgc ctt aag gcc gag tcc acc gtc gcg ccc       1392
Gly Val Met Thr Arg Gly Arg Leu Lys Ala Glu Ser Thr Val Ala Pro
        450                 455                 460 gaa gag gac acc gac gag gat tcc gac aac gaa atc cac aat ccg gcc       1440
Glu Glu Asp Thr Asp Glu Asp Ser Asp Asn Glu Ile His Asn Pro Ala
465                 470                 475                 480 gtg ttc acc tgg ccg ccc tgg cag gcc ggc atc ctg gcc cgc aac ctg       1488
Val Phe Thr Trp Pro Pro Trp Gln Ala Gly Ile Leu Ala Arg Asn Leu
                485                 490                 495 gtg ccc atg gtg gct acg gtt cag ggt cag aat ctg aag tac cag gaa       1536
Val Pro Met Val Ala Thr Val Gln Gly Gln Asn Leu Lys Tyr Gln Glu
                500                 505                 510 ttc ttc tgg gac gcc aac gac atc tac cgc atc ttc gcc gaa ttg gaa       1584
Phe Phe Trp Asp Ala Asn Asp Ile Tyr Arg Ile Phe Ala Glu Leu Glu
            515                 520                 525
```

-continued

```
ggc gta tgg cag ccc gct gcg caa ccc aaa cgt cgc cgc cac cgg caa      1632
Gly Val Trp Gln Pro Ala Ala Gln Pro Lys Arg Arg Arg His Arg Gln
530                 535                 540 gac gcc ttg ccc ggg cca tgc atc gcc tcg acg ccc aaa aag cac cga      1680
Asp Ala Leu Pro Gly Pro Cys Ile Ala Ser Thr Pro Lys Lys His Arg
545                 550                 555                 560 ggt                                                                   1683
Gly

<210> SEQ ID NO 2
<211> LENGTH: 561
<212> TYPE: PRT
<213> ORGANISM: Human cytomegalovirus

<400> SEQUENCE: 2

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320
```

```
Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly

<210> SEQ ID NO 3
<211> LENGTH: 1683
<212> TYPE: DNA
<213> ORGANISM: Artificial Sequence
<220> FEATURE:
<223> OTHER INFORMATION: codon-optimized sequence of hCMV pp65
<220> FEATURE:
<221> NAME/KEY: CDS
<222> LOCATION: (1)..(1683)

<400> SEQUENCE: 3 atg gag tcc cgc ggt cgc cgc tgt ccc gaa atg ata tcc gta ctg ggt      48
Met Glu Ser Arg Gly Arg Arg Cys Pro Glu Met Ile Ser Val Leu Gly
1               5                   10                  15 ccc att tcc ggg cac gtg ctg aaa gcc gtg ttt agt cgc ggc gat acc      96
Pro Ile Ser Gly His Val Leu Lys Ala Val Phe Ser Arg Gly Asp Thr
            20                  25                  30 ccc gtg ctg ccc cac gag acc cga ctc ctg cag acc ggt atc cac gta     144
Pro Val Leu Pro His Glu Thr Arg Leu Leu Gln Thr Gly Ile His Val
        35                  40                  45 cgc gtg agc cag ccc tcc ctg atc ttg gta tcc cag tac acc ccc gac     192
Arg Val Ser Gln Pro Ser Leu Ile Leu Val Ser Gln Tyr Thr Pro Asp
    50                  55                  60 tcc acc cca tgc cac cgc ggc gac aat cag ctg cag gtg cag cac acc     240
Ser Thr Pro Cys His Arg Gly Asp Asn Gln Leu Gln Val Gln His Thr
65                  70                  75                  80
```

| | |
|---|---|
| tac ttt acc ggc agc gag gtg gag aac gtg tcc gtc aac gtc cac aac<br>Tyr Phe Thr Gly Ser Glu Val Glu Asn Val Ser Val Asn Val His Asn<br>                    85                          90                    95 | 288 |
| ccc acc ggc cga agc atc tgc ccc agc cag gag ccc atg tcc atc tat<br>Pro Thr Gly Arg Ser Ile Cys Pro Ser Gln Glu Pro Met Ser Ile Tyr<br>                  100                        105                    110 | 336 |
| gtg tac gcc ctg ccc ctc aag atg ctg aac atc ccc agc atc aac gtg<br>Val Tyr Ala Leu Pro Leu Lys Met Leu Asn Ile Pro Ser Ile Asn Val<br>           115                        120                    125 | 384 |
| cac cac tac ccc tcc gcc gcc gag cgc aaa cac cga cac ctg ccc gta<br>His His Tyr Pro Ser Ala Ala Glu Arg Lys His Arg His Leu Pro Val<br>130                          135                        140 | 432 |
| gct gac gct gtg att cac gcc tcc ggc aag cag atg tgg cag gcc cgc<br>Ala Asp Ala Val Ile His Ala Ser Gly Lys Gln Met Trp Gln Ala Arg<br>145                          150                        155                    160 | 480 |
| ctc acc gtc tcc gga ctg gcc tgg acc cgc cag cag aac cag tgg aaa<br>Leu Thr Val Ser Gly Leu Ala Trp Thr Arg Gln Gln Asn Gln Trp Lys<br>                      165                        170                    175 | 528 |
| gag ccc gac gtc tac tac acc tca gcc ttc gtg ttt ccc acc aag gac<br>Glu Pro Asp Val Tyr Tyr Thr Ser Ala Phe Val Phe Pro Thr Lys Asp<br>                180                        185                    190 | 576 |
| gtg gca ctg cgg cac gtg gtg tgc gcc cac gag ctg gtt tgc tcc atg<br>Val Ala Leu Arg His Val Val Cys Ala His Glu Leu Val Cys Ser Met<br>          195                        200                    205 | 624 |
| gag aac acc cgc gca acc aag atg cag gtg ata ggt gac cag tac gtc<br>Glu Asn Thr Arg Ala Thr Lys Met Gln Val Ile Gly Asp Gln Tyr Val<br>210                          215                        220 | 672 |
| aag gtg tac ctg gag tcc ttc tgc gag gac gtg ccc tcc ggc aag ctc<br>Lys Val Tyr Leu Glu Ser Phe Cys Glu Asp Val Pro Ser Gly Lys Leu<br>225                          230                        235                    240 | 720 |
| ttt atg cac gtc acc ctg ggc tct gac gtg gaa gag gac ctg acc atg<br>Phe Met His Val Thr Leu Gly Ser Asp Val Glu Glu Asp Leu Thr Met<br>                  245                        250                    255 | 768 |
| acc cgc aac ccc caa ccc ttc atg cgc ccc cac gag cgc aac ggc ttt<br>Thr Arg Asn Pro Gln Pro Phe Met Arg Pro His Glu Arg Asn Gly Phe<br>            260                        265                    270 | 816 |
| acc gtg ttg tgt ccc aaa aat atg ata atc aaa ccc ggc aag atc tcc<br>Thr Val Leu Cys Pro Lys Asn Met Ile Ile Lys Pro Gly Lys Ile Ser<br>           275                        280                    285 | 864 |
| cac atc atg ctg gat gtg gct ttt acc tca cac gag cat ttt ggg ctg<br>His Ile Met Leu Asp Val Ala Phe Thr Ser His Glu His Phe Gly Leu<br>          290                        295                    300 | 912 |
| ctg tgt ccc aag agc atc ccc ggc ctg agc atc tca ggt aac ctg ttg<br>Leu Cys Pro Lys Ser Ile Pro Gly Leu Ser Ile Ser Gly Asn Leu Leu<br>305                          310                        315                    320 | 960 |
| atg aac ggg cag cag atc ttc ctg gag gta caa gcc ata cgc gag acc<br>Met Asn Gly Gln Gln Ile Phe Leu Glu Val Gln Ala Ile Arg Glu Thr<br>                  325                        330                    335 | 1008 |
| gtg gaa ctg cgc cag tac gat ccc gtg gct gcc ctc ttt ttc ttc gat<br>Val Glu Leu Arg Gln Tyr Asp Pro Val Ala Ala Leu Phe Phe Phe Asp<br>                340                        345                    350 | 1056 |
| atc gac ttg ctg ctg cag cgc ggg cct cag tac agc gag cac ccc acc<br>Ile Asp Leu Leu Leu Gln Arg Gly Pro Gln Tyr Ser Glu His Pro Thr<br>          355                        360                    365 | 1104 |
| ttc acc agc cag tat cgc atc cag ggc aag ctt gag tac cga cac acc<br>Phe Thr Ser Gln Tyr Arg Ile Gln Gly Lys Leu Glu Tyr Arg His Thr<br>370                          375                        380 | 1152 |
| tgg gac cgg cac gac gag ggt gcc gcc cag ggc gac gac gac gtc tgg<br>Trp Asp Arg His Asp Glu Gly Ala Ala Gln Gly Asp Asp Asp Val Trp | 1200 |

```
                385                 390                 395                 400
acc agc gga tcc gac tcc gac gaa gaa ctc gta acc acc gag cgc aag        1248
Thr Ser Gly Ser Asp Ser Asp Glu Glu Leu Val Thr Thr Glu Arg Lys
                    405                 410                 415 acc ccc cgc gtc acc ggc ggc gcc atg gcc ggc gcc tcc act tcc            1296
Thr Pro Arg Val Thr Gly Gly Ala Met Ala Gly Ala Ser Thr Ser
                420                 425                 430 gcc ggc cgc aaa cgc aaa tca gca tcc tcc gcc acc gcc tgc acc tcc        1344
Ala Gly Arg Lys Arg Lys Ser Ala Ser Ser Ala Thr Ala Cys Thr Ser
                    435                 440                 445 ggc gtt atg aca cgc ggc cgc ctt aag gcc gag tcc acc gtc gcc ccc        1392
Gly Val Met Thr Arg Gly Arg Leu Lys Ala Glu Ser Thr Val Ala Pro
                450                 455                 460 gaa gag gac acc gac gag gat tcc gac aac gaa atc cac aat ccc gcc        1440
Glu Glu Asp Thr Asp Glu Asp Ser Asp Asn Glu Ile His Asn Pro Ala
465                 470                 475                 480 gtg ttc acc tgg cca ccc tgg cag gcc ggc atc ctg gcc cgc aac ctg        1488
Val Phe Thr Trp Pro Pro Trp Gln Ala Gly Ile Leu Ala Arg Asn Leu
                    485                 490                 495 gtg ccc atg gtg gct acc gtt cag ggt cag aat ctg aag tac cag gaa        1536
Val Pro Met Val Ala Thr Val Gln Gly Gln Asn Leu Lys Tyr Gln Glu
                500                 505                 510 ttc ttc tgg gac gcc aac gac atc tac cgc atc ttc gcc gaa ttg gaa        1584
Phe Phe Trp Asp Ala Asn Asp Ile Tyr Arg Ile Phe Ala Glu Leu Glu
                    515                 520                 525 ggc gta tgg cag ccc gct gcc caa ccc aaa cgc cgc cgc cac cgg caa        1632
Gly Val Trp Gln Pro Ala Ala Gln Pro Lys Arg Arg Arg His Arg Gln
                530                 535                 540 gac gcc ttg ccc ggg cca tgc atc gcc tcc acc ccc aaa aag cac cga        1680
Asp Ala Leu Pro Gly Pro Cys Ile Ala Ser Thr Pro Lys Lys His Arg
545                 550                 555                 560 ggt                                                                    1683
Gly

<210> SEQ ID NO 4
<211> LENGTH: 561
<212> TYPE: PRT
<213> ORGANISM: Artificial Sequence
<220> FEATURE:
<223> OTHER INFORMATION: codon-optimized sequence of hCMV pp65

<400> SEQUENCE: 4

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
            35                  40                  45

Arg Val Ser Gln Pro Ser Leu Ile Leu Val Ser Gln Tyr Thr Pro Asp
        50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125
```

```
His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
                180                 185                 190

Val Ala Leu Arg His Val Val Cys Ala His Glu Leu Val Cys Ser Met
            195                 200                 205

Glu Asn Thr Arg Ala Thr Lys Met Gln Val Ile Gly Asp Gln Tyr Val
        210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
```

Gly

<210> SEQ ID NO 5
<211> LENGTH: 1671
<212> TYPE: DNA
<213> ORGANISM: Artificial Sequence
<220> FEATURE:
<223> OTHER INFORMATION: codon-optimized sequence of hCMV pp65

<400> SEQUENCE: 5

```
atggagtccc gcggtcgccg ctgtcccgaa atgatatccg tactgggtcc catttccggg      60
cacgtgctga aagccgtgtt tagtcgcggc gatacccccg tgctgcccca cgagacccga     120
ctcctgcaga ccggtatcca cgtacgcgtg agccagccct ccctgatctt ggtatcccag     180
tacacccccg actccacccc atgccaccgc ggcgacaatc agctgcaggt gcagcacacc     240
tactttaccg cagcgaggt ggagaacgtg tccgtcaacg tgcacaaccc caccggccga     300
agcatctgcc ccagccagga gcccatgtcc atctatgtgt acgccctgcc cctcaagatg     360
ctgaacatcc cagcatcaa cgtgcaccac taccctccg ccgccgagcg caaacaccga     420
cacctgcccg tagctgacgc tgtgattcac gcctccggca gcagatgtg gcaggcccgc     480
ctcaccgtct ccggactggc ctggaccccg cagcagaacc agtggaaaga gcccgacgtc     540
tactacacct cagccttcgt gtttcccacc aaggacgtgg cactgcggca cgtggtgtgc     600
gcccacgagc tggtttgctc catggagaac acccgcgcaa ccaagatgca ggtgataggt     660
gaccagtacg tcaaggtgta cctggagtcc ttctgcgagg acgtgccctc cggcaagctc     720
tttatgcacg tcaccctggg ctctgacgtg aagaggacc tgaccatgac ccgcaacccc     780
caacccttca tgcgccccca cgagcgcaac ggctttaccg tgttgtgtcc caaaaatatg     840
ataatcaaac ccggcaagat ctcccacatc atgctggatg tggcttttac ctcacacgag     900
cattttgggc tgctgtgtcc caagagcatc cccggcctga gcatctcagg taacctgttg    960
atgaacgggc agcagatctt cctggaggta caagccatac gcgagaccgt ggaactgcgc    1020
cagtacgatc ccgtggctgc cctcttcttt ttcgatatcg acttgctgct gcagcgcggg    1080
cctcagtaca gcgagcaccc caccttcacc agccagtatc gcatccaggg caagcttgag    1140
taccgacaca cctgggaccg gcacgacgag ggtgccgccc agggcgacga cgacgtctgg    1200
accagcggat ccgactccga cgaagaactc gtaaccaccg agcgcaagac ccccgcgtc    1260
accggcggcg gcgccatggc cggcgcctcc acttccgccg gctcagcatc ctccgccacc    1320
gcctgcacct ccggcgttat gacacgcggc cgccttaagg ccgagtccac cgtcgccccc    1380
gaagaggaca ccgacgagga ttccgacaac gaaatcccaa atcccgccgt gttcacctgg    1440
ccaccctggc aggccggcat cctggcccgc aacctggtgc ccatggtggc taccgttcag    1500
ggtcagaatc tgaagtacca ggaattcttc tgggacgcca cgacatcta ccgcatcttc    1560
gccgaattgg aaggcgtatg gcagcccgct gcccaaccca acgccgccg ccaccggcaa    1620
gacgccttgc ccgggccatg catcgcctcc acccccaaaa agcaccgagg t              1671
```

<210> SEQ ID NO 6
<211> LENGTH: 557
<212> TYPE: PRT
<213> ORGANISM: Artificial Sequence
<220> FEATURE:
<223> OTHER INFORMATION: codon-optimized sequence of hCMV pp65

<400> SEQUENCE: 6

-continued

```
Met Glu Ser Arg Gly Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Gly Ile His Val
            35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
    115                 120                 125

His His Tyr Pro Ser Ala Ala Glu Arg Lys His Arg His Leu Pro Val
130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
    195                 200                 205

Glu Asn Thr Arg Ala Thr Lys Met Gln Val Ile Gly Asp Gln Tyr Val
210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
    275                 280                 285

His Ile Met Leu Asp Val Ala Phe Thr Ser His Glu His Phe Gly Leu
290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
    355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
            405                 410                 415
```

```
              Thr Pro Arg Val Thr Gly Gly Ala Met Ala Gly Ala Ser Thr Ser
                          420                 425                 430

Ala Gly Ser Ala Ser Ala Thr Ala Cys Thr Ser Gly Val Met Thr
                          435                 440                 445

Arg Gly Arg Leu Lys Ala Glu Ser Thr Val Ala Pro Glu Glu Asp Thr
                          450                 455                 460

Asp Glu Asp Ser Asp Asn Glu Ile His Asn Pro Ala Val Phe Thr Trp
              465                 470                 475                 480

Pro Pro Trp Gln Ala Gly Ile Leu Ala Arg Asn Leu Val Pro Met Val
                              485                 490                 495

Ala Thr Val Gln Gly Gln Asn Leu Lys Tyr Gln Glu Phe Phe Trp Asp
                          500                 505                 510

Ala Asn Asp Ile Tyr Arg Ile Phe Ala Glu Leu Glu Gly Val Trp Gln
                          515                 520                 525

Pro Ala Ala Gln Pro Lys Arg Arg His Arg Gln Asp Ala Leu Pro
                          530                 535                 540

Gly Pro Cys Ile Ala Ser Thr Pro Lys Lys His Arg Gly
              545                 550                 555

<210> SEQ ID NO 7
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 7
atggagagca ggggcaggag gtgccccgag atgatcagcg tgctgggccc catcagcggc      60
cacgtgctga aggccgtgtt cagcaggggc gacaccccg tgctgcccca cgagaccagg     120
ctgctgcaga ccggcatcca cgtgagggtg agccagccca gcctgatcct ggtgagccag     180 tacaccccg acagcacccc ctgccacagg ggcgacaacc agctgcaggt gcagcacacc     240
tacttcaccg gcagcgaggt ggagaacgtg agcgtgaacg tgcacaaccc caccggcagg     300
agcatctgcc ccagccagga gcccatgagc atctacgtgt acgccctgcc cctgaagatg     360
ctgaacatcc ccagcatcaa cgtgcaccac taccccagcg ccgccgagag gaagcacagg     420
cacctgcccg tggccgacgc cgtgatccac gccagcggca gcagatgtg caggccagg      480 ctgaccgtga gcggcctggc ctggaccagg cagcagaacc agtggaagga gcccgacgtg     540
tactacacca cgcccttcgt gttccccacc aaggacgtgg ccctgaggca cgtggtgtgc     600
gcccacgagc tggtgtgcag catggagaac accagggcca ccaagatgca ggtgatcggc     660
gaccagtacg tgaaggtgta cctggagagc ttctgcgagg acgtgcccag cggcaagctg     720
ttcatgcacg tgaccctggg cagcgacgtg gaggaggacc tgaccatgac caggaacccc     780
cagcccttca tgaggccgcca cgagaggaac ggcttcaccg tgctgtgccc caagaacatg     840
atcatcaagc ccggcaagat cagccacatc atgctggacg tggccttcac cagccacgag     900
cacttcgggc tgctgtgccc caagagcatc cccggcctga gcatcagcgg caacctgctg     960
atgaacggcc agcagatctt cctggaggtg caggccatca gggagaccgt ggagctgagg    1020
cagtacgacc ccgtggccgc cctgttcttc ttcgacatcg acctgctgct gcagaggggc    1080
ccccagtaca gcgagcaccc caccttcacc agccagtaca ggatccaggg caagctggag    1140
tacaggcaca cctgggacag gcacgacgag ggcgccgccc agggcgacga cgacgtgtgg    1200
accagcggca gcgacagcga cgaggagctg gtgaccacca gaggaagac ccccaggggtg    1260
```

-continued

```
accggcggcg gcgccatggc cggcgccagc accagcgccg gcaggaagag gaagagcgcc   1320
agcagcgcca ccgcctgcac cagcggcgtg atgaccaggg gcaggctgaa ggccgagagc   1380
accgtggccc ccgaggagga caccgacgag gacagcgaca acgagatcca aaccccgcc    1440 gtgttcacct ggccccctg gcaggccggc atcctggcca ggaacctggt gcccatggtg    1500
gccaccgtgc agggccagaa cctgaagtac caggagttct tctgggacgc caacgacatc   1560
tacaggatct tcgccgagct ggaggcgtg tggcagcccg ccgccagcc caagaggagg    1620 aggcacaggc aggacgccct gcccggcccc tgcatcgcca gcaccccaa gaagcacagg   1680 ggc                                                                 1683

<210> SEQ ID NO 8
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 8
atggagagcc gcgggagaag atgtcccgag atgatcagtg tcctgggccc aatatctggc     60
cacgtgctga aggctgtctt ctcgagggga gataccag ttcttcctca cgaaaccaga     120
ctgctccaga caggtattca gtccgcgtg tctcagccgt cactcatcct tgttagccag     180
tacactccgg atagtactcc atgccatagg ggcgacaacc agctccaagt tcagcatacg    240
tattttacag ggtccgaggt ggagaatgtg agcgtcaatg tgcacaaccc caccggacgt    300
tcaatatgcc catctcagga acctatgtct atctacgttt atgcactgcc tttgaagatg    360
ctgaacatcc ccagtattaa tgttcaccat taccccctg ctgctgaacg caagcacagg    420
catctccccg tggccgacgc tgtgatccat gctagtggca aacagatgtg gcaggcacga    480
ttaacagtaa gcgggttggc atggacacgg cagcagaatc agtggaaaga gcccgacgta    540
tactatacca gtgcctttgt ctttcctacc aaggacgtcg ccttaagaca tgttgtctgc    600
gcgcacgagc tggtgtgtag catggaaaac actcgtgcaa ctaaaatgca ggtgattggc    660
gatcagtatg ttaaggtcta tctggagtca ttctgtgagg acgtcccatc cgggaaacta    720
ttcatgcacg tcactcttgg ttcggatgtg aagaagatc tgacaatgac ccggaacccc    780 caaccctta tgcggcctca cgaacggaac gggttcacag tgctatgccc caaaaatatg    840
atcattaaac ccgtaagat atcccatatc atgctcgatg tggcttcac ctcccacgaa    900 cacttcgggc tgctgtgtcc caagtccatc ccaggactca gcatatccgg caatttattg    960
atgaacggtc aacagatctt cctggaggtg caggcaatca gagaaacagt ggaactccgc   1020
cagtatgacc ctgtggcggc tctgtttttc tttgacattg atctgttgct tcaacgagga   1080
ccacaatatt ctgagcatcc aacatttact tcccagtacc gtatccaagg caagctcgaa   1140
tacaggcaca cgtgggacag gcacgacgag ggggctgccc aaggggacga tgacgtatgg   1200
acatccggct ccgatagtga tgaggagctt gtgaccaccg agcggaagac cccaagagtg   1260
acgggcggag gtgcaatggc cggagcatct accagcgccg gcggaagcg aaaatctgcc   1320 tcatcagcaa ctgcttgcac cagcggtgta atgacgaggg gacgcctaaa ggctgagagc   1380
accgtggccc ctgaggaaga tactgacgag gactcagaca cgaaattca caatcctgcc   1440 gtgttcacat ggcctccttg gcaggccgga attctggccc ggaacttggt accgatggtg   1500
gccactgttc agggccagaa cctgaaatac caggagtttt tctgggatgc caatgacatc   1560
tacagaattt ttgcggaact ggagggagtg tggcagccag ccgcacaacc caagcgccgg   1620
```

```
cgccataggc aggatgccct gccgggccct tgcattgcga gcaccccaaa aaagcaccga    1680
ggc                                                                 1683

<210> SEQ ID NO 9
<211> LENGTH: 1683
<212> TYPE: DNA
<213> ORGANISM: Artificial Sequence
<220> FEATURE:
<223> OTHER INFORMATION: codon-optimized sequence of hCMV pp65

<400> SEQUENCE: 9
atggaatctc gaggtagacg ttgtccggag atgatcagcg tgctaggacc aataagtggg      60
cacgtcctga aggctgtgtt ttcaaggggg gatacgccag tgctcccaca cgagacccgc     120
ctgctacaaa caggtattca cgttagggtc tcacagccca gcctaatttt ggttagccag     180
tatacacccg actccacccc ttgtcatcgc ggcgacaacc agctgcaagt ccagcatact     240
tatttcacag gcagcgaggt ggaaaatgtg tcggtcaatg tgcataaccc taccgggcgt     300
tccatctgcc cttcacagga gcctatgtct atctacgtgt atgctttacc tttgaagatg     360
ttaaacatcc cctctatcaa tgtgcaccat tatccttcag cggctgagcg aaacaccgc     420 cacttacccg tggctgacgc agtcatacac gcgagcggta agcagatgtg gcaagcacga     480
ctgacggtct ccggtctggc ttggactaga cagcagaatc agtggaagga acctgatgtg     540
tactacacca gcgcatttgt cttcccaacc aaagacgtgg cactgcgcca cgtagtgtgc     600
gcccatgaac tggtgtgttc catggagaac acccgggcaa ccaagatgca ggtaattggc     660
gatcagtatg tgaaagttta ccttgagtcc ttttgtgagg atgtaccag cggcaagctg     720 ttcatgcatg tgacgttggg cagtgacgtg aagaggacc tgacaatgac tcgaaatcca     780
caaccattta tgaggccgca cgaaagaaac gggtttacag tgctctgccc aaagaacatg     840
atcatcaagc ccgggaagat tagtcatatt atgctcgatg ttgccttcac cagtcacgaa     900
cattttggac tcctttgccc caaatccatc ccaggcttgt caatttcagg caatctcctc     960
atgaacggac agcagatttt cctggaggtg caagcgatcc gggagactgt agagctgaga    1020
cagtatgatc ctgttgcagc cctgttcttc ttcgatatcg accttctcct tcagcgaggc    1080
ccgcagtaca gcgaacaccc aaccttttaca tctcagtacc gcatccaagg gaaactggag    1140
tatcgtcata cctgggacag gcatgacgaa ggggccgctc aaggagacga tgatgtgtgg    1200
acaagtggct cggattccga tgaggagttg gtgacaaccg aaagaaagac tcccagggtt    1260
accggaggag gagcaatggc aggtgcttcc actagcgctg gcaggaaacg gaaaagcgcc    1320
tccagtgcca cagcctgcac ttctggcgtc atgacgaggg gcggctgaa agccgaatct    1380 actgtagccc ctgaggagga cactgacgag gattctgaca tgaaattca caatcccgcg    1440 gttttacat ggccccttg gcaggccgga attctggccc ggaaccttgt gcccatggtc    1500
gccacagtcc aaggccagaa cctgaagtac caggaatttt tctgggatgc aacgacata    1560 tacagaatct tcgcagaact ggagggagtt tggcagcccg ctgctcagcc taaacgagaa    1620
cggcacagac aggacgccct cccagggccg tgcatagcct ctaccccaaa gaagcaccgc    1680
ggt                                                                 1683

<210> SEQ ID NO 10
<211> LENGTH: 1683
<212> TYPE: DNA
<213> ORGANISM: Artificial Sequence
<220> FEATURE:
```

<223> OTHER INFORMATION: codon-optimized sequence of hCMV pp65

<400> SEQUENCE: 10

```
atggaatcgc gtggcaggcg atgtcccgaa atgatttcag tcttaggccc aatctccggg      60
cacgtgctca aagcagtctt ctccaggggg atacccccag tgctccctca cgagacgagg     120
cttctgcaga ccggcataca tgtcagagtt tctcagccca gccttatttt ggtatctcag     180
tacacccccgg acagtacacc gtgtcacaga ggagacaacc agctccaagt ccagcataca     240
tacttcacag gctcggaagt ggaaaacgtg tctgtgaacg tccataaccc aactggccgg     300
tcaatttgcc cctctcagga gcctatgagt atctatgtgt atgctctgcc ctcaaaatg      360
ctgaacatcc aagtattaa tgtccatcat taccctagcg cagccgagag aaagcatcgc     420
cacctgcctg tggctgacgc tgtgatacac gcttcaggta gcaaatgtg gcaggcccgc     480
cttacagtgt ctggattggc atggacacgg cagcagaacc agtggaagga gcccgatgtg     540
tactatacta gcgcttttgt gttccccacg aaagatgtcg ccttacgaca cgttgtatgc     600
gcacacgagc tagtgtgtag tatggagaac acacgtgcca ccaaaatgca ggtcatcggc     660
gatcaatacg tcaaggtgta cctggagagt ttttgcgaag atgttccttc cggcaaattg     720
ttcatgcatg tgaccctggg ttctgatgtt gaggaggatc tgacaatgac tcgaaatccc     780
cagcctttca tgcgccctca cgaacggaac gggtttacag tgctgtgccc gaagaacatg     840
attatcaaac ccggaaaaat tccccacatt atgttggatg tagcctttac agccatgaa      900
cacttcggac ttctctgtcc aaagtcaatt ccagggctgt ctataagcgg aaccttcta     960
atgaatggcc agcagatctt tctcgaggtg caggccataa gagagactgt ggagctccgg    1020
caatacgatc cggttgcggc cctcttcttt ttcgacatcg acctgttact gcagcgcggt    1080
ccacagtata gcgaacaccc aactttcacc agtcagtatc gtatccaagg taagctggag    1140
tatagacaca cgtgggatcg ccatgacgaa ggtgcagccc aaggcgacga cgacgtttgg    1200
acctccggat ctgactcaga tgaggagctg gttaccacag aaagaaagac tcccagggtc    1260
actggaggtg gggctatggc tggagcaagc actagcgcag gccggaaacg aaagtccgcc    1320
agctccgcca cagcttgcac ctcaggcgta atgacgcggg aagactgaa  agcccgagtcc    1380
actgtggcac ctgaagagga cacagacgaa gattccgaca tgaaatcca caatcccgca    1440
gtttttacct ggccacctg gcaggcgggg attctggcgc gcaatctggt gcccatggtg    1500
gctaccgtac aaggccagaa tttgaagtac caggagttct tttgggacgc caatgacatc    1560
tatagaatct ttgccgaact ggaggggtg tggcagccga ccgctcaacc aaagaggagg    1620
cgccaccggc aggatgcgct acccggacct tgcatcgcca gcacccctaa gaagcatagg    1680
ggg                                                                  1683
```

<210> SEQ ID NO 11
<211> LENGTH: 2718
<212> TYPE: DNA
<213> ORGANISM: Human cytomegalovirus
<220> FEATURE:
<221> NAME/KEY: CDS
<222> LOCATION: (1)..(2718)

<400> SEQUENCE: 11

```
atg gaa tcc agg atc tgg tgc ctg gta gtc tgc gtt aac ctg tgt atc        48
Met Glu Ser Arg Ile Trp Cys Leu Val Val Cys Val Asn Leu Cys Ile
1               5                   10                  15 gtc tgt ctg ggt gct gcg gtt tcc tct tct agt act tcc cat gca act       96
Val Cys Leu Gly Ala Ala Val Ser Ser Ser Ser Thr Ser His Ala Thr
```

-continued

```
                20                  25                  30
tct tct act cac aat gga agc cat act tct cgt acg tct gct caa    144
Ser Ser Thr His Asn Gly Ser His Thr Ser Arg Thr Thr Ser Ala Gln
         35                  40                  45 acc cgg tca gtc tat tct caa cac gta acg tct tct gaa gcc gtc agt    192
Thr Arg Ser Val Tyr Ser Gln His Val Thr Ser Ser Glu Ala Val Ser
     50                  55                  60 cat aga gcc aac gag act atc tac aac act acc ctc aag tac gga gat    240
His Arg Ala Asn Glu Thr Ile Tyr Asn Thr Thr Leu Lys Tyr Gly Asp
 65                  70                  75                  80 gtg gtg gga gtc aac act acc aag tac ccc tat cgc gtg tgt tct atg    288
Val Val Gly Val Asn Thr Thr Lys Tyr Pro Tyr Arg Val Cys Ser Met
                 85                  90                  95 gcc cag ggt acg gat ctt att cgc ttt gaa cgt aat atc atc tgc acc    336
Ala Gln Gly Thr Asp Leu Ile Arg Phe Glu Arg Asn Ile Ile Cys Thr
            100                 105                 110 tcg atg aag cct atc aat gaa gac ttg gat gag ggc atc atg gtg gtc    384
Ser Met Lys Pro Ile Asn Glu Asp Leu Asp Glu Gly Ile Met Val Val
        115                 120                 125 tac aag cgc aac atc gtg gcg cac acc ttt aag gta cgg gtc tac caa    432
Tyr Lys Arg Asn Ile Val Ala His Thr Phe Lys Val Arg Val Tyr Gln
    130                 135                 140 aag gtt ttg acg ttt cgt cgt agc tac gct tac atc tac acc act tat    480
Lys Val Leu Thr Phe Arg Arg Ser Tyr Ala Tyr Ile Tyr Thr Thr Tyr
145                 150                 155                 160 ctg ctg ggc agc aat acg gaa tac gtg gcg cct cct atg tgg gag att    528
Leu Leu Gly Ser Asn Thr Glu Tyr Val Ala Pro Pro Met Trp Glu Ile
                165                 170                 175 cat cac atc aac aag ttt gct caa tgc tac agt tcc tac agc cgc gtt    576
His His Ile Asn Lys Phe Ala Gln Cys Tyr Ser Ser Tyr Ser Arg Val
            180                 185                 190 ata gga ggc acg gtt ttc gtg gca tat cat agg gac agt tat gaa aac    624
Ile Gly Gly Thr Val Phe Val Ala Tyr His Arg Asp Ser Tyr Glu Asn
        195                 200                 205 aaa acc atg caa tta att ccc gac gat tat tcc aac acc cac agt acc    672
Lys Thr Met Gln Leu Ile Pro Asp Asp Tyr Ser Asn Thr His Ser Thr
    210                 215                 220 cgt tac gtg acg gtc aag gat cag tgg cac agc cgc ggc agc acc tgg    720
Arg Tyr Val Thr Val Lys Asp Gln Trp His Ser Arg Gly Ser Thr Trp
225                 230                 235                 240 ctc tat cgt gag acc tgt aat ctg aac tgt atg ctg acc atc act act    768
Leu Tyr Arg Glu Thr Cys Asn Leu Asn Cys Met Leu Thr Ile Thr Thr
                245                 250                 255 gcg cgc tcc aag tat cct tat cat ttt ttt gca act tcc acg ggt gat    816
Ala Arg Ser Lys Tyr Pro Tyr His Phe Phe Ala Thr Ser Thr Gly Asp
            260                 265                 270 gtg gtt tac att tct cct ttc tac aac gga acc aat cgc aat gcc agc    864
Val Val Tyr Ile Ser Pro Phe Tyr Asn Gly Thr Asn Arg Asn Ala Ser
        275                 280                 285 tac ttt gga gaa aac gcc gac aag ttt ttc att ttc ccg aac tac acc    912
Tyr Phe Gly Glu Asn Ala Asp Lys Phe Phe Ile Phe Pro Asn Tyr Thr
    290                 295                 300 atc gtt tcc gac ttt gga aga ccc aac gct gcg cca gaa acc cat agg    960
Ile Val Ser Asp Phe Gly Arg Pro Asn Ala Ala Pro Glu Thr His Arg
305                 310                 315                 320 ttg gtg gct ttt ctc gaa cgt gcc gac tcg gtg atc tct tgg gat ata   1008
Leu Val Ala Phe Leu Glu Arg Ala Asp Ser Val Ile Ser Trp Asp Ile
                325                 330                 335 cag gac gag aag aat gtc acc tgc cag ctc acc ttc tgg gaa gcc tcg   1056
```

```
                -continued

Gln Asp Glu Lys Asn Val Thr Cys Gln Leu Thr Phe Trp Glu Ala Ser
                     340                 345                 350 gaa cgt act atc cgt tcc gaa gcc gaa gac tcg tac cac ttt tct tct          1104
Glu Arg Thr Ile Arg Ser Glu Ala Glu Asp Ser Tyr His Phe Ser Ser
            355                 360                 365 gcc aaa atg act gca act ttt ctg tct aag aaa caa gaa gtg aac atg          1152
Ala Lys Met Thr Ala Thr Phe Leu Ser Lys Lys Gln Glu Val Asn Met
370                 375                 380 tcc gac tcc gcg ctg gac tgc gta cgt gat gag gct ata aat aag tta          1200
Ser Asp Ser Ala Leu Asp Cys Val Arg Asp Glu Ala Ile Asn Lys Leu
385                 390                 395                 400 cag cag att ttc aat act tca tac aat caa aca tat gaa aaa tac gga          1248
Gln Gln Ile Phe Asn Thr Ser Tyr Asn Gln Thr Tyr Glu Lys Tyr Gly
                405                 410                 415 aac gtg tcc gtc ttc gaa acc agc ggc ggt ctg gtg gtg ttc tgg caa          1296
Asn Val Ser Val Phe Glu Thr Ser Gly Gly Leu Val Val Phe Trp Gln
            420                 425                 430 ggc atc aag caa aaa tct ttg gtg gaa ttg gaa cgt ttg gcc aat cga          1344
Gly Ile Lys Gln Lys Ser Leu Val Glu Leu Glu Arg Leu Ala Asn Arg
        435                 440                 445 tcc agt ctg aat atc act cat agg acc aga aga agt acg agt gac aat          1392
Ser Ser Leu Asn Ile Thr His Arg Thr Arg Arg Ser Thr Ser Asp Asn
450                 455                 460 aat aca act cat ttg tcc agc atg gaa tcg gtg cac aat ctg gtc tac          1440
Asn Thr Thr His Leu Ser Ser Met Glu Ser Val His Asn Leu Val Tyr
465                 470                 475                 480 gcc cag ctg cag ttc acc tat gac acg ttg cgc ggt tac atc aac cgg          1488
Ala Gln Leu Gln Phe Thr Tyr Asp Thr Leu Arg Gly Tyr Ile Asn Arg
                485                 490                 495 gcg ctg gcg caa atc gca gaa gcc tgg tgt gtg gat caa cgg cgc acc          1536
Ala Leu Ala Gln Ile Ala Glu Ala Trp Cys Val Asp Gln Arg Arg Thr
            500                 505                 510 cta gag gtc ttc aag gaa ctc agc aag atc aac ccg tca gcc att ctc          1584
Leu Glu Val Phe Lys Glu Leu Ser Lys Ile Asn Pro Ser Ala Ile Leu
        515                 520                 525 tcg gcc att tac aac aaa ccg att gcc gcg cgt ttc atg ggt gat gtc          1632
Ser Ala Ile Tyr Asn Lys Pro Ile Ala Ala Arg Phe Met Gly Asp Val
530                 535                 540 ttg ggc ctg gcc agc tgc gtg acc atc aac caa acc agc gtc aag gtg          1680
Leu Gly Leu Ala Ser Cys Val Thr Ile Asn Gln Thr Ser Val Lys Val
545                 550                 555                 560 ctg cgt gat atg aac gtg aag gaa tcg cca gga cgc tgc tac tca cga          1728
Leu Arg Asp Met Asn Val Lys Glu Ser Pro Gly Arg Cys Tyr Ser Arg
                565                 570                 575 ccc gtg gtc atc ttt aat ttc gcc aac agc tcg tac gtg cag tac ggt          1776
Pro Val Val Ile Phe Asn Phe Ala Asn Ser Ser Tyr Val Gln Tyr Gly
            580                 585                 590 caa ctg ggc gag gac aac gaa atc ctg ttg ggc aac cac cgc act gag          1824
Gln Leu Gly Glu Asp Asn Glu Ile Leu Leu Gly Asn His Arg Thr Glu
        595                 600                 605 gaa tgt cag ctt ccc agc ctc aag atc ttc atc gcc ggg aac tcg gcc          1872
Glu Cys Gln Leu Pro Ser Leu Lys Ile Phe Ile Ala Gly Asn Ser Ala
610                 615                 620 tac gag tac gtg gac tac ctc ttc aaa cgc atg att gac ctc agc agt          1920
Tyr Glu Tyr Val Asp Tyr Leu Phe Lys Arg Met Ile Asp Leu Ser Ser
625                 630                 635                 640 atc tcc acc gtc gac agc atg atc gcc ctg gat atc gac ccg ctg gaa          1968
Ile Ser Thr Val Asp Ser Met Ile Ala Leu Asp Ile Asp Pro Leu Glu
                645                 650                 655
```

```
aat acc gac ttc agg gta ctg gaa ctt tac tcg cag aaa gag ctg cgt    2016
Asn Thr Asp Phe Arg Val Leu Glu Leu Tyr Ser Gln Lys Glu Leu Arg
            660                 665                 670 tcc agc aac gtt ttt gac ctc gaa gag atc atg cga gaa ttc aac tcg    2064
Ser Ser Asn Val Phe Asp Leu Glu Glu Ile Met Arg Glu Phe Asn Ser
            675                 680                 685 tac aag cag cgg gta aag tac gtg gag gac aag gta gtc gac ccg cta    2112
Tyr Lys Gln Arg Val Lys Tyr Val Glu Asp Lys Val Val Asp Pro Leu
            690                 695                 700 ccg ccc tac ctc aag ggt ctg gac gac ctc atg agc ggc ctg ggc gcc    2160
Pro Pro Tyr Leu Lys Gly Leu Asp Asp Leu Met Ser Gly Leu Gly Ala
705                 710                 715                 720 gcg gga aag gcc gtt ggc gta gcc att ggg gcc gtg ggt ggc gcg gtg    2208
Ala Gly Lys Ala Val Gly Val Ala Ile Gly Ala Val Gly Gly Ala Val
                725                 730                 735 gcc tcc gtg gtc gaa ggc gtt gcc acc ttc ctc aaa aac ccc ttc gga    2256
Ala Ser Val Val Glu Gly Val Ala Thr Phe Leu Lys Asn Pro Phe Gly
            740                 745                 750 gcc ttc acc atc atc ctc gtg gcc ata gcc gta gtc att atc act tat    2304
Ala Phe Thr Ile Ile Leu Val Ala Ile Ala Val Val Ile Ile Thr Tyr
            755                 760                 765 ttg atc tat act cga cag cgg cgt ctg tgc acg cag ccg ctg cag aac    2352
Leu Ile Tyr Thr Arg Gln Arg Arg Leu Cys Thr Gln Pro Leu Gln Asn
770                 775                 780 ctc ttt ccc tat ctg gtg tcc gcc gac ggg acc acc gtg acg tcg ggc    2400
Leu Phe Pro Tyr Leu Val Ser Ala Asp Gly Thr Thr Val Thr Ser Gly
785                 790                 795                 800 agc acc aaa gac acg tcg tta cag gct ccg cct tcc tac gag gaa agt    2448
Ser Thr Lys Asp Thr Ser Leu Gln Ala Pro Pro Ser Tyr Glu Glu Ser
                805                 810                 815 gtt tat aat tct ggt cgc aaa gga ccg gga cca ccg tcg tct gat gca    2496
Val Tyr Asn Ser Gly Arg Lys Gly Pro Gly Pro Pro Ser Ser Asp Ala
            820                 825                 830 tcc acg gcg gct ccg cct tac acc aac gag cag gct tac cag atg ctt    2544
Ser Thr Ala Ala Pro Pro Tyr Thr Asn Glu Gln Ala Tyr Gln Met Leu
            835                 840                 845 ctg gcc ctg gcc cgt ctg gac gca gag cag cga gcg cag cag aac ggt    2592
Leu Ala Leu Ala Arg Leu Asp Ala Glu Gln Arg Ala Gln Gln Asn Gly
850                 855                 860 aca gat tct ttg gac gga cag act ggc acg cag gac aag gga cag aag    2640
Thr Asp Ser Leu Asp Gly Gln Thr Gly Thr Gln Asp Lys Gly Gln Lys
865                 870                 875                 880 cct aac ctg cta gac cgg ctg cga cat cgc aaa aac ggc tac aga cac    2688
Pro Asn Leu Leu Asp Arg Leu Arg His Arg Lys Asn Gly Tyr Arg His
                885                 890                 895 ttg aaa gac tcc gac gaa gaa gag aac gtc                            2718
Leu Lys Asp Ser Asp Glu Glu Glu Asn Val
            900                 905
```

<210> SEQ ID NO 12
<211> LENGTH: 906
<212> TYPE: PRT
<213> ORGANISM: Human cytomegalovirus

<400> SEQUENCE: 12

```
Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
```

-continued

```
                35                  40                  45
Thr Arg Ser Val Tyr Ser Gln His Val Thr Ser Ser Glu Ala Val Ser
 50                  55                  60

His Arg Ala Asn Glu Thr Ile Tyr Asn Thr Thr Leu Lys Tyr Gly Asp
 65                  70                  75                  80

Val Val Gly Val Asn Thr Thr Lys Tyr Pro Tyr Arg Val Cys Ser Met
                 85                  90                  95

Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
                115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
                180                 185                 190

Ile Gly Gly Thr Val Phe Val Ala Tyr His Arg Asp Ser Tyr Glu Asn
                195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
                260                 265                 270

Val Val Tyr Ile Ser Pro Phe Tyr Asn Gly Thr Asn Arg Asn Ala Ser
                275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Glu Asp Ser Tyr His Phe Ser Ser
                355                 360                 365

Ala Lys Met Thr Ala Thr Phe Leu Ser Lys Lys Gln Glu Val Asn Met
                370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
                435                 440                 445

Ser Ser Leu Asn Ile Thr His Arg Thr Arg Arg Ser Thr Ser Asp Asn
450                 455                 460
```

```
Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
            485                 490                 495

Ala Leu Ala Gln Ile Ala Glu Ala Trp Cys Val Asp Gln Arg Arg Thr
        500                 505                 510

Leu Glu Val Phe Lys Glu Leu Ser Lys Ile Asn Pro Ser Ala Ile Leu
    515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Ile Ile Thr Tyr
        755                 760                 765

Leu Ile Tyr Thr Arg Gln Arg Arg Leu Cys Thr Gln Pro Leu Gln Asn
    770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880
```

```
Pro Asn Leu Leu Asp Arg Leu Arg His Arg Lys Asn Gly Tyr Arg His
            885                 890                 895
Leu Lys Asp Ser Asp Glu Glu Glu Asn Val
        900                 905

<210> SEQ ID NO 13
<211> LENGTH: 2139
<212> TYPE: DNA
<213> ORGANISM: Artificial Sequence
<220> FEATURE:
<223> OTHER INFORMATION: codon-optimized sequence of hCMV gB
<220> FEATURE:
<221> NAME/KEY: CDS
<222> LOCATION: (1)..(2139)

<400> SEQUENCE: 13 atg gaa tcc agg atc tgg tgc ctg gta gtc tgc gtt aac ctg tgt atc        48
Met Glu Ser Arg Ile Trp Cys Leu Val Val Cys Val Asn Leu Cys Ile
1               5                   10                  15 gtc tgt ctg ggt gct gcc gtt tcc tct tct agt act tcc cat gca act        96
Val Cys Leu Gly Ala Ala Val Ser Ser Ser Ser Thr Ser His Ala Thr
            20                  25                  30 tct tct act cac aat gga agc cat act tct cgc acc acc tct gct caa       144
Ser Ser Thr His Asn Gly Ser His Thr Ser Arg Thr Thr Ser Ala Gln
        35                  40                  45 acc cgg tca gtc tat tct caa cac gta acc tct tct gaa gcc gtc agt       192
Thr Arg Ser Val Tyr Ser Gln His Val Thr Ser Ser Glu Ala Val Ser
    50                  55                  60 cat aga gcc aac gag act atc tac aac act acc ctc aag tac gga gat       240
His Arg Ala Asn Glu Thr Ile Tyr Asn Thr Thr Leu Lys Tyr Gly Asp
65                  70                  75                  80 gtg gtg gga gtc aac act acc aag tac ccc tat cgc gtg tgt tct atg       288
Val Val Gly Val Asn Thr Thr Lys Tyr Pro Tyr Arg Val Cys Ser Met
                85                  90                  95 gcc cag ggt acc gat ctt att cgc ttt gaa cgc aat atc atc tgc acc       336
Ala Gln Gly Thr Asp Leu Ile Arg Phe Glu Arg Asn Ile Ile Cys Thr
            100                 105                 110 tcc atg aag cct atc aat gaa gac ttg gat gag ggc atc atg gtg gtc       384
Ser Met Lys Pro Ile Asn Glu Asp Leu Asp Glu Gly Ile Met Val Val
        115                 120                 125 tac aag cgc aac atc gtg gcc cac acc ttt aag gta cgg gtc tac caa       432
Tyr Lys Arg Asn Ile Val Ala His Thr Phe Lys Val Arg Val Tyr Gln
    130                 135                 140 aag gtt ttg acc ttt cgc cgc agc tac gct tac atc tac acc act tat       480
Lys Val Leu Thr Phe Arg Arg Ser Tyr Ala Tyr Ile Tyr Thr Thr Tyr
145                 150                 155                 160 ctg ctg ggc agc aat acc gaa tac gtg gcc cct cct atg tgg gag att       528
Leu Leu Gly Ser Asn Thr Glu Tyr Val Ala Pro Pro Met Trp Glu Ile
                165                 170                 175 cat cac atc aac aag ttt gct caa tgc tac agt tcc tac agc cgc gtt       576
His His Ile Asn Lys Phe Ala Gln Cys Tyr Ser Ser Tyr Ser Arg Val
            180                 185                 190 ata gga ggc acc gtt ttc gtg gca tat cat agg gac agt tat gaa aac       624
Ile Gly Gly Thr Val Phe Val Ala Tyr His Arg Asp Ser Tyr Glu Asn
        195                 200                 205 aaa acc atg caa tta att ccc gac gat tat tcc aac acc cac agt acc       672
Lys Thr Met Gln Leu Ile Pro Asp Asp Tyr Ser Asn Thr His Ser Thr
    210                 215                 220 cgc tac gtg acc gtc aag gat cag tgg cac agc cgc ggc agc acc tgg       720
Arg Tyr Val Thr Val Lys Asp Gln Trp His Ser Arg Gly Ser Thr Trp
225                 230                 235                 240
```

| | | |
|---|---|---|
| ctc tat cgc gag acc tgt aat ctg aac tgt atg ctg acc atc act act<br>Leu Tyr Arg Glu Thr Cys Asn Leu Asn Cys Met Leu Thr Ile Thr Thr<br>245 250 255 | | 768 |
| gcc cgc tcc aag tat cct tat cat ttt ttt gca act tcc acc ggt gat<br>Ala Arg Ser Lys Tyr Pro Tyr His Phe Phe Ala Thr Ser Thr Gly Asp<br>260 265 270 | | 816 |
| gtg gtt tac att tct cct ttc tac aac gga acc aat cgc aat gcc agc<br>Val Val Tyr Ile Ser Pro Phe Tyr Asn Gly Thr Asn Arg Asn Ala Ser<br>275 280 285 | | 864 |
| tac ttt gga gaa aac gcc gac aag ttt ttc att ttc ccc aac tac acc<br>Tyr Phe Gly Glu Asn Ala Asp Lys Phe Phe Ile Phe Pro Asn Tyr Thr<br>290 295 300 | | 912 |
| atc gtt tcc gac ttt gga aga ccc aac gct gcc cca gaa acc cat agg<br>Ile Val Ser Asp Phe Gly Arg Pro Asn Ala Ala Pro Glu Thr His Arg<br>305 310 315 320 | | 960 |
| ttg gtg gct ttt ctc gaa cgc gcc gac tcc gtg atc tct tgg gat ata<br>Leu Val Ala Phe Leu Glu Arg Ala Asp Ser Val Ile Ser Trp Asp Ile<br>325 330 335 | | 1008 |
| cag gac gag aag aat gtc acc tgc cag ctc acc ttc tgg gaa gcc tcc<br>Gln Asp Glu Lys Asn Val Thr Cys Gln Leu Thr Phe Trp Glu Ala Ser<br>340 345 350 | | 1056 |
| gaa cgc act atc cgc tcc gaa gcc gaa gac tcc tac cac ttt tct tct<br>Glu Arg Thr Ile Arg Ser Glu Ala Glu Asp Ser Tyr His Phe Ser Ser<br>355 360 365 | | 1104 |
| gcc aaa atg act gca act ttt ctg tct aag aaa caa gaa gtg aac atg<br>Ala Lys Met Thr Ala Thr Phe Leu Ser Lys Lys Gln Glu Val Asn Met<br>370 375 380 | | 1152 |
| tcc gac tcc gcc ctg gac tgc gta cgc gat gag gct ata aat aag tta<br>Ser Asp Ser Ala Leu Asp Cys Val Arg Asp Glu Ala Ile Asn Lys Leu<br>385 390 395 400 | | 1200 |
| cag cag att ttc aat act tca tac aat caa aca tat gaa aaa tac gga<br>Gln Gln Ile Phe Asn Thr Ser Tyr Asn Gln Thr Tyr Glu Lys Tyr Gly<br>405 410 415 | | 1248 |
| aac gtg tcc gtc ttc gaa acc agc ggc ggt ctg gtg gtg ttc tgg caa<br>Asn Val Ser Val Phe Glu Thr Ser Gly Gly Leu Val Val Phe Trp Gln<br>420 425 430 | | 1296 |
| ggc atc aag caa aaa tct ttg gtg gaa ttg gaa cgc ttg gcc aat cga<br>Gly Ile Lys Gln Lys Ser Leu Val Glu Leu Glu Arg Leu Ala Asn Arg<br>435 440 445 | | 1344 |
| tcc agt ctg aat atc act cat agg acc aga aga agt acc agt gac aat<br>Ser Ser Leu Asn Ile Thr His Arg Thr Arg Arg Ser Thr Ser Asp Asn<br>450 455 460 | | 1392 |
| aat aca act cat ttg tcc agc atg gaa tcc gtg cac aat ctg gtc tac<br>Asn Thr Thr His Leu Ser Ser Met Glu Ser Val His Asn Leu Val Tyr<br>465 470 475 480 | | 1440 |
| gcc cag ctg cag ttc acc tat gac acc ttg cgc ggt tac atc aac cgg<br>Ala Gln Leu Gln Phe Thr Tyr Asp Thr Leu Arg Gly Tyr Ile Asn Arg<br>485 490 495 | | 1488 |
| gcc ctg gcc caa atc gca gaa gcc tgg tgt gtg gat caa cgg cgc acc<br>Ala Leu Ala Gln Ile Ala Glu Ala Trp Cys Val Asp Gln Arg Arg Thr<br>500 505 510 | | 1536 |
| cta gag gtc ttc aag gaa ctc agc aag atc aac ccc tca gcc att ctc<br>Leu Glu Val Phe Lys Glu Leu Ser Lys Ile Asn Pro Ser Ala Ile Leu<br>515 520 525 | | 1584 |
| tcc gcc att tac aac aaa ccc att gcc gcc cgc ttc atg ggt gat gtc<br>Ser Ala Ile Tyr Asn Lys Pro Ile Ala Ala Arg Phe Met Gly Asp Val<br>530 535 540 | | 1632 |
| ttg ggc ctg gcc agc tgc gtg acc atc aac caa acc agc gtc aag gtg<br>Leu Gly Leu Ala Ser Cys Val Thr Ile Asn Gln Thr Ser Val Lys Val<br>545 550 555 560 | | 1680 |

```
ctg cgc gat atg aac gtg aag gaa tcc cca gga cgc tgc tac tca cga    1728
Leu Arg Asp Met Asn Val Lys Glu Ser Pro Gly Arg Cys Tyr Ser Arg
            565                 570                 575 ccc gtg gtc atc ttt aat ttc gcc aac agc tcc tac gtg cag tac ggt    1776
Pro Val Val Ile Phe Asn Phe Ala Asn Ser Ser Tyr Val Gln Tyr Gly
            580                 585                 590 caa ctg ggc gag gac aac gaa atc ctg ttg ggc aac cac cgc act gag    1824
Gln Leu Gly Glu Asp Asn Glu Ile Leu Leu Gly Asn His Arg Thr Glu
            595                 600                 605 gaa tgt cag ctt ccc agc ctc aag atc ttc atc gcc ggg aac tcc gcc    1872
Glu Cys Gln Leu Pro Ser Leu Lys Ile Phe Ile Ala Gly Asn Ser Ala
    610                 615                 620 tac gag tac gtg gac tac ctc ttc aaa cgc atg att gac ctc agc agt    1920
Tyr Glu Tyr Val Asp Tyr Leu Phe Lys Arg Met Ile Asp Leu Ser Ser
625                 630                 635                 640 atc tcc acc gtc gac agc atg atc gcc ctg gat atc gac ccc ctg gaa    1968
Ile Ser Thr Val Asp Ser Met Ile Ala Leu Asp Ile Asp Pro Leu Glu
            645                 650                 655 aat acc gac ttc agg gta ctg gaa ctt tac tcc cag aaa gag ctg cgc    2016
Asn Thr Asp Phe Arg Val Leu Glu Leu Tyr Ser Gln Lys Glu Leu Arg
            660                 665                 670 tcc agc aac gtt ttt gac ctc gaa gag atc atg cgc gaa ttc aac tcc    2064
Ser Ser Asn Val Phe Asp Leu Glu Glu Ile Met Arg Glu Phe Asn Ser
            675                 680                 685 tac aag cag cgg gta aag tac gtg gag gac aag gta gtc gac cca cta    2112
Tyr Lys Gln Arg Val Lys Tyr Val Glu Asp Lys Val Val Asp Pro Leu
            690                 695                 700 cct ccc tac ctc aag ggt ctg gac gac                                2139
Pro Pro Tyr Leu Lys Gly Leu Asp Asp
705                 710

<210> SEQ ID NO 14
<211> LENGTH: 713
<212> TYPE: PRT
<213> ORGANISM: Artificial Sequence
<220> FEATURE:
<223> OTHER INFORMATION: codon-optimized sequence of hCMV gB

<400> SEQUENCE: 14

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
            85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
```

-continued

```
            145                 150                 155                 160
Leu Leu Gly Ser Asn Thr Glu Tyr Val Ala Pro Met Trp Glu Ile
                165                 170                 175
His His Ile Asn Lys Phe Ala Gln Cys Tyr Ser Ser Tyr Ser Arg Val
                180                 185                 190
Ile Gly Gly Thr Val Phe Val Ala Tyr His Arg Asp Ser Tyr Glu Asn
                195                 200                 205
Lys Thr Met Gln Leu Ile Pro Asp Asp Tyr Ser Asn Thr His Ser Thr
    210                 215                 220
Arg Tyr Val Thr Val Lys Asp Gln Trp His Ser Arg Gly Ser Thr Trp
225                 230                 235                 240
Leu Tyr Arg Glu Thr Cys Asn Leu Asn Cys Met Leu Thr Ile Thr Thr
                245                 250                 255
Ala Arg Ser Lys Tyr Pro Tyr His Phe Phe Ala Thr Ser Thr Gly Asp
                260                 265                 270
Val Val Tyr Ile Ser Pro Phe Tyr Asn Gly Thr Asn Arg Asn Ala Ser
                275                 280                 285
Tyr Phe Gly Glu Asn Ala Asp Lys Phe Phe Ile Phe Pro Asn Tyr Thr
                290                 295                 300
Ile Val Ser Asp Phe Gly Arg Pro Asn Ala Ala Pro Glu Thr His Arg
305                 310                 315                 320
Leu Val Ala Phe Leu Glu Arg Ala Asp Ser Val Ile Ser Trp Asp Ile
                325                 330                 335
Gln Asp Glu Lys Asn Val Thr Cys Gln Leu Thr Phe Trp Glu Ala Ser
                340                 345                 350
Glu Arg Thr Ile Arg Ser Glu Ala Glu Asp Ser Tyr His Phe Ser Ser
                355                 360                 365
Ala Lys Met Thr Ala Thr Phe Leu Ser Lys Lys Gln Glu Val Asn Met
                370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
                420                 425                 430
Gly Ile Lys Gln Lys Ser Leu Val Glu Leu Glu Arg Leu Ala Asn Arg
                435                 440                 445
Ser Ser Leu Asn Ile Thr His Arg Thr Arg Ser Thr Ser Asp Asn
                450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
                500                 505                 510
Leu Glu Val Phe Lys Glu Leu Ser Lys Ile Asn Pro Ser Ala Ile Leu
                515                 520                 525
Ser Ala Ile Tyr Asn Lys Pro Ile Ala Ala Arg Phe Met Gly Asp Val
                530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
```

-continued

```
Pro Val Val Ile Phe Asn Phe Ala Asn Ser Ser Tyr Val Gln Tyr Gly
            580                 585                 590
Gln Leu Gly Glu Asp Asn Glu Ile Leu Leu Gly Asn His Arg Thr Glu
        595                 600                 605
Glu Cys Gln Leu Pro Ser Leu Lys Ile Phe Ile Ala Gly Asn Ser Ala
    610                 615                 620
Tyr Glu Tyr Val Asp Tyr Leu Phe Lys Arg Met Ile Asp Leu Ser Ser
625                 630                 635                 640
Ile Ser Thr Val Asp Ser Met Ile Ala Leu Asp Ile Asp Pro Leu Glu
                645                 650                 655
Asn Thr Asp Phe Arg Val Leu Glu Leu Tyr Ser Gln Lys Glu Leu Arg
            660                 665                 670
Ser Ser Asn Val Phe Asp Leu Glu Glu Ile Met Arg Glu Phe Asn Ser
        675                 680                 685
Tyr Lys Gln Arg Val Lys Tyr Val Glu Asp Lys Val Val Asp Pro Leu
    690                 695                 700
Pro Pro Tyr Leu Lys Gly Leu Asp Asp
705                 710
```

<210> SEQ ID NO 15
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 15

| | | | | |
|---|---|---|---|---|
| atggagagca | ggatctggtg | cctggtggtg | tgcgtgaacc | tgtgcatcgt | gtgcctgggc | 60 |
| gccgccgtga | gcagcagcag | caccagccac | gccaccagca | gcacccacaa | cggcagccac | 120 |
| accagcagga | ccaccagcgc | ccagaccagg | agcgtgtaca | gccagcacgt | gaccagcagc | 180 |
| gaggccgtga | gccacagggc | caacgagacc | atctacaaca | ccaccctgaa | gtacggcgac | 240 |
| gtggtgggcg | tgaacaccac | caagtacccc | tacagggtgt | gcagcatggc | ccagggcacc | 300 |
| gacctgatca | ggttcgagag | gaacatcatc | tgcaccagca | tgaagcccat | caacgaggac | 360 |
| ctggacgagg | gcatcatggt | ggtgtacaag | aggaacatcg | tggcccacac | cttcaaggtg | 420 |
| agggtgtacc | agaaggtgct | gaccttcagg | aggagctacg | cctacatcta | caccacctac | 480 |
| ctgctgggca | gcaacaccga | gtacgtggcc | ccccccatgt | gggagatcca | ccacatcaac | 540 |
| aagttcgccc | agtgctacag | cagctacagc | agggtgatcg | cggcaccgt | gttcgtggcc | 600 |
| taccacaggg | acagctacga | gaacaagacc | atgcagctga | tccccgacga | ctacagcaac | 660 |
| acccacagca | ccaggtacgt | gaccgtgaag | gaccagtggc | acagcagggg | cagcacctgg | 720 |
| ctgtacaggg | agacctgcaa | cctgaactgc | atgctgacca | tcaccaccgc | caggagcaag | 780 |
| tacccctacc | acttcttcgc | caccagcacc | ggcgacgtgg | tgtacatcag | ccccttctac | 840 |
| aacggcacca | acaggaacgc | cagctacttc | ggcgagaacg | ccgacaagtt | cttcatcttc | 900 |
| cccaactaca | ccatcgtgag | cgacttcggc | aggcccaacg | ccgcccccga | acccacaggg | 960 |
| ctggtggcct | tcctggagag | ggccgacagc | gtgatcagct | gggacatcca | ggacgagaag | 1020 |
| aacgtgacct | gccagctgac | cttctgggag | gccagcgaga | ggaccatcag | gagcgaggcc | 1080 |
| gaggacagct | accacttcag | cagcgccaag | atgaccgcca | ccttcctgag | caagaagcag | 1140 |
| gaggtgaaca | tgagcgacag | cgccctggac | tgcgtgaggg | acgaggccat | caacaagctg | 1200 |
| cagcagatct | tcaacaccag | ctacaaccag | acctacgaga | agtacggcaa | cgtgagcgtg | 1260 |

```
ttcgagacca gcggcggcct ggtggtgttc tggcagggca tcaagcagaa gagcctggtg    1320
gagctggaga ggctggccaa caggagcagc ctgaacatca cccacaggac caggaggagc    1380
accagcgaca caacaccac ccacctgagc agcatggaga gcgtgcacaa cctggtgtac     1440
gcccagctgc agttcaccta cgacaccctg aggggctaca tcaacagggc cctggcccag    1500
atcgccgagg cctggtgcgt ggaccagagg aggaccctgg aggtgttcaa ggagctgagc    1560
aagatcaacc ccagcgccat cctgagcgcc atctacaaca agcccatcgc cgccaggttc    1620
atgggcgacg tgctgggcct ggccagctgc gtgaccatca accagaccag cgtgaaggtg    1680
ctgagggaca tgaacgtgaa ggagagcccc ggcaggtgct acagcaggcc cgtggtgatc    1740
ttcaacttcg ccaacagcag ctacgtgcag tacggccagc tgggcgagga caacgagatc    1800
ctgctgggca ccacaggac cgaggagtgc cagctgccca gcctgaagat cttcatcgcc    1860
ggcaacagcg cctacgagta cgtggactac ctgttcaaga ggatgatcga cctgagcagc    1920
atcagcaccg tggacagcat gatcgccctg gacatcgacc ccctggagaa caccgacttc    1980
agggtgctgg agctgtacag ccagaaggag ctgaggagca gcaacgtgtt cgacctggag    2040
gagatcatga gggagttcaa cagctacaag cagagggtga agtacgtgga ggacaaggtg    2100 gtggacccc tgcccccta cctgaagggc ctggacgacc tgatgagcgg cctgggcgcc     2160
gccggcaagg ccgtgggcgt ggccatcggc gccgtgggcg gcgccgtggc cagcgtggtg    2220
gagggcgtgg ccaccttcct gaagaacccc ttcggcgcct tcaccatcat cctggtggcc    2280
atcgccgtgg tgatcatcac ctacctgatc tacaccaggc agaggaggct gtgcacccag    2340
cccctgcaga acctgttccc ctacctggtg agcgccgacg gcaccaccgt gaccagcggc    2400
agcaccaagg acaccagcct gcaggccccc cccagctacg aggagagcgt gtacaacagc    2460
ggcaggaagg gccccggccc cccagcagc gacgccagca ccgccgcccc cccctacacc     2520
aacgagcagg cctaccagat gctgctggcc ctggccaggc tggacgccga gcagggcc     2580 cagcagaacg gcaccgacag cctggacggc cagaccggca cccaggacaa gggccagaag    2640
cccaacctgc tggacaggct gaggcacagg aagaacggct acaggcacct gaaggacagc    2700
gacgaggagg agaacgtg                                                  2718
```

<210> SEQ ID NO 16  
<211> LENGTH: 2718  
<212> TYPE: DNA  
<213> ORGANISM: Artificial Sequence  
<220> FEATURE:  
<223> OTHER INFORMATION: codon-optimized sequence of hCMV gB

<400> SEQUENCE: 16

```
atggaatcca ggatctggtg tctcgtcgtc tgtgtcaacc tttgtatcgt ttgcttggga    60
gctgccgtta gtagcagctc cacaagtcat gccaccagca gtacccataa cggtagccac    120
acctcacgga caacgagcgc tcagactcgt tccgtgtact cgcagcacgt tacctcctca    180
gaggcagtgt ccatcgcgc taacgaaact atctacaaca ccacactcaa gtatggcgac    240
gtagtgggtg taaatacgac aaaatacccca tatagagtgt gctcaatggc ccagggcacc    300
gatctgatcc ggttcgagag aaatataatc tgcacctcta tgaaacctat caatgaggat    360
ctggacgagg ggatcatggt ggtgtataag agaaatattg tcgcccatac ctttaaagtg    420
cgcgtttatc aaaaggtgtt aactttcaga aggtcctacg cttatatcta caccacgtac    480
ctgctcggct ccaatacaga gtacgtcgct cctcccatgt gggaaattca ccatatcaac    540
```

```
aagttcgccc agtgctactc ctcttactca cgcgtgatcg gagggaccgt gttcgtggca    600
tatcaccgag attcttacga aaacaagaca atgcagctga tccctgatga ctactctaat    660
acacactcaa cccgttatgt gaccgtaaag gatcaatggc actcccgcgg gtctacctgg    720
ctctacaggg aaacgtgcaa cctgaattgt atgctgacaa taacgactgc taggtcaaag    780 taccccctacc acttttttgc aacctctacc ggcgacgtgg tttatattag tcctttctac    840
aacggaacca accgtaatgc gagttatttc ggtgaaaacg cagacaagtt tttcattttc    900
cccaactata ctatcgtgag tgacttcgga agacctaatg cagccccaga gactcatcgc    960
ctggtggcct tcctcgaaag agccgatagc gtgatctcct gggatattca ggacgagaag    1020
aacgtgactt gccaactcac cttttgggag gcgtctgagc gcactatacg aagcgaagcc    1080
gaagactctt atcatttcag cagtgcaaag atgcagcca ctttcttgtc caaaaaacag     1140
gaggttaaca tgtctgactc agcgctagac tgtgtgcggg acgaggcgat caacaaactg    1200
caacaaatat tcaacacgag ctacaaccag acctacgaga gtatggcaa tgtgtcagta     1260 tttgagacta gcggcggact ggtagtattt tggcagggga ttaaacagaa gtctctcgtc    1320
gaactcgagc ggctggccaa tcgcagtagt ctgaacatca cacacaggac acgaaggtct    1380
acttccgata ataataccac ccacctctcc tctatggagt cggtgcacaa cctggtgtac    1440
gctcagttgc agtttacata cgacaccctg cgcgggtata ttaacagagc gctggcacag    1500
atcgccgaag catggtgcgt cgaccaacgt cgaacgctgg aggtcttcaa ggagctatcc    1560
aagattaacc caagtgccat tctatctgca atttacaata agccgattgc cgctaggttt    1620
atgggcgatg ttctgggact ggcgagctgt gtgactataa accaaacgtc agtcaaggtg    1680
cttagggaca tgaacgttaa ggaatcccct ggccggtgtt attcgcggcc tgttgtcata    1740
tttaattttg ccaattcctc ttacgtgcag tacggccagt taggcgagga caacgaaatt    1800
ttattgggca atcatcgcac cgaggaatgc cagttgccga gcctgaaaat ctttatagct    1860
gggaacagcg cttacgagta cgtcgactat ctctttaagc ggatgattga tctgagctcg    1920
atcagcacag tcgactctat gatcgccctg gatattgacc cgctggagaa tacagatttc    1980
agagtgcttg aattatattc acagaaagag ctgcggagct caaatgtgtt cgatcttgag    2040
gaaattatgc gggaattcaa cagctacaag caacgggtca agtacgtgga ggacaaggtg    2100
gtggacccac tgccccccta cttgaaaggt ctggatgatc tcatgagcgg tcttggagcg    2160
gctggcaaag ccgttggagt agcaatcggc gccgttggag gggccgtggc ttctgtagtg    2220
gagggcgttg ctacctttt gaagaacccc ttcgggccct tactatcat tctagtcgct     2280 attgcagtcg tgataatcac atatttgatc tatactcggc agagacgctt atgcacacag    2340
ccccttcaga atctcttccc ctatctggtc tccgcagatg gacaacagt gacaagtggc     2400 tcgactaagg ataccagctt gcaagctccc ccaagttacg aagagagcgt ttataactcc    2460
ggtaggaaag gaccaggtcc acctagctca gatgcatcaa ccgctgcccc accctatact    2520
aatgagcagg cctatcagat gctgcttgca ctcgccagac tggacgccga gcagcgagcc    2580
cagcagaatg gacagactc cctcgacggg cagactggaa cccaggataa aggacagaaa    2640
cctaatctgc ttgaccgact aagcacacagg aaaaatggct acaggcacct taaagatagt   2700
gatgaagaag agaacgtc                                                   2718
```

<210> SEQ ID NO 17
<211> LENGTH: 2718
<212> TYPE: DNA
<213> ORGANISM: Artificial Sequence -continued
<220> FEATURE:
<223> OTHER INFORMATION: codon-optimized sequence of hCMV gB

<400> SEQUENCE: 17

```
atggagagcc ggatttggtg tctggtcgtg tgcgtgaacc tgtgcatcgt ctgtttgggc      60
gctgccgttt catcctccag tacttcccat gctacatcct cgacacacaa tggctcacat     120
accagcagaa ctacttctgc acaaactcgc tccgtgtact cacagcacgt cacttctagc     180
gaagcagtgt cccacagggc aaacgaaacg atctacaaca ccaccctgaa gtatggtgac     240
gtggtggggg tgaacaccac taaatatcct tatagagttt gtagtatggc acaagggaca     300
gatctgatca ggttcgagcg aaacattatt tgcacctcca tgaagcctat aaacgaagat     360
ctggacgagg gcatcatggt ggtgtacaag cgtaatatag tcgcccatac ctttaaggta     420
agggtgtacc agaaggtcct cacatttcgc agaagctatg cctatattta cactacctat     480
ctactgggct ccaacactga atacgttgca cccccccatgt gggaaattca ccacatcaat     540
aaattcgccc agtgttattc cagctattct agggttatag gaggcaccgt gtttgtggcc     600
taccaccggg atagctacga gaataagact atgcagctca tccctgacga ctacagcaat     660
acacattcca caagatacgt caccgtcaag gatcagtggc attctagggg atctacatgg     720
ctttatcgcg agacatgcaa cttgaactgt atgcttacca tcaccacagc gcgttctaaa     780
tacccatatc attttttgc gactagtacg ggagacgtgg tgtatatctc accgttttat     840
aacggtacta accgtaatgc tagctatttt ggcgagaatg cagataaatt ttttatcttc     900
cccaactaca caatcgtaag tgacttcgga aggcccaatg ccgcccccga aacgcacagg     960
ctggtggcct tcctcgagcg agccgatagc gtaatttcat gggatataca ggatgagaaa    1020
aatgtgacct gccagcttac cttctgggaa gcttcagaga ggactatccg gagtgaagcc    1080
gaggattcct atcacttttc cagtgctaag atgacggcaa cctttctctc aaagaagcag    1140
gaggtgaaca tgagcgactc ggctcttgat tgcgtgcggg acgaagcaat caacaaactg    1200
cagcaaatct tcaacaccag ctacaaccag acatacgaaa aatatggaaa tgtgagcgtc    1260
ttcgagacta gcggtgggct ggtggtgttc tggcagggaa ttaagcagaa gtccttggtg    1320
gaactggagc ggctggctaa ccggtcgtct ctaaatatca cccacagaac acgacgctct    1380
acgtctgata ataacaccac acacctcagc agcatggaat ctgttcacaa cctcgtctac    1440
gcccaactac agttcaccta tgacactttg agggggtata tcaatagagc tttagcccaa    1500
attgccgaag cctggtgtgt ggatcaacgg agaacactgg aggtttttaa ggagctctca    1560
aagattaacc cttcagcgat actgagcgcc atttacaata agccaatcgc agctagattc    1620
atgggtgacg tattgggctt agcaagttgt gttaccataa atcagacctc cgtgaaggtc    1680
ttacgcgaca tgaatgttaa ggagagccct gggcggtgct actcacggcc agttgtaatc    1740
ttcaatttcg caaactcctc atatgtccag tatggccaac taggagagga caacgagatt    1800
ctgctcggca accataggac agaggagtgc caactaccct ccctgaaaat tttcatcgct    1860
gggaattcgg cctatgagta cgtcgattac ctcttcaaac ggatgattga tctgagttct    1920
attagtaccg tggactccat gatcgctctt gacatagatc cactcgagaa taccgacttc    1980
cgggtccttg aactgtatag ccagaaagag cttcgctctt ctaacgtctt tgacttggaa    2040
gaaattatgc gagaatttaa ttcatataag cagcgtgtta aatacgttga agataaggtt    2100
gtggacccgt tacctcctta cctcaaaggc cttgacgatc tcatgagcgg gctcggcgca    2160
gccgggaaag cggtaggagt ggccatcggt gccgttggag gcgccgtagc cagtgtcgtg    2220
```

-continued

| | |
|---|---|
| gaaggagtag caacgttcct gaaaaacccc ttcggtgctt ttacaattat cctcgtggcg | 2280 |
| atcgccgtgg tgatcattac ctacctgata tacactcgcc agcgacgcct gtgcacacaa | 2340 |
| ccattgcaga acttgtttcc ctacctggtc tcggcggacg ggactaccgt gacatctggg | 2400 |
| agtaccaaag atacgagctt acaggctccc ccatcttacg aggagtcagt gtacaattcc | 2460 |
| ggtagaaagg gtcctggccc tccgagtagt gacgctagca ccgctgcgcc cccatacaca | 2520 |
| aacgagcagg cctaccagat gctgctggcc ctggccagac tggatgctga gcagagagca | 2580 |
| cagcagaatg gaactgactc cctggatggg cagacaggca cgcaagataa gggccagaaa | 2640 |
| ccaaacttgc tggaccgcct tcgacaccgc aaaaatggct acaggcatct gaaggactct | 2700 |
| gacgaagaag agaatgtc | 2718 |

<210> SEQ ID NO 18
<211> LENGTH: 2718
<212> TYPE: DNA
<213> ORGANISM: Artificial Sequence
<220> FEATURE:
<223> OTHER INFORMATION: codon-optimized sequence of hCMV gB

<400> SEQUENCE: 18

```
atggagagta ggatttggtg tctggtggtt tgcgtcaacc tttgcatcgt gtgcctgggg     60
gcagctgttt cgtcgtctag cactagccat gccacctcta gtactcacaa cgggtcacac    120
acatctcgga ccacatccgc acagaccagg agcgtataca gccagcatgt tacaagttcg    180
gaggcagtga gtcatcgagc aaatgagacc atctataata ccacactcaa gtatggcgac    240
gtcgtgggcg tgaatacaac caagtatcct taccgggtgt gcagcatggc acagggtacc    300
gatctcattc gcttcgagcg gaacattatc tgtacgagca tgaagcctat taacgaggac    360
ctcgatgaag gtatcatggt tgtttataaa cgcaatattg ttgcccacac gtttaaagtg    420
agagtttacc agaaggtgct gacattcagg aggtcgtacg cttacattta tactacatat    480
ctattagggt ccaacacaga gtacgtggcc ccgcccatgt gggaaatcca ccatatcaat    540
aagttcgctc agtgttattc ttcgtattcc agggtgatcg gcgggaccgt atttgtggct    600
taccacagag actcctacga gaacaaaaca atgcaactga ttcccgatga ctactctaat    660
actcacagca ctcgctacgt gactgtcaag gatcagtggc actctagggg ctcaacctgg    720
ctgtacaggg aaacatgtaa tctgaattgc atgctgacca ttactactgc acgcagcaag    780
tatccctatc actttttcgc cacctccaca ggggatgtcg tttatatcag cccattttac    840
aacggcacca atagaaacgc ttcctacttt ggagaaaatg ctgataaatt cttcatattc    900
ccgaattaca ctatcgtgag tgatttcggc cgaccaaacg cggcgcccga aacccacaga    960
ctggttgcct tccttgaacg ggctgacagc gttatcagtt gggatatcca ggatgagaag   1020
aacgtgacct gccagctgac tttttgggaa gcatcagaga ggaccattag gtccgaagcc   1080
gaggactcct accatttcag cagtgctaaa atgaccgcca ctttcctgtc aaaaaagcag   1140
gaggtgaaca tgtcagactc tgcactggat tgtgtccggg acgaagcaat caacaagctg   1200
cagcagatat tcaatacctc ctacaaccaa acctacgaaa aatacggcaa tgtgtcagtg   1260
tttgagacgt ctggcggact ggtggtattt tggcagggaa taaaacagaa atccctcgtc   1320
gagttggagc gcttagccaa cagaagtagc ctgaacatca ctcacaggac acgccggtca   1380
acgagtgata ataataccac ccacctgagc agcatggagt ccgtccataa cctagtgtac   1440
gcccaactcc aattcactta tgacacactt cgaggttaca ttaaccgagc actcgcccag   1500
attgcagagg cctggtgtgt tgatcagcgg agaaccttgg aagtgtttaa ggaactctct   1560
```

-continued

```
aagataaacc cttccgctat cttatccgcc atttataata aacctatcgc agcacgcttc      1620
atgggtgacg tactggggct tgcctcttgt gtgacgatca accagacatc tgtgaaagtc      1680
ctgcgggata tgaatgtcaa ggagtcacca ggacgttgct acagccgccc agtcgtgatt      1740
tttaacttcg ctaattccag ctatgtgcaa tatgggcagt tgggagagga caatgagatc      1800
ctccttggta atcatcgcac tgaagaatgc cagttgcctt ctctgaagat ctttatcgcc      1860
ggcaacagcg cgtatgagta cgtagattac ctctttaagc gtatgataga cctttcctca      1920
atctccacag ttgatagtat gattgccctg gacatcgacc ccctggagaa cactgatttc      1980
agagtcctcg agttgtattc tcagaaggaa ttaagatcct ctaacgtatt tgacctcgag      2040
gagattatgc gcgaatttaa tagctacaag caacgagtca aatatgtgga agataaggtc      2100
gtggacccac taccgcccta tctaaagggg ctggacgacc tgatgagtgg gttaggagcg      2160
gccggaaaag ccgtgggagt ggcgattggt gctgtgggcg gggctgtagc cagtgtggtc      2220
gagggagtcg ctacctttct caagaatccc ttcgcgcgt ttacaatcat tctggtggcc       2280
atagctgttg tcataatcac gtacttgata tacacccggc agagacggct gtgcactcag      2340
cctctgcaaa atcttttccc ttatctagtc tctgccgacg ggacaaccgt aacaagcggc      2400
agcacaaaag atacttcact ccaggccccc ccatcctacg aagaatcagt gtataactcc      2460
ggccgaaaag gacccggccc tccaagctca gacgcatcaa ccgccgcccc ccttacacc      2520 aacgagcagg cttaccagat gttgttggct ctcgcccgtc tggatgcgga acagcgtgcc      2580
caacaaaacg gaacggacag tcttgatggc cagacgggta cacaagacaa gggccagaag      2640
ccaaaccttc tggacaggtt gcggcacaga aaaaacggtt atagacatct gaaagactct      2700
gatgaggagg aaaatgtg                                                    2718
```

<210> SEQ ID NO 19
<211> LENGTH: 1473
<212> TYPE: DNA
<213> ORGANISM: Human cytomegalovirus
<220> FEATURE:
<221> NAME/KEY: CDS
<222> LOCATION: (1)..(1473)

<400> SEQUENCE: 19

```
atg gag tcc tct gcc aag aga aag atg gac cct gat aat cct gac gag       48
Met Glu Ser Ser Ala Lys Arg Lys Met Asp Pro Asp Asn Pro Asp Glu
1               5                   10                  15 ggc cct tcc tcc aag gtg cca cgg ccc gag aca ccc gtg acc aag gcc       96
Gly Pro Ser Ser Lys Val Pro Arg Pro Glu Thr Pro Val Thr Lys Ala
                20                  25                  30 acg acg ttc ctg cag act atg ttg agg aag gag gtt aac agt cag ctg      144
Thr Thr Phe Leu Gln Thr Met Leu Arg Lys Glu Val Asn Ser Gln Leu
            35                  40                  45 agt ctg gga gac ccg ctg ttt cca gag ttg gcc gaa gaa tcc ctc aaa      192
Ser Leu Gly Asp Pro Leu Phe Pro Glu Leu Ala Glu Glu Ser Leu Lys
        50                  55                  60 act ttt gaa caa gtg acc gag gat tgc aac gag aac ccc gag aaa gat      240
Thr Phe Glu Gln Val Thr Glu Asp Cys Asn Glu Asn Pro Glu Lys Asp
65                  70                  75                  80 gtc ctg gca gaa ctc gtc aaa cag att aag gtt cga gtg gac atg gtg      288
Val Leu Ala Glu Leu Val Lys Gln Ile Lys Val Arg Val Asp Met Val
                85                  90                  95 cgg cat aga atc aag gag cac atg ctg aaa aaa tat acc cag acg gaa      336
Arg His Arg Ile Lys Glu His Met Leu Lys Lys Tyr Thr Gln Thr Glu
                100                 105                 110
```

```
gag aaa ttc act ggc gcc ttt aat atg atg gga gga tgt ttg cag aat       384
Glu Lys Phe Thr Gly Ala Phe Asn Met Met Gly Gly Cys Leu Gln Asn
        115                 120                 125 gcc tta gat atc tta gat aag gtt cat gag cct ttc gag gag atg aag       432
Ala Leu Asp Ile Leu Asp Lys Val His Glu Pro Phe Glu Glu Met Lys
130                 135                 140 tgt att ggg cta act atg cag agc atg tat gag aac tac att gta cct       480
Cys Ile Gly Leu Thr Met Gln Ser Met Tyr Glu Asn Tyr Ile Val Pro
145                 150                 155                 160 gag gat aag cgg gag atg tgg atg gct tgt att aag gag ctg cat gat       528
Glu Asp Lys Arg Glu Met Trp Met Ala Cys Ile Lys Glu Leu His Asp
                165                 170                 175 gtg agc aag ggc gcc gct aac aag ttg ggg ggt gca ctg cag gct aag       576
Val Ser Lys Gly Ala Ala Asn Lys Leu Gly Gly Ala Leu Gln Ala Lys
            180                 185                 190 gcc cgt gct aaa aag gat gaa ctt agg aga aag atg atg tat atg tgc       624
Ala Arg Ala Lys Lys Asp Glu Leu Arg Arg Lys Met Met Tyr Met Cys
        195                 200                 205 tac agg aat ata gag ttc ttt acc aag aac tca gcc ttc cct aag acc       672
Tyr Arg Asn Ile Glu Phe Phe Thr Lys Asn Ser Ala Phe Pro Lys Thr
210                 215                 220 acc aat ggc tgc agt cag gcc atg gcg gca ctg cag aac ttg cct cag       720
Thr Asn Gly Cys Ser Gln Ala Met Ala Ala Leu Gln Asn Leu Pro Gln
225                 230                 235                 240 tgc tcc cct gat gag att atg gct tat gcc cag aaa ata ttt aag att       768
Cys Ser Pro Asp Glu Ile Met Ala Tyr Ala Gln Lys Ile Phe Lys Ile
                245                 250                 255 ttg gat gag gag aga gac aag gtg ctc acg cac att gat cac ata ttt       816
Leu Asp Glu Glu Arg Asp Lys Val Leu Thr His Ile Asp His Ile Phe
            260                 265                 270 atg gat atc ctc act aca tgt gtg gaa aca atg tgt aat gag tac aag       864
Met Asp Ile Leu Thr Thr Cys Val Glu Thr Met Cys Asn Glu Tyr Lys
        275                 280                 285 gtc act agt gac gct tgt atg atg acc atg tac ggg ggc atc tct ctc       912
Val Thr Ser Asp Ala Cys Met Met Thr Met Tyr Gly Gly Ile Ser Leu
290                 295                 300 tta agt gag ttc tgt cgg gtg ctg tgc tgc tat gtc tta gag gag act       960
Leu Ser Glu Phe Cys Arg Val Leu Cys Cys Tyr Val Leu Glu Glu Thr
305                 310                 315                 320 agt gtg atg ctg gcc aag cgg cct ctg ata acc aag cct gag gtt atc      1008
Ser Val Met Leu Ala Lys Arg Pro Leu Ile Thr Lys Pro Glu Val Ile
                325                 330                 335 agt gta atg aag cgc gcc att gag gag atc tgc atg aag gtc ttt gcc      1056
Ser Val Met Lys Arg Arg Ile Glu Glu Ile Cys Met Lys Val Phe Ala
            340                 345                 350 cag tac att ctg ggg gcc gat cct ctg aga gtc tgc tct cct agt gtg      1104
Gln Tyr Ile Leu Gly Ala Asp Pro Leu Arg Val Cys Ser Pro Ser Val
        355                 360                 365 gat gac cta cgg gcc atc gcc gag gag tca gat gag gaa gag gct att      1152
Asp Asp Leu Arg Ala Ile Ala Glu Glu Ser Asp Glu Glu Glu Ala Ile
370                 375                 380 gta gcc tac act ttg gcc acc gct ggt gtc agc tcc tct gat tct ctg      1200
Val Ala Tyr Thr Leu Ala Thr Ala Gly Val Ser Ser Ser Asp Ser Leu
385                 390                 395                 400 gtg tca ccc cca gag tcc cct gta ccc gcg act atc cct ctg tcc tca      1248
Val Ser Pro Pro Glu Ser Pro Val Pro Ala Thr Ile Pro Leu Ser Ser
                405                 410                 415 gta att gtg gct gag aac agt gat cag gaa gaa agt gag cag agt gat      1296
Val Ile Val Ala Glu Asn Ser Asp Gln Glu Glu Ser Glu Gln Ser Asp
```

-continued

```
              420                 425                 430
gag gaa gag gag gag ggt gct cag gag gag cgg gag gac act gtg tct    1344
Glu Glu Glu Glu Glu Gly Ala Gln Glu Glu Arg Glu Asp Thr Val Ser
            435                 440                 445 gtc aag tct gag cca gtg tct gag ata gag gaa gtt gcc cca gag gaa    1392
Val Lys Ser Glu Pro Val Ser Glu Ile Glu Glu Val Ala Pro Glu Glu
450                 455                 460 gag gag gat ggt gct gag gaa ccc acc gcc tct gga ggc aag agc acc    1440
Glu Glu Asp Gly Ala Glu Glu Pro Thr Ala Ser Gly Gly Lys Ser Thr
465                 470                 475                 480 cac cct atg gtg act aga agc aag gct gac cag                        1473
His Pro Met Val Thr Arg Ser Lys Ala Asp Gln
                485                 490
```

<210> SEQ ID NO 20
<211> LENGTH: 491
<212> TYPE: PRT
<213> ORGANISM: Human cytomegalovirus

<400> SEQUENCE: 20

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Val Lys Gln Ile Lys Val Arg Val Asp Met Val
                85                  90                  95

Arg His Arg Ile Lys Glu His Met Leu Lys Lys Tyr Thr Gln Thr Glu
            100                 105                 110

Glu Lys Phe Thr Gly Ala Phe Asn Met Met Gly Gly Cys Leu Gln Asn
        115                 120                 125

Ala Leu Asp Ile Leu Asp Lys Val His Glu Pro Phe Glu Glu Met Lys
    130                 135                 140

Cys Ile Gly Leu Thr Met Gln Ser Met Tyr Glu Asn Tyr Ile Val Pro
145                 150                 155                 160

Glu Asp Lys Arg Glu Met Trp Met Ala Cys Ile Lys Glu Leu His Asp
                165                 170                 175

Val Ser Lys Gly Ala Ala Asn Lys Leu Gly Gly Ala Leu Gln Ala Lys
            180                 185                 190

Ala Arg Ala Lys Lys Asp Glu Leu Arg Arg Lys Met Met Tyr Met Cys
        195                 200                 205

Tyr Arg Asn Ile Glu Phe Phe Thr Lys Asn Ser Ala Phe Pro Lys Thr
    210                 215                 220

Thr Asn Gly Cys Ser Gln Ala Met Ala Ala Leu Gln Asn Leu Pro Gln
225                 230                 235                 240

Cys Ser Pro Asp Glu Ile Met Ala Tyr Ala Gln Lys Ile Phe Lys Ile
                245                 250                 255

Leu Asp Glu Glu Arg Asp Lys Val Leu Thr His Ile Asp His Ile Phe
            260                 265                 270

Met Asp Ile Leu Thr Thr Cys Val Glu Thr Met Cys Asn Glu Tyr Lys
        275                 280                 285
```

-continued

```
Val Thr Ser Asp Ala Cys Met Met Thr Met Tyr Gly Gly Ile Ser Leu
    290                 295                 300
Leu Ser Glu Phe Cys Arg Val Leu Cys Cys Tyr Val Leu Glu Glu Thr
305                 310                 315                 320
Ser Val Met Leu Ala Lys Arg Pro Leu Ile Thr Lys Pro Glu Val Ile
                325                 330                 335
Ser Val Met Lys Arg Arg Ile Glu Glu Ile Cys Met Lys Val Phe Ala
            340                 345                 350
Gln Tyr Ile Leu Gly Ala Asp Pro Leu Arg Val Cys Ser Pro Ser Val
        355                 360                 365
Asp Asp Leu Arg Ala Ile Ala Glu Glu Ser Asp Glu Glu Ala Ile
    370                 375                 380
Val Ala Tyr Thr Leu Ala Thr Ala Gly Val Ser Ser Asp Ser Leu
385                 390                 395                 400
Val Ser Pro Pro Glu Ser Pro Val Pro Ala Thr Ile Pro Leu Ser Ser
                405                 410                 415
Val Ile Val Ala Glu Asn Ser Asp Gln Glu Glu Ser Glu Gln Ser Asp
            420                 425                 430
Glu Glu Glu Glu Glu Gly Ala Gln Glu Glu Arg Glu Asp Thr Val Ser
        435                 440                 445
Val Lys Ser Glu Pro Val Ser Glu Ile Glu Glu Val Ala Pro Glu Glu
    450                 455                 460
Glu Glu Asp Gly Ala Glu Glu Pro Thr Ala Ser Gly Gly Lys Ser Thr
465                 470                 475                 480
His Pro Met Val Thr Arg Ser Lys Ala Asp Gln
                485                 490

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer T7

<400> SEQUENCE: 21
taatacgact cactataggg                                              20

<210> SEQ ID NO 22
<211> LENGTH: 18
<212> TYPE: DNA
<213> ORGANISM: Artificial Sequence
<220> FEATURE:
<223> OTHER INFORMATION: oligonucleotide primer 65-delta-rev

<400> SEQUENCE: 22
aggatgctga gccggcgg                                                18

<210> SEQ ID NO 23
<211> LENGTH: 23
<212> TYPE: DNA
<213> ORGANISM: Artificial Sequence
<220> FEATURE:
<223> OTHER INFORMATION: oligonucleotide primer M13rev

<400> SEQUENCE: 23
cccagtcacg acgttgtaaa acg                                          23

<210> SEQ ID NO 24
<211> LENGTH: 18
```

-continued

```
<210> SEQ ID NO 24
<211> LENGTH: 18
<212> TYPE: DNA
<213> ORGANISM: Artificial Sequence
<220> FEATURE:
<223> OTHER INFORMATION: oligonucleotide primer 65-delta-for

<400> SEQUENCE: 24
ccgccggctc agcatcct                                                       18

<210> SEQ ID NO 25
<211> LENGTH: 22
<212> TYPE: DNA
<213> ORGANISM: Artificial Sequence
<220> FEATURE:
<223> OTHER INFORMATION: oligonucleotide primer VR1051FOR

<400> SEQUENCE: 25
gagcagtact cgttgctgcc gc                                                  22

<210> SEQ ID NO 26
<211> LENGTH: 32
<212> TYPE: DNA
<213> ORGANISM: Artificial Sequence
<220> FEATURE:
<223> OTHER INFORMATION: oligonucleotide primer hCMVpp65-R

<400> SEQUENCE: 26
gttacgtcta gatcaacctc ggtgcttttt gg                                       32

<210> SEQ ID NO 27
<211> LENGTH: 28
<212> TYPE: DNA
<213> ORGANISM: Artificial Sequence
<220> FEATURE:
<223> OTHER INFORMATION: oligonucleotide primer hCMVgB-R

<400> SEQUENCE: 27
tctagatcag tcgtccagac ccttgagg                                            28

<210> SEQ ID NO 28
<211> LENGTH: 1236
<212> TYPE: DNA
<213> ORGANISM: Artificial Sequence
<220> FEATURE:
<223> OTHER INFORMATION: codon-optimized IE1 sequence
<220> FEATURE:
<221> NAME/KEY: CDS
<222> LOCATION: (16)..(1227)

<400> SEQUENCE: 28
gatatcgccg ccacc atg gag tct agc gcc aag agg aag atg gac ccc gac          51
                Met Glu Ser Ser Ala Lys Arg Lys Met Asp Pro Asp
                  1               5                  10 aac cct gat gag ggc cct agc agc aag gtg ccc cgg gtg aag cag atc           99
Asn Pro Asp Glu Gly Pro Ser Ser Lys Val Pro Arg Val Lys Gln Ile
         15                  20                  25 aag gtg cgg gtg gac atg gtg cgg cac agg atc aag gaa cac atg ctg          147
Lys Val Arg Val Asp Met Val Arg His Arg Ile Lys Glu His Met Leu
     30                  35                  40 aag aag tac acc cag acc gag gag aag ttc acc ggc gcc ttc aat atg          195
Lys Lys Tyr Thr Gln Thr Glu Glu Lys Phe Thr Gly Ala Phe Asn Met
 45                  50                  55                  60 atg ggc ggc tgc ctg cag aat gcc ctg gac atc ctg gac aag gtg cac          243
Met Gly Gly Cys Leu Gln Asn Ala Leu Asp Ile Leu Asp Lys Val His
                 65                  70                  75 gag ccc ttc gag gag atg aag tgc atc ggc ctg acc atg cag agc atg          291
```

-continued

```
                Glu Pro Phe Glu Glu Met Lys Cys Ile Gly Leu Thr Met Gln Ser Met
                            80                  85                  90 tac gag aac tac atc gtg ccc gag gac aag agg gag atg tgg atg gcc         339
Tyr Glu Asn Tyr Ile Val Pro Glu Asp Lys Arg Glu Met Trp Met Ala
        95                  100                 105 tgc atc gac gag ctg cgg cgg aag atg atg tac atg tgc tac cgg aac         387
Cys Ile Asp Glu Leu Arg Arg Lys Met Met Tyr Met Cys Tyr Arg Asn
110                 115                 120 atc gag ttc ttc acc aag aac agc gcc ttc ccc aag acc acc aac gga         435
Ile Glu Phe Phe Thr Lys Asn Ser Ala Phe Pro Lys Thr Thr Asn Gly
125                 130                 135                 140 tgc tct cag gcc atg gcc gcc ctg cag aat ctg cct cag tgc agc ccc         483
Cys Ser Gln Ala Met Ala Ala Leu Gln Asn Leu Pro Gln Cys Ser Pro
                145                 150                 155 gat gag atc atg gcc tac gcc cag aag atc ttc aag atc ctg gac gag         531
Asp Glu Ile Met Ala Tyr Ala Gln Lys Ile Phe Lys Ile Leu Asp Glu
                160                 165                 170 gag agg gat aag gtg ctg acc cac atc gac cac atc ttc atg gac atc         579
Glu Arg Asp Lys Val Leu Thr His Ile Asp His Ile Phe Met Asp Ile
            175                 180                 185 ctg acc acc tgc gtg gag acc atg tgc aac gag tac aag gtg acc agc         627
Leu Thr Thr Cys Val Glu Thr Met Cys Asn Glu Tyr Lys Val Thr Ser
            190                 195                 200 gac gcc tgc atg atg aca atg tac ggc ggc atc agc ctg ctg agc gag         675
Asp Ala Cys Met Met Thr Met Tyr Gly Gly Ile Ser Leu Leu Ser Glu
205                 210                 215                 220 ttc tgc aga gtg ctg tgc tgc tac gtg ctg gag gag acc tct gtg atg         723
Phe Cys Arg Val Leu Cys Cys Tyr Val Leu Glu Glu Thr Ser Val Met
                225                 230                 235 ctg gcc aag agg ccc ctg atc acc aag cct gag gtg atc agc gtg atg         771
Leu Ala Lys Arg Pro Leu Ile Thr Lys Pro Glu Val Ile Ser Val Met
                240                 245                 250 aag cgg cgg atc gag gag atc tgc atg aag gtg ttc gcc cag tac atc         819
Lys Arg Arg Ile Glu Glu Ile Cys Met Lys Val Phe Ala Gln Tyr Ile
            255                 260                 265 ctg gga gcc gac cct ctg aga gtg tgt agc ccc agc gtg gat gac ctg         867
Leu Gly Ala Asp Pro Leu Arg Val Cys Ser Pro Ser Val Asp Asp Leu
            270                 275                 280 aga gcc atc gcc gag gaa tct gat gaa gag gag gcc atc gtg gcc tat         915
Arg Ala Ile Ala Glu Glu Ser Asp Glu Glu Glu Ala Ile Val Ala Tyr
285                 290                 295                 300 aca ctg gcc aca gcc ggc gtg tct agc agc gat agc ctg gtg agc cct         963
Thr Leu Ala Thr Ala Gly Val Ser Ser Ser Asp Ser Leu Val Ser Pro
                305                 310                 315 cct gag tct cct gtg cct gcc aca atc cct ctg agc agc gtg atc gtg         1011
Pro Glu Ser Pro Val Pro Ala Thr Ile Pro Leu Ser Ser Val Ile Val
                320                 325                 330 gcc gag aac agc gat cag gag gag agc gag cag tct gat gag gaa gag         1059
Ala Glu Asn Ser Asp Gln Glu Glu Ser Glu Gln Ser Asp Glu Glu Glu
            335                 340                 345 gaa gag gga gcc cag gag gag aga gag gat acc gtg agc gtg aag agc         1107
Glu Glu Gly Ala Gln Glu Glu Arg Glu Asp Thr Val Ser Val Lys Ser
350                 355                 360 gag cct gtg agc gag atc gaa gag gtg gcc cct gag gaa gag gag gat         1155
Glu Pro Val Ser Glu Ile Glu Glu Val Ala Pro Glu Glu Glu Glu Asp
365                 370                 375                 380 ggc gcc gag gag cct aca gcc agc ggc ggc aag tca aca cac ccc atg         1203
Gly Ala Glu Glu Pro Thr Ala Ser Gly Gly Lys Ser Thr His Pro Met
                385                 390                 395
```

```
gtg acc aga agc aag gcc gac cag taaggatcc                              1236
Val Thr Arg Ser Lys Ala Asp Gln
            400
```

<210> SEQ ID NO 29
<211> LENGTH: 404
<212> TYPE: PRT
<213> ORGANISM: Artificial Sequence
<220> FEATURE:
<223> OTHER INFORMATION: codon-optimized IE1 sequence

<400> SEQUENCE: 29

```
Met Glu Ser Ser Ala Lys Arg Lys Met Asp Pro Asp Asn Pro Asp Glu
1               5                   10                  15

Gly Pro Ser Ser Lys Val Pro Arg Val Lys Gln Ile Lys Val Arg Val
            20                  25                  30

Asp Met Val Arg His Arg Ile Lys Glu His Met Leu Lys Lys Tyr Thr
        35                  40                  45

Gln Thr Glu Glu Lys Phe Thr Gly Ala Phe Asn Met Met Gly Gly Cys
    50                  55                  60

Leu Gln Asn Ala Leu Asp Ile Leu Asp Lys Val His Glu Pro Phe Glu
65                  70                  75                  80

Glu Met Lys Cys Ile Gly Leu Thr Met Gln Ser Met Tyr Glu Asn Tyr
                85                  90                  95

Ile Val Pro Glu Asp Lys Arg Glu Met Trp Met Ala Cys Ile Asp Glu
            100                 105                 110

Leu Arg Arg Lys Met Met Tyr Met Cys Tyr Arg Asn Ile Glu Phe Phe
        115                 120                 125

Thr Lys Asn Ser Ala Phe Pro Lys Thr Thr Asn Gly Cys Ser Gln Ala
    130                 135                 140

Met Ala Ala Leu Gln Asn Leu Pro Gln Cys Ser Pro Asp Glu Ile Met
145                 150                 155                 160

Ala Tyr Ala Gln Lys Ile Phe Lys Ile Leu Asp Glu Glu Arg Asp Lys
                165                 170                 175

Val Leu Thr His Ile Asp His Ile Phe Met Asp Ile Leu Thr Thr Cys
            180                 185                 190

Val Glu Thr Met Cys Asn Glu Tyr Lys Val Thr Ser Asp Ala Cys Met
        195                 200                 205

Met Thr Met Tyr Gly Gly Ile Ser Leu Leu Ser Glu Phe Cys Arg Val
    210                 215                 220

Leu Cys Cys Tyr Val Leu Glu Glu Thr Ser Val Met Leu Ala Lys Arg
225                 230                 235                 240

Pro Leu Ile Thr Lys Pro Glu Val Ile Ser Val Met Lys Arg Arg Ile
                245                 250                 255

Glu Glu Ile Cys Met Lys Val Phe Ala Gln Tyr Ile Leu Gly Ala Asp
            260                 265                 270

Pro Leu Arg Val Cys Ser Pro Ser Val Asp Asp Leu Arg Ala Ile Ala
        275                 280                 285

Glu Glu Ser Asp Glu Glu Glu Ala Ile Val Ala Tyr Thr Leu Ala Thr
    290                 295                 300

Ala Gly Val Ser Ser Ser Asp Ser Leu Val Ser Pro Pro Glu Ser Pro
305                 310                 315                 320

Val Pro Ala Thr Ile Pro Leu Ser Ser Val Ile Val Ala Glu Asn Ser
                325                 330                 335

Asp Gln Glu Glu Ser Glu Gln Ser Asp Glu Glu Glu Glu Glu Gly Ala
            340                 345                 350
```

Gln Glu Glu Arg Glu Asp Thr Val Ser Val Lys Ser Glu Pro Val Ser
            355                 360                 365

Glu Ile Glu Glu Val Ala Pro Glu Glu Glu Asp Gly Ala Glu Glu
        370                 375                 380

Pro Thr Ala Ser Gly Gly Lys Ser Thr His Pro Met Val Thr Arg Ser
385                 390                 395                 400

Lys Ala Asp Gln

<210> SEQ ID NO 30
<211> LENGTH: 1236
<212> TYPE: DNA
<213> ORGANISM: Artificial Sequence
<220> FEATURE:
<223> OTHER INFORMATION: codon-optimized IE1 sequence
<220> FEATURE:
<221> NAME/KEY: CDS
<222> LOCATION: (16)..(1227)

<400> SEQUENCE: 30

```
gaattcgccg ccacc atg gag tcc tct gcc aag aga aag atg gac cct gat        51
                 Met Glu Ser Ser Ala Lys Arg Lys Met Asp Pro Asp
                  1               5                  10 aat cct gac gag ggc cct tcc tcc aag gtg cca cgg gtc aaa cag att        99
Asn Pro Asp Glu Gly Pro Ser Ser Lys Val Pro Arg Val Lys Gln Ile
        15                  20                  25 aag gtt cga gtg gac atg gtg cgg cat aga atc aag gag cac atg ctg       147
Lys Val Arg Val Asp Met Val Arg His Arg Ile Lys Glu His Met Leu
 30                  35                  40 aaa aaa tat acc cag acg gaa gag aaa ttc act ggc gcc ttt aat atg       195
Lys Lys Tyr Thr Gln Thr Glu Glu Lys Phe Thr Gly Ala Phe Asn Met
45                  50                  55                  60 atg gga gga tgt ttg cag aat gcc tta gat atc tta gat aag gtt cat       243
Met Gly Gly Cys Leu Gln Asn Ala Leu Asp Ile Leu Asp Lys Val His
                 65                  70                  75 gag cct ttc gag gag atg aag tgt att ggg cta act atg cag agc atg       291
Glu Pro Phe Glu Glu Met Lys Cys Ile Gly Leu Thr Met Gln Ser Met
         80                  85                  90 tat gag aac tac att gta cct gag gat aag cgg gag atg tgg atg gct       339
Tyr Glu Asn Tyr Ile Val Pro Glu Asp Lys Arg Glu Met Trp Met Ala
             95                 100                 105 tgt att gat gaa ctt agg aga aag atg atg tat atg tgc tac agg aat       387
Cys Ile Asp Glu Leu Arg Arg Lys Met Met Tyr Met Cys Tyr Arg Asn
    110                 115                 120 ata gag ttc ttt acc aag aac tca gcc ttc cct aag acc acc aat ggc       435
Ile Glu Phe Phe Thr Lys Asn Ser Ala Phe Pro Lys Thr Thr Asn Gly
125                 130                 135                 140 tgc agt cag gcc atg gcg gca ctg cag aac ttg cct cag tgc tcc cct       483
Cys Ser Gln Ala Met Ala Ala Leu Gln Asn Leu Pro Gln Cys Ser Pro
                145                 150                 155 gat gag att atg gct tat gcc cag aaa ata ttt aag att ttg gat gag       531
Asp Glu Ile Met Ala Tyr Ala Gln Lys Ile Phe Lys Ile Leu Asp Glu
        160                 165                 170 gag aga gac aag gtg ctc acg cac att gat cac ata ttt atg gat atc       579
Glu Arg Asp Lys Val Leu Thr His Ile Asp His Ile Phe Met Asp Ile
    175                 180                 185 ctc act aca tgt gtg gaa aca atg tgt aat gag tac aag gtc act agt       627
Leu Thr Thr Cys Val Glu Thr Met Cys Asn Glu Tyr Lys Val Thr Ser
190                 195                 200 gac gct tgt atg atg acc atg tac ggg ggc atc tct ctc tta agt gag       675
Asp Ala Cys Met Met Thr Met Tyr Gly Gly Ile Ser Leu Leu Ser Glu
```

```
ttc tgt cgg gtg ctg tgc tgc tat gtc tta gag gag act agt gtg atg      723
Phe Cys Arg Val Leu Cys Cys Tyr Val Leu Glu Glu Thr Ser Val Met
            225                 230                 235 ctg gcc aag cgg cct ctg ata acc aag cct gag gtt atc agt gta atg      771
Leu Ala Lys Arg Pro Leu Ile Thr Lys Pro Glu Val Ile Ser Val Met
        240                 245                 250 aag cgc cgc att gag gag atc tgc atg aag gtc ttt gcc cag tac att      819
Lys Arg Arg Ile Glu Glu Ile Cys Met Lys Val Phe Ala Gln Tyr Ile
    255                 260                 265 ctg ggg gcc gat cct ctg aga gtc tgc tct cct agt gtg gat gac cta      867
Leu Gly Ala Asp Pro Leu Arg Val Cys Ser Pro Ser Val Asp Asp Leu
270                 275                 280 cgg gcc atc gcc gag gag tca gat gag gaa gag gct att gta gcc tac      915
Arg Ala Ile Ala Glu Glu Ser Asp Glu Glu Glu Ala Ile Val Ala Tyr
285                 290                 295                 300 act ttg gcc acc gct ggt gtc agc tcc tct gat tct ctg gtg tca ccc      963
Thr Leu Ala Thr Ala Gly Val Ser Ser Ser Asp Ser Leu Val Ser Pro
            305                 310                 315 cca gag tcc cct gta ccc gcg act atc cct ctg tcc tca gta att gtg     1011
Pro Glu Ser Pro Val Pro Ala Thr Ile Pro Leu Ser Ser Val Ile Val
        320                 325                 330 gct gag aac agt gat cag gaa gaa agt gag cag agt gat gag gaa gag     1059
Ala Glu Asn Ser Asp Gln Glu Glu Ser Glu Gln Ser Asp Glu Glu Glu
    335                 340                 345 gag gag ggt gct cag gag gag cgg gag gac act gtg tct gtc aag tct     1107
Glu Glu Gly Ala Gln Glu Glu Arg Glu Asp Thr Val Ser Val Lys Ser
350                 355                 360 gag cca gtg tct gag ata gag gaa gtt gcc cca gag gaa gag gag gat     1155
Glu Pro Val Ser Glu Ile Glu Glu Val Ala Pro Glu Glu Glu Glu Asp
365                 370                 375                 380 ggt gct gag gaa ccc acc gcc tct gga ggc aag agc acc cac cct atg     1203
Gly Ala Glu Glu Pro Thr Ala Ser Gly Gly Lys Ser Thr His Pro Met
            385                 390                 395 gtg act aga agc aag gct gac cag tgaggatcc                           1236
Val Thr Arg Ser Lys Ala Asp Gln
            400
```

<210> SEQ ID NO 31
<211> LENGTH: 404
<212> TYPE: PRT
<213> ORGANISM: Artificial Sequence
<220> FEATURE:
<223> OTHER INFORMATION: codon-optimized IE1 sequence

<400> SEQUENCE: 31

```
Met Glu Ser Ser Ala Lys Arg Lys Met Asp Pro Asp Asn Pro Asp Glu
1               5                   10                  15

Gly Pro Ser Ser Lys Val Pro Arg Val Lys Gln Ile Lys Val Arg Val
            20                  25                  30

Asp Met Val Arg His Arg Ile Lys Glu His Met Leu Lys Lys Tyr Thr
        35                  40                  45

Gln Thr Glu Glu Lys Phe Thr Gly Ala Phe Asn Met Met Gly Gly Cys
    50                  55                  60

Leu Gln Asn Ala Leu Asp Ile Leu Asp Lys Val His Glu Pro Phe Glu
65                  70                  75                  80

Glu Met Lys Cys Ile Gly Leu Thr Met Gln Ser Met Tyr Glu Asn Tyr
                85                  90                  95

Ile Val Pro Glu Asp Lys Arg Glu Met Trp Met Ala Cys Ile Asp Glu
```

-continued

```
                100                 105                 110
Leu Arg Arg Lys Met Met Tyr Met Cys Tyr Arg Asn Ile Glu Phe Phe
            115                 120                 125

Thr Lys Asn Ser Ala Phe Pro Lys Thr Thr Asn Gly Cys Ser Gln Ala
        130                 135                 140

Met Ala Ala Leu Gln Asn Leu Pro Gln Cys Ser Pro Asp Glu Ile Met
145                 150                 155                 160

Ala Tyr Ala Gln Lys Ile Phe Lys Ile Leu Asp Glu Glu Arg Asp Lys
                165                 170                 175

Val Leu Thr His Ile Asp His Ile Phe Met Asp Ile Leu Thr Thr Cys
            180                 185                 190

Val Glu Thr Met Cys Asn Glu Tyr Lys Val Thr Ser Asp Ala Cys Met
        195                 200                 205

Met Thr Met Tyr Gly Gly Ile Ser Leu Leu Ser Glu Phe Cys Arg Val
210                 215                 220

Leu Cys Cys Tyr Val Leu Glu Glu Thr Ser Val Met Leu Ala Lys Arg
225                 230                 235                 240

Pro Leu Ile Thr Lys Pro Glu Val Ile Ser Val Met Lys Arg Arg Ile
                245                 250                 255

Glu Glu Ile Cys Met Lys Val Phe Ala Gln Tyr Ile Leu Gly Ala Asp
            260                 265                 270

Pro Leu Arg Val Cys Ser Pro Ser Val Asp Asp Leu Arg Ala Ile Ala
        275                 280                 285

Glu Glu Ser Asp Glu Glu Ala Ile Val Ala Tyr Thr Leu Ala Thr
            290                 295                 300

Ala Gly Val Ser Ser Ser Asp Ser Leu Val Ser Pro Pro Glu Ser Pro
305                 310                 315                 320

Val Pro Ala Thr Ile Pro Leu Ser Ser Val Ile Val Ala Glu Asn Ser
                325                 330                 335

Asp Gln Glu Glu Ser Glu Gln Ser Asp Glu Glu Glu Glu Glu Gly Ala
            340                 345                 350

Gln Glu Glu Arg Glu Asp Thr Val Ser Val Lys Ser Glu Pro Val Ser
        355                 360                 365

Glu Ile Glu Glu Val Ala Pro Glu Glu Glu Asp Gly Ala Glu Glu
    370                 375                 380

Pro Thr Ala Ser Gly Gly Lys Ser Thr His Pro Met Val Thr Arg Ser
385                 390                 395                 400

Lys Ala Asp Gln

<210> SEQ ID NO 32
<211> LENGTH: 9
<212> TYPE: PRT
<213> ORGANISM: Homo sapiens

<400> SEQUENCE: 32

Ala Tyr Ala Gly Leu Phe Thr Pro Leu
1               5

<210> SEQ ID NO 33
<211> LENGTH: 20
<212> TYPE: DNA
<213> ORGANISM: Artificial
<220> FEATURE:
<223> OTHER INFORMATION: synthetic primer 2944S

<400> SEQUENCE: 33
```

```
ctgcgcctta tccggtaact                                              20

<210> SEQ ID NO 34
<211> LENGTH: 20
<212> TYPE: DNA
<213> ORGANISM: Artificial
<220> FEATURE:
<223> OTHER INFORMATION: synthetic primer 5876

<400> SEQUENCE: 34
cagtgaggca cctatctcag                                              20

<210> SEQ ID NO 35
<211> LENGTH: 20
<212> TYPE: DNA
<213> ORGANISM: Artificial
<220> FEATURE:
<223> OTHER INFORMATION: synthetic primer 5760

<400> SEQUENCE: 35
caccatgagt gacgactgaa                                              20

<210> SEQ ID NO 36
<211> LENGTH: 20
<212> TYPE: DNA
<213> ORGANISM: Artificial
<220> FEATURE:
<223> OTHER INFORMATION: synthetic primer 5761

<400> SEQUENCE: 36
ttaatcgcgg cctcgagcaa                                              20

<210> SEQ ID NO 37
<211> LENGTH: 20
<212> TYPE: DNA
<213> ORGANISM: Artificial
<220> FEATURE:
<223> OTHER INFORMATION: synthetic primer 5762

<400> SEQUENCE: 37
ggctcatgtc caacattacc                                              20

<210> SEQ ID NO 38
<211> LENGTH: 20
<212> TYPE: DNA
<213> ORGANISM: Artificial
<220> FEATURE:
<223> OTHER INFORMATION: synthetic primer 931S

<400> SEQUENCE: 38
gagacgccat ccacgctgtt                                              20

<210> SEQ ID NO 39
<211> LENGTH: 20
<212> TYPE: DNA
<213> ORGANISM: Artificial
<220> FEATURE:
<223> OTHER INFORMATION: synthetic primer 5874

<400> SEQUENCE: 39
cagacttagg cacagcacaa                                              20

<210> SEQ ID NO 40
<211> LENGTH: 20
<212> TYPE: DNA
<213> ORGANISM: Artificial
```

```
<220> FEATURE:
<223> OTHER INFORMATION: synthetic primer 5104

<400> SEQUENCE: 40
gagcgaggaa gcggaagagt                                                  20

<210> SEQ ID NO 41
<211> LENGTH: 20
<212> TYPE: DNA
<213> ORGANISM: Artificial
<220> FEATURE:
<223> OTHER INFORMATION: synthetic primer 3054A

<400> SEQUENCE: 41
ccgcctacat acctcgctct                                                  20

<210> SEQ ID NO 42
<211> LENGTH: 20
<212> TYPE: DNA
<213> ORGANISM: Artificial
<220> FEATURE:
<223> OTHER INFORMATION: synthetic primer 5767

<400> SEQUENCE: 42
gagcattacg ctgacttgac                                                  20

<210> SEQ ID NO 43
<211> LENGTH: 20
<212> TYPE: DNA
<213> ORGANISM: Artificial
<220> FEATURE:
<223> OTHER INFORMATION: synthetic primer 5768

<400> SEQUENCE: 43
atgcctcttc cgaccatcaa                                                  20

<210> SEQ ID NO 44
<211> LENGTH: 20
<212> TYPE: DNA
<213> ORGANISM: Artificial
<220> FEATURE:
<223> OTHER INFORMATION: synthetic primer 5770

<400> SEQUENCE: 44
ggcggtaatg ttggacatga                                                  20

<210> SEQ ID NO 45
<211> LENGTH: 20
<212> TYPE: DNA
<213> ORGANISM: Artificial
<220> FEATURE:
<223> OTHER INFORMATION: synthetic primer 847A

<400> SEQUENCE: 45
ggcggagttg ttacgacatt                                                  20

<210> SEQ ID NO 46
<211> LENGTH: 20
<212> TYPE: DNA
<213> ORGANISM: Artificial
<220> FEATURE:
<223> OTHER INFORMATION: synthetic primer 5772

<400> SEQUENCE: 46
cattgtgctg tgcctaagtc                                                  20
```

```
<210> SEQ ID NO 47
<211> LENGTH: 20
<212> TYPE: DNA
<213> ORGANISM: Artificial
<220> FEATURE:
<223> OTHER INFORMATION: synthetic primer GA seqF1

<400> SEQUENCE: 47
ccagaccgag gagaagttca                                          20

<210> SEQ ID NO 48
<211> LENGTH: 20
<212> TYPE: DNA
<213> ORGANISM: Artificial
<220> FEATURE:
<223> OTHER INFORMATION: synthetic primer GA seqF2

<400> SEQUENCE: 48
tgctggagga gacctctgtg                                          20

<210> SEQ ID NO 49
<211> LENGTH: 20
<212> TYPE: DNA
<213> ORGANISM: Artificial
<220> FEATURE:
<223> OTHER INFORMATION: synthetic primer GA seqR2

<400> SEQUENCE: 49
tcgatccgcc gcttcatcac                                          20

<210> SEQ ID NO 50
<211> LENGTH: 1236
<212> TYPE: DNA
<213> ORGANISM: Homo sapiens

<400> SEQUENCE: 50
gaattcgccg ccaccatgga gtcctctgcc aagagaaaga tggaccctga taatcctgac    60
gagggccctt cctccaaggt gccacgggtc aaacagatta aggttcgagt ggacatggtg   120
cggcatagaa tcaaggagca catgctgaaa aaatataccc agacggaaga gaaattcact   180
ggcgccttta atatgatggg aggatgtttg cagaatgcct agatatctt agataaggtt   240 catgagcctt tcgaggagat gaagtgtatt gggctaacta tgcagagcat gtatgagaac   300
tacattgtac ctgaggataa gcgggagatg tggatggctt gtattgatga acttaggaga   360
aagatgatgt atatgtgcta caggaatata gagttcttta ccaagaactc agccttccct   420
aagaccacca atggctgcag tcaggccatg gcggcactgc agaacttgcc tcagtgctcc   480
cctgatgaga ttatggctta tgcccagaaa atatttaaga ttttggatga ggagagagac   540
aaggtgctca cgcacattga tcacatattt atggatatcc tcactacatg tgtggaaaca   600
atgtgtaatg agtacaaggt cactagtgac gcttgtatga tgaccatgta cggggggcatc   660 tctctcttaa gtgagttctg tcgggtgctg tgctgctatg tcttagagga gactagtgtg   720
atgctggcca gcggcctct gataaccaag cctgaggtta tcagtgtaat gaagcgccgc   780
attgaggaga tctgcatgaa ggtctttgcc cagtacattc tggggccga tcctctgaga   840 gtctgctctc ctagtgtgga tgacctacgg gccatcgccg aggagtcaga tgaggaagag   900
gctattgtag cctacacttt ggccaccgct ggtgtcagct cctctgattc tctggtgtca   960
cccccagagt ccctgtacc cgcgactatc cctctgtcct cagtaattgt ggctgagaac  1020
agtgatcagg aagaaagtga gcagagtgat gaggaagagg aggagggtgc tcaggaggag  1080
```

-continued

```
cgggaggaca ctgtgtctgt caagtctgag ccagtgtctg agatagagga agttgcccca    1140
gaggaagagg aggatggtgc tgaggaaccc accgcctctg gaggcaagag cacccaccct    1200
atggtgacta gaagcaaggc tgaccagtga ggatcc                              1236
```